US008637706B2

(12) United States Patent
Dalton et al.

(10) Patent No.: US 8,637,706 B2
(45) Date of Patent: Jan. 28, 2014

(54) NUCLEAR RECEPTOR BINDING AGENTS

(75) Inventors: James T. Dalton, Lakeland, TN (US);
Christina Barrett, Oakland, TN (US);
Duane D. Miller, Germantown, TN (US); Seoung-Soo Hong, Collierville, TN (US); Yali He, Germantown, TN (US); Michael L. Mohler, Memphis, TN (US); Ramesh Narayanan, Cordova, TN (US); Zhongzhi Wu, Collierville, TN (US)

(73) Assignee: Gtx, Inc., Memphis, TN (US)

( * ) Notice: Subject to any disclaimer, the term of this patent is extended or adjusted under 35 U.S.C. 154(b) by 157 days.

(21) Appl. No.: 13/362,242

(22) Filed: Jan. 31, 2012

(65) Prior Publication Data
US 2012/0157539 A1   Jun. 21, 2012

Related U.S. Application Data

(63) Continuation-in-part of application No. 11/785,251, filed on Apr. 16, 2007, now Pat. No. 8,158,828, which is a continuation-in-part of application No. 11/604,884, filed on Nov. 28, 2006, now abandoned.

(60) Provisional application No. 60/739,898, filed on Nov. 28, 2005.

(51) Int. Cl.
*C07C 233/65* (2006.01)
*A61K 31/165* (2006.01)

(52) U.S. Cl.
USPC ............ 564/179; 564/171; 514/617; 514/619

(58) Field of Classification Search
USPC .................... 564/171, 174, 179; 514/619
See application file for complete search history.

(56) References Cited

U.S. PATENT DOCUMENTS

| | | | |
|---|---|---|---|
| 3,413,339 A | 11/1968 | Scherrer | |
| 3,625,972 A | 12/1971 | Schulenberg | |
| 3,838,131 A | 9/1974 | Gauthier et al. | |
| 3,838,134 A | 9/1974 | Gauthier et al. | |
| 3,960,886 A | 6/1976 | Schulenberg | |
| 4,373,017 A | 2/1983 | Maukawa et al. | |
| 5,081,112 A * | 1/1992 | Tsutsumi et al. | 514/119 |
| 5,480,656 A | 1/1996 | Okada et al. | |
| 5,491,173 A | 2/1996 | Toivola et al. | |
| 5,575,987 A | 11/1996 | Kamei et al. | |
| 5,631,020 A | 5/1997 | Okada et al. | |
| 5,643,607 A | 7/1997 | Okada et al. | |
| 5,716,640 A | 2/1998 | Kamei et al. | |
| 5,814,342 A | 9/1998 | Okada et al. | |
| 6,036,976 A | 3/2000 | Takechi et al. | |
| 6,166,013 A | 12/2000 | Coghlan et al. | |
| 6,518,301 B1 | 2/2003 | Bariaam et al. | |
| 6,632,447 B1 | 10/2003 | Steiner et al. | |
| 7,001,911 B2 | 2/2006 | Salvati et al. | |
| 7,118,552 B2 | 10/2006 | Shaw et al. | |
| 7,220,247 B2 | 5/2007 | Shaw et al. | |
| 7,500,964 B2 | 3/2009 | Shaw et al. | |
| 2002/0119953 A1 | 8/2002 | Brugnara et al. | |
| 2002/0156301 A1 | 10/2002 | Kaneko et al. | |
| 2002/0192310 A1 | 12/2002 | Bland et al. | |
| 2003/0153625 A1 | 8/2003 | Steiner | |
| 2004/0082813 A1 | 4/2004 | Iwakuma | |
| 2005/0182143 A1 | 8/2005 | Anttila | |
| 2006/0287282 A1 | 12/2006 | Steiner et al. | |
| 2006/0287359 A1 | 12/2006 | Danso-Danquah et al. | |
| 2007/0265296 A1 | 11/2007 | Dalton et al. | |
| 2009/0062341 A1 | 3/2009 | Dalton et al. | |
| 2009/0156614 A1 | 6/2009 | Dalton et al. | |

FOREIGN PATENT DOCUMENTS

| | | |
|---|---|---|
| DE | 269 213 | 1/1914 |
| DE | 269213 | 1/1914 |
| DE | 2228351 | 12/1972 |
| EP | 0501656 | 9/1992 |
| EP | 1 193 250 | 4/2002 |
| EP | 1193250 | 4/2002 |
| EP | 1 593 665 | 11/2005 |
| FR | 4333 | 9/1966 |
| FR | 1536400 | 7/1967 |
| FR | 1.557.928 | 2/1969 |
| FR | 7699 | 2/1970 |
| FR | 2.098.587 | 4/1972 |
| GB | 2126576 | 3/1984 |
| GB | 2305173 | 2/1997 |
| GB | 2305177 | 2/1997 |
| JP | 49127938 A | 12/1974 |
| JP | 2002322162 | 11/2002 |
| JP | 2004307380 | 11/2004 |
| JP | 2005-255981 | 9/2005 |

(Continued)

OTHER PUBLICATIONS

Supplementary European Search Report for European Patent Application No. EP 06 83 8432 dated Mar. 11, 2011.
European Search Report for European Patent Application No. 12 15 0818 dated Apr. 5, 2012.
Carter et al., John, Wiley & Sons, 2$^{nd}$ Edition, 361-365, 1981.
Australian Office Action for Australian Patent Application No. 2006318400 dated Oct. 25, 2011.
Australian Office Action dated Oct. 25, 2011 cited reference in AU Patent Application No. 2006318400, D19 CAS RN-79777-72-1, Benzamide, 2, 4-dichloro-N, N-bis (2-chlorophenyl), Chemical Library, Dec. 15, 2004.
Gilman et al., Synthesis of some 5, 10-dihydrophenazasiline derivatives, Journal of Organic Chemistry, 1961, vol. 26, pp. 2013-2017.
Australian Office Action cited dated Oct. 25, 2011 reference in AU Patent Application No. 2006318400, D21 RN 663217-19-14, Benzamide, N-[3, 5-bis (1,1-dimethylethyl)-4-hydroxyphenyl]-2-chloro-N-(4-methylphenyl), Chemical Library Supplier, Mar. 15, 2004.

(Continued)

*Primary Examiner* — Shailendra Kumar
(74) *Attorney, Agent, or Firm* — Mark S. Cohen; Pearl Cohen Zedek Latzer Baratz

(57) ABSTRACT

The present invention relates to a novel class of selective estrogen receptor modulators (SERMs). The SERM compounds are applicable for use in the prevention and/or treatment of a variety of diseases and conditions including prevention and treatment of cancers such as prostate and breast cancer, osteoporosis, hormone-related diseases, hot flashes or vasomotor symptoms, neurological disorders, cardiovascular disease and obesity.

30 Claims, 15 Drawing Sheets

(56) References Cited

FOREIGN PATENT DOCUMENTS

| | | |
|---|---|---|
| WO | WO 96/07402 | 3/1996 |
| WO | WO 97/30047 | 8/1997 |
| WO | WO 01/44161 | 6/2001 |
| WO | WO 02/28853 | 4/2002 |
| WO | WO 2004/009552 | 1/2004 |
| WO | WO 2004/026823 | 4/2004 |

OTHER PUBLICATIONS

Australian Office Action dated Oct. 25, 2011cited reference in AU Patent Application No. 2006318400, D22 CAS RN 409111-68-8, Benzeneacetic acid, 2, 2'-[4-chlorobenzoyll)iminio]bis-, dimethylester.

Grimshaw et al., Electrochemical Reactions, Part 20, Intramolecular Cyclization During the Reduction of 2-chloro-NN-Diphenylbenzamides, Journal of the Chemical Society, Perkin Transactions 1: Organic and Bio-Organic Chemistry (1972-1999) (1977), (22), 2456.

Birchall et al., Rearrangements of Diphenylamine Derivatives, II, Rearrangement o Some N-aroyldiphenylamines and the Intermolecular Character of the Reaction, Journal of the Chemical Society [Section] C: Organic 1968, vol. 23, pp. 2900-2904.

Jamison et al., Some Derivatives of Diphenylamine and a New Synthesis of N-arylanthranilic Acids and of Acridones, Journal of the Chemical Society, 1937, pp. 1954-1959.

Ivakhnenko et al., Synthesis and Transformations of Phenoxyl Biradicals, Zhurnal Organicheskoi Khimii, 1990, vol. 26(3), pp. 616-623.

Hey et al. Internuclear Cyclization, XIII, Decomposition of Diazonium Salts Rearrangement from N-(omicron-aminobenzoyl) Diphenylamines. New Molecular Rearrangement, Journal of the Chemical Society, 1959, pp. 1563-1572.

Tozer et al., Rearrangement of the o-Carbamyl Derivaties of Diphenly ether, Journal of the Chemical Society, 1938, pp. 2052-2056.

Chapman et al., Beckmann Change, I, The Spontaneous Rearrangement of oxime picryl ethers, Journal of the Chemical Society, 1933, pp. 806-811.

Australian Office Action dated Oct. 25, 2011 cited reference in AU Patent Application No. 2006318400, D31 CAS RN 300668-84-4, Benzamide, N-(3-bromophenyl_-N-(4-bromophenyl)-2-nitro, Chemical Library Supplier, Nov. 1, 2000.

Heine et al., The Reactions of an o-Quinone Monoimide with some phenols, Journal of Organic Chemistry, 1990, vol. 55(13), pp. 4039-4043.

Carter et al., Arylation with 1, 3-dinitroarnes and copper (I) tert-butoxide Scope and Limitations, Journal of Chemical Research, Synopses, 1985, vol. 5, pp. 136-137.

Froehlich et al., Process for Preparation of Anthranilamides, Ger (East), 1989, p. 7.

Australian Office Action for Australian Patent Application No. 2011226856 dated Dec. 23, 2011.

Hellwinkel et al., Carbanionically induced [1,3]-migrations of π-and Coorrdinatively Unsaturated Groups, Chemische Berichte, 1983, vol. 116, No. 10, pp. 3375-3405.

Boltze et al., The Chemistry of Etofenamate, a Novel Anti-inflammatory Agent from the Series N-arylanthranilic Acid Derivatives, Arzneimittel-Forschung, 1977 vol. 27, No. 6B, pp. 1300-1312.

Grigorovskii et al., The Formation of 9-Chloroacridines from Diphenylamine-2-Carboxylic Acids and Phosphorus Oxychlorid, Zhurnal Prikladnoi Khimii, 1950, vol. 23, pp. 197-204.

Alibhai, et al (2006) "Prevention and Management of Osteoporosis in Men Receiving Androgen Deprivation Therapy: A Survey of Urologists and Radiation Oncologists." Urology, vol. 68, pp. 126-131.

Angelo, et al (1968) Nouvelles solutions ioniques radiclaires et leur emplol., Bull de la Soc. Chim. De France, No. 9, 3855-3856.

Berthelot, et al (1985) Stereochimie des complexes du chlorure d'iode avec les bases carbonylees, Can. J. Chem, vol. 63, 1985, pp. 958-962.

Chadwick, et al (2005) "Identification of pathway-selective estrogen receptor ligands that inhibit NF-κB transcriptional activity." PNAS, vol. 102, No. 7, pp. 2543-2548.

Fotsis, et al (1993) "Genistein, a Dietary-Derived Inhibitor of in vitro Angiogensis." PNAS, vol. 90, pp. 2690-2694.

Grease, et al (2001) Photochemical Synthesis of N-Arylbenzophenanthridine Selective Estrogen Receptor Modulators (SERMS). J. Med. Chem. 44, 2857-2860.

Gustafson (2006) "ERβ scientific visions translate to clinical uses." Climacteric, vol. 9, pp. 156-160.

Harris (2006) "The unexpected science of estrogen receptor-β selective agonists: a new class of anti-inflammatory agents?" Nuclear Receptor Signaling, vol. 4, 012-016.

Harris (2006) "Estrogen Receptor-β: Recent Lessons from in Vivo Studies." Molecular Endocrinology, vol. 21, No. 1, pp. 1-13.

Harris, et al (2006) "Evaluation of an Estrogen Receptor-β Agonist in Animal Models of Human Disease." Endocrinology, vol. 144, No. 10, pp. 4241-4249.

Hayashi, et al (1997) "Genistein, a Protein Tyrosine Kinase Inhibitor, Ameliorates Retinal Degeneration After Ischemia-Reperfusion Injury in a Rat." Investigative Ophthalmology and Visual Science, vol. 38, No. 6, pp. 1193-1202.

Heim, et al (2006) "They Phytoestrogen Genistein Enhances Osteogenesis and Represses Adipogenic Differentiation of Human Primary Bone Marrow Stromal Cells." Endocrinology, vol. 145, No. 2, pp. 848-859.

Yu, et al (2006) "Salutary effects of estrogen receptor-β agonist on lung injury after trauma-hemorrhage." Am. J. Physiol. Lung Cell Mol. Physiol., vol. 290, pp. L1004-L1009.

Steigman et al., The Anhydrides of N-aryl Anthranilic Acids II, Journal of Organic Chemistry, 1937, vol. 2, pp. 211-212.

Ho, et al (2004) "Estrogens and Anti-Estrogens: Key Mediators of Prostat Carcinogenesis and New Therapeutic Candidates." Journal of Cellular Biochemistry, vol. 91, pp. 491-503.

Kai, et al (2004) "Soybean Isoflavones Eliminate Nifedipine-Induced Flushing of Tail Skin in Ovariectomized Mice." J Pharmacol. Sci., vol. 95, pp. 476-478.

Lutty, et al (1999) "Changes in Choriocapillaris and Retinal Pigment Epithelium (RPE) in Age-Related Macular Degeneration." Molecular Vision, vol. 5, No. 35, pages.

Morani, et al (2006) "Lung dysfunction causes systematic hypoxia in estrogen receptor β knockout (ERβ$^{-/-}$) mice." PNAS. vol. 103, No. 18, pp. 7165-7169.

Norman, et al (2006) "Benzopyrans Are Selective Estrogen Receptor β Agonists with Novel Activity in Models of Benign Prostate Hyperplasia." J Med. Chem., vol. 49, pp. 6155-6157.

Nakajima, et al (2001) "Normalization of Retinal Vascular Permeability in Experimental Diabetes with Genistein." Investigative Ophthalmology and Visual Science, vol. 42, No. 9, pp. 2110-2114.

Rhodes, et al (2005) "ERβ-selective SERMs produce mnemonic-enhancing effects in the inhibitory avoidance and water maze tasks." Neurobiology of Learning and Memory, vol. 85, pp. 183-191.

Safe, et al (2006) "The role of xenoestrogenic compounds in the development of breast cancer." TRENDS in Pharmacological Sciences, vol. 27, No. 8.

Shen, et al (2006) "Expression of Estrogen Receptors-α and -β in Bladder Cancer Cell Lines and Human Bladder Tumor Tissue." American Cancer Society.

Trotter, et al (2006) "Design and Synthesis of Novel Isoquinoline-3-nitrilies as Orally Bioavailable Kv1.5 Antagonists for the Treatment of Atrial Fibrillation." American Chemical Society.

Vivacqua, et al (2006) "The G Protein-Coupled Receptor GPR30 Mediates the Proliferative Effects Induced by 17β-Estradiol and Hydroxytamoxifen in Endometrial Cancer Cells." Molecular Endocrinology, vol. 20, No. 3, pp. 631-646.

Walf, et al (2006) "Aggression, mood and affect." Frontiers in Neuroendocrinology, vol. 27.

Xu, et al (2006) "Effects of genistein on angiotensin-converting enzyme in rats." Life Sciences, vol. 79, pp. 828-837.

Grimshaw, et al "Intramolecular Cyclisation during the reduction of 2-chloro-NN-diphenylbenzamides" Electrochemical Reactions, Part 20, vol. 22, 1977, p. 2456.

(56) References Cited

OTHER PUBLICATIONS

Kenneth et al., "The kinetics of the thermal rearrangement of phenyl benzanilimino ethers", Journal of the American Chemical Society, 1955, 77, 2205-9.
Chapman et al., "New method for preparing substituted diphenylamines", Journal of the Chemical Society, 1929, pp. 569-572.
Schroeter et al., "Dimolecular Anhydrides of Anthranilic Acid", Justis Liebigs Annalen der Chemie, 1909, 367, pp. 101-168.
Clark et al., "Synthetic studies on 5-(3,4-dimethoxyphenyl)-5, 6-dihydrophenanthridin-6-ol, an analog of perloline", Australian Journal of Chemistry, 1982, 35(8), pp. 1645-1653.
Hoeft Eugen et al., "Reactions of nitrogen-containing compounds with molecular oxygen II. Partially hydrogenated, benxocondensed isoquinolines", justus Liebids Annalen de Chemie, 1966, 697, pp. 181-187.
Migel et al., "Estimate of the energy characteristics of the electronic-vibrational interactions in N-methylphenanthridone molecules" Zhurnal Fizicheskoi Khimii, 1986 62(9), pp. 2533-2537.
Hellwinkel et al., "Heterocyclic synthese via carbanionically induced rearrangement reactions", Tetrahedron, 1983, 39(12), 2073-84.
Datta et al., "Studies on Enamides. Part 4. Photochemical Investigations of N-Aroyldiphenylamines", Tetrahedron, 1990, 46(19), 6821-30.
Joseph et al., "Rearrangement of nitrones to amides using chlorosulfonyl isocyanate", Tetrahedron, 1986, 42(21), 5979-83.
Fong et al., "The effect of side chain confirmation on the carbon-13 substituent chemical shifts of N-substituted benzamides", Australian Journal of Chemistry, 1981, 34(6), 1205-1214.
Scherowsky et al., "Reactions of heterocyclic onium salts with electron-rich multiple bond systems", Chemische Berichte, 1983, 116(1), pp. 186-196.
El-Taweel et al., "Studies with polyfunctionally substituted heteroarenes: New synthesis of benzo[c]quinolinones and pyrano[3,2,c]quinoline derivatives", Bollettino Chimico Farmaceutico, 1998, 137(8), pp. 325-333.
Mintas Mhaden et al., "Sterically hindered N-aryl-2 (1H)-quinolones and N-aryl-6-(5H)-phenanthridinones: separation of enantiomers and barriers to racemization", Journal of the Chemical Society, Perkin Transactions 2: Physical Organic Chemistry (1972-1999) (4), 1990, pp. 619-624.
Derneter et al., "Dual fluorescence and intramolecular charge transfer with N-Phenylphenanthridinones", Journal of Physical Chemistry a, 2001, 105 (19), 4611-4621.
Moynehan et al.,t, Proceedings of the Chemical Society, Lodon 209, 1957.
Hey et al., "Internuclear cyclization. XIII. Decomposition of diazonium salts prepared from N-(0-aminobenzoyl) diphenylamines. New molecular rearrangement", Journal of the Chemistry Society, 1959, pp. 1563-1572.
Wolff, "Burger's Medical Chemistry $4^{th}$ Ed. Part I", Wiley: New York, 1979, 336-337.
Wolff, "Burger's Medicinal Chemistry $5^{th}$ Ed. Part I", Wiley: 1996, pp. 975-977.
Banker et al., "Modern Pharmaceutics, 3 Ed." 1996, pp. 451 and 596.
West, "Solid state chemistry and its applications" Wiley, 1988, pp. 358 and 365.
Ohnmacht et al., "N-Aryl-3,3,3-trifluoro-2-hydroxy-2-methylpropanamides: potassium Channel Openers. Modifications on the Western Region", J. Med. Chem., 1996, 39, 4592-4601.
International Search Report of Application No. PCT/US06/45451; Date of Mailing Feb. 29, 2008.
Eurasian Search Report of Application No. 200801461; Date of Mailing Oct. 29, 2008.
International Search Report of Application No. PCT/US10/25032; Date of Mailing Apr. 8, 2010.
International Search Report of Application No. PCT/US08/04908; Date of Mailing Sep. 26, 2008.
Datti et al., "Studies on Enamides. Part-4: Photochemical Investigations of N-Aroyldiphenylamines", Tetrahedron, vol. 46, No. 19, 1990, pp. 6821-6830.
Heine et al., "The reactions of an o-Quinone Monoimide with some phenols", Journal of Organic Chemistry, vol. 55, No. 13, 1990, pp. 4039-4043.
Harris et al., "Sequential N-Arylation of primary amines as a route to alkyldiarylamines", Journal of Organic Chemistry, vol. 64, 1999, pp. 6019-6022.
Ohta et al., "Reaction of N,O-Diacylarylhydroxylamine with carbon nucleophiles", 1978, Tetrahedron Letters, pp. 1983-1986.
Piutti et al., "Azione dell'anidride ftalica sulfa p- e m-ossidiffenilammina", Gazzetta Chimica Italiana, vol. 28, 1898, pp. 370-382.
Hellwinkel et al., "Ein bequemes Eintopfverfahren zur Synthese von 1,2-Benzisothiazol-1, 1-dioxiden", No. 5, 1989, pp. 394-395.
Lam et al., "Copper-promoted C—N bond cross-coupling with phenylstannane", Tetrahedron Letters 43, 2002, 3091-3094.
Smith (2008) *Current Prostate Reports*. 6:149-154.
Suzuki et al., (2008) *Int. J. Clin. Oncol.* 13: 401-410.
Sharifi, N. et al., (2005) *JAMA*. 294(2): 238-244.
Presti, J.C. Jr. (1996) JAMA. 275(15): 1153-6.
Tsourdi et al., 2008, *Fertility and Sterility* doi: 10.1016.

* cited by examiner

NUCLEAR RECEPTOR BINDING AGENTS

CROSS REFERENCE TO RELATED APPLICATIONS

This application is a Continuation-In-Part application of U.S. patent application Ser. No. 11/785,251 filed Apr. 16, 2007 now U.S. Pat. No. 8,158,828, which is a Continuation-In-Part application of U.S. patent application Ser. No. 11/604,884 filed Nov. 28, 2006 now abandoned, which claims the benefit of U.S. Provisional Application Ser. No. 60/739,898, filed Nov. 28, 2005, which are all hereby incorporated by reference in their entirety.

FIELD OF THE INVENTION

The present invention relates to a novel class of nuclear receptor binding agents (NRBAs). The NRBA compounds are applicable for use in the prevention and/or treatment of a variety of diseases and conditions including, inter alia, prevention and treatment of hormone-related diseases, cancers, inflammation, osteoporosis, peripheral vascular disease, neurological disorders, ocular disorders, cardiovascular disease and obesity.

BACKGROUND OF THE INVENTION

The nuclear hormone receptor superfamily of ligand activated transcription factors is present in various tissues, and responsible for a multitude of effects in these tissues.

The nuclear receptor (NR) superfamily presently comprises approximately 48 different proteins, most of which are believed to function as ligand activated transcription factors, exerting widely different biological responses by regulating gene expression. Members of this family include receptors for endogenous small, lipophilic molecules, such as steroid hormones, retinoids, vitamin D and thyroid hormone.

The nuclear receptor (NR) superfamily includes the steroid nuclear receptor subfamily, such as the mineralocorticoid receptor (MR) (or aldosterone receptor), the estrogen receptors (ER), ER alpha and ER beta, the androgen receptor (AR), the progesterone receptors (PR), glucocorticoid receptors (GR) and others. Also closely related in structure are the estrogen related receptors (ERRs) ERR-alpha, ERR-beta and ERR-gamma. The steroid nuclear receptors perform important functions in the body some of which are related to the transcriptional homeostasis of electrolyte and water balance, growth, development and wound healing, fertility, stress responses, immunological function, and cognitive functioning. The effects may be mediated by cytosolic or nuclear events. The effects may be mediated by cytosolic or nuclear events. Accordingly, compounds that modulate (i.e. antagonize, agonize, partially antagonize, partially agonize) the activity of steroid nuclear receptors are important pharmaceutical agents that have specific utility in a number of methods, as well as for the treatment and prevention of a wide range of diseases and disorders modulated by the activity of steroid nuclear receptors.

Members of the steroid nuclear receptor sub-family exhibit significant homology to each other and possess closely related DNA and ligand binding domains.

Given the close similarity in ligand binding domains of the steroid nuclear receptors, it is not surprising that many naturally occurring and synthetic molecules possess the ability to modulate the activity of more than one steroid nuclear receptor.

SUMMARY OF THE PRESENT INVENTION

In one embodiment, this invention provides a nuclear receptor binding agent (NRBA), which in one embodiment is a selective estrogen receptor modulator (SERM) compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula I:

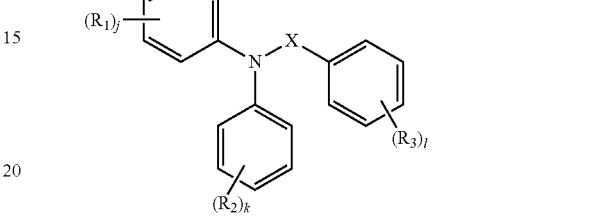

wherein
X is CO, CS, $(CH_2)_q$, branched alkyl, branched alkyl with haloalkyl side chain, haloalkyl, $C(O)(CH_2)_q$, SO, or $SO_2$;

$R_1$, $R_2$ and $R_3$ are independently, hydrogen, halogen, aldehyde, COOH, CHNOH, $CH=CHCO_2H$, hydroxyalkyl, hydroxyl, alkoxy, cyano, nitro, $CF_3$, $NH_2$, NHR, NHCOR, $N(R)_2$, sulfonamide, $SO_2R$, alkyl, aryl, protected hydroxyl, $OCH_2CH_2NR_4R_5$, Z-Alk-Q, Z-Alk-$NR_4R_5$, Z-Alk-heterocycle or $OCH_2CH_2$-heterocycle in which the heterocycle is a 3-7 membered substituted or unsubstituted heterocyclic ring, optionally aromatic, or $R_1$, $R_2$ or $R_3$ together with the benzene ring to which the R-group is attached comprises a fused ring system represented by structure A

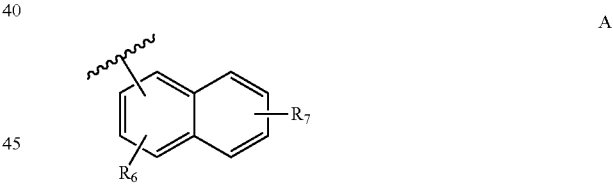

wherein;
$R_6$ and $R_7$ are independently $R_1$, $R_2$ or $R_3$;
R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;
$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;
Z is O, NH, $CH_2$ or

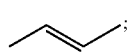;

Q is $SO_3H$, $CO_2H$, $CO_2R$, $NO_2$, tetrazole, $SO_2NH_2$ or $SO_2NHR$;
j, k, l are independently 1-5;
q is 1-5;

Alk is linear alkyl of 1-7 carbons, branched alkyl of 1-7 carbons, or cyclic alkyl of 3-8 carbons; and if X is $(CH_2)_q$, CO or $C(O)(CH_2)_q$, and $R_2$ is $OCH_2CH_2NR_4R_5$, or $OCH_2CH_2$-heterocycle when k is 1, then $R_1$ or $R_3$ is not hydrogen, lower alkyl (1-4 carbons), lower alkoxy (1-4 carbons), halogen, nitro or amino;

if X is $(CH_2)_q$, CO or $C(O)(CH_2)_q$, and $R_3$ is $OCH_2CH_2NR_4R_5$, or $OCH_2CH_2$-heterocycle when l is one, then $R_1$ or $R_2$ is not hydrogen, lower alkyl (1-4 carbons), lower alkoxy (1-4 carbons), halogen, nitro or amino.

In one embodiment, this invention provides a NRBA, which in one embodiment is a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula I:

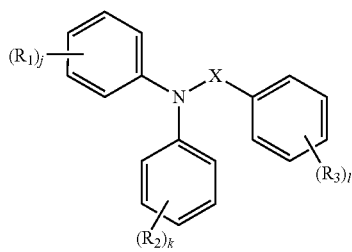

(I)

wherein

X is CS, branched alkyl, branched alkyl with haloalkyl side chain, haloalkyl, SO, or $SO_2$;

$R_1$, $R_2$ and $R_3$ are independently, hydrogen, halogen, aldehyde, COOH, CHNOH, CH=$CHCO_2H$, hydroxyalkyl, hydroxyl, alkoxy, cyano, nitro, $CF_3$, $NH_2$, NHR, NHCOR, $N(R)_2$, sulfonamide, $SO_2R$, alkyl, aryl, protected hydroxyl, $OCH_2CH_2NR_4R_5$, $Z(CH_2)_qQ$, Z-Alk-$NR_4R_5$, Z-Alk-heterocycle or $OCH_2CH_2$-heterocycle in which the heterocycle is a 3-7 membered substituted or unsubstituted heterocyclic ring, optionally aromatic;

or $R_1$, $R_2$ or $R_3$ together with the benzene ring to which the R-group is attached comprises a fused ring system represented by structure A

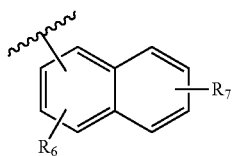

A wherein $R_6$ or $R_7$ are independently $R_1$, $R_2$ or $R_3$;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;

Z is O, NH, $CH_2$, or

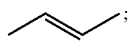;

Q is $SO_3H$, $CO_2H$, $CO_2R$, $NO_2$, tetrazole, $SO_2NH_2$, or $SO_2NHR$;

j, k, l are independently 1-5;

q is 1-5;

Alk is linear alkyl of 1-7 carbons, branched alkyl of 1-7 carbons or cyclic alkyl of 3-8 carbons.

In one embodiment this invention provides a NRBA, which in one embodiment is a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula II:

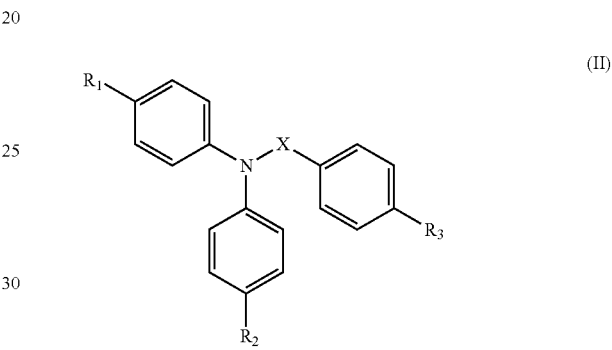

(II)

X is CO, CS, $(CH_2)_q$, branched alkyl, branched alkyl with haloalkyl side chain, haloalkyl, $C(O)(CH_2)_q$, SO, or $SO_2$;

$R_1$, $R_2$ and $R_3$ are independently, hydrogen, halogen, aldehyde, COOH, CHNOH, CH=$CHCO_2H$, hydroxyalkyl, hydroxyl, alkoxy, cyano, nitro, $CF_3$, $NH_2$, NHR, NHCOR, $N(R)_2$, sulfonamide, $SO_2R$, alkyl, aryl, protected hydroxyl, $OCH_2CH_2NR_4R_5$, Z-Alk-Q, Z-Alk-$NR_4R_5$, Z-Alk-heterocycle or $OCH_2CH_2$-heterocycle in which the heterocycle is a 3-7 membered substituted or unsubstituted heterocyclic ring, optionally aromatic, or $R_1$, $R_2$ or $R_3$ together with the benzene ring to which the R-group is attached comprises a fused ring system represented by structure A

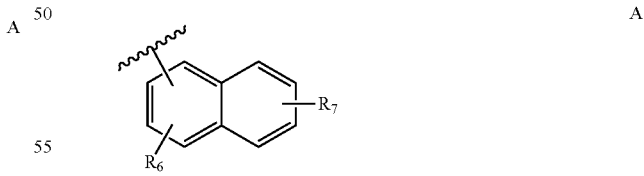

A wherein $R_6$ and $R_7$ are independently $R_1$, $R_2$ or $R_3$;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;

Z is O, NH, CH$_2$, or

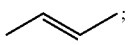;

Q is SO$_3$H, CO$_2$H, CO$_2$R, NO$_2$, tetrazole, SO$_2$NH$_2$, or SO$_2$NHR; q is 1-5;
Alk is linear alkyl of 1-7 carbons, branched alkyl of 1-7 carbons or cyclic alkyl of 3-8 carbons; and
if X is (CH$_2$)$_q$, CO or C(O)(CH$_2$)$_q$, and R$_2$ is OCH$_2$CH$_2$NR$_4$R$_5$, or OCH$_2$CH$_2$-heterocycle when k is 1, then R$_1$ or R$_3$ is not hydrogen, lower alkyl (1-4 carbons), lower alkoxy (1-4 carbons), halogen, nitro or amino;
if X is (CH$_2$)$_q$, CO or C(O)(CH$_2$)$_q$, and R$_3$ is OCH$_2$CH$_2$NR$_4$R$_5$, or OCH$_2$CH$_2$-heterocycle when l is one, then R$_1$ or R$_2$ is not hydrogen, lower alkyl (1-4 carbons), lower alkoxy (1-4 carbons), halogen, nitro or amino.

In one embodiment this invention provides a NRBA, which in one embodiment is a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula II:

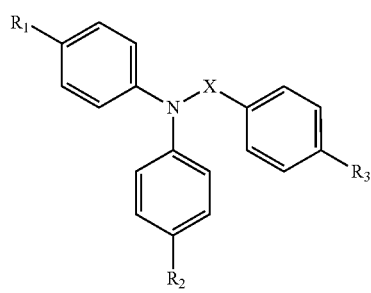

(II)

wherein
X is CS, branched alkyl, branched alkyl with haloalkyl side chain, haloalkyl, SO, or SO$_2$;
R$_1$, R$_2$ and R$_3$ are independently, hydrogen, halogen, aldehyde, COOH, CHNOH, CH=CHCO$_2$H, hydroxyalkyl, hydroxyl, alkoxy, cyano, nitro, CF$_3$, NH$_2$, NHR, NHCOR, N(R)$_2$, sulfonamide, SO$_2$R, alkyl, aryl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered substituted or unsubstituted heterocyclic ring, optionally aromatic,
or R$_1$, R$_2$ or R$_3$ together with the benzene ring to which the R-group is attached comprises a fused ring system represented by structure A

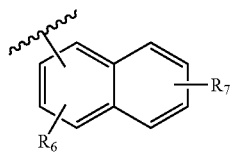

A wherein R$_6$ or R$_7$ are independently R$_1$, R$_2$ or R$_3$;
R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$, or OH;

R$_4$ and R$_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;
Z is O, NH, CH$_2$, or

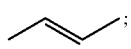;

Q is SO$_3$H, CO$_2$H, CO$_2$R, NO$_2$, tetrazole, SO$_2$NH$_2$, or SO$_2$NHR;
Alk is linear alkyl of 1-7 carbons, branched alkyl of 1-7 carbons or cyclic alkyl of 3-8 carbons.

In another embodiment this invention provides a NRBA, which in one embodiment is a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula III:

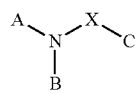

(III)

wherein
A is a ring selected from

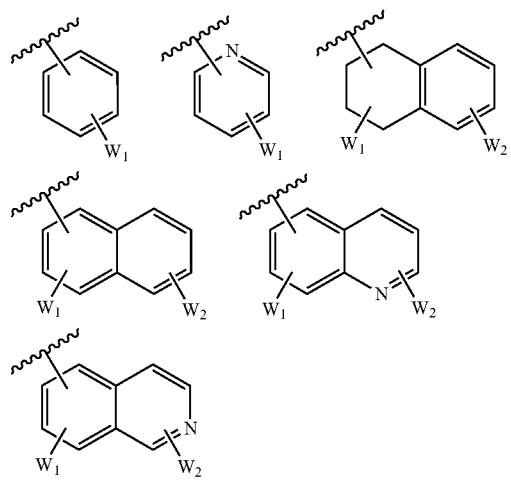

B is a ring selected from

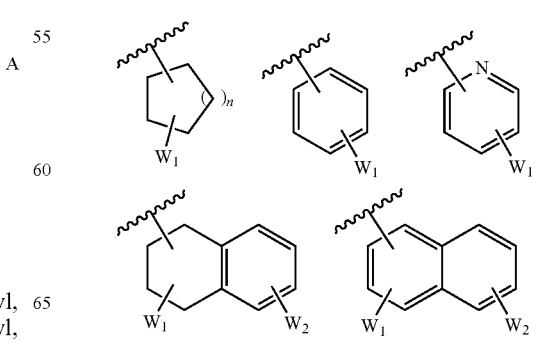

-continued

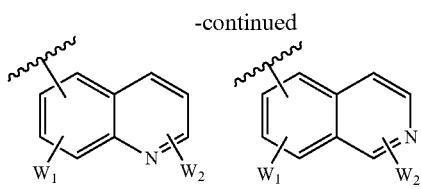

C is a ring selected from

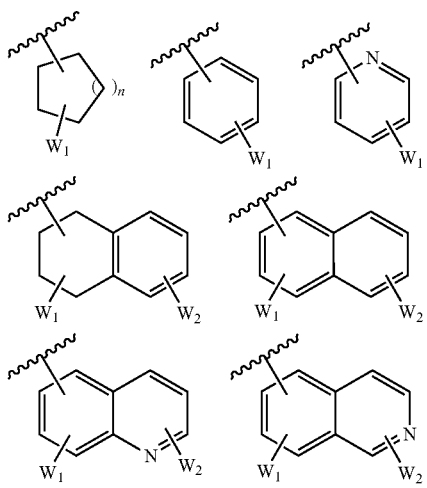

X is CO, CS, (CH$_2$)$_q$, branched alkyl, branched alkyl with haloalkyl side chain, haloalkyl, C(O)(CH$_2$)$_q$, SO, or SO$_2$;

W$_1$ and W$_2$ are independently, hydrogen, halogen, aldehyde, COOH, CHNOH, CH=CHCO$_2$H, hydroxyalkyl, hydroxyl, alkoxy, cyano, nitro, CF$_3$, NH$_2$, NHR, NHCOR, N(R)$_2$, sulfonamide, SO$_2$R, alkyl, aryl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered substituted or unsubstituted heterocyclic ring, optionally aromatic;

R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$, or OH;

R$_4$ and R$_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;

Z is O, NH, CH$_2$, or

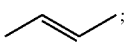

Q is SO$_3$H, CO$_2$H, CO$_2$R, NO$_2$, tetrazole, SO$_2$NH$_2$, or SO$_2$NHR; q is 1-5;
n is 0-5;
Alk is linear alkyl of 1-7 carbons, branched alkyl of 1-7 carbons, or cyclic alkyl of 3-8 carbons;
A, B and C cannot simultaneously be a benzene ring; and
if X is (CH$_2$)$_q$, CO or C(O)(CH$_2$)$_q$, A is pyridyl ring and B and C are phenyl rings and C is substituted with OCH$_2$CH$_2$NR$_4$R$_5$, or OCH$_2$CH$_2$-heterocycle, then A or B is not substituted with hydrogen, lower alkyl (1-4 carbons), lower alkoxy (1-4 carbons), halogen, nitro or amino;
If X is (CH$_2$)$_q$, CO or C(O)(CH$_2$)$_q$, A is pyridyl ring and B and C are phenyl rings and B is substituted with OCH$_2$CH$_2$NR$_4$R$_5$, or OCH$_2$CH$_2$-heterocycle, then A or C is not substituted with hydrogen, lower alkyl (1-4 carbons), lower alkoxy (1-4 carbons), halogen, nitro or amino.

In another embodiment, this invention provides, a NRBA, which in one embodiment is a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula IV:

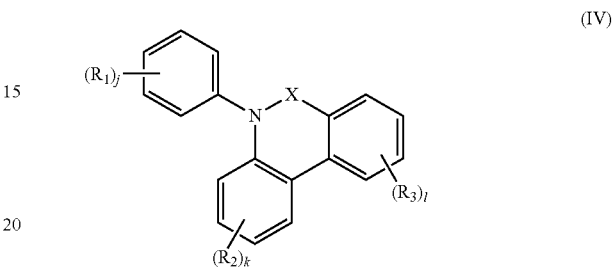

(IV)

wherein
X is CO, CS, (CH$_2$)$_q$, branched alkyl, branched alkyl with haloalkyl side chain, haloalkyl, C(O)(CH$_2$)$_q$, SO, or SO$_2$;

R$_1$, R$_2$ and R$_3$ are independently, hydrogen, halogen, aldehyde, COOH, CHNOH, CH=CHCO$_2$H, hydroxyalkyl, hydroxyl, alkoxy, cyano, nitro, CF$_3$, NH$_2$, NHR, NHCOR, N(R)$_2$, sulfonamide, SO$_2$R, alkyl, aryl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered substituted or unsubstituted heterocyclic ring, optionally aromatic, or R$_1$, R$_2$ and R$_3$ together with the benzene ring to which the R-group is attached comprises a fused ring system represented by structure A

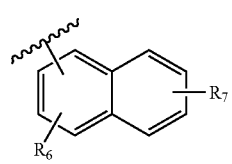

A wherein
R$_6$ and R$_7$ independently are R$_1$, R$_2$ or R$_3$;
R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$, or OH;
R$_4$ and R$_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;
Z is O, NH, CH$_2$, or

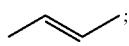

Q is SO$_3$H, CO$_2$H, CO$_2$R, NO$_2$, tetrazole, SO$_2$NH$_2$, or SO$_2$NHR;
j, k, l are independently 1-5;
q is 1-5;

Alk is linear alkyl of 1-7 carbons, branched alkyl of 1-7 carbons or cyclic alkyl of 3-8 carbons.

In another embodiment, this invention provides a NRBA, which in one embodiment is a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula V:

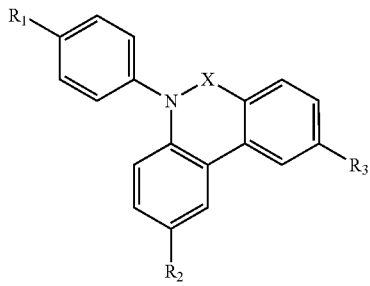
(V)

X is CO, CS, $(CH_2)_q$, branched alkyl, branched alkyl with haloalkyl side chain, haloalkyl, $C(O)(CH_2)_q$, SO, or $SO_2$;

$R_1$, $R_2$ and $R_3$ are independently, hydrogen, halogen, aldehyde, COOH, CHNOH, CH=CHCO$_2$H, hydroxyalkyl, hydroxyl, alkoxy, cyano, nitro, CF$_3$, NH$_2$, NHR, NHCOR, N(R)$_2$, sulfonamide, SO$_2$R, alkyl, aryl, protected hydroxyl group, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered substituted or unsubstituted heterocyclic ring, optionally aromatic, or $R_1$, $R_2$ and $R_3$ together with the benzene ring to which the R-group is attached comprises a fused ring system represented by structure A

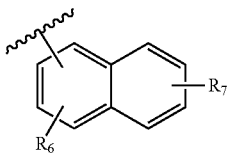
A wherein
$R_6$ and $R_7$ independently are $R_1$, $R_2$ or $R_3$;
R is alkyl, hydrogen, haloalkyl, dihaloalkyl, trihaloalkyl, CH$_2$F, CHF$_2$, CF$_3$, CF$_2$CF$_3$, aryl, phenyl, halogen, CN, NO$_2$, alkenyl or OH;
$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;
Z is O, NH, CH$_2$, or

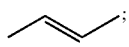;

Q is SO$_3$H, CO$_2$H, CO$_2$R, NO$_2$, tetrazole, SO$_2$NH$_2$, or SO$_2$NHR; q is 1-5;
Alk is linear alkyl of 1-7 carbons, branched alkyl of 1-7 carbons, or cyclic alkyl of 3-8 carbons.

In one embodiment this invention provides a NRBA, which in one embodiment is a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula VI:

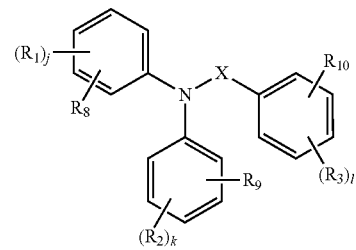
VI wherein
X is CO, CS, $(CH_2)_9$, branched alkyl, branched alkyl with haloalkyl side chain, haloalkyl, $C(O)(CH_2)_q$, SO, or $SO_2$;

$R_1$, $R_2$, $R_3$, $R_8$, $R_9$, and $R_{10}$ are independently hydrogen, halogen, aldehyde, COOH, CHNOH, CH=CHCO$_2$H, hydroxyalkyl, hydroxyl, alkoxy, cyano, nitro, CF$_3$, NH$_2$, NHR, NHCOR, N(R)$_2$, sulfonamide, SO$_2$R, alkyl, aryl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered substituted or unsubstituted heterocyclic ring, optionally aromatic, or $R_1$, $R_2$ or $R_3$ together with the benzene ring to which the R-group is attached comprises a fused ring system represented by structure A

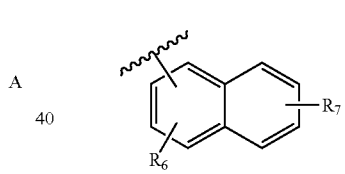
A wherein
$R_6$ and $R_7$ are independently $R_1$, $R_2$ or $R_3$;
R is alkyl, hydrogen, haloalkyl, dihaloalkyl, trihaloalkyl, CH$_2$F, CHF$_2$, CF$_3$, CF$_2$CF$_3$, aryl, phenyl, halogen, CN, NO$_2$, alkenyl or OH;
$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;
Z is O, NH, CH$_2$, or

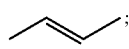;

Q is SO$_3$H, CO$_2$H, CO$_2$R, NO$_2$, tetrazole, SO$_2$NH$_2$, or SO$_2$NHR;
j, k, l are independently 1-4;
q is 1-5;
Alk is linear alkyl of 1-7 carbons, branched alkyl of 1-7 carbons, or cyclic alkyl of 3-8 carbons; and
if X is $(CH_2)_q$, CO or $C(O)(CH_2)_q$, and $R_2$ is OCH$_2$CH$_2$NR$_4$R$_5$, or OCH$_2$CH$_2$-heterocycle when k is 1, and R₉ is hydrogen, lower alkyl (1-4 carbons), lower alkoxy (1-4 carbons), halogen, nitro or amino, then R₁ or R₃ is not hydrogen, lower alkyl (1-4 carbons), lower alkoxy (1-4 carbons), halogen, nitro or amino;

if X is $(CH_2)_q$, CO or $C(O)(CH_2)_q$, and R₃ is $OCH_2CH_2NR_4R_5$, or $OCH_2CH_2$-heterocycle when 1 is one, and R₁₀ is hydrogen, lower alkyl (1-4 carbons), lower alkoxy (1-4 carbons), halogen, nitro or amino;

then R₁ or R₂ is not hydrogen, lower alkyl (1-4 carbons), lower alkoxy (1-4 carbons), halogen, nitro or amino.

In another embodiment, the 3-7 membered substituted or unsubstituted heterocyclic ring, optionally aromatic, is represented by the structure of formula B:

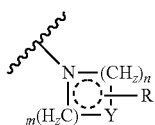

B wherein Y is $CH_2$, CH, bond, O, S, NH, N or NR;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

if B is aryl, then z is 1; and if B is cycloalkyl, then z is 2;

M is 0-4;

n is 0-4;

wherein m and n cannot both be zero.

In one embodiment B is substituted or unsubstituted piperidine; in another embodiment B is substituted or unsubstituted pyrrolidine; in another embodiment B is substituted or unsubstituted morpholine; in another embodiment B is substituted or unsubstituted piperazine.

In one embodiment this invention provides a NRBA, which in one embodiment is a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula VII:

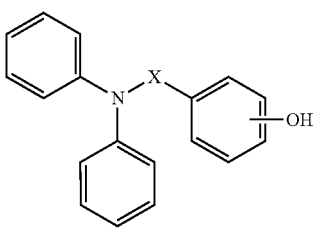

(VII)

wherein X is CS, $(CH_2)_q$, branched alkyl, branched alkyl with haloalkyl side chain, haloalkyl, $C(O)(CH_2)_q$, SO, or $SO_2$;

or X is CO, and OH is meta or ortho.

In another embodiment this invention provides a NRBA, which in one embodiment is a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula VIII:

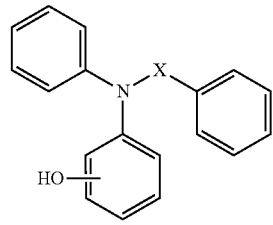

(VIII)

wherein X is CS, $(CH_2)_q$, branched alkyl, branched alkyl with haloalkyl side chain, haloalkyl, $C(O)(CH_2)_q$, SO, or $SO_2$;

or X is CO, and OH is meta or ortho.

In another embodiment, this invention provides a NRBA, which in one embodiment is a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula IX:

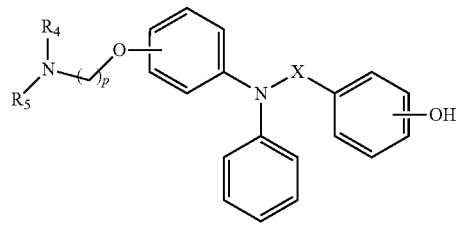

IX wherein X is CO, CS, $(CH_2)_q$, branched alkyl, branched alkyl with haloalkyl side chain, haloalkyl, $C(O)(CH_2)_q$, SO, or $SO_2$;

R₄ and R₅ are independently hydrogen, phenyl, an alkyl group of 1 to 6 carbon atoms, a 3 to 7 membered cycloalkyl, a 3 to 7 membered heterocycloalkyl, a 3 to 7 membered heteroaryl group, or R₄ and R₅ form together with the nitrogen atom a 3-7 heterocyclic ring, optionally aromatic, is represented by the structure of formula B:

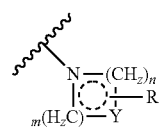

B wherein Y is $CH_2$, CH, bond, O, S, NH, N or NR;
if B is aryl then z is 1; and if B is cycloalkyl z is 2;
m is 0-4;
n is 0-4;
wherein m and n cannot both be zero;
q is 1-5;
p is 1-4;
R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$ or OH.

In another embodiment, this invention provides a NRBA, which in one embodiment is a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula X:

wherein

X is CO, CS, $(CH_2)_q$, branched alkyl, branched alkyl with haloalkyl side chain, haloalkyl, $C(O)(CH_2)_q$, SO, or $SO_2$;

$R_1, R_2, R_3, R_8, R_9, R_{10}, R_{11}, R_{12}$ and $R_{13}$ are independently hydrogen, halogen, aldehyde, COOH, CHNOH, CH=CHCO$_2$H, hydroxyalkyl, hydroxyl, alkoxy, cyano, nitro, CF$_3$, NH$_2$, NHR, NHCOR, N(R)$_2$, sulfonamide, SO$_2$R, alkyl, aryl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered substituted or unsubstituted heterocyclic ring, optionally aromatic, or $R_1, R_2$ or $R_3$ together with the benzene ring to which the R-group is attached comprises a fused ring system represented by structure A wherein $R_6$ and $R_7$ are independently is $R_1, R_2$ or $R_3$;

R is alkyl, hydrogen, haloalkyl, dihaloalkyl, trihaloalkyl, CH$_2$F, CHF$_2$, CF$_3$, CF$_2$CF$_3$, aryl, phenyl, halogen, CN, NO$_2$, alkenyl or OH;

$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group; or $R_4$ and $R_5$ form together with the nitrogen atom a 3-7 heterocyclic ring, optionally aromatic, is represented by the structure of formula B:

wherein Y is CH$_2$, CH, bond, O, S, NH, N or NR;
if B is aryl then z is 1; and if B is cycloalkyl z is 2;
m is 0-4;
n is 0-4;
wherein m and n cannot both be zero;
q is 1-5;
p is 1-4;
R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$ or OH;

Z is O, NH, CH$_2$, or

X

Q is SO$_3$H, CO$_2$H, CO$_2$R, NO$_2$, tetrazole, SO$_2$NH$_2$, or SO$_2$NHR;
j, k, l are independently 1-3;
q is 1-5;
Alk is linear alkyl of 1-7 carbons, branched alkyl of 1-7 carbons, or cyclic alkyl of 3-8 carbons; and if X is $(CH_2)_q$, CO or $C(O)(CH_2)_q$, and $R_2$ is OCH$_2$CH$_2$NR$_4$R$_5$, or OCH$_2$CH$_2$-heterocycle when k is 1, and $R_9$ and $R_{12}$ are hydrogen, lower alkyl (1-4 carbons), lower alkoxy (1-4 carbons), halogen, nitro or amino, then $R_1$ or $R_3$ is not hydrogen, lower alkyl (1-4 carbons), lower alkoxy (1-4 carbons), halogen, nitro or amino;

if X is $(CH_2)_q$, CO or $C(O)(CH_2)_q$, and $R_3$ is OCH$_2$CH$_2$NR$_4$R$_5$, or OCH$_2$CH$_2$-heterocycle when l is one, and $R_{10}$ and $R_{13}$ are hydrogen, lower alkyl (1-4 carbons), lower alkoxy (1-4 carbons), halogen, nitro or amino;

then $R_1$ or $R_2$ is not hydrogen, lower alkyl (1-4 carbons), lower alkoxy (1-4 carbons), halogen, nitro or amino In one embodiment this invention provides a method of reducing circulating lipid levels in a male subject with prostate cancer having undergone Androgen Deprivation Therapy (ADT), said method comprising administering to said subject a composition comprising a nuclear receptor binding agent (NRBA) compound or its pharmaceutically acceptable salt, hydrate, N-oxide, or any combination thereof.

In one embodiment, this invention provides a method of treating atherosclerosis and its associated diseases including cardiovascular disorders, cerebrovascular disorders, peripheral vascular disorders, and intestinal vascular disorders in a subject with prostate cancer having undergone Androgen Deprivation Therapy (ADT), comprising administering to said subject a composition comprising a nuclear receptor binding agent (NRBA) compound or its pharmaceutically acceptable salt, hydrate, N-oxide, or any combination thereof.

In one embodiment, this invention provides a method of treating ischemia in a tissue of a subject with prostate cancer having undergone Androgen Deprivation Therapy (ADT), comprising administering to said subject a composition comprising a nuclear receptor binding agent (NRBA) compound or its pharmaceutically acceptable salt, hydrate, N-oxide, or any combination thereof.

In another embodiment this invention provides a method of (i) treating and preventing osteoporosis; (ii) treating, preventing or reducing the risk of mortality from cardiovascular disease in a subject; (iii) improving a lipid profile; (iv) reducing the incidence of, inhibiting, suppressing, or treating androgen-deprivation induced osteoporosis, bone fractures and/or loss of bone mineral density (BMD) in men having prostate cancer; (v) ameliorating symptoms and/or clinical complications associated with menopause in a female subject; (vi) treating, preventing or reducing the severity of Alzheimer's disease; (vii) treating, preventing, suppressing, inhibiting, or reducing the incidence of hot flashes, gynecomastia, and/or hair loss in a male; (viii) treating, suppressing, inhibiting or reducing the risk of developing prostate cancer in a subject with prostate cancer; (ix) treating, suppressing, inhibiting or reducing the amount of precancerous precursors of prostate adenocarcinoma lesions; (x) treating, suppressing, inhibiting or reducing the risk of developing breast cancer in a subject; (xi) treating, suppressing, inhibiting or reducing the risk of developing colon cancer in a subject; (xii) treating, suppressing, inhibiting or reducing the risk of developing leukemia in a subject; (xiii) treating, suppressing, inhibiting or reducing the risk of developing bladder cancer in a subject; (xiv) treating, suppressing, inhibiting or reducing the incidence of inflammation in a subject; (xv) treating, suppressing, inhibiting or reducing the incidence of neurological disorders in a subject; (xvi) treating, suppressing, inhibiting or reducing the incidence of ocular disorders, (xvii) reducing the lipid profile of a male subject with prostate cancer having undergone ADT, (xviii) treating, suppressing, inhibiting or reducing the risk of atherosclerosis of a male subject with prostate cancer having undergone ADT. (xix) treating, suppressing, inhibiting or reducing the risk of ischemia of a male subject with prostate cancer having undergone ADT using the nuclear receptor binding agents (NRBAs) of the invention, which in one embodiment are SERM compounds.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE PRESENT INVENTION

Figure 1:
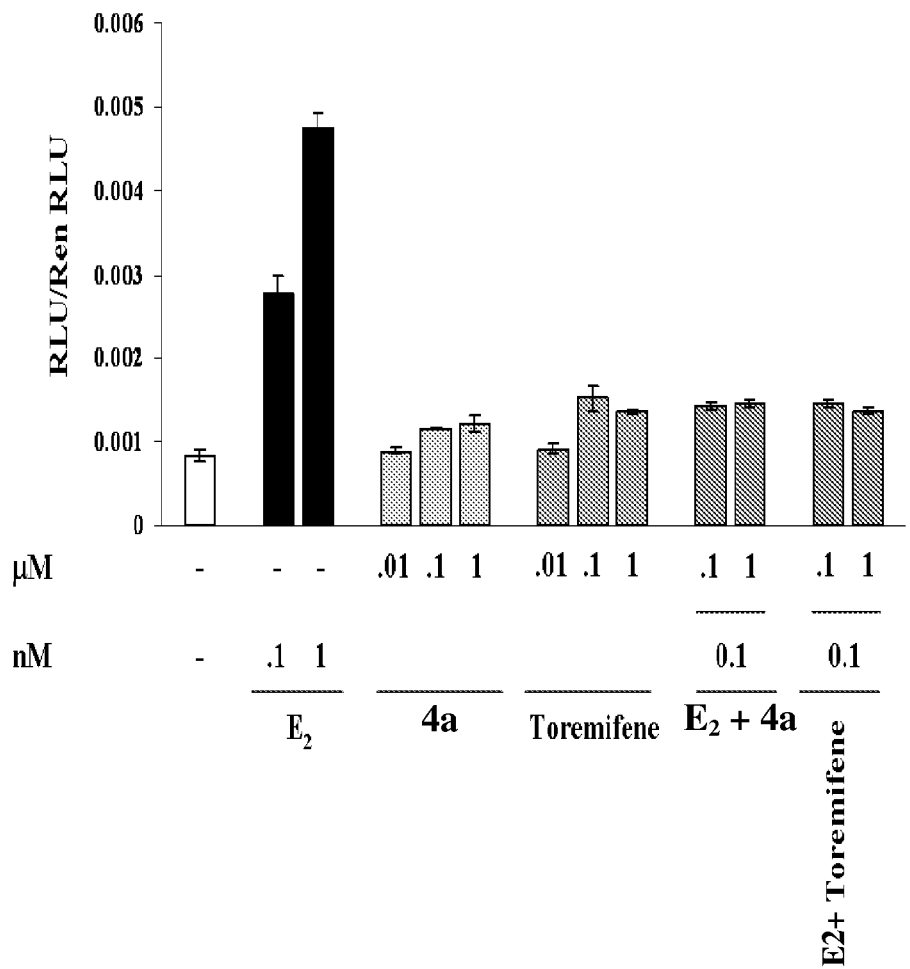
FIG. 1: Effects of the indicated compounds on ER-α transactivation. COS or 293 cells plated in DME without phenol red+10% charcoal stripped fetal bovine serum (csFBS) at 90,000 cells per well of 24 well plates were transfected with 0.25 µg ERE-LUC, 0.02 µg CMV-LUC (*Renilla*) and 25 ng of ER-α by lipofectamine. Twenty four hours after transfection, the cells were treated as indicated in the figure, harvested 48 hrs after transfection and were assayed for firefly and *renilla* luciferase.

The present invention provides, in some embodiments, novel NRBAs, which in some embodiments are SERM compounds, and compositions comprising the same.

This invention provides, in some embodiments, NRBAs, which in one embodiment are SERMs. In one embodiment, the phrase "Selective Estrogen Receptor Modulator" or "SERM" refers to a compound that affects estrogen receptor activity. In one embodiment, a SERM exhibits activity as an agonist, or, in another embodiment, as an antagonist, or in another embodiment, as a partial agonist, or in another embodiment, as a partial antagonist of the estrogen receptor. In one embodiment, the SERM exerts its effects on the estrogen receptor (e.g., ERα, ERβ or ERRs) in a tissue-dependent manner. In some embodiments, the SERMs of this invention can act as estrogen receptor agonists in some tissues (e.g., bone, brain, and/or heart) and as antagonists in other tissue types, for example in the breast and/or uterine lining.

In one embodiment, a SERM of this invention will have an $IC_{50}$ or $EC_{50}$ with respect to ERα and/or ERβ of up to about 10 μM as determined using the ERα and/or ERβ transactivation assays, as known in the art, or, in other embodiments, as described herein (Example 1, 2). In some embodiments, the SERMs exhibit $IC_{50}$ or $EC_{50}$ values (as agonists or antagonists) of not more than about 5 μM. Representative compounds of the present invention have been discovered to exhibit agonist or antagonist activity with respect to the estrogen receptor. Compounds of the present invention exhibit, in some embodiments, an antagonist or agonist $IC_{50}$ or $EC_{50}$ with respect to ERα and/or ERβ of no more than about 5 μM, or in some embodiments, no more than about 500 nM, or in other embodiments, not more than about 1 nM, as measured in ERα and/or ERβ transactivation assays. The term "$IC_{50}$" refers, in some embodiments, to a concentration of the SERM which reduces the activity of a target (e.g., ERα or ERβ) to half-maximal level. The term "$EC_{50}$" refers, in some embodiments, to a concentration of the SERM that produces a half-maximal effect In some embodiments of this invention, the compounds of this invention are characterized by a structure comprising a phenyl group added to bisphenolic agonists, thus forming triphenyl agents. In some embodiments, the triphenyl groups are rigidly held by an amide bond. In addition to the triphenyl moiety, in some embodiments, the SERMs may be characterized by a structure comprising a basic side chain (tertiary amine), which in some embodiments, is present as an N-substituted ethanolamine sidechain appended to one or two of the phenolic ether groups.

SERMs:

In one embodiment, the present invention provides a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula I:

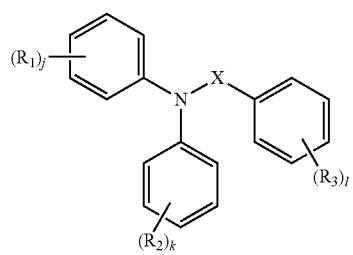

(I)

wherein

X is CO, CS, $(CH_2)_q$, branched alkyl, branched alkyl with haloalkyl side chain, haloalkyl, $(C)O(CH_2)_q$, SO, or $SO_2$;

$R_1$, $R_2$ and $R_3$ are independently, hydrogen, halogen, aldehyde, COOH, CHNOH, CH=$CHCO_2H$, hydroxyalkyl, hydroxyl, alkoxy, cyano, nitro, $CF_3$, $NH_2$, NHR, NHCOR, $N(R)_2$, sulfonamide, $SO_2R$, alkyl, aryl, protected hydroxyl, $OCH_2CH_2NR_4R_5$, Z-Alk-Q, Z-Alk-$NR_4R_5$, Z-Alk-heterocycle or $OCH_2CH_2$-heterocycle in which the heterocycle is a 3-7 membered substituted or unsubstituted heterocyclic ring, optionally aromatic, or $R_1$, $R_2$ or $R_3$ together with the benzene ring to which the R-group is attached comprises a fused ring system represented by structure A

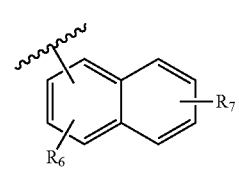

A wherein $R_6$ and $R_7$ are independently $R_1$, $R_2$ or $R_3$;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;

Z is O, NH, $CH_2$, or

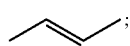;

Q is $SO_3H$, $CO_2H$, $CO_2R$, $NO_2$, tetrazole, $SO_2NH_2$, or $SO_2NHR$;

j, k, l are independently 1-5;

q is 1-5;

Alk is linear alkyl of 1-7 carbons, branched alkyl of 1-7 carbons, or cyclic alkyl of 3-8 carbons; and if X is $(CH_2)_q$, CO or $C(O)(CH_2)_q$, and $R_2$ is $OCH_2CH_2NR_4R_5$, or $OCH_2CH_2$-heterocycle when k is 1, then $R_1$ or $R_3$ is not hydrogen, lower alkyl (1-4 carbons), lower alkoxy (1-4 carbons), halogen, nitro or amino;

if X is $(CH_2)_q$, CO or $C(O)(CH_2)_q$, and $R_3$ is $OCH_2CH_2NR_4R_5$, or $OCH_2CH_2$-heterocycle when l is one, then $R_1$ or $R_2$ is not hydrogen, lower alkyl (1-4 carbons), lower alkoxy (1-4 carbons), halogen, nitro or amino.

In another embodiment, this invention provides a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula I:

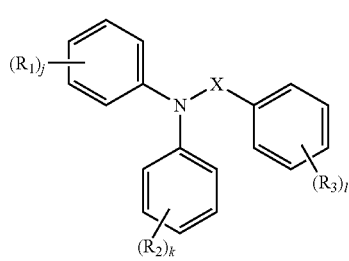

(I)

wherein

X is CS, branched alkyl, branched alkyl with haloalkyl side chain, haloalkyl, SO, or $SO_2$;

$R_1$, $R_2$ and $R_3$ are independently, hydrogen, halogen, aldehyde, COOH, CHNOH, CH=CHCO$_2$H, hydroxyalkyl, hydroxyl, alkoxy, cyano, nitro, CF$_3$, NH$_2$, NHR, NHCOR, N(R)$_2$, sulfonamide, SO$_2$R, alkyl, aryl, protected hydroxyl, OCH$_2$CH$_2$NR$_4$R$_5$, Z(CH$_2$)$_q$Q, Z-Alk-NR$_4$R$_5$, Z-Alk-heterocycle or OCH$_2$CH$_2$-heterocycle in which the heterocycle is a 3-7 membered substituted or unsubstituted heterocyclic ring, optionally aromatic, or $R_1$, $R_2$ or $R_3$ together with the benzene ring to which the R-group is attached comprises a fused ring system represented by structure A

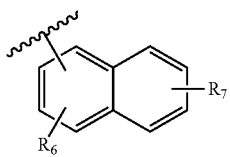

wherein $R_6$ or $R_7$ are independently $R_1$, $R_2$ or $R_3$;

R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$, or OH;

$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;

Z is O, NH, CH$_2$, or

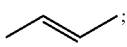;

Q is SO$_3$H, CO$_2$H, CO$_2$R, NO$_2$, tetrazole, SO$_2$NH$_2$, or SO$_2$NHR;

j, k, l are independently 1-5;

q is 1-5;

Alk is linear alkyl of 1-7 carbons, branched alkyl of 1-7 carbons, or cyclic alkyl of 3-8 carbons.

In another embodiment this invention provides a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula II:

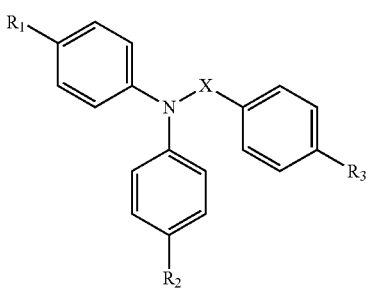

X is CO, CS, (CH$_2$)$_q$, branched alkyl, branched alkyl with haloalkyl side chain, haloalkyl, C(O)(CH$_2$)$_q$, SO, or SO$_2$;

$R_1$, $R_2$ and $R_3$ are independently, hydrogen, halogen, aldehyde, COOH, CHNOH, CH=CHCO$_2$H, hydroxyalkyl, hydroxyl, alkoxy, cyano, nitro, CF$_3$, NH$_2$, NHR, NHCOR, N(R)$_2$, sulfonamide, SO$_2$R, alkyl, aryl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered substituted or unsubstituted heterocyclic ring, optionally aromatic, or $R_1$, $R_2$ or $R_3$ together with the benzene ring to which the R-group is attached comprises a fused ring system represented by structure A

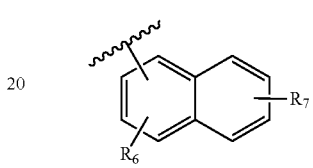

wherein $R_6$ and $R_7$ are independently $R_1$, $R_2$ or $R_3$;

R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$, or OH;

$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;

Z is O, NH, CH$_2$, or

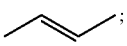;

Q is SO$_3$H, CO$_2$H, CO$_2$R, NO$_2$, tetrazole, SO$_2$NH$_2$, or SO$_2$NHR;

q is 1-5;

Alk is linear alkyl of 1-7 carbons, branched alkyl of 1-7 carbons, or cyclic alkyl of 3-8 carbons; and if X is (CH$_2$)$_q$, CO or C(O)(CH$_2$)$_q$, and $R_2$ is OCH$_2$CH$_2$NR$_4$R$_5$, or OCH$_2$CH$_2$-heterocycle when k is 1, then $R_1$ or $R_3$ is not hydrogen, lower alkyl (1-4 carbons), lower alkoxy (1-4 carbons), halogen, nitro or amino;

if X is (CH$_2$)$_q$, CO or C(O)(CH$_2$)$_q$, and $R_3$ is OCH$_2$CH$_2$NR$_4$R$_5$, or OCH$_2$CH$_2$-heterocycle when l is one, then $R_1$ or $R_2$ is not hydrogen, lower alkyl (1-4 carbons), lower alkoxy (1-4 carbons), halogen, nitro or amino.

In another embodiment, according to this aspect of the invention, X is CO and $R_1$, $R_2$ and $R_3$ are OH, or in another embodiment X is CO and $R_1$ is OCH$_2$CH$_2$-piperidine HCl salt, $R_2$ is H and $R_3$ is OH.

In another embodiment this invention provides a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula II:

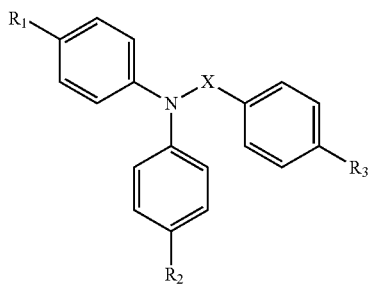
(II)

wherein
- X is CS, branched alkyl, branched alkyl with haloalkyl side chain, haloalkyl, SO, or $SO_2$;
- $R_1$, $R_2$ and $R_3$ are independently, hydrogen, halogen, aldehyde, COOH, CHNOH, $CH=CHCO_2H$, hydroxyalkyl, hydroxyl, alkoxy, cyano, nitro, $CF_3$, $NH_2$, NHR, NHCOR, $N(R)_2$, sulfonamide, $SO_2R$, alkyl, aryl, protected hydroxyl, $OCH_2CH_2NR_4R_5$, Z-Alk-Q, Z-Alk-$NR_4R_5$, Z-Alk-heterocycle or $OCH_2CH_2$-heterocycle in which the heterocycle is a 3-7 membered substituted or unsubstituted heterocyclic ring, optionally aromatic,
- or $R_1$, $R_2$ or $R_3$ together with the benzene ring to which the R-group is attached comprises a fused ring system represented by structure A

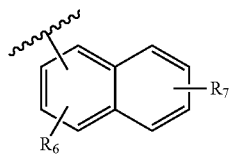
A wherein $R_6$ and $R_7$ are independently $R_1$, $R_2$ or $R_3$;
R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;
$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;
Z is O, NH, $CH_2$, or

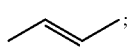;

Q is $SO_3H$, $CO_2H$, $CO_2R$, $NO_2$, tetrazole, $SO_2NH_2$, or $SO_2NHR$;
Alk is linear alkyl of 1-7 carbons, branched alkyl of 1-7 carbons, or cyclic alkyl of 3-8 carbons.

In another embodiment the present invention provides, a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula III:

(III)

wherein
A is a ring selected from

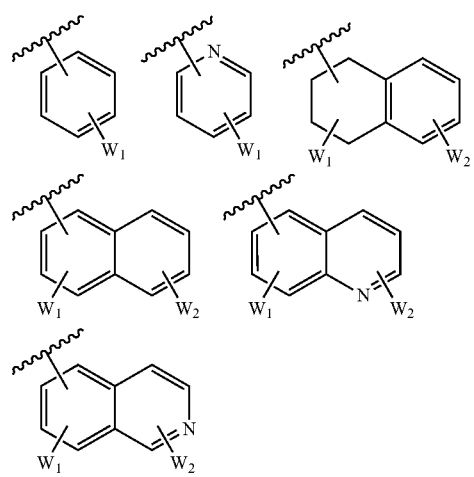

B is a ring selected from

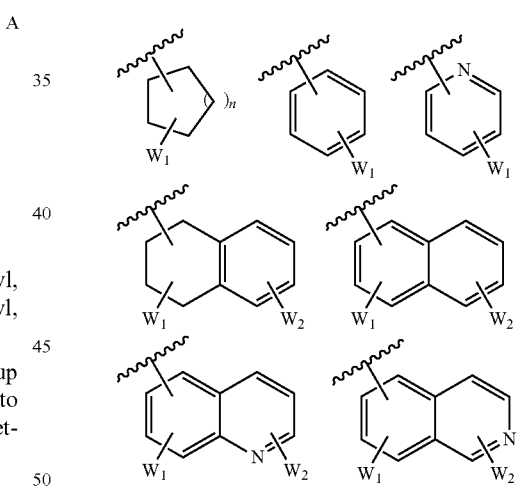

C is a ring selected from

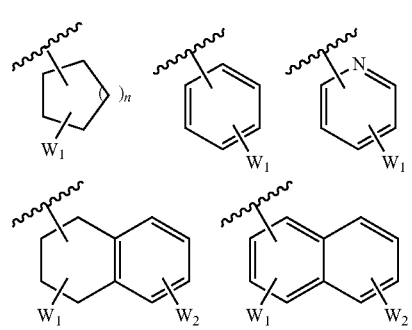

-continued

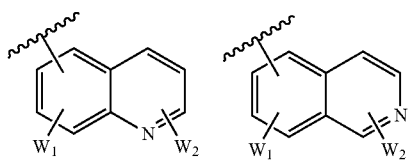

X is CO, CS, $(CH_2)_q$, branched alkyl, branched alkyl with haloalkyl side chain, haloalkyl, $C(O)(CH_2)_q$, SO, or $SO_2$;

$W_1$ and $W_2$ are independently, hydrogen, halogen, hydroxyl, aldehyde, COOH, CHNOH, CH=CHCO$_2$H, hydroxyalkyl, alkoxy, cyano, nitro, $CF_3$, $NH_2$, NHR, NHCOR, $N(R)_2$, sulfonamide, $SO_2R$, alkyl, aryl, protected hydroxyl, $OCH_2CH_2NR_4R_5$, Z-Alk-Q, Z-Alk-NR$_4$R$_5$, Z-Alk-heterocycle or $OCH_2CH_2$-heterocycle in which the heterocycle is a 3-7 membered substituted or unsubstituted heterocyclic ring, optionally aromatic;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;

Z is O, NH, $CH_2$, or

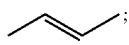;

Q is $SO_3H$, $CO_2H$, $CO_2R$, $NO_2$, tetrazole, $SO_2NH_2$, or $SO_2NHR$;

q is 1-5;

n is 0-5;

Alk is linear alkyl of 1-7 carbons, branched alkyl of 1-7 carbons, or cyclic alkyl of 3-8 carbons;

and A, B and C cannot simultaneously be a benzene ring; and if X is $(CH_2)_q$, CO or $C(O)(CH_2)_q$, A is pyridyl ring and B and C are phenyl rings and C is substituted with $OCH_2CH_2NR_4R_5$, or $OCH_2CH_2$-heterocycle, then A or B is not substituted with hydrogen, lower alkyl (1-4 carbons), lower alkoxy (1-4 carbons), halogen, nitro or amino;

If X is $(CH_2)_q$, CO or $C(O)(CH_2)_q$, A is pyridyl ring and B and C are phenyl rings and B is substituted with $OCH_2CH_2NR_4R_5$, or $OCH_2CH_2$-heterocycle, then A or C is not substituted with hydrogen, lower alkyl (1-4 carbons), lower alkoxy (1-4 carbons), halogen, nitro or amino.

In another embodiment this invention provides a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula IV:

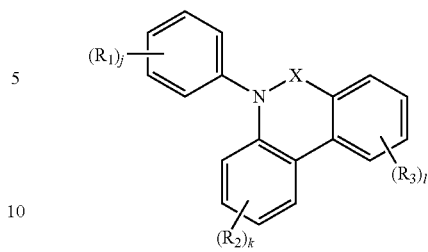

wherein

X is CO, CS, $(CH_2)_q$, branched alkyl, branched alkyl with haloalkyl side chain, haloalkyl, $C(O)(CH_2)_q$, SO, or $SO_2$;

$R_1$, $R_2$ and $R_3$ are independently, hydrogen, halogen, hydroxyl, aldehyde, COOH, CHNOH, CH=CHCO$_2$H, hydroxyalkyl, alkoxy, cyano, nitro, $CF_3$, $NH_2$, NHR, NHCOR, $N(R)_2$, sulfonamide, $SO_2R$, alkyl, aryl, protected hydroxyl, $OCH_2CH_2NR_4R_5$, Z-Alk-Q, Z-Alk-NR$_4$R$_5$, Z-Alk-heterocycle or $OCH_2CH_2$-heterocycle in which the heterocycle is a 3-7 membered substituted or unsubstituted heterocyclic ring, optionally aromatic, or $R_1$, $R_2$ and $R_3$ together with the benzene ring to which the R-group is attached comprises a fused ring system represented by structure A

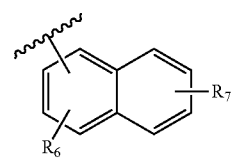

wherein $R_6$ and $R_7$ are independently $R_1$, $R_2$ or $R_3$;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;

Z is O, NH, $CH_2$, or

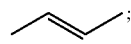;

Q is $SO_3H$, $CO_2H$, $CO_2R$, $NO_2$, tetrazole, $SO_2NH_2$, or $SO_2NHR$;

j, k, l are independently is 1-5;

q is 1-5;

Alk is linear alkyl of 1-7 carbons, branched alkyl of 1-7 carbons, or cyclic alkyl of 3-8 carbons.

In another embodiment, this invention provides a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula V:

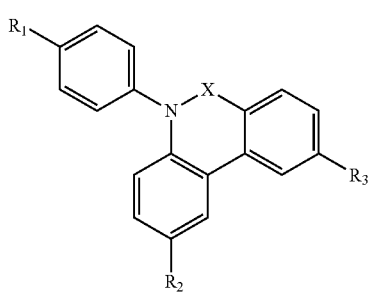 (V)

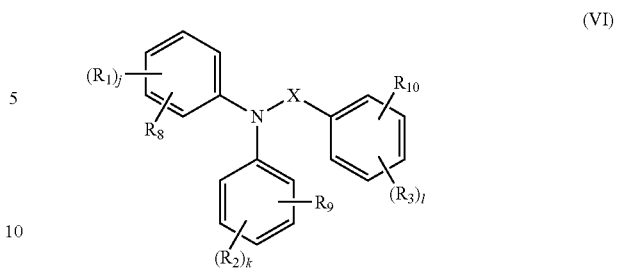 (VI)

X is CO, CS, $(CH_2)_q$, branched alkyl, branched alkyl with haloalkyl side chain, haloalkyl, $C(O)(CH_2)_q$, SO, or $SO_2$;

$R_1$, $R_2$ and $R_3$ are independently, hydrogen, aldehyde, COOH, CHNOH, CH=CHCO$_2$H, hydroxyalkyl, halogen, hydroxyl, alkoxy, cyano, nitro, $CF_3$, $NH_2$, NHR, NHCOR, $N(R)_2$, sulfonamide, $SO_2R$, alkyl, aryl, protected hydroxyl group, $OCH_2CH_2NR_4R_5$, Z-Alk-Q, Z-Alk-NR$_4$R$_5$, Z-Alk-heterocycle or $OCH_2CH_2$-heterocycle in which the heterocycle is a 3-7 membered substituted or unsubstituted heterocyclic ring, optionally aromatic, or $R_1$, $R_2$ and $R_3$ together with the benzene ring to which the R-group is attached comprises a fused ring system represented by structure A

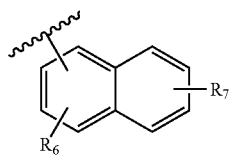 A wherein $R_6$ or $R_7$ are independently $R_1$, $R_2$ or $R_3$;

R is alkyl, hydrogen, haloalkyl, dihaloalkyl, trihaloalkyl, $CH_2F$, $CHF_2$, $CF_3$, $CF_2CF_3$, aryl, phenyl, halogen, CN, $NO_2$, alkenyl or OH;

$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;

Z is O, NH, $CH_2$, or

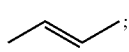;

Q is $SO_3H$, $CO_2H$, $CO_2R$, $NO_2$, tetrazole, $SO_2NH_2$, or $SO_2NHR$;

q is 1-5;

Alk is linear alkyl of 1-7 carbons, branched alkyl of 1-7 carbons, or cyclic alkyl of 3-8 carbons.

In another embodiment, this invention provides a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula VI:

wherein

X is CO, CS, $(CH_2)_9$, branched alkyl, branched alkyl with haloalkyl side chain, haloalkyl, $C(O)(CH_2)_q$, SO, or $SO_2$;

$R_1$, $R_2$, $R_3$, $R_8$, $R_9$, and $R_{10}$ are independently hydrogen, halogen, aldehyde, COOH, CHNOH, CH=CHCO$_2$H, hydroxyalkyl, hydroxyl, alkoxy, cyano, nitro, $CF_3$, $NH_2$, NHR, NHCOR, $N(R)_2$, sulfonamide, $SO_2R$, alkyl, aryl, protected hydroxyl, $OCH_2CH_2NR_4R_5$, Z-Alk-Q, Z-Alk-NR$_4$R$_5$, Z-Alk-heterocycle or $OCH_2CH_2$-heterocycle in which the heterocycle is a 3-7 membered substituted or unsubstituted heterocyclic ring, optionally aromatic, or $R_1$, $R_2$ or $R_3$ together with the benzene ring to which the R-group is attached comprises a fused ring system represented by structure A

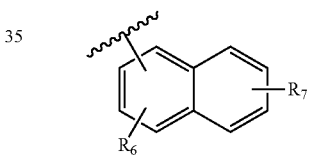 A wherein $R_6$ and $R_7$ are independently is $R_1$, $R_2$ or $R_3$;

R is alkyl, hydrogen, haloalkyl, dihaloalkyl, trihaloalkyl, $CH_2F$, $CHF_2$, $CF_3$, $CF_2CF_3$, aryl, phenyl, halogen, CN, $NO_2$, alkenyl or OH;

$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group;

Z is O, NH, $CH_2$, or

;

Q is $SO_3H$, $CO_2H$, $CO_2R$, $NO_2$, tetrazole, $SO_2NH_2$, or $SO_2NHR$;

j, k, l are independently 1-4;

q is 1-5;

Alk is linear alkyl of 1-7 carbons, branched alkyl of 1-7 carbons, or cyclic alkyl of 3-8 carbons; and if X is $(CH_2)_q$, CO or $C(O)(CH_2)_q$, and $R_2$ is $OCH_2CH_2NR_4R_5$, or $OCH_2CH_2$-heterocycle when k is 1, and $R_9$ is hydrogen, lower alkyl (1-4 carbons), lower alkoxy (1-4 carbons), halogen, nitro or amino, then $R_1$ or $R_3$ is not hydrogen, lower alkyl (1-4 carbons), lower alkoxy (1-4 carbons), halogen, nitro or amino;

if X is $(CH_2)_q$, CO or $C(O)(CH_2)_q$, and $R_3$ is $OCH_2CH_2NR_4R_5$, or $OCH_2CH_2$-heterocycle when 1 is 1, and $R_{10}$ is hydrogen, lower alkyl (1-4 carbons), lower alkoxy (1-4 carbons), halogen, nitro or amino;

then $R_1$ or $R_2$ is not hydrogen, lower alkyl (1-4 carbons), lower alkoxy (1-4 carbons), halogen, nitro or amino.

In one embodiment of this invention, the 3-7 membered substituted or unsubstituted heterocyclic ring, optionally aromatic, is represented by the structure of formula B:

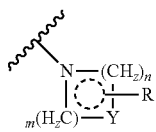

B wherein Y is $CH_2$, CH, bond, O, S, NH, N or NR;

R is alkyl, hydrogen, haloalkyl, dihaloalkyl, trihaloalkyl, $CH_2F$, $CHF_2$, $CF_3$, $CF_2CF_3$, aryl, phenyl, halogen, CN, $NO_2$, alkenyl or OH;

if B is aryl then z is 1; and if B is cycloalkyl z is 2;

m is 0-4;

n is 0-4;

wherein m and n cannot both be zero.

In one embodiment B is substituted or unsubstituted piperidine; in another embodiment B is substituted or unsubstituted pyrrolidine; in another embodiment B is substituted or unsubstituted morpholine; in another embodiment B is substituted or unsubstituted piperazine.

In one embodiment this invention provides a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula VII:

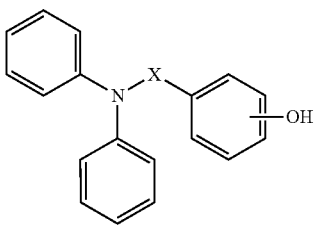

(VII)

wherein X is CS, $(CH_2)_q$, branched alkyl, branched alkyl with haloalkyl side chain, haloalkyl, $C(O)(CH_2)_q$, SO, or $SO_2$;

or X is CO, and OH is meta or ortho.

In another embodiment this invention provides a selective estrogen receptor modulator (SERM) compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula VIII:

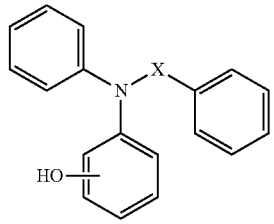

(VIII)

wherein X is CS, $(CH_2)_q$, branched alkyl, branched alkyl with haloalkyl side chain, haloalkyl, $C(O)(CH_2)_q$, SO, or $SO_2$;

or X is CO, and OH is meta or ortho.

In another embodiment, this invention provides a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula IX:

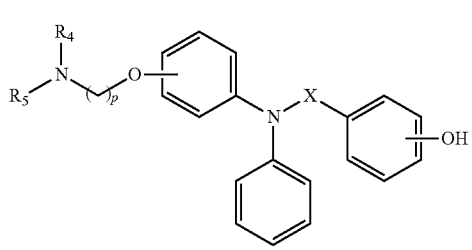

IX wherein X is CO, CS, $(CH_2)_q$, branched alkyl, branched alkyl with haloalkyl side chain, haloalkyl, $C(O)(CH_2)_q$, SO, or $SO_2$;

$R_4$ and $R_5$ are independently hydrogen, phenyl, an alkyl group of 1 to 6 carbon atoms, a 3 to 7 membered cycloalkyl, a 3 to 7 membered heterocycloalkyl, a 3 to 7 membered heteroaryl group, or $R_4$ and $R_5$ form together with the nitrogen atom a 3-7 heterocyclic ring, optionally aromatic, is represented by the structure of formula B:

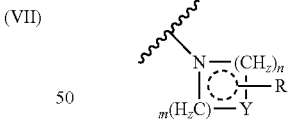

B wherein Y is $CH_2$, CH, bond, O, S, NH, N or NR;

if B is aryl then z is 1; and if B is cycloalkyl z is 2;

m is 0-4;

is 0-4;

wherein m and n cannot both be zero;

q is 1-5;

p is 1-4;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$ or OH.

In one embodiment B is substituted or unsubstituted piperidine; in another embodiment B is substituted or unsubstituted pyrrolidine; in another embodiment B is substituted or unsubstituted morpholine; in another embodiment B is substituted or unsubstituted piperazine.

In another embodiment, this invention provides a SERM compound or its prodrug, analog, isomer, metabolite, derivative, pharmaceutically acceptable salt, pharmaceutical product, polymorph, crystal, impurity, N-oxide, ester, hydrate or any combination thereof, represented by the structure of formula X:

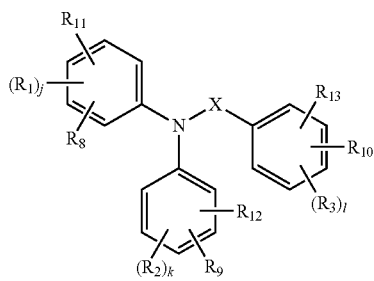

X wherein

X is CO, CS, $(CH_2)_q$, branched alkyl, branched alkyl with haloalkyl side chain, haloalkyl, $C(O)(CH_2)_q$, SO, or $SO_2$;

$R_1, R_2, R_3, R_8, R_9, R_{10}, R_{11}, R_{12}$ and $R_{13}$ are independently hydrogen, halogen, aldehyde, COOH, CHNOH, $CH=CHCO_2H$, hydroxyalkyl, hydroxyl, alkoxy, cyano, nitro, $CF_3$, $NH_2$, NHR, NHCOR, $N(R)_2$, sulfonamide, $SO_2R$, alkyl, aryl, protected hydroxyl, $OCH_2CH_2NR_4R_5$, Z-Alk-Q, Z-Alk-$NR_4R_5$, Z-Alk-heterocycle or $OCH_2CH_2$-heterocycle in which the heterocycle is a 3-7 membered substituted or unsubstituted heterocyclic ring, optionally aromatic, or $R_1$, $R_2$ or $R_3$ together with the benzene ring to which the R-group is attached comprises a fused ring system represented by structure A

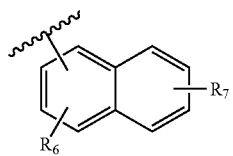

A wherein $R_6$ and $R_7$ are independently is $R_1$, $R_2$ or $R_3$;

R is alkyl, hydrogen, haloalkyl, dihaloalkyl, trihaloalkyl, $CH_2F$, $CHF_2$, $CF_3$, $CF_2CF_3$, aryl, phenyl, halogen, CN, $NO_2$, alkenyl or OH;

$R_4$ and $R_5$ are independently hydrogen, phenyl, an alkyl group of 1 to 6 carbon atoms, a 3 to 7 membered cycloalkyl, a 3 to 7 membered heterocycloalkyl, or a 3 to 7 membered heteroaryl group; or $R_4$ and $R_5$ form together with the nitrogen atom a 3-7 heterocyclic ring, optionally aromatic, is represented by the structure of formula B:

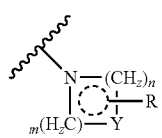

B wherein Y is $CH_2$, CH, bond, O, S, NH, N or NR;
if B is aryl then z is 1; and if B is cycloalkyl z is 2;
m is 0-4;
n is 0-4;
wherein m and n cannot both be zero;
q is 1-5;
p is 1-4;
R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$ or OH.
Z is O, NH, $CH_2$, or $\diagup\!\!\!\diagdown\!\!\!\diagup$ ;

Q is $SO_3H$, $CO_2H$, $CO_2R$, $NO_2$, tetrazole, $SO_2NH_2$, or $SO_2NHR$;
j, k, l are independently 1-3;
q is 1-5;
Alk is linear alkyl of 1-7 carbons, branched alkyl of 1-7 carbons, or cyclic alkyl of 3-8 carbons; and
if X is $(CH_2)_q$, CO or $C(O)(CH_2)_q$, and $R_2$ is $OCH_2CH_2NR_4R_5$, or $OCH_2CH_2$-heterocycle when k is 1, and $R_9$ and $R_{12}$ are hydrogen, lower alkyl (1-4 carbons), lower alkoxy (1-4 carbons), halogen, nitro or amino, then
$R_1$ or $R_3$ is not hydrogen, lower alkyl (1-4 carbons), lower alkoxy (1-4 carbons), halogen, nitro or amino;
if X is $(CH_2)_q$, CO or $C(O)(CH_2)_q$, and $R_3$ is $OCH_2CH_2NR_4R_5$, or $OCH_2CH_2$-heterocycle when l is one, and $R_{10}$ and $R_{13}$ are hydrogen, lower alkyl (1-4 carbons), lower alkoxy (1-4 carbons), halogen, nitro or amino;
then $R_1$ or $R_2$ is not hydrogen, lower alkyl (1-4 carbons), lower alkoxy (1-4 carbons), halogen, nitro or amino.

In one embodiment the NRBA or SERM compound of this invention is 4-methoxy-N,N-bis-(4-methoxyphenyl)-benzamide (2a). In one embodiment the NRBA or SERM compound of this invention is 3-methoxy-N,N-bis-(4-methoxyphenyl)-benzamide (2b). In one embodiment the NRBA or SERM compound of this invention is 4-methoxy-N-(4-methoxyphenyl)-N-(3-methoxyphenyl)-benzamide (2c). In one embodiment the NRBA or SERM compound of this invention is N,N-bis-(4-methoxyphenyl)-benzamide (2d). In one embodiment the NRBA or SERM compound of this invention is 4-Methoxy-N,N-diphenyl-benzamide (2e). In one embodiment the NRBA or SERM compound of this invention is 3-methoxy-N,N-diphenyl-benzamide (2f). In one embodiment the NRBA or SERM compound of this invention is N,N-diphenyl-benzamide (2g). In one embodiment the NRBA or SERM compound of this invention is N-(4-methoxyphenyl)-N-phenyl-benzamide (2h). In one embodiment the NRBA or SERM compound of this invention is N-(3-methoxyphenyl)-N-phenyl-benzamide (2i). In one embodiment the NRBA or SERM compound of this invention is 4-methoxy-N-(4-methoxyphenyl)-N-phenyl-benzamide (2j). In one embodiment the NRBA or SERM compound of this invention is 4-methoxy-N-(3-methoxyphenyl)-N-phenyl-benzamide (2k). In one embodiment the NRBA or SERM compound of this invention is N,N-bis(4-methoxyphenyl)-4-fluorobenzamide (2l). In one embodiment the NRBA or SERM compound of this invention is 4-methoxy-N,N-diphenyl-sulfonamide (2m). In one embodiment the NRBA or SERM compound of this invention is 4-methoxy-N-(4-methoxyphenyl)-N-(4-fluorophenyl)-benzamide (2n). In one embodiment the NRBA or SERM compound of this invention is 4-methoxy-N-(4-methoxyphenyl)-N-(1-naphthyl)-benzamide (2o). In one embodiment the NRBA or SERM compound of this invention is N-(4-methoxyphenyl)-N-(4-benzyloxyphenyl)-1-naphthylamide (2p). In one embodiment the NRBA or SERM compound of this invention is 4-chloro-N-(4-methoxyphenyl)-N-(4-benzyloxyphenyl)-benzamide (2q). In one embodiment the NRBA or SERM compound of this invention is 4-cyano-N-(4-methoxyphenyl)-N-(4-benzyloxyphenyl)-benzamide (2r). In one embodiment the NRBA or SERM compound of this invention is N-(4-methoxyphenyl)-N-(4-benzyloxyphenyl)-2-naphthylamide (2s). In one embodiment the NRBA or SERM compound of this invention is 4-(benzyloxy)-N-[4-(benzyloxy)phenyl]-N-(4-methoxyphenyl)benzamide (2t). In one embodiment the NRBA or SERM compound of this invention is N-[4-(benzyloxy)phenyl]-4-methoxy-N-(4-methoxyphenyl)benzamide (2u). In one embodiment the NRBA or SERM compound of this invention is N-[4-(benzyloxy)phenyl]-N-biphenyl-4-yl-4-methoxybenzamide (2v). In one embodiment the NRBA or SERM compound of this invention is 4-cyano-N-(4-methoxyphenyl)-N-phenylbenzamide (2w). In one embodiment the NRBA or SERM compound of this invention is 3-methoxy-N-(4-methoxyphenyl)-N-phenylbenzamide (2x). In one embodiment the NRBA or SERM compound of this invention is 4-cyano-N-(3-methoxyphenyl)-N-phenylbenzamide (2y). In one embodiment the NRBA or SERM compound of this invention is 4-cyano-N,N-diphenylbenzamide (2z). In another embodiment the NRBA or SERM compound of this invention is 4-hydroxy-N,N-bis-(4-hydroxyphenyl)-benzamide (3a). In one embodiment the NRBA or SERM compound of this invention is 3-hydroxy-N-bis-(4-hydroxyphenyl)-benzamide (3b). In one embodiment the NRBA or SERM compound of this invention is 4-hydroxy-N-(4-hydroxyphenyl)-N-(3-hydroxyphenyl)-benzamide (3c). In one embodiment the NRBA or SERM compound of this invention is N,N-bis-(4-hydroxyphenyl)-benzamide (3d). In another embodiment the NRBA or SERM compound of this invention is 4-hydroxy-N,N-diphenyl-benzamide (3e). In another embodiment the NRBA or SERM compound of this invention is 3-hydroxy-N,N-diphenyl-benzamide (3f). In another embodiment the NRBA or SERM compound of this invention is N-(4-hydroxyphenyl)-N-phenyl-benzamide (3g). In another embodiment the NRBA or SERM compound of this invention is N-(3-hydroxyphenyl)-N-phenyl-benzamide (3h). In another embodiment the NRBA or SERM compound of this invention is 4-hydroxy-N-(4-hydroxyphenyl)-N-phenyl-benzamide (3i). In one embodiment the NRBA or SERM compound of this invention is 4-hydroxy-N-(3-hydroxyphenyl)-N-phenyl-benzamide (3j). In one embodiment the NRBA or SERM compound of this invention is N,N-bis(4-hydroxyphenyl)-4-fluoro-benzamide (3k). In one embodiment the NRBA or SERM compound of this invention is 4-hydroxy-N,N-diphenyl-phenyl-sulfonamide (3l). In another embodiment the NRBA or SERM compound of this invention is 4-hydroxy-N-(4-hydroxyphenyl)-N-(4-fluorophenyl)-benzamide (3m). In another embodiment the NRBA or SERM compound of this invention is N,N-bis(4-hydroxyphenyl)-1-naphthylamide (3n). In one embodiment the NRBA or SERM compound of this invention is 4-hydroxy-N-(1-naphthyl)-N-(4-hydroxyphenyl)-benzamide (3o). In one embodiment the NRBA or SERM compound of this invention is 4-cyano-N,N-bis(4-hydroxyphenyl)-benzamide (3p). In one embodiment the NRBA or SERM compound of this invention is 3-Cyano-N,N-bis(4-hydroxyphenyl)-benzamide (3q). In another embodiment the NRBA or SERM compound of this invention is N,N-bis(4-hydroxyphenyl)-2-naphthylamide (3r). In one embodiment the NRBA or SERM compound of this invention is 4-cyano-N-[4-(2-piperidin-1-ylethoxy)-phenyl]-N-(4-hydroxyphenyl)-benzamide (3s). In another embodiment the NRBA or SERM compound of this invention is 3-chloro-N-[4-(2-piperidin-1-ylethoxy)-phenyl]-N-(4-hydroxyphenyl)-benzamide (3t). In one embodiment the NRBA or SERM compound of this invention is N-biphenyl-4-yl-N-(4-hydroxyphenyl)-4-methoxybenzamide (3u). In one embodiment the NRBA or SERM compound of this invention is N-biphenyl-4-yl-4-hydroxy-N-(4-hydroxyphenyl)-benzamide (3v). In one embodiment the NRBA or SERM compound of this invention is 4-hydroxy-N-(4-hydroxyphenyl)-N-[4-(2-piperidin-1-ylethoxy)phenyl]-benzamide (3w). In another embodiment the NRBA or SERM compound of this invention is 3-hydroxy-N-(4-hydroxyphenyl)-N-phenyl-benzamide (3x). In one embodiment the NRBA or SERM compound of this invention is N-biphenyl-4-yl-4-hydroxy-N-[4-(2-piperidin-1-ylethoxy)phenyl]-benzamide (3y). In another embodiment the NRBA or SERM compound of this invention is N-(4-hydroxyphenyl)-N-[4-(2-piperidin-1-ylethoxy)-phenyl]-benzamide (4a). In another embodiment the NRBA or SERM compound of this invention is N-(phenyl)-N-[4-(2-piperidin-1-ylethoxy)-phenyl]-benzamide (4b). In another embodiment the NRBA or SERM compound of this invention is N,N-diphenyl-[3-(2-piperidinylethoxy)]-benzamide hydrochloride (4c). In another embodiment the NRBA or SERM compound of this invention is N,N-diphenyl-[3-(2-piperidinylethoxy)]-benzamide hydrochloride (4d). In another embodiment the NRBA or SERM compound of this invention is N-(4-hydroxyphenyl)-N-phenyl-[4-(2-piperidin-1-ylethoxy)]-benzamide hydrochloride (4e). In one embodiment the NRBA or SERM compound of this invention is N,N-diphenyl-bis[4-(2-piperidin-1-ylethoxy)-phenyl]-sulfonamide hydrochloride (4f). In another embodiment the NRBA or SERM compound of this invention is N-(4-fluorophenyl)-N-[4-hydroxyphenyl]-[4-(2-piperidin-1-ylethoxy)]-benzamide (4g). In another embodiment the NRBA or SERM compound of this invention is N-(4-hydroxyphenyl)-N-[4-(2-piperidin-1-ylethoxy)-phenyl]-4-fluororo-benzamide hydrochloride (4h). In one embodiment the NRBA or SERM compound of this invention is 3-(2-piperidin-1-ylethoxy)-N,N-bis(4-hydroxyphenyl)-benzamide (4i). In another embodiment the NRBA or SERM compound of this invention is 4-cyano-N-[4-(2-piperidin-1-ylethoxy)-phenyl]-N-(4-methoxyphenyl)-benz amide (4j). In another embodiment the NRBA or SERM compound of this invention is 4-chloro-N-[4-(2-piperidin-1-ylethoxy)-phenyl]-N-(4-methoxyphenyl)-benzamide (4k) In one embodiment the NRBA or SERM compound of this invention is 4-cyano-N-[4-(2-piperidin-1-ylethoxy)-phenyl]-N-(4-methoxyphenyl)-benzamide (4l). In another embodiment the NRBA or SERM compound of this invention is 3-chloro-N-[4-(2-piperidin-1-ylethoxy)-phenyl]-N-(4-methoxyphenyl)-benzamide (4m). In another embodiment the NRBA or SERM compound of this invention is 4-methoxy-N-(4-methoxyphenyl)-N-[4-(2-piperidin-1-ylethoxy)phenyl]-benzamide (4n). In one embodiment the NRBA or SERM compound of this invention is N-biphenyl-4-yl-N-(4-hydroxyphenyl)-4-(2-piperidin-1-ylethoxy)-benzamide (4o). In another embodiment the NRBA or SERM compound of this invention is 4-methoxy-N-phenyl-N-[4-(2-piperidin-1-ylethoxy)phenyl]-benzamide (4p). In another embodiment the NRBA or SERM compound of this invention is N-(4-hydroxyphenyl)-N-phenyl-3-(2-piperidin-1-ylethoxy)-benzamide (4q). In another embodiment the NRBA or SERM compound of this invention is N-(4-fluorophenyl)-N-[4-(2-piperidin-1-ylethoxy)-phenyl]-[4-(2-piperidin-1-ylethoxy)]-benzamide dihydrochloride (4r). In another embodiment the NRBA or SERM compound of this invention is N,N-bis[4-(2-piperidin-1-ylethoxy)-phenyl]-4-fluorobenzamide dihydrochloride (4s). In another embodiment the NRBA or SERM compound of this invention is N,N-bis[4-(2-piperidin-1-ylethoxy)-phenyl]-benzamide dihydrochloride (4t). In another embodiment the NRBA or SERM compound of this invention is N-[4-(2-piperidin-1-ylethoxy)-phenyl]-N-phenyl-[4-(2-piperidin-1-ylethoxy)]-benzamide dihydrochloride (4u). In one embodiment the NRBA or SERM compound of this invention is 4-chloro-N-[4-hydroxyphenyl]-N-(4-methoxyphenyl)-benzamide (5a). In one embodiment the NRBA or SERM compound of this invention is 4-cyano-N-[4-hydroxyphenyl]-N-(4-methoxyphenyl)-benzamide (5b). In one embodiment the NRBA or SERM compound of this invention is 3-chloro-N-[4-hydroxyphenyl]-N-(4-methoxyphenyl)-benzamide (5c). In one embodiment the NRBA or SERM compound of this invention is 4-hydroxy-N-(4-hydroxyphenyl)-N-(4-methoxyphenyl)-benzamide (5d). In one embodiment the NRBA or SERM compound of this invention is N-(4-hydroxyphenyl)-4-methoxy-N-(4-methoxyphenyl)-benzamide (5e). In one embodiment the NRBA or SERM compound of this invention is 2-(N-(4-methoxyphenyl)-4-methylphenylsulfonamido)ethyl 4-methylbenzenesulfonate (6a). In one embodiment the NRBA or SERM compound of this invention is (R)-3-bromo-2-hydroxy-N-(4-methoxyphenyl)-2-methylpropanamide (6b). In one embodiment the NRBA or SERM compound of this invention is (S)-2-hydroxy-N,3-bis(4-methoxyphenyl)-2-methylpropanamide (6c). In one embodiment the NRBA or SERM compound of this invention is (S)-2-hydroxy-3-(4-methoxyphenoxy)-N-(4-methoxyphenyl)-2-methylpropanamide (6d). In one embodiment the NRBA or SERM compound of this invention is (R)-3-bromo-2-hydroxy-N-(4-hydroxyphenyl)-2-methylpropanamide (6e). In one embodiment the NRBA or SERM compound of this invention is (S)-2-hydroxy-3-(4-hydroxyphenoxy)-N-(4-hydroxyphenyl)-2-methylpropanamide (6f). In one embodiment the NRBA or SERM compound of this invention is (S)-2-hydroxy-N,3-bis(4-hydroxyphenyl)-2-methylpropanamide (6g). In another embodiment the NRBA or SERM compound of this invention is 5-[4-methoxy-phenyl]-5H-phenanthridin-6-one (7a). In another embodiment the NRBA or SERM compound of this invention is 5-[4-hydroxy-phenyl]-5H-phenanthridin-6-one (7b). In one embodiment the NRBA or SERM compound of this invention is 5-[4-(2-piperidin-1-ylethoxy)-phenyl]-5H-phenanthridin-6-one (7c). In another embodiment the NRBA or SERM compound of this invention is cyclohexane-carboxylic acid bis(4-hydroxyphenyl)-amide (8b). In another embodiment the NRBA or SERM compound of this invention is 4-cyano-N-(4-hydroxyphenyl)-N-phenylbenzamide (10a). In another embodiment the NRBA or SERM compound of this invention is N-(biphenyl-4-yl)-4-cyano-N-(4-methoxyphenyl)-benzamide (10b). In another embodiment the NRBA or SERM compound of this invention is N,N-bis(4-hydroxyphenyl)biphenyl-4-carboxamide (10c). In another embodiment the NRBA or SERM compound of this invention is N,N-bis(4-hydroxyphenyl)-3,4-dimethylbenzamide (10d). In another embodiment the NRBA or SERM compound of this invention is N-(biphenyl-4-yl)-4-cyano-N-(4-hydroxyphenyl)-benzamide (10e). In another embodiment the NRBA or SERM compound of this invention is 3-fluoro-4-hydroxy-N-(4-hydroxyphenyl)-N-phenylbenzamide (10f). In another embodiment the NRBA or SERM compound of this invention is 4-fluoro-3-hydroxy-N,N-bis(4-hydroxyphenyl)-benzamide (10 g). In another embodiment the NRBA or SERM compound of this invention is 4-hydroxy-N,N-bis(4-hydroxyphenyl)-3,5-dimethylbenzamide (10i). In another embodiment the NRBA or SERM compound of this invention is N,N-bis(4-hydroxyphenyl)-2,3-dimethylbenzamide (10j). In another embodiment the NRBA or SERM compound of this invention is 3-fluoro-4-hydroxy-N,N-bis(4-hydroxyphenyl)-benzamide (10k). In another embodiment the NRBA or SERM compound of this invention is N,N-bis(4-hydroxyphenyl)-4-propylbenzamide (10l). In another embodiment the NRBA or SERM compound of this invention is 3,4-dihydroxy-N,N-bis(4-hydroxyphenyl)-benzamide (10m). In another embodiment the NRBA or SERM compound of this invention is 4-hydroxy-N,N-bis(4-hydroxyphenyl)-3-methylbenzamide (10n). In another embodiment the NRBA or SERM compound of this invention is N-(4-hydroxyphenyl)-N-(4-(2-(piperidin-1-yl)ethoxy)phenyl)-4-propylbenzamide (10o). In another embodiment the NRBA or SERM compound of this invention is N-(4-hydroxyphenyl)-2,3-dimethyl-N-(4-(2-(piperidin-1-yl)ethoxy)phenyl)-benzamide (10p). In another embodiment the NRBA or SERM compound of this invention is N,N-bis(4-hydroxyphenyl)-2,4-dimethylbenzamide (10q). In another embodiment the NRBA or SERM compound of this invention is N,N-bis(4-hydroxyphenyl)-3,5-dimethylbenzamide (10r). In another embodiment the NRBA or SERM compound of this invention is N,N-bis(4-hydroxyphenyl)-4-methylbenzamide (10s). In another embodiment the NRBA or SERM compound of this invention is 4,4'-(2,3-dimethyl-benzylazanediyl)diphenol (10t). In another embodiment the NRBA or SERM compound of this invention is 4-formyl-N,N-bis(4-hydroxyphenyl)-benzamide (10u). In another embodiment the NRBA or SERM compound of this invention is 4-hydroxy-N-(4-hydroxyphenyl)benzamide (10v). In another embodiment the NRBA or SERM compound of this invention is N-cyclohexyl-4-hydroxy-N-(4-hydroxyphenyl)benzamide (10w). In another embodiment the NRBA or SERM compound of this invention is 4-((4-fluorophenyl)(4-hydroxybenzyl)amino)phenol (10x). In another embodiment the NRBA or SERM compound of this invention is N-(4-(2-(dimethylamino)ethoxy)phenyl)-N-(4-hydroxy-phenyl)-benzamide (10y). In another embodiment the NRBA or SERM compound of this invention is 3-Cyano-N-(4-hydroxyphenyl)-N-(4-(2-(piperidin-1-yl)ethoxy)phenyl)-benzamide (10z). In another embodiment the NRBA or SERM compound of this invention is N-(4-hydroxyphenyl)-N-(4-(2-(pyrrolidin-1-yl)ethoxy)phenyl)benzamide (11a). In another embodiment the NRBA or SERM compound of this invention is N,N-bis(4-hydroxyphenyl)-4-(trifluoromethyl)-benzamide (11b). In another embodiment the NRBA or SERM compound of this invention is N-(4-hydroxyphenyl)-N-(4-(2-(piperidin-1-yl)ethoxy)phenyl)-4-(trifluoromethyl)-benzamide (11c). In another embodiment the NRBA or SERM compound of this invention is N,N-bis(4-hydroxyphenyl)-4-nitro-benzamide (11d). In another embodiment the NRBA or SERM compound of this invention is 3-fluoro-N,N-bis(4-hydroxyphenyl)-benzamide (11e). In another embodiment the NRBA or SERM compound of this invention is N-(4-hydroxyphenyl)-N-(4-(2-(piperidin-1-yl)ethoxy)phenyl)-1-naphthamide (11f). In another embodiment the NRBA or SERM compound of this invention is 3-fluoro-N-(4-hydroxyphenyl)-N-(4-(2-(piperidin-1-yl)ethoxy)phenyl)benzamide (11g). In another embodiment the NRBA or SERM compound of this invention is N-(4-hydroxyphenyl)-4-nitro-N-(4-(2-(piperidin-1-yl)ethoxy)phenyl)benzamide (11h). In another embodiment the NRBA or SERM compound of this invention is N,N-bis(4-hydroxyphenyl)-4-methoxy-1-naphthamide (11i). In another embodiment the NRBA or SERM compound of this invention is N-(4-hydroxyphenyl)-N-(4-(2-(piperidin-1-yl)ethoxy)phenyl)-2-naphthamide (11j). In another embodiment the NRBA or SERM compound of this invention is 2-hydroxy-N,N,2-tris(4-hydroxyphenyl)-propanamide (11k). In another embodiment the NRBA or SERM compound of this invention is 4-((hydroxyimino)methyl)-N, N-bis(4-hydroxyphenyl) benzamide (11l). In another embodiment the NRBA or SERM compound of this invention is N-(4-hydroxyphenyl)-2,4-dimethyl-N-(4-(2-(piperidin-1-yl)ethoxy)phenyl)benzamide (11m). In another embodiment the NRBA or SERM compound of this invention is N-(4-hydroxyphenyl)-3,5-dimethyl-N-(4-(2-(piperidin-1-yl)ethoxy)phenyl)benzamide (11n). In another embodiment the NRBA or SERM compound of this invention is 4-((2,3-dimethylbenzyl)(4-(2-(piperidin-1-yl)ethoxy)phenyl)amino)phenol (11o). In another embodiment the NRBA or SERM compound of this invention is N,N-bis(4-hydroxyphenyl)-4-pentylbenzamide (11p). In another embodiment the NRBA or SERM compound of this invention is N-(4-hydroxyphenyl)-4-pentyl-N-(4-(2-(piperidin-1-yl)ethoxy)phenyl)benzamide (11q). In another embodiment the NRBA or SERM compound of this invention is 4-tert-butyl-N,N-bis(4-hydroxyphenyl)benzamide (11r). In another embodiment the NRBA or SERM compound of this invention is 4-tert-butyl-N-(4-hydroxyphenyl)-N-(4-(2-(piperidin-1-yl)ethoxy)phenyl)benzamide (11s). In another embodiment the NRBA or SERM compound of this invention is 3-{4-[bis-(4-hydroxy-phenyl)-carbamoyl]-phenyl}-acrylic acid (11t). In another embodiment the NRBA or SERM compound of this invention is 3-{4-[bis-(4-hydroxy-phenyl)-carbamoyl]-phenyl}-propionic acid (11u). In another embodiment the NRBA or SERM compound of this invention is N,N-bis-(4-hydroxy-phenyl)-4-(3-hydroxy-propyl)-benzamide (11v). In another embodiment the NRBA or SERM compound of this invention is N-(4-hydroxyphenyl)-4-(3-hydroxypropyl)-N-(4-methoxyphenyl)-benzamide (11w). In another embodiment the NRBA or SERM compound of this invention is 4-fluoro-N,N-bis(4-hydroxyphenyl)-2-(trifluoromethyl)-benzamide (11x). In another embodiment the NRBA or SERM compound of this invention is 3-fluoro-N-(4-fluorophenyl)-4-hydroxy-N-(4-hydroxyphenyl)benzamide (11y). In another embodiment the NRBA or SERM compound of this invention is N-(4-hydroxyphenyl)-4-methyl-N-(4-(2-(piperidin-1-yl)ethoxy)phenyl)benzamide (11z). In another embodiment the NRBA or SERM compound of this invention is N,N-bis(4-hydroxyphenyl)-isonicotin-amide (11aa). In another embodiment the NRBA or SERM compound of this invention is N-(4-hydroxyphenyl)-N-(4-(2-(piperidin-1-yl)ethoxy)phenyl)-isonicotinamide (11ab). In another embodiment, this invention provides a composition comprising a NRBA or SERM compound as described herein, or any combination thereof.

In another embodiment, the SERM compound for use in the methods of this invention may be represented by the structure of formula XI:

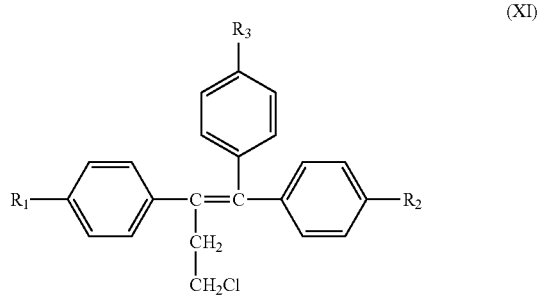

(XI)

wherein $R_1$ and $R_2$, which can be the same or different, are H or OH, $R_3$ is $OCH_2CH_2OH$, $OCH_2CH_2NR_4R_5$, wherein $R_4$ and $R_5$, which can be the same or different, are H, an alkyl group of 1 to about 4 carbon atoms or forms together with the nitrogen a cyclic 5-8 membered ring; and their pharmaceutically acceptable carrier, diluents, salts, esters, or N-oxides, and mixtures thereof.

In another embodiment, the SERM compound is toremifene

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. In another embodiment, the cyclic alkyl group has 3-8 carbons. In another embodiment, the cyclic alkyl group has 3-12 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, alkoxy carbonyl, amido, alkylamido, dialkylamido, nitro, amino, alkylamino, dialkylamino, carboxyl, thio and/or thioalkyl.

An "alkenyl" group refers, in another embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. Examples of alkenyl groups are ethenyl, propenyl, butenyl, cyclohexenyl, etc. The alkenyl group may be unsubstituted or substituted by a halogen, hydroxy, alkoxy carbonyl, amido, alkylamido, dialkylamido, nitro, amino, alkylamino, dialkylamino, carboxyl, thio and/or thioalkyl.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 6 membered ring. In another embodiment, the aryl group is a 5 membered ring. In another embodiment, the aryl group is 2-4 fused ring system.

A "aldehyde" group refers, in one embodiment to an alkyl, or alkenyl substituted by a formyl group, wherein the alkyl or alkenyl are as defined hereinabove. In another embodiment, the aldehyde group is an aryl, or phenyl group substituted by a formyl group, wherein the aryl is as defined hereinabove. Examples of aldehydes are: formyl, acetal, propanal, butanal, pentanal, benzaldehyde. In another embodiment, the aldehyde group is a formyl group.

A "haloalkyl" group refers, in another embodiment, to an alkyl group as defined above, which is substituted by one or more halogen atoms, e.g. by F, Cl, Br or I.

A "hydroxyl" group refers, in another embodiment, to an OH group. It is understood by a person skilled in the art that when $R_1$, $R_2$ or $R_3$ in the compounds of the present invention is OR, then R is not OH.

In one embodiment, the term "halo" refers to a halogen, such as F, Cl, Br or I.

In another embodiment, the phrase "phenol" refers to an alcohol (OH) derivative of benzene.

A "heterocycle" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 4-8 membered ring. In another embodiment, the heterocycle group may be unsubstituted or substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring.

Reference to protected hydroxyl, in some embodiments, includes the incorporation of a substituent bonded to the oxygen moiety of the benzene ring, wherein the substituent may be readily removed. In some embodiments, phenolic protecting groups may comprise a: methyl ether, methoxymethyl (MOM) ether, benzoyloxymethyl (BOM) ether, methoxyethoxymethyl (MEM) ether, 2-(trimethylsilyl)ethoxymethyl(SEM) ether, methylthiomethyl (MTM) ether, phenylthiomethyl (PTM) ether, azidomethyl ether, cyanomethyl ether, 2,2-dichloro-1,1-difluoroethyl ether, 2-chloroethyl ether, 2-bromoethyl ether, tetrahydropyranyl (THP) ether, 1-ethoxyethyl (EE) ether, phenacyl ether, 4-bromophenacyl ether, cyclopropylmethyl ether, allyl ether, propargyl ether, isopropyl ether, cyclohexyl ether, t-butyl ether, benzyl ether, 2,6-dimethylbenzyl ether, 4-methoxybenzyl ether, o-nitrobenzyl ether, 2,6dichlorobenzyl ether, 3,4dichlorobenzyl ether, 4-(dimethylamino)carbonylbenzyl ether, 4-methylsulfinylbenzyl ether, 4-anthrylmethyl ether, 4-picolyl ether, heptafluoro-p-tolyl, tetrafluoro-4-pyridyl ether, trimethylsilyl (TMS) ether, t-butyldimethylsilyl (TBDMS) ether, t-butyldiphenylsilyl (TBDPS) ether, triisopropylsilyl (TIPS) ether, aryl formate, arylacetate, aryl levulinate, arylpivaloate, aryl benzoate, aryl 9-fluorenecarboxylate, aryl methyl carbonate, 1-adamantyl carbonate, t-butyl carbonate, 4-methylsulfinylbenzyl carbonate, 2,4-dimethylpent-3-yl carbonate, aryl 2,2,2trichloroethyl carbonate, aryl benzyl carbonate, aryl carbamate, dimethylphosphinyl ester (Dmp-OAr), dimethylphosphinothionyl ester (Mpt-OAr), diphenylphosphinothionyl ester (Dpt-OAr), aryl methanesulfonate, aryl toluenesulfonate or aryl 2-formylbenzenesulfonate.

In one embodiment, this invention provides a NRBA or SERM compound and/or analog, derivative, isomer, metabolite, pharmaceutically acceptable salt, pharmaceutical product, hydrate, N-oxide, prodrug, ester, polymorph, impurity or crystal or combinations thereof. In one embodiment, this invention provides an analog of the NRBA or SERM compound. In another embodiment, this invention provides a derivative of the NRBA or SERM compound. In another embodiment, this invention provides an isomer of the NRBA or SERM compound. In another embodiment, this invention provides a metabolite of the NRBA or SERM compound. In another embodiment, this invention provides a pharmaceutically acceptable salt of the NRBA or SERM compound. In another embodiment, this invention provides a pharmaceutical product of the NRBA or SERM compound. In another embodiment, this invention provides a hydrate of the NRBA or SERM compound. In another embodiment, this invention provides an N-oxide of the NRBA or SERM compound. In another embodiment, this invention provides a prodrug of the NRBA or SERM compound. In another embodiment, this invention provides an ester of the NRBA or SERM compound. In another embodiment, this invention provides a polymorph of the NRBA or SERM compound. In another embodiment, this invention provides a crystal of the NRBA or SERM compound. In another embodiment, this invention provides an impurity of the NRBA or SERM compound. In another embodiment, this invention provides composition comprising a NRBA or SERM compound, as described herein, or, in another embodiment, a combination of an analog, derivative, isomer, metabolite, pharmaceutically acceptable salt, pharmaceutical product, hydrate, N-oxide, prodrug, polymorph, ester, impurity or crystal of the NRBA or SERM compounds of the present invention.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the NRBA or SERM compound. It will be appreciated by those skilled in the art that the NRBA or SERMs of the present invention contain at least one chiral center. Accordingly, the NRBA or SERMs used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or mixtures thereof, and use of these for any application is to be considered within the scope of this invention.

In one embodiment, the NRBAs or SERMs are the pure (R)-isomers. In another embodiment, the NRBAs or SERMs are the pure (S)-isomers. In another embodiment, the NRBAs or SERMs are a mixture of the (R) and the (S) isomers. In another embodiment, the NRBAs or SERMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase), and such methods are to be considered as part of this invention. In some embodiments, synthesis of such racemic forms may be accomplished by methods described and exemplified herein, or via appropriate modification thereof, as will be understood by one skilled in the art.

In one embodiment, the NRBAs or SERMs are the pure (E)-isomers. In another embodiment, the NRBAs or SERMs are the pure (Z)-isomers. In another embodiment, the NRBAs or SERMs are a mixture of the (E) and the (Z) isomers.

The invention includes "pharmaceutically acceptable salts" of the compounds of this invention, which may be produced, by reaction of a compound of this invention with an acid or base.

Suitable pharmaceutically-acceptable salts of amines of Formula I-XI may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrate, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilate, algenate, alkane carboxylates, substituted alkane carboxylates, alginates, benzenesulfonates, benzoates, bisulfates, butyrates, bicarbonates, bitartrates, carboxilate, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonate gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoate, hydrofluorate, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, mitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or phenols may be selected from ammonium, alkali metals to include lithium, sodium, potassium, cesium; alkaline earch metals to include calcium, magnesium, aluminium; zinc, barium, cholines, quaternary ammoniums.

In another embodiment, examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment, the pharmaceutically acceptable salt of a NRBA compound comprising a piperidine ring is an HCl salt. In another embodiment, the pharmaceutically acceptable salt of a NRBA compound comprising a pyrrolidine ring is an HCl salt. In another embodiment, the pharmaceutically acceptable salt of a NRBA compound comprising a morpholine ring is an HCl salt. In another embodiment, the pharmaceutically acceptable salt of a NRBA compound comprising a piperazine ring is an HCl salt.

This invention provides, in some embodiments, derivatives of the NRBA or SERM compounds. In one embodiment, the term "derivatives" refers to ether derivatives, acid derivatives, amide derivatives, ester derivatives or others, as known in the art. In another embodiment, this invention further includes hydrates of the NRBA or SERM compounds. In one embodiment, the term "hydrate" refers to hemihydrate, monohydrate, dihydrate, trihydrate or others, as known in the art.

This invention provides, in other embodiments, metabolites of the NRBA or SERM compounds. In one embodiment, the term "metabolite" refers to any substance produced from another substance by metabolism or a metabolic process.

In some embodiments, a NRBA or SERM of this invention will comprise the compounds listed in Table 1. In some embodiments, the NRBAs or SERMs of this invention will have an affinity for a nuclear hormone receptor, with varying affinity. In some embodiments of this invention, NRBAs or SERMs of this invention will vary in terms of their activity, for example, some NRBAs or SERMs possessing greater anabolic activity, some exhibiting greater activity with regard to anti-estrogenic activity, etc. It is to be understood that all such NRBAs or SERMs are to be considered as part of this invention.

In some embodiments, the NRBAs or SERMs of this invention may exhibit affinity for or binding to a nuclear receptor, which in some embodiments, is an estrogen receptor α and/or estrogen receptor β molecule. In some embodiments, the NRBAs or SERMs of this invention may exhibit agonist activity. In some embodiments, the NRBAs or SERMs of this invention may exhibit antagonist activity. Agonist and antagonist activity for representative NRBAs are exemplified in the Examples herein, wherein such agonist and/or antagonist activity under specific experimental conditions is provided, representing only some embodiments of this invention. It is to be understood that while the indicated compounds may exhibit a particular activity (for example, compound 3v is an agonist) under the experimental conditions employed, as a function, in some embodiments of the particular cells utilized, etc., such compounds may possess alternate, varied, or partial activity in different experimental settings. In some embodiments, the NRBAs or SERMs of this invention may exhibit agonist activity for a particular receptor, and antagonist activity for a different receptor, or vice versa, or in some embodiments, the NRBAs or SERMs of this invention may exhibit agonist activity for a particular receptor under certain experimental conditions, yet exhibit antagonist activity for the same receptor under different experimental conditions, or vice versa, or in some embodiments, the NRBAs or SERMs of this invention may exhibit agonist activity for a particular receptor in a particular tissue, yet exhibit antagonist activity for the same receptor in a different tissue, or vice versa, etc.

Steroid nuclear hormone receptors are known to have rapid, tissue-specific effects that are mediated by cell-surface and cytosolic receptors through protein-protein interaction or phosphorylation of kinases, which are known as non-genomic effects. For instance, SERMs are known to have distinct rapid effects in the cardiovascular and central nervous systems which may be mediated by distinct receptors. Putative receptors for these non-genomic effects include a variety of G-protein coupled receptors (GPCRs) such as GPR130 for SERMs, as well as cell-membrane associated or cytosolic nuclear receptors. NRBA and SERMs of this invention may also bind to receptors involved in these non-genomic effects allowing differential pharmacological exploitation of genomic, non-genomic, and tissue-selective steroid receptor activities. As such these NRBA and SERMs may have a wide variety of specific and targeted steroid responses broadening their potential to have beneficial medical properties In some embodiments, a NRBA of this invention is a non-genomic agonist, or in some embodiments, a non-genomic antagonist, or in some embodiments, a non-genomic partial agonist of a nuclear receptor. In some embodiments, the NRBAs of this invention are tissue selective, non-genomic nuclear receptors, such as for example, estrogen or androgen receptor agonists, or in some embodiments, tissue selective, non-genomic nuclear receptor antagonists, or in some embodiments, tissue selective, non-genomic nuclear receptor partial agonists. In some embodiments, the NRBAs of this invention are non-selective non-genomic nuclear receptors, such as for example, estrogen or androgen receptor agonists, or in some embodiments, non-selective non-genomic nuclear receptor antagonists, or in some embodiments, non-selective non-genomic nuclear receptor partial agonists. In some embodiments, the NRBAs of this invention are non-selective genomic nuclear receptors, such as for example, estrogen or androgen receptor agonists, or in some embodiments, antagonists, or in some embodiments, partial agonists. In some embodiments, the NRBAs of this invention are tissue selective genomic nuclear receptor modulators, such as for example, estrogen or androgen receptor agonists, or in some embodiments, antagonists, or in some embodiments, partial agonists. In some embodiments, the NRBAs of this invention are genomic agents which selectively transactivate nuclear receptor-regulated genes. In some embodiments, selective transactivation is in a tissue selective manner. In some embodiments, the NRBAs of this invention are genomic agents which selectively transrepress nuclear receptor-regulated genes. In some embodiments, selective tranrepression is in a tissue selective manner.

This invention provides, in other embodiments, pharmaceutical products of the NRBA or SERM compounds. The term "pharmaceutical product" refers, in other embodiments, to a composition suitable for pharmaceutical use (pharmaceutical composition), for example, as described herein.

In one embodiment, this invention provides a method of binding any NRBA or SERM compound of this invention to an estrogen receptor or an estrogen related receptors, comprising the step of contacting an estrogen receptor with said NRBA or SERM. In another embodiment, this invention provides a method of binding any NRBA or SERM compound of this invention to a nuclear hormone receptor or one related thereto.

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compound of this invention, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

The pharmaceutical compositions containing the compounds of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitonealy, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the SARM compounds are formulated in a capsule. In accordance with this embodiment, the compositions of the present invention comprise in addition to a compound of this invention and the inert carrier or diluent, a hard gelatin capsule.

In one embodiment, the micronized capsules comprise particles containing a compound of this invention, wherein the term "micronized" used herein refers to particles having a particle size is of less than 100 microns, or in another embodiment, less than 60 microns, or in another embodiment, less than 36 microns, or in another embodiment, less than 16 microns, or in another embodiment, less than 10 microns, or in another embodiment, less than 6 microns.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of a compound as herein described over a period of time. In a further embodiment, the pharmaceutical compositions are administered intravaginally.

In another embodiment, the active compound can be delivered in a vesicle, in particular a liposome (see Langer, Science 249:1627-1633 (1990); Treat et al., in Liposomes in the Therapy of Infectious Disease and Cancer, Lopez-Berestein and Fidler (eds.), Liss, New York, pp. 363-366 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In one embodiment, the compositions of this invention may include, a compound of this invention or any combination thereof, together with one or more pharmaceutically acceptable excipients.

It is to be understood that this invention encompasses any embodiment of a compound as described herein, which in some embodiments is referred to as "a compound of this invention".

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sobitan esters, stearic acids), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), coloring agents, lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the compound of this invention is released over a period of time after administration. Controlled or sustained release compositions include formulation in lipophilic depots (e.g. fatty acids, waxes, oils). In another embodiment, the composition is an immediate release composition, i.e. a composition in which all of the compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:607 (1980); Saudek et al., N. Engl. J. Med. 321: 674 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 116-138 (1984). Other controlled release systems are discussed in the review by Langer (Science 249:1627-1633 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compounds solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the compounds of this invention or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the compounds of this invention or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the compound will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In one embodiment, this invention provides pharmaceutical compositions comprising a compound of this invention. In one embodiment, such compositions are useful for oral testosterone replacement therapy.

In one embodiment, this invention also provides a composition comprising two or more compounds of this invention, or polymorphs, isomers, hydrates, salts, N-oxides, etc., thereof. The present invention also relates to compositions and a pharmaceutical compositions which comprises a compound of this invention alone or in combination with a progestin or estrogen, or in another embodiment, chemotherapeutic compound, osteogenic or myogenic compound, or other agents suitable for the applications as herein described. In one embodiment, the compositions of this invention will comprise a suitable carrier, diluent or salt.

In one embodiment, the methods of this invention may comprise administration of a compound of this invention at various dosages. In one embodiment, the compound of this invention is administered at a dosage of 0.1-200 mg per day. In one embodiment, the compound of this invention is administered at a dose of 0.1-10 mg, or in another embodiment, 0.1-26 mg, or in another embodiment, 0.1-60 mg, or in another embodiment, 0.3-16 mg, or in another embodiment, 0.3-30 mg, or in another embodiment, 0.6-26 mg, or in another embodiment, 0.6-60 mg, or in another embodiment, 0.76-16 mg, or in another embodiment, 0.76-60 mg, or in another embodiment, 1-6 mg, or in another embodiment, 1-20 mg, or in another embodiment, 3-16 mg, or in another embodiment, 30-60 mg, or in another embodiment, 30-76 mg, or in another embodiment, 100-2000 mg.

In one embodiment, the methods of this invention may comprise administration of a compound of this invention at various dosages. In one embodiment, the compound of this invention is administered at a dosage of 1 mg. In another embodiment the compound of this invention is administered at a dosage of 6 mg, 10 mg, 16 mg, 20 mg, 26 mg, 30 mg, 36 mg, 40 mg, 46 mg, 60 mg, 66 mg, 60 mg, 66 mg, 70 mg, 76 mg, 80 mg, 86 mg, 90 mg, 96 mg or 100 mg.

In one embodiment, the present invention provides methods of use comprising the administration of a pharmaceutical composition comprising a) any embodiment of a compound as described herein; and b) a pharmaceutically acceptable carrier or diluent; which is to be understood to include an analog, isomer, metabolite, derivative, pharmaceutically acceptable salt, N-oxide, hydrate or any combination thereof of a compound as herein described.

In some embodiments, the present invention provides methods of use of a pharmaceutical composition comprising a) any embodiment of the compounds as described herein, including an analog, isomer, metabolite, derivative, pharmaceutically acceptable salt, pharmaceutical product, N-oxide, hydrate thereof or any combination thereof; b) a pharmaceutically acceptable carrier or diluent; c) a flow-aid; and d) a lubricant.

In another embodiment, the present invention provides methods of use of a pharmaceutical composition comprising a) any embodiment of the compounds as described herein, including an analog, isomer, metabolite, derivative, pharmaceutically acceptable salt, pharmaceutical product, N-oxide, hydrate thereof or any combination thereof; b) lactose monohydrate; c) microcrystalline cellulose; d) magnesium stearate; and e) colloidal silicon dioxide.

In some embodiments, the methods of this invention make use of compositions comprising compounds of this invention, which offer the advantage that the compounds are nonsteroidal ligands for the androgen receptor, and exhibit anabolic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides compounds and compositions, including any embodiment described herein, for use in any of the methods of this invention, as described herein. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In some embodiments, the methods of this invention make use of compositions comprising compounds of this invention, which offer the advantage that the compounds are nonsteroidal ligands for the androgen receptor, and exhibit anabolic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides compounds and compositions, including any embodiment described herein, for use in any of the methods of this invention. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In some embodiments, the compositions will further comprise a 5a-Reductase Inhibitors, a SARM or SARMs, a selective estrogen receptor modulator (SERM), an aromatase inhibitor, such as but not limited to anastrazole, exemestane, or letrozole; a GnRH agonist or antagonist, a steroidal or nonsteroidal GR ligand, a steroidal or nonsteroidal PR ligand, a steroidal or nonsteroidal AR antagonist, a 17-aldoketoreductase inhibitor or 17b-hydroxysteroid dehydrogenase inhibitor. Such compositions may be used, in some embodiments, for treating a hormone dependent condition, such as, for example, infertility, neoplasia of a hormone-responsive cancer, for example, a gonadal cancer, or a urogenital cancer.

In some embodiments, the composition will comprise the compounds as described herein, as well as another therapeutic compound, including inter alia, a 5ARI such as finasteride, dutasteride, izonsteride; other SARMs, such as, RU-58642, RU-56279, WS9761 A and B, RU-59063, RU-58841, bexlosteride, LG-2293, L-245976, LG-121071, LG-121091, LG-121104, LGD-2226, LGD-2941, YM-92088, YM-175735, LGD-1331, BMS-357597, BMS-391197, S-40503, BMS-482404, EM-4283, EM-4977, BMS-564929, BMS-391197, BMS-434588, BMS-487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, ACP-105; SERMs, such as tamoxifene, 4-hydroxytamoxifene, idoxifene, toremifene, ospemifene, droloxifene, raloxifene, arzoxifene, bazedoxifene, PPT (1,3,5-Tris(4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstibestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, Ban zhi lian, CT-101, CT-102, VG-101; GnRH agonists or antagonists, such as, leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, acyline; FSH agonist/antagonist, LH agonist/antagonists, aromatase inhibitors, such as, letrozole, anastrazole, atamestane, fadrozole, minamestane, exemestane, plomestane, liarozole, NKS-01, vorozole, YM-511, finrozole, 4-hydroxyandrostenedione, aminogluethimide, rogletimide; Steroidal or nonsteroidal glucocorticoid receptor ligands, such as, ZK-216348, ZK-243149, ZK-243185, LGD-5552, mifepristone, RPR-106541, ORG-34517, GW-215864X, Sesquicillin, CP-472555, CP-394531, A-222977, AL-438, A-216054, A-276575, CP-394531, CP-409069, UGR-07; Steroidal or nonsteroidal progesterone receptor ligands; Steroidal or nonsteroidal AR antagonists such as flutamide, hydroxyflutamide, bicalutamide, nilutamide, hydroxysteroid dehydrogenase inhibitors, PPAR ligand such as bezafibrate, fenofibrate, gemfibrozil; PPARγ ligands such as darglitazone, pioglitazone, rosiglitazone, isaglitazone, rivoglitazone, netoglitazone; Dual acting PPAR ligands, such as naveglitazar, farglitazar, tesaglitazar, ragaglitazar, oxeglitazar, PN-2034, PPAR δ; a 17-ketoreductase inhibitors, 3β-DHΔ4, 6-isomerase inhibitors, 3β-DHΔ4,5-isomerase inhibitors, 17,20 desmolase inhibitors, p450c17 inhibitors, p450ssc inhibitors, 17,20-lyase inhibitors, or combinations thereof.

In some embodiments, the compositions will further comprise Ghrelin receptor ligand or growth hormone analogues and secretagogues, IGF-1, IGF-1 analogues and secretagogues, Myostatin Analogues, Proteasome Inhibitors, Androgenic/Anabolic Steroid, EnbrelMelanocortin 4 Receptor Agonist, Insulins, or combinations thereof. Such compositions may be used, in some embodiments, for treating sarcopenia or a musculoskeletal condition.

In some embodiments, the composition will comprise the compounds as described herein, as well as another therapeutic compound, including inter alia, Ghrelin receptor ligand or growth hormone analogues and secretagogues, such as, pralmorelin, examorelin, tabimorelin, capimorelin, capromorelin, ipamorelin, EP-01572, EP-1572, JMV-1843, an androgenic/Anabolic Steroid such as Testosterone/Oxandrolone; a melanocortin 4 receptor agonist, such as Bremelanotide, a Ghrelin or analogue thereof, such as human ghrelin, CYT-009-GhrQb, L-692429, GHRP-6, SK&F-110679, U-75799E), leptin (metreleptin, pegylated leptin; a leptin receptor agonist, such as LEP(116-130), OB3, [D-Leu4]-OB3, rAAV-leptin, AAV-hOB, rAAVhOB; an insulin (short-, intermediate-, and long acting formulations; a cortisol or corticosteroid, or a combination thereof.

The invention contemplates, in some embodiments, administration of compositions comprising the individual agents, administered separately and by similar or alternative routes, formulated as appropriately for the route of administration. The invention contemplates, in some embodiments, administration of compositions comprising the individual agents, administered in the same formulation. The invention contemplates, in some embodiments, staggered administration, concurrent administration, of administration of the various agents over a course of time, however, their effects are synergistic in the subject.

It is to be understood that any of the above means, timings, routes, or combinations thereof, of administration of two or more agents is to be considered as being encompassed by the phrase "administered in combination", as described herein.

In one embodiment, the compound of this invention is administered in combination with an anti-cancer agent. In one embodiment, the anti-cancer agent is a monoclonal antibody. In some embodiments, the monoclonal antibodies are used for diagnosis, monitoring, or treatment of cancer. In one embodiment, monoclonal antibodies react against specific antigens on cancer cells. In one embodiment, the monoclonal antibody acts as a cancer cell receptor antagonist. In one embodiment, monoclonal antibodies enhance the patient's immune response. In one embodiment, monoclonal antibodies act against cell growth factors, thus blocking cancer cell growth. In one embodiment, anti-cancer monoclonal antibodies are conjugated or linked to anti-cancer drugs, radioisotopes, other biologic response modifiers, other toxins, or a combination thereof. In one embodiment, anti-cancer monoclonal antibodies are conjugated or linked to a compound of this invention as described hereinabove.

In another embodiment, the present invention includes compounds and compositions in which a compound of the invention is either combined with, or covalently bound to, an agent bound to a targeting agent, such as a monoclonal antibody (e.g., a murine or humanized monoclonal antibody). In one embodiment, the agent bound to a targeting agent is a cytotoxic agent. It will be appreciated that the latter combination may allow the introduction of cytotoxic agents into for example cancer cells with greater specificity. Thus, the active form of the cytotoxic agent (i.e., the free form) will be present only in cells targeted by the antibody. Of course, the compounds of the invention may also be combined with monoclonal antibodies that have therapeutic activity against cancer.

In one embodiment, the compound is administered in combination with a selective tyrosine kinase inhibitor. In some embodiments, the selective tyrosine kinase inhibitor inhibits catalytic sites of cancer promoting receptors thereby inhibiting tumor growth. In one embodiment, a selective tyrosine kinase inhibitor modulates growth factor signaling. In some embodiments, the selective tyrosine kinase inhibitor targets EGFR (ERB B/HER) family members. In one embodiment, the selective tyrosine kinase inhibitor is a BCR-ABL tyrosine kinase inhibitor. In one embodiment, the selective tyrosine kinase inhibitor is an epidermal growth factor receptor tyrosine kinase inhibitor. In one embodiment, the selective tyrosine kinase inhibitor is a vascular endothelial growth factor tyrosine kinase inhibitor. In one embodiment, the selective tyrosine kinase inhibitor is a Platelet Derived Growth Factor (PDGF) inhibitor.

In one embodiment, the compound is administered in combination with a cancer vaccine. In one embodiment, the cancer vaccine is a therapeutic vaccine thus, treating an existing cancer. In some embodiments, the cancer vaccine is a prophylactic vaccine thus, preventing the development of cancer. In one embodiment, both types of vaccines have the potential to reduce the burden of cancer. In one embodiment, treatment or therapeutic vaccines are administered to cancer patients and are designed to strengthen the body's natural defenses against cancers that have already developed. In one embodiment, therapeutic vaccines may prevent additional growth of existing cancers, prevent the recurrence of treated cancers, or eliminate cancer cells not killed by prior treatments. In some embodiments, prevention or prophylactic vaccines are administered to healthy individuals and are designed to target cancer in individuals who present high risk for the disease. In one embodiment, the cancer vaccine is an antigen/adjuvant vaccine. In one embodiment, the cancer vaccine is a whole cell tumor vaccine. In one embodiment, the cancer vaccine is a dendritic cell vaccine. In one embodiment, the cancer vaccine comprises viral vectors and/or DNA vaccines. In one embodiment, the cancer vaccine is an idiotype vaccine.

In one embodiment, the compound is administered in combination with an anti-cancer chemotherapeutic agent. In one embodiment, the anti-cancer chemotherapeutic agent is an alkylating agent, such as but not limited to cyclophosphamide. In one embodiment, the anti-cancer chemotherapeutic agent is a cytotoxic antibiotic such as but not limited to doxorubicin. In one embodiment, the anti-cancer chemotherapeutic agent is an antimetabolite, such as but not limited to methotrexate. In one embodiment, the anti-cancer chemotherapeutic agent is a vinca alkaloid, such as but not limited to vindesine. In some embodiments, the anti-cancer chemotherapeutic agents include platinum compounds such as but not limited to carboplatin, and taxanes such as docetaxel. In one embodiment, the anti-cancer chemotherapeutic agent is an aromatase inhibitor such as but not limited to anastrazole, exemestane, or letrozole.

In one embodiment, the compound is administered in combination with a Bax activity modulator such as alisol B acetate. In one embodiment, the compound is administered in combination with an angiotensin II receptor blocker such as losartan. In one embodiment, the compound is administered in combination with selenium, green tea cachecins, saw palmetto, lycopene, vitamin D, dietary soy, genistein or isoflavone.

In one embodiment, the compound is administered in combination with antineoplastic agents, such as alkylating agents, antibiotics, hormonal antineoplastics and antimetabolites. Examples of useful alkylating agents include alkyl sulfonates such as busulfan, improsulfan and piposulfan; aziridines, such as a benzodizepa, carboquone, meturedepa and uredepa; ethylenimines and methylmelamines such as altretamine, triethylenemelamine, triethylenephosphoramide, triethylenethiophos-phoramide and trimethylolmelamine; nitrogen mustards such as chlorambucil, chlomaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, ranimustine, dacarbazine, mannomustine, mitobronitol, mitolactol and pipobroman. More such agents will be known to those having skill in the medicinal chemistry and oncology arts.

In some embodiments, other agents suitable for combination with the compounds of this invention include protein synthesis inhibitors such as abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine, modeccin, neomycin, norvaline, pactamycin, paromomycine, puromycin, ricin, α-sarcin, shiga toxin, showdomycin, sparsomycin, spectinomycin, streptomycin, tetracycline, thiostrepton and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine, β-1-D-arabinoside, amethopterin, aminopterin, 2-aminopurine, aphidicolin, 8-azaguanine, azaserine, 6-azauracil, 2'-azido-2'-deoxynucliosides, 5-bromodeoxycytidine, cytosine, β-1-D-arabinoside, diazooxynorleucine, dideoxynucleosides, 5-fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin and streptolydigin also can be combined with the compounds of the invention to provide pharmaceutical compositions.

In one embodiment, the compound is administered in combination with a vaccine for prostate cancer, Alisol B acetate, angiotensin II receptor blocker, or others known in the art. In one embodiment, the compound is administered in combination with an agent to decrease prostate (benign or malignant) hypertrophy, such as, for example, Selenium, green tea cachecins, saw palmetto, lycopene, vitamin D, dietary soy, genistein and isoflavone food product and others.

In one embodiment, the compound is administered in combination with an immunomodulating agent. In one embodiment, the immunomodulating agent is an immunosuppressive agent. In one embodiment, immunosuppressive agents comprise corticosteroids, cyclosporine, azathioprine, methotrexate, cyclophosphamide, tacrolimus-FK-506, anti-thymocyte globulin, mycophenylate moeftil, or a combination thereof. In one embodiment, the corticosteroid is a glucocorticoid.

In one embodiment, the immunomodulating agent is an immunostimulatory agent. In one embodiment, the immunostimulatory agent is a specific immunostimulator thus, provides antigenic specificity during an immune response, such as a vaccine or any antigen. In one embodiment, the immunostimulatory agent is a non-specific immunostimulator thus, acting irrespective of antigenic specificity to augment immune response of other antigen or stimulate components of the immune system without antigenic specificity. In one embodiment, the non-specific immunostimulator is Freund's complete adjuvant. In one embodiment, the non-specific immunostimulator is Freund's incomplete adjuvant. In one embodiment, the non-specific immunostimulator is a montanide ISA adjuvant. In one embodiment, the non-specific immunostimulator is a Ribi's adjuvant. In one embodiment, the non-specific immunostimulator is a Hunter's TiterMax. In one embodiment, the non-specific immunostimulator is an aluminum salt adjuvant. In one embodiment, the non-specific immunostimulator is a nitrocellulose-adsorbed protein. In one embodiment, the non-specific immunostimulator is a Gerbu Adjuvant.

In one embodiment, the compound is administered in combination with an agent, which treats bone diseases, disorders or conditions, such as osteoporosis, bone fractures, etc., and this invention comprises methods of treating the same, by administering the compounds as herein described, alone or in combination with other agents.

In one embodiment, bone turnover markers have been demonstrated as an effective, validated tool for the clinical scientist to monitor bone activity. In another embodiment, urinary hydroxyproline, serum alkaline phosphatase, tartrate-resistant acid phosphatase, and osteocalcin levels, along with the urinary calcium-creatinine ratio are used as bone turnover markers. In another embodiment osteocalcin levels is used as a bone formation marker. In another embodiment c-telopeptide is used as a bone resorption marker.

In one embodiment, this invention provides for the treatment, prevention, suppression or inhibition of, or the reduction of the risk of developing a skeletal-related event (SRE), such as bone fractures, surgery of the bone, radiation of the bone, spinal cord compression, new bone metastasis, bone loss, or a combination thereof in a subject with cancer, comprising administering to the a compound as herein described and/or its analog, derivative, isomer, metabolite, pharmaceutically acceptable salt, pharmaceutical product, hydrate, N-oxide, or any combination thereof. The invention relates, inter alia to treatment of an SRE with the compound of this invention in a subject with prostate cancer undergoing or having undergone androgen deprivation therapy (ADT).

In one embodiment, the skeletal-related events treated using the methods provided herein and/or utilizing the compositions provided herein, are fractures, which in one embodiment, are pathological fractures, non-traumatic fractures, vertebral fracture, non-vertebral fractures, morphometric fractures, or a combination thereof. In some embodiments, fractures may be simple, compound, transverse, greenstick, or comminuted fractures. In one embodiment, fractures may be to any bone in the body, which in one embodiment, is a fracture in any one or more bones of the arm, wrist, hand, finger, leg, ankle, foot, toe, hip, collar bone, or a combination thereof.

In another embodiment, the methods and/or compositions provided herein, are effective in treatment, prevention, suppression, inhibition or reduction of the risk of skeletal-related events such as pathologic fractures, spinal cord compression, hypercalcemia, bone-related pain, or their combination.

In another embodiment, the skeletal-related events sought to be treated using the methods provided herein and/or utilizing the compositions provided herein, comprise the necessity for bone surgery and/or bone radiation, which in some embodiments, is for the treatment of pain resulting in one embodiment from bone damage, or nerve compression. In another embodiment, the skeletal-related events sought to be treated using the methods provided herein and/or utilizing the compositions provided herein, comprise spinal cord compression, or the necessity for changes in antineoplastic therapy, including changes in hormonal therapy, in a subject. In some embodiments, skeletal-related events sought to be treated using the methods provided herein and/or utilizing the compositions provided herein, comprise treating, suppressing, preventing, reducing the incidence of, or delaying progression or severity of bone metastases, or bone loss. In one embodiment, bone loss may comprise osteoporosis, osteopenia, or a combination thereof. In one embodiment, skeletal-related events may comprise any combination of the embodiments listed herein.

In one embodiment, the methods provided herein and/or utilizing the compositions provided herein, are effective in reducing metastases to the bone, such as in terms of number of foci, the size of foci, or a combination thereof. According to this aspect of the invention and in one embodiment, provided herein is a method of preventing or inhibiting cancer metastasis to bone in a subject, comprising the step of administering to the subject a composition comprising toremifene, raloxifene, tamoxifen or an analogue, functional derivative, metabolite or a combination thereof, or a pharmaceutically acceptable salt thereof. In one embodiment, such metabolites may comprise ospemifene, fispemifene or their combination. In one embodiment, the cancer is prostate cancer.

A person skilled in the art would readily recognize that changes in the antineoplastic therapy according to the methods provided herein, utilizing the compositions provided herein may be conducted as a function of, or adjusted or varied as a function of, inter-alia, the severity of the underlying disease, the source of the underlying disease, the extent of the patients' pain and source of the patients' pain, as well as the stage of the disease. The therapeutic changes may include in certain embodiments, changes in the route of administration (e.g. intracavitarily, intraartialy, intratumoraly etc.), forms of the compositions administered (e.g. tablets, elixirs, suspensions etc.), changes in dosage and the like. Each of these changes are well recognized in the art and are encompassed by the embodiments provided herein.

In one embodiment, the skeletal-related events are a result of cancer therapy. In one embodiment, the skeletal-related events are a result of hormone deprivation therapy, while in another embodiment, they are a product of androgen deprivation therapy (ADT).

In one embodiment, the compounds of this invention are useful in prevention or reversal of androgen-deprivation therapy (ADT) induced side effects such as reduced muscle mass, reduced muscle strength, frailty, hypogonadism, osteoporosis, osteopenia, decreased BMD and/or decreased bone mass.

In males, while the natural decline in sex-hormones at maturity (direct decline in androgens as well as lower levels of estrogens derived from peripheral aromatization of androgens) is associated with the frailty of bones, this effect is more pronounced in males who have undergone androgen deprivation therapy.

Such agents for combined use may comprise a SERM, as herein described, a bisphosphonate, for example, alendronate, tiludroate, clodroniate, pamidronate, etidronate, alendronate, zolendronate, cimadronate, neridronate, minodronic acid, ibandronate, risedronate, homoresidronate, a calcitonin, for example, salmon, Elcatonin, SUN-8577, TJN-135; a Vitamin D or derivative (ZK-156979); a Vitamin D receptor ligand or analogues thereof, such as calcitriol, topitriol, ZK-150123, TEI-9647, BXL-628, Ro-26-9228, BAL-2299, Ro-65-2299, DP-035, an estrogen, estrogen derivative, or conjugated estrogen; an antiestrogen, progestin, synthetic estrogen/progestin; a RANK ligand mAb, for example, denosumab or AMG162 (Amgen); an $\alpha v\beta 3$ integrin receptor antagonist; an osteoclast vacuolar ATPase inhibitor; an antagonist of VEGF binding to osteoclast receptors; a calcium receptor antagonist; PTh (parathyroid hormone) or analogues thereof, PTHrP analogues (parathyroid hormone-related peptide), Cathepsin K inhibitors (AAE581); Strontium ranelate; Tibolone; HCT-1026, PS K3471; Gallium maltolate; Nutropin AQ; Prostaglandins, p38 protein kinase inhibitor; a bone morphogenetic protein; an inhibitor of BMP antagonism, an. HMG-CoA reductase inhibitor, a Vitamin K or derivative, an antiresorptive, an Ipriflavone, a fluoride salt, dietary calcium supplement, Osteoprotegerin, or any combination thereof. In one embodiment, the combined administration of a SARM as herein described, Osteoprotegerin and parathyroid hormone is contemplated for treating any disease, disorder or condition of the bone.

In one embodiment, the immunomodulating agent is an anti-inflammatory agent. In one embodiment, the anti-inflammatory agent is a non-steroidal anti-inflammatory agent. In one embodiment, the non-steroidal anti-inflammatory agent is a cox-1 inhibitor. In one embodiment, the non-steroidal anti-inflammatory agent is a cox-2 inhibitor. In one embodiment, the non-steroidal anti-inflammatory agent is a cox-1 and cox-2 inhibitor. In some embodiments, non-steroidal anti-inflammatory agents include but are not limited to aspirin, salsalate, diflunisal, ibuprofen, fenoprofen, flubiprofen, fenamate, ketoprofen, nabumetone, piroxicam, naproxen, diclofenac, indomethacin, sulindac, tolmetin, etodolac, ketorolac, oxaprozin, or celecoxib. In one embodiment, the anti-inflammatory agent is a steroidal anti-inflammatory agent. In one embodiment, the steroidal anti-inflammatory agent is a corticosteroid.

In one embodiment, the immunomodulating agent is an anti-rheumatic agent. In one embodiment, the anti-rheumatic agent is a non-steroidal anti-inflammatory agent. In one embodiment, the anti-rheumatic agent is a corticosteroid. In one embodiment, the corticosteroid is prednisone or dexamethasone. In one embodiment, the anti-rheumatic agent is a disease modifying anti-rheumatic drug. In one embodiment, the disease modifying anti-rheumatic drug is a slow-acting anti-rheumatic drug. In one embodiment, the disease modifying anti-rheumatic drug is an antimalarial agent. In one embodiment, disease modifying anti-rheumatic drugs include but are not limited to chloroquine, hydroxychloroquine, methotrexate, sulfasalazine, cyclosporine, azathioprine, cyclophosphamide, azathioprine, sulfasalazine, penicillamine, aurothioglucose, gold sodium thiomalate, or auranofin. In one embodiment, the anti-rheumatic agent is an immunosuppressive cytotoxic drug. In one embodiment, immunosuppressive cytotoxic drugs include but are not limited to methotrexate, mechlorethamine, cyclophosphamide, chlorambucil, or azathioprine.

In one embodiment, the compound is administered in combination with an antidiabetic agent. In one embodiment, the antidiabetic agent is a sulfonylurea. In one embodiment, sulfonylureas include but are not limited to tolbutamide, acetohexamide, tolazamide, chlorpropamide, glipizide, glyburide, glimepiride, or gliclazide. In one embodiment, the antidiabetic agent is a meglitinide. In one embodiment, meglitinides include but are not limited to prandin or nateglinide. In one embodiment, the antidiabetic agent is a biguanide. In one embodiment, biguanides include but are not limited to metformin In one embodiment, the antidiabetic agent is a thiazolidinedione. In one embodiment, thiazolidinediones include but are not limited to rosiglitazone, pioglitazone, or troglitazone. In one embodiment, the antidiabetic agent is an alpha glucosidase inhibitor. In one embodiment, alpha glucosidase inhibitors include but are not limited to miglitol or acarbose. In one embodiment, the antidiabetic agent is PPAR$\alpha/\gamma$ ligand, dipeptidylpeptidase 4 (DPP-4) inhibitor, SGLT (sodium-dependent glucose transporter 1) inhibitor, or FBPase (fructose 1,6-bisphosphatase) inhibitor. In one embodiment, the antidiabetic agent is insulin. In one embodiment, the insulin is rapid-acting insulin. In one embodiment, the insulin is short-acting insulin. In one embodiment, the insulin is intermediate-acting insulin. In one embodiment, the insulin is intermediate- and short-acting insulin mixtures. In one embodiment, the insulin is long-acting insulin. In one embodiment, the antidiabetic agents are inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DPP4) inhibitors such as those disclosed in WO 0168603, which are incorporated by reference.

In one embodiment, the compound is administered in combination with an agent treating the nervous system. In one embodiment, the agent treating the nervous system is an agent treating the autonomic nervous system. In one embodiment, the agent treating the autonomic nervous system is an adrenomimetic drug. In one embodiment, the adrenomimetic drug is a beta-adrenoceptor agonist, alpha-adrenoceptor agonist, or a combination thereof. In one embodiment, the adrenomimetic drug is a catecholamine. In one embodiment, adrenomimetic drugs include but are not limited to isoproterenol, norepinephrine, epinephrine, amphetamine, ephedrine, or dopamine. In one embodiment, the adrenomimetic drug is a directly acting adrenomimetic drug. In some embodiments, directly acting adrenomimetic drugs include but are not limited to phenylephrine, metaraminol, or methoxamine.

In one embodiment, the agent treating the autonomic nervous system is an adrenoceptor antagonist. In one embodiment, the adrenoceptor antagonist is a haloalkylamine, imidazoline, or quinazoline. In one embodiment, haloalkylamines include but are not limited to phenoxybenzamine. In one embodiment, imidazolines include but are not limited to phentolamine or tolazoline. In one embodiment, quinazolines include but are not limited to prazosine, terazosin, doxazosin, or trimazosin. In one embodiment, the adrenoceptor antagonist has a combined alpha and beta blocking activity. In one embodiment, the combined alpha and beta blocking agent is labetalol, bucindolol, carvedilol, or medroxalol.

In one embodiment, the agent treating the autonomic nervous system is a cholinomimetic agent. In one embodiment, the cholinomimetic agent is a direct-acting parasympathomimetic drug. In one embodiment, direct-acting parasympathomimetic drugs include but are not limited to methacholine, pilocarpine, carbachol, or bethanechol.

In one embodiment, the agent treating the autonomic nervous system is a cholinesterase inhibitor. In one embodiment, the cholinesterase inhibitor is a quaternary ammonium agent. In one embodiment, quaternary ammonium agents include but are not limited to edrophonium or ambenonium. In one embodiment, the cholinesterase inhibitor is a carbamate such as physostigmine, pyridostigmine, neostigmine, or rivastigmine. In one embodiment, the cholinesterase inhibitor is an organophosphate agent. In one embodiment, the inhibitor targets acetylcholine in the central nervous system such as tacrine, donepezil, or galanthamine.

In one embodiment, the agent treating the autonomic nervous system is a muscarinic blocking agent. In one embodiment, the muscarinic blocking agent is a belladonna alkaloid such as atropine or scopolamine.

In one embodiment, the agent treating the autonomic nervous system is a gangilionic blocking agent. In one embodiment, gangilionic blocking agents include but are not limited to nicotine, trimethaphan, or mecamylamine.

In one embodiment, the agent treating the nervous system is an agent treating the central nervous system. In one embodiment, the agent treating the central nervous system is a local anesthetic agent. In one embodiment, local anesthetic agents include but are not limited to benzocaine, chloroprocaine, cocaine, procaine, bupivacaine, levobupivacaine, lidocaine, mepivacaine, prilocalne, or ropivacaine. In one embodiment, the agent treating the central nervous system is a general anaesthetic agent. In one embodiment, general anesthetic agents include but are not limited to esflurane, sevoflurane, isoflurane, halothane, enflurane, methoxyflurane, xenon, propofol, etomidate, methohexital, midazolam, diazepamor, ketamine, thiopentone/thiopental, or lidocaine/prilocalne.

In one embodiment, the agent treating the central nervous system is an analgesic agent. In some embodiments, analgesic agents include but are not limited to paracetamol or non-steroidal anti-inflammatory agent. In some embodiments, analgesic agents include opiates or morphinomimetics such as morphine, pethidine, oxycodone, hydrocodone, diamorphine, tramadol, or buprenorphine. In some embodiments, a combination of two or more analgesics is desired.

In one embodiment, the agent treating the central nervous system is a muscle relaxant or vasoconstrictor agent. In one embodiment, muscle relaxants include but are not limited to methocarbamol, baclofen, carisoprodol, chlorzoxazone, cyclobenzaprine, dantrolene, metaxalone, orphenadrine, amyl nitrite, pancuronium, tizanidine, clonidine, or gabapentin. In one embodiment, vasoconstrictor agents include but are not limited to antihistamines, adrenalin dimethylarginine, caffeine, *cannabis*, catecholamines, decongestants, pseudoephedrinse, norepinephrines, tetrahydrozoline, or thromboxane.

In one embodiment, the agent treating the central nervous system is an antiemetic drug. In one embodiment, the antiemetic drug is a 5-HT3 receptor antagonist such as dolasetron, granisetron, ondansetron, or tropisetron. In one embodiment, the antiemetic drug is a dopamine antagonist such as domperidone droperidol, haloperidol, chlorpromazine, promethazine, or metoclopramide. In one embodiment, the antiemetic drug is an antihistamine such as cyclizine, diphenhydramine, dimenhydrinate, or meclizine. In one embodiment, the antiemetic drug is a cannabinoid such as *cannabis* or marinol.

In one embodiment, the agent treating the central nervous system is a sedative agent. In one embodiment, the sedative agent is an antidepressant agent such as mirtazapine or trazodone. In one embodiment, the sedative agent is a barbiturate such as secobarbital, pentobarbital, or amobarbital. In one embodiment, the sedative agent is a benzodiazepine such as diazepam, clonazepam, alprazolam, temazepam, chlordiazepoxide, flunitrazepam, lorazepam, or clorazepate. In one embodiment, the sedative agent is an imidazopyridines such as zolpidem or alpidem. In one embodiment, the sedative agent is a Pyrazolopyrimidine such as zaleplon. In one embodiment, the sedative agent is an antihistamine such as diphenhydramine, dimenhydrinate, or doxylamine. In one embodiment, the sedative agent is an antipsychotic agent such as ziprasidone, risperidone, quetiapine, clozapine, prochlorperazine, perphenazine, loxapine, trifluoperazine, thiothixene, haloperidol, or fluphenazine. In one embodiment, the sedative agent is an herbal sedative such as valerian plant mandrake, or kava. In some embodiments, the sedative agent is eszopiclone, ramelteon, methaqualone, ethchlorvynol, chloral hydrate, meprobamate, glutethimide, methyprylon, gamma-hydroxybutyrate, ethyl alcohol, methyl trichloride, zopiclone, or diethyl ether.

In one embodiment, the agent treating the central nervous system is a neurodegenerative disorder medication. In one embodiment, the neurodegenerative disorder medication is an acetylcholinesterase inhibitor such as tacrine, donepezil, galanthamine, or rivastigmine. In one embodiment, the neurodegenerative disorder medication is an N-methyl-D-aspartate (NMDA) antagonist such as memantine. In one embodiment, the neurodegenerative disorder medication reduces damage to motor neurons such as riluzole. In one embodiment, the neurodegenerative disorder medication silences the gene that causes the progression of the disease. In one embodiment, the agent treating the central nervous system is an antiepileptic drug (AED). In some embodiments, antiepileptic agents include sodium channel blockers, GABA receptor agonists, GABA reuptake inhibitors, GABA transaminase inhibitor, AEDs with a potential GABA mechanism of action, glutamate blockers, or AEDs with other mechanisms of action. In some embodiments, antiepileptic agents include but are not limited to carbamazepine, fosphenytoin, oxcarbazepine, lamotrigine, zonisamide, clobazam, clonazepam, phenobarbital, primidone, tiagabine, vigabatrin, gabapentin, valproate, felbamate, topiramate, levetiracetam, or pregabalin.

In one embodiment, the agent treating the central nervous system is an anti-addiction drug. In one embodiment, the anti-addiction is an anti-alcoholism drug such as disulfiram. In one embodiment, the anti-addiction drug is a serotonin uptake inhibitor, dopaminergic agonist, or opioid antagonist.

In one embodiment, the agent treating the central nervous system is an agent treating Alzheimer disease. In some embodiments, agents treating Alzheimer's disease include but are not limited to a cholinesterase inhibitor, gamma secreatse inhibitor, or a beta lowering drug.

In one embodiment, the agent treating the central nervous system is an agent treating mild cognitive impairment. In some embodiments, agents treating mild cognitive impairment include but are not limited to an AMPA regulator.

In one embodiment, the agent treating the central nervous system is an agent treating Parkinson's disease. In some embodiments, agents treating Parkinson's disease include but are not limited to a dopaminergic drugs, amantadine, benztropine, biperiden, bromocriptine, entacapone, carbidopa/levodopa, selegiline/deprenyl, iphenhydramine, pergolide, procyclidine, selegiline, or trihexyphenidyl.

In one embodiment, the compound is administered with an agent, which treats Alzheimer's disease, such as cholinesterase inhibitors, gamma secreatse inhibitors, A-beta lowering drugs; or an agent, which treats mild cognitive impairment (MCI)— such as AMPA regulators, or an agent, which treats Parkinson's Disease, such as dopaminergic drugs, or an agent, which treats Major Depression, such as SSRI's, SNRI's, for example, duloxetine, or an agent, which treats sexual dysfunction, such as PDE5 inhibitors.

In one embodiment, the compound is administered in combination with an agent treating the cardiovascular system. In one embodiment, the agent treating the cardiovascular system is treating a congestive heart failure. In one embodiment, the agent treating congestive heart failure is an angiotensin converting enzyme (ACE) inhibitor such as benazepril, captopril, cilazapril, enalapril, fosinopril, lisinopril, moexipril, perindopril, quinapril, ramipril, trandolapril, or enalaprilat. In one embodiment, the agent treating congestive heart failure is a beta-blocker such as acebutolol, atenolol, betaxolol hydrochloride, bisoprolol fumarate, carteolol hydrochloride, carvedilol, celiprolol hydrochloride, esmolol hydrochloride, labetalol hydrochloride, levobunolol, metoprolol tartrate, metipranolol, nadolol, nebivolol, oxprenolol hydrochloride, pindolol, propranolol hydrochloride, sotalol hydrochloride, or timolol maleate. In one embodiment, the agent treating congestive heart failure is digoxin. In one embodiment, the agent treating congestive heart failure is a diuretic such as thiazide diuretic, loop diuretic, potassium-sparing diuretic, or a combination thereof. In some embodiments, thiazide diuretics include but are not limited to bendrofluazide, bendroflumethiazide, benzthiazide, chlorothiazide, chlorthalidone, cyclopenthiazide, Diucardin®, Diuril®, Enduron®, Esidrix®, Exna®, HCTZ, Hydrochlorothiazide, HydroDIURIL®, HYDROFLUMETHIAZIDE, Hydromox®, Hygroton®, indapamide, Lozol®, methyclothiazide, metolazone, Mykrox®, Naqua®, Naturetin®, Oretic®, polythiazide, quinethazone, Renese®, trichlormethiazide, xipamide, or Zaroxolyn®. In some embodiments, loop diuretics include but are not limited to furosemide/frusemide, bumetanide, or torasemide. In some embodiments, potassium-sparing diuretics include but are not limited to amiloride, triamterene, aldosterone antagonists, or spironolactone.

In one embodiment, the agent treating the cardiovascular system is an anti-arrhythmic agent. In one embodiment, the anti-arrhythmic agent is a sodium channel blocker, beta-adrenergic blocker, calcium channel blocker, or an agent that prolong repolarization. In one embodiment, sodium channel blockers include but are not limited to quinidine, procainamide, disopyramide, lidocaine, tocainide, mexiletine, encainide, or flecainide. In one embodiment, beta-adrenergic blockers include but are not limited to propranolol, acebutolol, esmolol, or sotalol. In one embodiment, agents that prolong repolarization include but are not limited to sotalol or amiodarone. In one embodiment, calcium channel blockers include but are not limited to verapamil, diltiazem, nifedipine, or mebefradil. In one embodiment, the anti-arrhythmic agent is adenosine or digoxin.

In one embodiment, the agent treating the cardiovascular system is an anti-anginal agent. In one embodiment, the anti-anginal agent is an antiplatelet agent, adrenoceptor antagonist, calcium channel blocker, or a vasodilator. In some embodiments, the adrenoceptor antagonists and calcium channel blockers comprise agents as described hereinabove. In one embodiment, the antiplatelet agent is a cyclooxygenase inhibitor, ADP inhibitor, phosphodiesterase (I) inhibitor, glycoprotein IIb/IIIa inhibitor, or an adenosine reuptake inhibitor. In one embodiment, cyclooxygenase inhibitors include but are not limited to acetylsalicylic acid or an acetylsalicylic acid in combination with dipyridimole. In one embodiment, ADP inhibitors include but are not limited to clopidogrel, CS-747, or ticlopdipine. In one embodiment, phosphodiesterase III inhibitors include but are not limited to cilostazol. In one embodiment, glycoprotein IIb/IIIa inhibitors include but are not limited to abciximab, rheopro, eptifibatide, integrilin, tirofiban, or aggrastat. In one embodiment, adenosine reuptake inhibitors include but are not limited to dipyridimole. In one embodiment, vasodilator agents include but are not limited to isosorbide dinitrate, isosorbide mononitrate, or nitroglycerine. In one embodiment, cardiac glycosides such as digitalis or ouabain may be used in combination with a SARM compound.

In one embodiment, the agent treating the cardiovascular system is a vasocative agent or an inotrope. In one embodiment, vasocative agents or inotropes include but are not limited to digoxin, dopamine, dobutamine, hydralazine, prazosin, carvedilol, nitroprusside, nitroglycerin, captopril, lisinopril, nifedipine, diltiazem, hydrochlorothiazide, furosemide, spironolactone, AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), or nitrates.

In one embodiment, the agent treating the cardiovascular system is an anticoagulant agent. In one embodiment, the anticoagulant agent is a coumarin derivative or an unfractionated heparin. In one embodiment, coumarin derivatives include but are not limited to warfarin.

In one embodiment, the agent treating the cardiovascular system is a fibrinolytic agent such as streptokinase, urokinase, alteplase, anistreplase, prourokinase, reteplase, tenecteplase, lanoteplase, staphylokinase, vampire, or alfimeprase.

In one embodiment, the agent treating the cardiovascular system is a hypercholesterolemic agent such as niacin-lovastatin, colestipol HCl, fluvastatin sodium, atorvastatin calcium, simvastatin, gemfibrozil, lovastatin, pravastatin sodium, cholestyramine, cholestyramine light, fenofibrate, colesevelam HCl, or ezetimibe.

In one embodiment, the compound of this invention is administered in combination with an agent treating the gastrointestinal system. In one embodiment, the agent treating the gastrointestinal (GI) system is enhancing GI motility. In one embodiment, the agent enhancing GI motility is a prokinetic agent such as metoclopramide, cisapride, tegaserod, or erythromycin. In one embodiment, the agent treating the GI system is decreasing GI motility. In one embodiment, the agent decreasing GI motility is an opioid such as morphine, diphenoxylate, loperamide hydrochloride, or opium.

In one embodiment, the agent treating the GI system is an adsorbent or a bulking agent. In one embodiment, the adsorbent is kaolin or other hydrated aluminum silicate clays. In one embodiment, the hydrated aluminum silicate clay is further combined with pectin. In one embodiment, adsorbents or a bulking agents comprise bismuth subsalicylate, methylcellulose, psyllium derivative, or calcium polycarbophil.

In one embodiment, the agent treating the GI system is a stool softener. In one embodiment, stool softeners include but are not limited to mineral oil, docusate dioctyl sodium sulfosuccinate, dioctyl calcium sulfosuccinate, or dioctyl potassium sulfosuccinate.

In one embodiment, the agent treating the GI system is a laxative. In one embodiment, the agent treating the GI system is a bulk forming laxative as described hereinabove. In one embodiment, the laxative is an osmotic laxative such as lactulose, sorbitol, or polyethylene glycol. In one embodiment, the laxative is a saline laxative such as milk of magnesia, magnesium citrate, sodium phosphate, docusate potassium, sorbitol, sodium phosphate-biphosphate, or visicol.

In one embodiment, the agent treating the GI system is a cathartic stimulant. In one embodiment, the cathartic stimulant is an anthraquinone derivative such as cascara, aloe, senna, or rhubarb. In one embodiment, the cathartic stimulant is phenolphthalein, castor oil, or bisacodyl.

In one embodiment, the agent treating the GI system is an emetic agent. In one embodiment, the emetic agent is ipecac or apomorphine. In one embodiment, the agent treating the GI system is an anti-emetic agent such as antihistamine, anticholinergic agent, benzodiazepine, cannabinoid, dopamine antagonist, phenothiazine derivative, or 5-HT3 antagonist such as ondansetron or granisetron.

In one embodiment, the agent treating the GI system is an antacid. In one embodiment the antacid pharmaceutical preparation comprises buffering agents such as sodium bicarbonate, calcium carbonate, magnesium hydroxide, or aluminum hydroxide.

In one embodiment, the agent treating the GI system is an H2-receptor antagonist. In some embodiments, the H2-receptor antagonist is cimetidine, ranitidine, famotidine, or nizatidine.

In one embodiment, the agent treating the GI system is a proton pump inhibitor. In some embodiments, the proton pump inhibitor is omeprazole, lansoprazole, pantoprazole, rebeprazole, or esomeprazole In one embodiment, the agent treating the GI system is an agent treating inflammation. In one embodiment, the agent treating inflammation is 5-amino-salicylate, corticosteroid, metronidazole, ciprofloxacin, infiximab, budesonide, or anti-TNF alpha antibody.

In one embodiment, the compound of this invention is administered in combination with an agent treating a metabolic disease, disorder or condition, which in some embodiments refers to metabolic syndrome. In some embodiments, such agents comprise, inter alia, pancreatic lipase inhibitors, such as for example, orlistat, cetilistat, serotonin and norepinephrine reuptake inhibitors, such as sibutramine, insulin-sensitizers such as biguanides (metformin) or PPAR agonists, dual-acting PPAR agonists (muraglitazar, tesaglitazar, naveglitazar), PPAR-delta agonists (GW-501516), DPP-IV Inhibitors (vildagliptin, sitagliptin), alpha glucosidase inhibitors (acarbose), anti-diabetic combinations (ActoPlusMet, AvandaMet, metformin/pioglitazone, metformin/rosiglitazone, Glucovance, etc.), glucagon-like peptide-1 analogues (exenatide, liraglutide), amylin analogues (pramlintide), statins (atorvastatin, simvastatin, rosuvastatin, pravastatin, fluvastatin, lovastatin, pitavastatin), cholesterol absorption inhibitors (ezetimibe), nicotinic acid derivatives (immediate release and controlled release niacins, niaslo, etc.), antidyslipidemic fixed combinations (simvastatin/ezetimibe, lovastatin/nicotinic acid, atorvastatin/amlodipine, atorvastatin/torcetrapib, simvastatin/nicotinic acid (ER)), ACE inhibitors (ramipril, captopril, lisinopril), AT-II receptor antagonists (valsartan, telmisartan), cannabinoid receptor antagonists (rimonabant), cholesteryl ester transfer protein or CETP Inhibitors (JTT-705, CETi-1), beta3 adrenergic agonists, PPARa ligands, or combinations thereof.

In one embodiment, the compound is administered in combination with an agent treating a dermatological disorder. In one embodiment, the agent treating a dermatological disorder is a corticosteroid or glucocorticosteroid such as betamethasone dipropionate, clobetasol, diflorasone, amcinonide, desoximetasone, fluocinonide, aclometasone, desonide triamcinolone, fluticasone, halobetasol, mometasone, or hydrocortisone. In one embodiment, the agent treating a dermatological disorder is a retinoid such as isotretinoin, acitretin, tretinoin, adapalene, tazarotene, bexarotene, alitretinoin, or beta-carotene.

In one embodiment, the agent treating a dermatological disorder is photochemotherapy agent. In one embodiment, the photochemotherapy agent is PUVA or psoralen such as oxsoralen. In one embodiment, the agent treating a dermatological disorder is a photodynamic agent such as porphyrin.

In one embodiment, the agent treating a dermatological disorder is daspone, thalidomide, anti-malarial agent, antimicrobial agent, or antifungal agent. In one embodiment, the anti-malarial agent is chloroquine or hydroxychloroquine.

In one embodiment, the agent treating a dermatological disorder is an antibiotic. In one embodiment, the antibiotic is a systemic antibiotic such as griseofulvin, ketoconazole, fluconazole, itraconazole, terbinafine, or potassium iodide. In one embodiment, the antibiotic is a topical antifungal agent. In some embodiment, topical antifungal agents include but are not limited to ciclopirox, clotrimazole, econazole, ketoconazole, miconazole, naftifine, oxiconazole, terbinafine, or tolnaftate.

In one embodiment, the agent treating a dermatological disorder is an antiviral agent such as interferon alpha. In one embodiment, the agent treating a dermatological disorder is an antiscabies agent such as pyrethrin or pyrethroid. In one embodiment, the agent treating a dermatological disorder is an immunosuppressive agent such as mycophenolate motefil or 6-thioguanine. In one embodiment, the agent treating a dermatological disorder is a topical immunosuppressive agent such as tacrolimus, pimecrolimus, imiquimod, 5-fluorouracil, or mechlorethamine. In one embodiment, the agent treating a dermatological disorder is an antihistamine such as doxepin. In one embodiment, the agent treating a dermatological disorder is treating pigmentation such as hydroquinone or monobenzone. In one embodiment, the agent treating a dermatological disorder is a protein or a recombinant protein such as becaplermin, etanercept, denileukin diftitox, or botulinum toxin. In one embodiment, the agent treating a dermatological disorder is capsaicin, anthralin, benzoyl peroxide, or calcipotriene.

In one embodiment, the agent treating a dermatological disorder is a keratolytic agent. In one embodiment, the agent treating a dermatological disorder is selenium sulfide. In one embodiment, the agent treating or preventing a dermatological disorder is a sunscreen. In one embodiment, the sunscreen absorbs UVB, UVA, or a combination thereof.

In one embodiment, the agent treating a dermatological disorder may be a growth factor such as epidermal growth factor (EGF), transforming growth factor-α (TGF-α), platelet derived growth factor (PDGF), fibroblast growth factors (FGFs) including acidic fibroblast growth factor (α-FGF) and basic fibroblast growth factor (β-FGF), transforming growth factor-β (TGF-β) and insulin like growth factors (IGF-1 and IGF-2), or any combination thereof.

In one embodiment, the compound is administered in combination with an anti-infective agent. In one embodiment, the anti-infective agent is an antibiotic agent. In one embodiment the antibiotic is a beta-lactam antibiotic. In one embodiment beta-lactam antibiotics include but are not limited to penicillin, benzathine penicillin, benzylpenicillin, amoxicillin, procaine penicillin, dicloxacillin, amoxicillin, flucloxacillin, ampicillin, methicillin, azlocillin, carbenicillin, ticarcillin, mezlocillin, piperacillin, phenoxymethylpenicillin, co-amoxiclav, cephalosporin, cefalexin, cephalothin, cefazolin, cefaclor, cefuroxime, cefamandole, cefotetan, cefoxitin, ceftriaxone, cefotaxime, ceftazidime, cefepime, cefpirome, imipenem, meropenem, ertapenem, faropenem, monobactam, aztreonam, or carbapenem.

In one embodiment the antibiotic is a tetracycline antibiotic. In one embodiment tetracycline antibiotics include but are not limited to tetracycline, chlortetracycline, demeclocycline, doxycycline, lymecycline, minocycline, or oxytetracycline.

In one embodiment the antibiotic is a macrolide antibiotic. In one embodiment macrolide antibiotics include but are not limited to erythromycin, azithromycin, oxithromycin, dirithromycin, clarithromycin, josamycin, oleandomycin, kitasamycin, spiramycin, tylosin/tylocine, troleandomycin, carbomycin, cethromycin, or telithromycin.

In one embodiment the antibiotic is an aminoglycoside antibiotic. In one embodiment, aminoglycoside antibiotics include but are not limited to gentamicin, tobramycin, faropenem, imipenem, kanamycin, neomycin, ertapenem, apramycin, paromomycin sulfate, streptomycin, or amikacin.

In one embodiment the antibiotic is a quinolone antibiotic. In one embodiment quinolone antibiotics include but are not limited to ciprofloxacin, norfloxacin, lomefloxacin, enoxacin, ofloxacin, ciprofloxacin, levofloxacin, sparfloxacin, gatifloxacin, moxifloxacin, trovafloxacin, or alatrofloxacin.

In one embodiment the antibiotic is a cyclic peptide antibiotic. In one embodiment cyclic peptide antibiotics include but are not limited to vancomycin, streptogramins, Microcin J25, Bacteriocin AS-48, RTD-1, or polymyxins.

In one embodiment the antibiotic is a lincosamide antibiotic. In one embodiment lincosamide antibiotics include but are not limited to clindamycin.

In one embodiment, the antibiotic is an oxazolidinone antibiotic. In one embodiment oxazolidinone antibiotics include but are not limited to linezolid, U-100592, DA-7867, AZD2563, or U-100766.

In one embodiment, the antibiotic is a sulfa antibiotic. In one embodiment, sulfa antibiotics include but are not limited to sulfisoxazole.

In one embodiment, the antibiotic is an antiseptic agent. In one embodiment, antiseptic agents include but are not limited to alcohols, chlorhexidine, chlorine, hexachlorophene, iodophors, chloroxylenol (PCMX), quaternary ammonium compounds, or triclosan.

In one embodiment, the antibiotic is an anti-tuberculosis agent. In one embodiment an anti-tuberculosis agents include but are not limited to ethambutol, rifabutin, isoniazid, rifampicin, pyrazinamide, or rifampin In one embodiment, the antibiotic is an antifungal agent. In one embodiment, antifungal agents include but are not limited to terbinafine, flucytosine, fluconazole, itraconazole, ketoconazole, ravuconazole, posaconazole, voriconazole, caspofungin, micafungin, v-echinocandin, amphotericin B, amphotericin B lipid complex (ABLC), amphotericin B colloidal dispersion (ABCD), liposomal amphoterician b (l-Amb), liposomal nystatin, or griseofulvin.

In one embodiment, the antibiotic is an antiprotozoal agent. In one embodiment the antiprotozoal agent is an antimalarial agent. In one embodiment, antimalarial agents include but are not limited to chloroquine, mefloquine, proguanil, pyrimethamine with dapsone, pyrimethamine with sulfadoxine, quinine, or primaquine. In one embodiment, the antiprotozoal agent is an amoebicide. In one embodiment, amoebicides include but are not limited to metronidazole, timidazole, or diloxanide furoate. In one embodiment, the antiprotozoal agent is an antigiadial agent. In one embodiment, antigiadial agents include but are not limited to metronidazole, timidazole, or mepacrine. In one embodiment, the antiprotozoal agent is a leishmanicide. In one embodiment, leishmanicides include but are not limited to sodium stibogluconate. In one embodiment, the antibiotic is an antithelmintic agent.

In one embodiment, the antibiotic is an antiviral agent. In one embodiment, antiviral agents include but are not limited to abacavir, acyclovir, amantadine, didanosine, emtricitabine, enfuvirtide, entecavir, lamivudine, nevirapine, oseltamivir, ribavirin, rimantadine, stavudine, valaciclovir, vidarabine, zalcitabine, or zidovudine. In one embodiment, the antiviral agent is a nucleotide analog reverse transcriptase inhibitor. In one embodiment, nucleotide analog reverse transcriptase inhibitors include but are not limited totenofovir or adefovir. In one embodiment, the antiviral agent is a protease inhibitor. In one embodiment, protease inhibitors include but are not limited to saquinavir, ritonavir, indinavir, nelfinavir, amprenavir, lopinavir, fosamprenavir, or tipranavir. In one embodiment, the antiviral agent is a fusion inhibitor such as enfuvirtide. In one embodiment, a combination of antiviral or antiretroviral agents is desired. In one embodiment, antiviral or antiretroviral agents or a combination thereof, further comprise hydroxyurea, resveratrol, grapefruit, ritonavir, leflunomide, or a combination thereof.

In one embodiment, the compound is administered in combination with an agent treating the liver. In one embodiment, the compound is administered in combination with a statin. In some embodiment, statins include but are not limited to atorvastatin, fluvastatin, lovastatin, pravastatin, simvastatin, or rosuvastatin.

In one embodiment, the compound is administered in combination with a bile acid sequestrant. In some embodiment, bile acid sequestrants include but are not limited to cholestyramine, colestipol, or colesevelam.

In one embodiment, the compound is administered in combination with a cholesterol absorption inhibitor. In some embodiment, cholesterol absorption inhibitors include but are not limited to ezetimibe.

In one embodiment, the compound is administered in combination with a nicotinic acid agent. In some embodiments, nicotinic acid agents include but are not limited to niacin, niacor, or slo-niacin.

In one embodiment, the compound is administered in combination with a fibrate. In some embodiments, fibrates include but are not limited to gemfibrozil, or fenofibrate.

In one embodiment, the agent treating the liver is cortisone, cortisol or corticosterone. In some embodiments, the agent treating the liver is colchicine, methotrexate, ursodeoxycholic acid, or penicillamine.

In one embodiment, the compound is administered in with an agent treating the kidney. In one embodiment, the agent treating the kidney is a diuretic. In some embodiments, diuretics include but are not limited to organomercurial, ethacrynic acid, frusemide, humetanide, piretanide, muzolimine, chlorothiazide and thiazide, phthalimidine, chlorthalidone, clorexolone, quinazolinone, quinethazone, metolazone ilenzenesulphonamide, mefruside, chlorobenzamide, clopamidesalicylamide, xipamide, xanthine, aminophylline, carbonic anhydrase inhibitor, acetazolamide mannitol, potassium-sparing compound, aldosterone antagonist, spironolactone and canrenoate, pteridines, pyrazine, carboxamide-triamterene, or amiloride. In one embodiment, the agent treating the kidney is a steroid.

In one embodiment, the agent treating the kidney is erythropoietin. In one embodiment, erythropoietin is obtained by natural sources (e.g., urinary erythropoietin; See U.S. Pat. No. 3,865,801), or is a recombinantly produced protein and analogs thereof, for example, as described in U.S. Pat. Nos. 5,441,868, 5,547,933, 5,618,698 and 5,621,080 as well as human erythropoietin analogs with increased glycosylation and/or changes in the amino acid sequence as those described in European Patent Publication No. EP 668351 and the hyperglycosylated analogs having 1-14 sialic acid groups and changes in the amino acid sequence described in PCT Publication No. WO 91/05867. In one embodiment, erythropoietin-like polypeptides are administered in combination with the compounds of this invention. In some embodiments, erythropoietin-like polypeptides comprise darbepoietin (from Amgen; also known as Aranesp and novel erthyropoiesis stimulating protein (NESP)).

In one embodiment, the SARM compound is administered in with an agent treating a metabolic disease. In some embodiments, agents treating a metabolic disease include but are not limited to a vitamin, Coenzyme Q10, glucosidase alfa, sodium bicarbonate, bisphosphonate, biotin, allopurinol, levodopa, diazepam, phenobarbital, haloperidol, folic acid, antioxidants, activators of cation channels haptoglobin, or carnitine.

In one embodiment, the agent treating a metabolic disease is a pancreatic lipase inhibitor such as orlistat or cetilistat, Serotonin or norepinephrine reuptake inhibitor such as sibutramine, insulin-sensitizers such as biguanide, PPAR agonist, Dual-acting PPAR agonist such as muraglitazar, tesaglitazar, or naveglitazar, PPAR-delta agonist such as GW-501516, DPP-IV Inhibitor such as vildagliptin or sitagliptin, alpha glucosidase inhibitor such as acarbose, antidiabetic combination such as ActoPlusMet, AvandaMet, metformin/pioglitazone, metformin/rosiglitazone, or Glucovance, Glucagon-like peptide-1 analogue such as exenatide or liraglutide, Amylin analogue such as pramlintide, statin such as atorvastatin, simvastatin, rosuvastatin, pravastatin, fluvastatin, lovastatin, or pitavastatin, Cholesterol absorption inhibitor such as ezetimibe, Nicotinic acid derivative such as niacin or niaslo, antidyslipidemic fixed combination such as simvastatin/ezetimibe, lovastatin/nicotinic acid, atorvastatin/amlodipine, or atorvastatin/torcetrapib, simvastatin/nicotinic acid, ACE inhibitor such as ramipril, captopril, or lisinopril, AT-II receptor antagonist such as valsartan or telmisartan, cannabinoid receptor antagonist such as rimonabant, cholesteryl ester transfer protein or CETP Inhibitor such as JTT-705, CETi-1, or beta-3 adrenergic agonist.

In one embodiment, the compound is administered with an agent treating a wasting disease. In some embodiments, agents treating a wasting disease include but are not limited to corticosteroids, anabolic steroids, cannabinoids, metoclopramid, cisapride, medroxyprogesterone acetate, megestrol acetate, cyproheptadine, hydrazine sulfate, pentoxifylline, thalidomide, anticytokine antibodies, cytokine inhibitors, eicosapentaenoic acid, indomethacin, ibuprofen, melatonin, insulin, growth hormone, clenbuterol, porcine pancreas extract, IGF-1, IGF-1 analogue and secretagogue, myostatin analogue, proteasome inhibitor, testosterone, oxandrolone, enbrel, melanocortin 4 receptor agonist, or a combination thereof.

In one embodiment, the agent treating a wasting disease is a ghrelin receptor ligand, growth hormone analogue, or a secretagogue. In some embodiments, ghrelin receptor ligands, growth hormone analogues, or secretagogues include but are not limited to pralmorelin, examorelin, tabimorelin, capimorelin, capromorelin, ipamorelin, EP-01572, EP-1572, or JMV-1843.

In one embodiment, growth promoting agents such as but not limited to TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890 are utilized as agents treating a wasting disease.

In other embodiments, agents treating a wasting disease may comprise growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or, in other embodiments, with growth hormone releasing factor and its analogs or growth hormone and its analogs, or with alpha-adrenergic agonists, such as clonidine or serotinin 5-HTD agonists, such as sumatriptan, or agents which inhibit somatostatin or its release, such as physostigmine and pyridostigmine. In some embodiments, agents treating a wasting disease may comprise parathyroid hormone, PTH(1-34) or bisphosphonates, such as MK-217 (alendronate). In other embodiments, agents treating wasting disease may further comprise estrogen, a selective estrogen receptor modulator, such as tamoxifene or raloxifene, or other androgen receptor modulators, such as those disclosed in Edwards, J. P. et. al., Bio. Med. Chem. Let., 9, 1003-1008

(1999) and Hamann, L. G. et. al., J. Med. Chem., 42, 210-212 (1999). In some embodiments, agents treating a wasting disease may further comprise a progesterone receptor agonists ("PRA"), such as levonorgestrel, medroxyprogesterone acetate (MPA). In some embodiments, agents treating a wasting disease may include nutritional supplements, such as those described in U.S. Pat. No. 5,179,080, which, in other embodiments are in combination with whey protein or casein, amino acids (such as leucine, branched amino acids and hydroxymethylbutyrate), triglycerides, vitamins (e.g., A, B6, B 12, folate, C, D and E), minerals (e.g., selenium, magnesium, zinc, chromium, calcium and potassium), carnitine, lipoic acid, creatinine, B-hyroxy-B-methylbutyriate (Juven) and coenzyme Q. In one embodiment, agents treating a wasting disease may further comprise antiresorptive agents, vitamin D analogues, elemental calcium and calcium supplements, cathepsin K inhibitors, MMP inhibitors, vitronectin receptor antagonists, Src SH2 antagonists, vacular-H+-ATPase inhibitors, ipriflavone, fluoride, tibolone, prostanoids, 17-beta hydroxysteroid dehydrogenase inhibitors and Src kinase inhibitors.

In one embodiment, the compound is administered in with an agent treating the endocrine system. In some embodiments, agents treating the endocrine system include but are not limited to radioactive iodine, antithyroid agent, thyroid hormone supplement, growth hormone, cabergoline, bromocriptine, thyroxine, gonadotropin, glucocorticoid, glucocorticoid analogue, corticotrophin, metyrapone, aminoglutethimide, mitotane, ketoconazole, mifepristone, dexamethasone somatostatin analogue, gonadotropin-releasing hormone analogue, leuprolide, goserelin, antidiuretic hormone, antidiuretic hormone analogue, oxytocin, calcium supplement, vitamin D, or a combination thereof.

In one embodiment, the agent treating the endocrine system is a 5-alpha-reductase inhibitor. In some embodiments, 5-alpha-reductase inhibitors include but are not limited to finasteride, dutasteride, or izonsteride.

In one embodiment, the agent treating the endocrine system is a SARM compound. In some embodiments, SARMs include but are not limited to RU-58642, RU-56279, WS9761 A and B, RU-59063, RU-58841, bexlosteride, LG-2293, L-245976, LG-121071, LG-121091, LG-121104, LGD-2226, LGD-2941, YM-92088, YM-175735, LGD-1331, BMS-357597, BMS-391197, S-40503, BMS-482404, EM-4283, EM-4977, BMS-564929, BMS-391197, BMS-434588, BMS-487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, or ACP-105.

In one embodiment, the additional agent treating the endocrine system is a SERM compound. In some embodiments, SERMs include but are not limited to tamoxifene, 4-hydroxytamoxifene, idoxifene, toremifene, ospemifene, droloxifene, raloxifene, arzoxifene, bazedoxifene, PPT (1,3,5-Tris (4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstibestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, Ban zhi lian, CT-101, CT-102, or VG-101.

In one embodiment, the agent treating the endocrine system is a gonadotropin-releasing hormone agonist or antagonist. In some embodiments, gonadotropin-releasing hormone agonists or antagonists include but are not limited to leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, or acyline.

In one embodiment, the agent treating the endocrine system is a luteinizing hormone agonist or antagonist. In some embodiments, luteinizing hormone agonists or antagonists include but are not limited to letrozole, anastrazole, atamestane, fadrozole, minamestane, exemestane, plomestane, liarozole, NKS-01, vorozole, YM-511, finrozole, 4-hydroxyandrostenedione, aminogluethimide, or rogletimide. In one embodiment, the agent treating the endocrine system is a follicle stimulating hormone agonist or antagonist. In one embodiment, the agent treating the endocrine system is a luteinizing hormone releasing hormone (LHRH) or a LHRH analog.

In one embodiment, the agent treating the endocrine system is a steroidal or nonsteroidal glucocorticoid receptor ligand. In some embodiments, nonsteroidal glucocorticoid receptor ligands include but are not limited to ZK-216348, ZK-243149, ZK-243185, LGD-5552, mifepristone, RPR-106541, ORG-34517, GW-215864X, Sesquicillin, CP-472555, CP-394531, A-222977, AL-438, A-216054, A-276575, CP-394531, CP-409069, or UGR-07.

In one embodiment, the agent treating the endocrine system is a steroidal or non-steroidal progesterone receptor ligand. In one embodiment, the agent treating the endocrine system is a steroidal or nonsteroidal androgen receptor antagonist. In some embodiments, steroidal or nonsteroidal androgen receptor antagonists include but are not limited to flutamide, hydroxyflutamide, bicalutamide, nilutamide, or hydroxysteroid dehydrogenase inhibitor.

In one embodiment, the agent treating the endocrine system is a peroxisome proliferator-activated receptor ligand. In some embodiments, peroxisome proliferator-activated receptor ligands include but are not limited to bezafibrate, fenofibrate, gemfibrozil, darglitazone, pioglitazone, rosiglitazone, isaglitazone, rivoglitazone, netoglitazone, naveglitazar, farglitazar, tesaglitazar, ragaglitazar, oxeglitazar, or PN-2034.

In one embodiment, an agent treating the endocrine system is a human growth hormone. In some embodiments, human growth hormones include but are not limited to somatotropin or analogues.

In one embodiment, the agent treating the endocrine system is a ghrelin. In some embodiments, ghrelins include but are not limited to human ghrelin, CYT-009-GhrQb, L-692429, GHRP-6, SK&F-110679, or U-75799E.

In one embodiment, the agent treating the endocrine system is a leptin. In some embodiments, leptins include but are not limited to metreleptin or pegylated leptin. In one embodiment, an agent treating the endocrine system is a leptin receptor agonist. In some embodiments, leptin receptor agonists include but are not limited to LEP(116-130), OB3, [D-Leu4]-OB3, rAAV-leptin, AAV-hOB, or rAAVhOB.

In one embodiment, the SARM compound is administered with an inhibitor of an enzyme involved in the androgen biosynthetic pathway. In some embodiments, inhibitors of enzymes involved in the androgen biosynthetic pathway include but are not limited to 17-ketoreductase inhibitor, 3-DH4,6-isomerase inhibitor, 3-DH4,5-isomerase inhibitor, 17,20 desmolase inhibitor, p450c17 inhibitor, p450ssc inhibitor, or 17,20-lyase inhibitor.

In one embodiment, the compound of this invention is administered with an agent treating osteoporosis. In some embodiments, osteoporosis is induced by alcohol and/or smoking. In some embodiments, agents treating osteoporosis include but are not limited to SERMs, calcitonin, vitamin D, vitamin D derivatives, vitamin D receptor ligand, vitamin D receptor ligand analogue, estrogen, estrogen derivative, conjugated estrogen, antiestrogen, progestin, synthetic estrogen, synthetic progestin, RANK ligand monoclonal antibody, integrin receptor antagonist, osteoclast vacuolar ATPase inhibitor, antagonist of VEGF binding to osteoclast receptors, calcium receptor antagonist, parathyroid hormone, parathyroid hormone analogue, parathyroid hormone-related peptide, cathepsin K inhibitor, strontium ranelate, tibolone, HCT-1026, PSK3471, gallium maltolate, nutropin AQ, prostaglandin, p38 protein kinase inhibitor, bone morphogenetic protein (BMP), inhibitor of BMP antagonism, HMG-CoA reductase inhibitor, vitamin K, vitamin K derivative, ipriflavone, fluoride salts, dietary calcium supplement, or osteoprotegerin.

In one embodiment, the agent treating osteoporosis is a calcitonin. In some embodiments, calcitonins include but are not limited to salmon, elcatonin, SUN-8577, or TJN-135.

In one embodiment, the agent treating osteoporosis is a vitamin D receptor ligand or analogue. In some embodiments, vitamin D receptor ligands or analogues include but are not limited to calcitriol, topitriol, ZK-150123, TEI-9647, BXL-628, Ro-26-9228, BAL-2299, Ro-65-2299, or DP-035.

In one embodiment, the compound of this invention is administered with an agent treating pharmacotherapy induced hypogonadal and/or osteopenic and/or sarcopenic state. In some embodiments, agents treating pharmacotherapy induced hypogonadal and/or osteopenic and/or sarcopenic states include but are not limited to opioids, narcotics, opiates, opioids, methadone, kadian, D2 dopamine receptor antagonist, zotepine, haloperidol, amisulpride, risperidone, anti-epileptic agent, valproic acid, carbamazepine, oxcarbamazepine, chemotherapeutic agent, methotrexate, cyclophosphamide, ifosfamide, adriamycin, doxorubicin, glucocorticoids, cyclosporine, L-thyroxine, SERMs, AI, fulvestrant, gonadotropin-releasing hormone agent, androgen depravation agent, prolactinemia-inducing agent, serotonergic antidepressant, selective serotonin reuptake inhibitor, monoamine oxidase inhibitor, tricyclic antidepressant, antihypertensive agents, methyldopa, reserpine, clonidine, verapamil, antidopaminergic agent, anti-emetic agent, metoclopramide, H2 receptor antagonist, cimetidine, ranitidine, estrogen, or amphetamine.

In one embodiment, the compound of this invention is administered with a vitamin. In some embodiments, vitamins include but are not limited to vitamin D, vitamin E, vitamin K, vitamin B, vitamin C, or a combination thereof.

In one embodiment, the compound of this invention is administered with a behavior-modulating agent. In some embodiments, behavior-modulating agents include but are not limited to an anti-anxiety agent, anti-psychotic agent, anti-depressant, beta-blocker, beta-2 agonist, anticholinergic bronchodilator, theophylline, aminophylline, nedocromil sodium, sodium cromoglycate, leukotriene receptor antagonist, corticosteroid, expectorant, mucolytic agent, antihistamine, pseudoephedrine, methylphenidate, amphetamine, buspirone, benzodiazepine, dextroamphetamine, tricyclic antidepressant, serotonin reuptake inhibitor, phenothiazines, benztropine, bupropion, propranolol, lithium, venlafaxine, haloperidol, buspirone, or a neuraminidase inhibitor.

In one embodiment, the behavior-modulating agent is a benzodiazepine. In one embodiment, benzodiazepines comprise alprazolam, chlordiazepoxide, diazepam, flurazepam, lorazepam, oxazepam, temazepam, or triazolam.

In one embodiment, the behavior-modulating agent is a phenothiazine. In one embodiment, phenothiazines comprise fluphenazine, perphenazine, thioridazine, or trifluoperazine.

In one embodiment, the behavior-modulating agent is a tricyclic antidepressant or a serotonin reuptake inhibitor. In one embodiment, tricyclic antidepressants or serotonin reuptake inhibitors comprise phenothiazine, protriptyline, fluoxetine, paroxetine, or sertraline.

In one embodiment, the compound of this invention is administered with an agent treating a connective tissue. In some embodiments, agents treating a connective tissue include but are not limited to an anti-malaria agent, a cytotoxic agent, a steroid, corticosteroid, lupus medication, imuran, cytoxan, anti-rheumatic agent, corticosteroid, nifedipine, aspirin, colchicine, captopril, penicillamine, azathioprine, methotrexate, cyclophosphamide, prednisone, nicardipine, or a non-steroidal anti-inflammatory agent.

In one embodiment, the compound of this invention is administered with an agent treating an ophthalmic disease. In some embodiments, agents treating an ophthalmic disease include but are not limited to betagan, betimol, timoptic, betoptic, betoptic, ocupress, optipranolol, xalatan, alphagan, azopt, trusopt, cospot, pilocar, pilagan, propine, opticrom, acular, livostin, alomide, emadine, patanol, alrex, poly-pred, pred-g, dexacidin, erythromycin, maxitrol, tobradex, blephamide, FML, ocufen, voltaren, profenal, pred forte, econpred plus, eflone, flarex, inflamase forte, betadine, gramicidin, prednisolone, betaxolol, humorsol, proparacaine, betoptic, hylartin, inflamase mild, lotemax, flurbiprofen, chloramphenicol, methazolamide, timolol, ciloxan, terramycin, ciprofloxacin, miostat, triamcinolone, miconazole, tobramycin, physostimine, gentamicin, pilocarpine, bacitracin, goniosol, polymyxin, oxytetracycline, viroptic, vexol, suprofen, celluvisc, polytrim, illotycin, ciloxan, ocuflox, brinzolamide, cefazolin, tobrex, latanoprost, indocyanine, trifluridine, phenylephrine, demecarium, neomycin, tropicamide, dexamethasone, neptazane, dipivefrin, ocuflox, vidarabine, dorzolamide, ofloxacin, epinephrine, acyclovir, carbonic anhydrase inhibitor, antihistamine vitamin A, vitamin C, vitamin E, zinc, copper, atropine, or garamycin.

In one embodiment, the compound of this invention is administered in with a gene therapy agent. In some embodiments, gene therapy agents include but are not limited to an antisense agent, or a replacement gene.

In some embodiments, any of the compositions of this invention will comprise a compound of this invention, in any form or embodiment as described herein. In some embodiments, any of the compositions of this invention will consist of a compound of this invention, in any form or embodiment as described herein. In some embodiments, of the compositions of this invention will consist essentially of a compound of this invention, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a compound as herein described, alone or as part of the combined therapy or using the compositions of this invention represent additional embodiments of this invention.

Biological Activity of Selective Androgen Modulator Compounds

The compounds of this invention may be useful, in some embodiments, for oral testosterone replacement therapy. In other embodiments, appropriately substituted compounds are useful for a) male contraception; b) treatment of a variety of hormone-related conditions, for example conditions associated with ADAM, such as fatigue, depression, decreased libido, sexual dysfunction, erectile dysfunction, hypogonadism, osteoporosis, hair loss, obesity, sarcopenia, osteopenia, benign prostate hyperplasia, and alterations in mood and cognition; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; e) treatment of prostate cancer, imaging of prostate cancer; decreasing the incidence of, halting or causing a regression of prostate cancer; f) treatment of diabetes type I; g) treatment of diabetes type II; h) suppressing or inhibiting or reducing the incidence of diabetes i) treatment of glucose intolerance; j) treatment of hyperinsulinemia; k) treatment of insulin resistance l) treatment of diabetic nephropathy; m) treatment of diabetic neuropathy; n) treatment of diabetic retinopathy; o) treatment of fatty liver condition; p) treatment of cachexia; q) oral androgen replacement and/or other clinical therapeutic and/or diagnostic areas, including any embodiment of what is encompassed by the term "treating" as described herein.

In some embodiments, the compounds of this invention possess in vivo tissue selective androgenic and anabolic activity, which is accordingly utilized for particular applications, as will be appreciated by one skilled in the art.

In one embodiment, this invention provides: a) a method of treating a subject having a muscle wasting disorder; b) a method of treating a subject suffering from malnutrition; c) a method of treating a bone-related disorder in a subject; d) a method of increasing a bone mass in a subject; e) a method of improving the lipid profile in a subject; f) a method of treating atherosclerosis and its associated diseases; g) a method of improving dexterity and movement in a subject; h) a method of treating a subject having dwarfism; i) a method of treating a subject having dysmenorrhea; j) a method of treating a subject having dysparunia; k) a method of treating a subject having dysspermtogenic sterility; comprising the step of administering to said subject a compound of this invention and/or an analog, derivative, isomer, metabolite, pharmaceutically acceptable salt, pharmaceutical product, hydrate, N-oxide, prodrug, polymorph, impurity or crystal of said compound, or any combination thereof.

In some embodiments, the compounds as described herein and/or compositions comprising the same may be used for applications and treating diseases in which the improvement of cognition, reduction or treatment of depression, or other neuroprotective effects are desired.

In one embodiment, "Cognition" refers to the process of knowing, specifically the process of being aware, knowing, thinking, learning and judging. Cognition is related to the fields of psychology, linguistics, computer science, neuroscience, mathematics, ethology and philosophy. In one embodiment, "mood" refers to a temper or state of the mind As contemplated herein, alterations mean any change for the positive or negative, in cognition and/or mood.

In one embodiment, "depression" refers to an illness that involves the body, mood and thoughts that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

In one embodiment, the methods of this invention are useful a subject, which is a human. In another embodiment, the subject is a mammal. In another embodiment the subject is an animal. In another embodiment the subject is an invertebrate. In another embodiment the subject is a vertebrate.

In one embodiment, the subject is male. In another embodiment, the subject is female. In some embodiments, while the methods as described herein may be useful for treating either males or females, females may respond more advantageously to administration of certain compounds, for certain methods, as described and exemplified herein.

In some embodiments, while the methods as described herein may be useful for treating either males or females, males may respond more advantageously to administration of certain compounds, for certain methods, as described herein.

In some embodiments, the compounds as described herein and/or compositions comprising the same may be used for applications in or treating hair loss, alopecia, androgenic alopecia, alopecia areata, alopecia secondary to chemotherapy, alopecia secondary to radiation therapy, alopecia induced by scarring or alopecia induced by stress. In one embodiment, "hair loss", or "alopecia", refers to baldness as in the very common type of male-pattern baldness. Baldness typically begins with patch hair loss on the scalp and sometimes progresses to complete baldness and even loss of body hair. Hair loss affects both males and females.

In some embodiments, the compounds as described herein and/or compositions comprising the same may be used for applications in, or treating diseases or conditions associated with a subject having anemia. In one embodiment, "anemia" refers to the condition of having less than the normal number of red blood cells or less than the normal quantity of hemoglobin in the blood, reduced hematocrit or reduced mean corpuscular volume, or reduced corpuscular size. The oxygen-carrying capacity of the blood is decreased in anemia. In some embodiments, treating anemia may also refer herein to treating underlying factors resulting in anemia, such as for example: a) hemorrhage (bleeding); b) hemolysis (excessive destruction of red blood cells); c) underproduction of red blood cells; and d) not enough normal hemoglobin. In some embodiments, treating anemia in this invention refers to treating any form thereof, including aplastic anemia, benzene poisoning, Fanconi anemia, hemolytic disease of the newborn, hereditary spherocytosis, iron deficiency anemia, osteoporosis, pernicious anemia, aplastic anemia, hemolytic anemia, sickle cell anemia, renal anemia, thalassemia, myelodysplastic syndrome, and a variety of bone marrow diseases.

In some embodiments, the compounds as described herein and/or compositions comprising the same may be used for applications in and/or treating diseases and/or conditions associated with problems with a subject's libido, or erectile dysfunction in a subject. In one embodiment, "libido", may refer to sexual desire.

In one embodiment, the term "erectile" refers to the ability to be erect or upright. An erectile tissue is a tissue, which is capable of being greatly dilated and made rigid by the distension of the numerous blood vessels, which it contains.

In another embodiment of the present invention, a method is provided for hormonal therapy in a patient (i.e., one suffering from an androgen-dependent condition) which includes contacting an androgen receptor of a patient with a compound and/or a non steroidal agonist of the present invention and/or its analog, derivative, isomer, metabolite, pharmaceutically acceptable salt, pharmaceutical product, polymorph, crystal, impurity, hydrate, N-oxide or any combination thereof, in an amount effective to bind the compound to the androgen receptor and effect a change in an androgen-dependent condition.

In one embodiment of this invention, a method is provided for hormone replacement therapy in a patient (i.e., one suffering from an androgen-dependent condition) which includes administering a compound as herein described and/or its analog, derivative, isomer, metabolite, pharmaceutically acceptable salt, pharmaceutical product, polymorph, crystal, impurity, hydrate, N-oxide or any combination thereof, to a subject, in an amount sufficient to effect a change in a hormone-dependent condition in the subject.

Androgen-dependent conditions which may be treated with the compounds and/or compositions as herein described, comprising the methods of the present invention include those conditions which are associated with aging, hypogonadism, sarcopenia, diminished erythropoiesis, osteoporosis, and any other conditions dependent upon low androgen (e.g., testosterone) or estrogen levels.

Androgen-dependent conditions which may be treated with the compounds and/or compositions as herein described, and comprising a method of the invention, may comprise conditions characterized by elevated androgen or estrogen levels, including hirsutism, infertility, polycystic ovarian syndrome, endometrial carcinoma, breast cancer, male pattern baldness, prostate cancer, testicular cancer, and others, as will be known to one skilled in the art. For such conditions, the subject may be administered a compound as herein described, alone or in combination with another therapeutic agent, as will be appreciated by one skilled in the art.

In one embodiment, this invention provides methods for the treatment of a cancer in a subject, reduction of incidence or severity or pathogenesis of a cancer in a subject, delaying progression, prolonging remission or delaying onset of cancer in a subject, comprising the step of administering to the subject a compound as herein described and/or its analog, derivative, isomer, metabolite, pharmaceutically acceptable salt, pharmaceutical product, polymorph, crystal, impurity, hydrate, N-oxide or any combination thereof. In some embodiments, such cancers are hormone-dependent or androgen receptor dependent tumors (malignant or benign) associated with reproductive tissue in males or females, such as cancer of the prostate, ovary, breast, uterus, testicle, or others.

In some embodiments, this invention provides methods for the treatment of a precancerous precursor or lesion in a subject, reduction of incidence of precancerous precursors or lesions in a subject, comprising the step of administering to the subject a compound as herein described and/or its analog, derivative, isomer, metabolite, pharmaceutically acceptable salt, pharmaceutical product, polymorph, crystal, impurity, hydrate, N-oxide or any combination thereof. In some embodiments, such precancerous precursors are androgen receptor dependent tumors found in hormone-responsive tissue or are associated with reproductive tissue in males or females, such as in the prostate, ovary, breast, uterus, testicle, or others. In some embodiments, such precancerous precursors comprise any local intraepithelial neoplasia, for example, of the prostate, the cervix, etc. In some embodiments, such methods are useful in treating neoplasia or pre-neoplasia, dysplasia or hyperplasia in a tissue, such as in reproductive tissue in males or females.

In one embodiment, this invention provides compounds, compositions and/or methods of use thereof in treating benign prostate hyperplasia (BPH). "BPH (benign prostate hyperplasia)" is a nonmalignant enlargement of the prostate gland, and is the most common non-malignant proliferative abnormality found in any internal organ and the major cause of morbidity in the adult male. BPH occurs in over 75% of men over 50 years of age, reaching 88% prevalence by the ninth decade. BPH frequently results in a gradual squeezing of the portion of the urethra which traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure.

In another embodiment, the invention provides a method of treating, delaying onset, reducing the incidence of or reducing the severity of prostate cancer in a subject with prostate cancer comprising administering a compound of formula (I)-(XI), to said subject.

In some embodiments ER-β agonists are useful treating, delaying onset, reducing the incidence of or reducing the severity of prostate cancer in a subject. In another embodiment, ER-β agonist of this invention is compound 3a, listed in Table 1. In another embodiment, ER-β agonist of this invention is compound 3d, listed in Table 1. In another embodiment, ER-β agonist of this invention is compound 3e, listed in Table 1. In another embodiment, ER-β agonist of this invention is compound 3l, listed in Table 1. In another embodiment, ER-β agonist of this invention is compound 3g, listed in Table 1. In another embodiment, ER-β agonist of this invention is compound 3j, listed in Table 1. In another embodiment, ER-β agonist of this invention is compound 3i, listed in Table 1, or any combination thereof. In another embodiment, ER-β agonist of this invention is compound 4a, listed in Table 1. In another embodiment, ER-β agonist of this invention is compound 4h, listed in Table 1. In another embodiment, ER-β agonist of this invention is compound 4u, listed in Table 1. In another embodiment, ER-β agonist of this invention is compound 10o, listed in Table 1. In another embodiment, ER-β agonist of this invention is compound 10d, listed in Table 1. In another embodiment, ER-β agonist of this invention is compound 10f, listed in Table 1. In another embodiment, ER-β agonist of this invention is compound 10l, listed in Table 1. In another embodiment, ER-β agonist of this invention is compound 10w, listed in Table 1, or any combination thereof.

In one embodiment, the method comprises administering prodrug, ester, analog, isomer, metabolite, derivative, pharmaceutically acceptable salt, pharmaceutical product, polymorph, crystal, impurity, N-oxide, hydrate or any combination thereof of the compound of formula (I)-(XI) to the subject. In another embodiment, the compound is 3a, 3d, 3e, 3l, 3g, 3j, 3i, 4a, 4d, 4u, 10o, 10d, 10f, 10l, or 10w.

In some embodiments, the method comprises administering a composition comprising a compound of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof, to the subject. In another embodiment, the compound is 3a, 3d, 3e, 3l, 3g, 3j, 3i, 4a, 4d, 4u, 10o, 10d, 10f, 10l, or 10w.

In another embodiment, the invention provides a method of reducing the risk of developing prostate cancer in a mammalian subject comprising administering a compound of formula (I)-(XI) or its prodrug, analog, isomer, metabolite, derivative, pharmaceutically acceptable salt, pharmaceutical product, ester, polymorph, crystal, impurity, N-oxide, hydrate or any combination thereof to the subject. In some embodiments ER-β agonists are useful in reducing the risk of developing prostate cancer in a mammalian subject. In another embodiment, ER-β agonist of this invention is compound 3a, listed in Table 1. In another embodiment, ER-β agonist of this invention is compound 3d, listed in Table 1. In another embodiment, ER-β agonist of this invention is compound 3e, listed in Table 1. In another embodiment, ER-β agonist of this invention is compound 3l, listed in Table 1. In another embodiment, ER-β agonist of this invention is compound 3g, listed in Table 1. In another embodiment, ER-β agonist of this invention is compound 3j, listed in Table 1. In another embodiment, ER-β agonist of this invention is compound 3i, listed in Table 1, or any combination thereof. In another embodiment, ER-β agonist of this invention is compound 4a, listed in Table 1. In another embodiment, ER-β agonist of this invention is compound 4h, listed in Table 1. In another embodiment, ER-β agonist of this invention is compound 4u, listed in Table 1. In another embodiment, ER-β agonist of this invention is compound 10o, listed in Table 1. In another embodiment, ER-β agonist of this invention is compound 10d, listed in Table 1. In another embodiment, ER-β agonist of this invention is compound 10f, listed in Table 1. In another embodiment, ER-β agonist of this invention is compound 10l, listed in Table 1. In another embodiment, ER-β agonist of this invention is compound 10w, listed in Table 1, or any combination thereof.

In another embodiment, the invention provides a method of treating, delaying onset, reducing the incidence of or reducing the number precancerous precursors of prostate adenocarcinoma lesions in a mammalian subject comprising administering a compound of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof to the subject. In another embodiment, the precancerous precursor of prostate adenocarcinoma is prostate intraepithelial neoplasia (PIN). In some embodiments ER-β agonists are useful in treating, delaying onset, reducing the incidence of or reducing the number precancerous precursors of prostate adenocarcinoma lesions in a mammalian subject. In another embodiment, ER-β agonist of this invention is compound 3a, listed in Table 1. In another embodiment, ER-β agonist of this invention is compound 3d, listed in Table 1. In another embodiment, ER-β agonist of this invention is compound 3e, listed in Table 1. In another embodiment, ER-β agonist of this invention is compound 3l, listed in Table 1. In another embodiment, ER-β agonist of this invention is compound 3g, listed in Table 1. In another embodiment, ER-β agonist of this invention is compound 3j, listed in Table 1. In another embodiment, ER-β agonist of this invention is compound 3i, listed in Table 1, or any combination thereof. In another embodiment, ER-β agonist of this invention is compound 4a, listed in Table 1. In another embodiment, ER-β agonist of this invention is compound 4h, listed in Table 1. In another embodiment, ER-β agonist of this invention is compound 4u, listed in Table 1. In another embodiment, ER-β agonist of this invention is compound 10o, listed in Table 1. In another embodiment, ER-β agonist of this invention is compound 10d, listed in Table 1. In another embodiment, ER-β agonist of this invention is compound 10f, listed in Table 1. In another embodiment, ER-β agonist of this invention is compound 10l, listed in Table 1. In another embodiment, ER-β agonist of this invention is compound 10w, listed in Table 1, or any combination thereof.

In another embodiment, the invention provides a method of treating, preventing, suppressing, inhibiting, or reducing the incidence of testicular cancer in a mammalian subject comprising administering a compound of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof to the subject. In another embodiment, the invention provides a method of treating, preventing, suppressing, inhibiting, or reducing the incidence of a urogenital disorder, disease or condition in a mammalian subject comprising administering a compound of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof to the subject. In some embodiments ER-β agonists are useful in treating, preventing, suppressing, inhibiting, or reducing the incidence of testicular cancer in a mammalian subject. In another embodiment, ER-β agonist of this invention is compound 3a, listed in Table 1. In another embodiment, ER-β agonist of this invention is compound 3d, listed in Table 1. In another embodiment, ER-β agonist of this invention is compound 3e, listed in Table 1. In another embodiment, ER-β agonist of this invention is compound 3l, listed in Table 1. In another embodiment, ER-β agonist of this invention is compound 3g, listed in Table 1. In another embodiment, ER-β agonist of this invention is compound 3j, listed in Table 1. In another embodiment, ER-β agonist of this invention is compound 3i, listed in Table 1, or any combination thereof. In another embodiment, ER-β agonist of this invention is compound 4a, listed in Table 1. In another embodiment, ER-β agonist of this invention is compound 4h, listed in Table 1. In another embodiment, ER-β agonist of this invention is compound 4u, listed in Table 1. In another embodiment, ER-β agonist of this invention is compound 10o, listed in Table 1. In another embodiment, ER-β agonist of this invention is compound 10d, listed in Table 1. In another embodiment, ER-β agonist of this invention is compound 10f, listed in Table 1. In another embodiment, ER-β agonist of this invention is compound 10l, listed in Table 1. In another embodiment, ER-β agonist of this invention is compound 10w, listed in Table 1, or any combination thereof.

In one embodiment, according to these aspects of the invention, the methods are appropriate for treating, suppressing, inhibiting, reducing the risk of developing latent prostate cancer.

It is to be understood that any of the methods may be effected via the administration of a composition comprising the indicated compound or compounds, and represents embodiments of this invention.

In some embodiments, this invention provides compounds, compositions and methods of use thereof in the treatment of a cancer, or a precancerous precursor thereof or a hyperplasia. In some embodiments, such neoplasia, preneoplasias or hyperplasias may be of any cell type, such as, for example, an epithelial cell. In some embodiments, such cancers, precancerous lesions or hyperplastic lesions, which may be positively affected by the NRBAs or compositions of this invention may comprise those of thyroid, liver, bladder, kidney, head and neck tissue, pancreas, urogenital tract, GI tract, nervous and supporting tissue, or combinations thereof. In some embodiments, compounds and compositions of this invention are beneficial when administered at an early, preneoplastic stage. In some embodiments, the compounds and compositions of this invention are beneficial when administered at latter stages of disease, for example, in the prevention of metastasis from a primary focus. In some embodiments, the compounds, compositions and methods of this invention are beneficial when administered at any, or at multiple stages of carcinogenesis in a subject, or pre-cancerous stages or combinations thereof.

In one embodiment, the invention provides a method of treating, preventing the recurrence, inhibiting, reducing the incidence of, delaying onset, reducing the recurrence of, or reducing the severity of a carcinoma in a subject, comprising administering a compound of formula (I)-(XI), which in some embodiments is a SERM, or its prodrug, analog, isomer, metabolite, derivative, pharmaceutically acceptable salt, pharmaceutical product, polymorph, crystal, impurity, N-oxide, ester, hydrate or any combination thereof, to the subject.

In another embodiment of the present invention, the method for treating benign prostate hyperplasia (BPH) in a subject, comprises the step of administering to the subject a compound as herein described and/or its analog, derivative, isomer, metabolite, pharmaceutically acceptable salt, pharmaceutical product, polymorph, crystal, impurity, hydrate, N-oxide or any combination thereof, in an amount effective to treat BPH in the subject.

In some embodiments, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, or reducing pathogenesis of cachexia and/or cachexia associated with cancer in a subject. In another embodiment, the cancer comprise adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof.

In another embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, delaying the onset of lung cancer.

In another embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, delaying the onset of non small cell lung cancer.

Colon cancer is the second most frequently diagnosed malignancy in the United States, as well as the second most common cause of cancer death. Cholesterol-rich diets have had a significant epidemiological association with cancers of the colon, which in turn may be influenced by the administration of compounds which modulate nuclear hormone binding agents, in particular, compounds which modulate receptors binding components of the steroidogenic pathway, in particular SERMs, as described herein.

In one embodiment, the invention provides a method of treating, preventing the recurrence, inhibiting, reducing the incidence of, delaying onset, reducing the recurrence of, or reducing the severity of colon cancer in a subject, comprising administering a compound of formula (I)-(XI), which in some embodiments is a SERM, or its prodrug, analog, isomer, metabolite, derivative, pharmaceutically acceptable salt, pharmaceutical product, polymorph, crystal, impurity, N-oxide, ester, hydrate or any combination thereof, to the subject.

In some embodiments ER-β agonists are useful in treating, preventing the recurrence, inhibiting, reducing the incidence of, delaying onset, reducing the recurrence of, or reducing the severity of colon cancer in a subject. In another embodiment, ER-β agonist of this invention is compound 3a, listed in Table 1. In another embodiment, ER-β agonist of this invention is compound 3d, listed in Table 1. In another embodiment, ER-β agonist of this invention is compound 3e, listed in Table 1. In another embodiment, ER-β agonist of this invention is compound 3l, listed in Table 1. In another embodiment, ER-β agonist of this invention is compound 3g, listed in Table 1. In another embodiment, ER-β agonist of this invention is compound 3j, listed in Table 1. In another embodiment, ER-β agonist of this invention is compound 3i, listed in Table 1, or any combination thereof. In another embodiment, ER-β agonist of this invention is compound 4a, listed in Table 1. In another embodiment, ER-β agonist of this invention is compound 4h, listed in Table 1. In another embodiment, ER-β agonist of this invention is compound 4u, listed in Table 1. In another embodiment, ER-β agonist of this invention is compound 10o, listed in Table 1. In another embodiment, ER-β agonist of this invention is compound 10d, listed in Table 1. In another embodiment, ER-β agonist of this invention is compound 10f, listed in Table 1. In another embodiment, ER-β agonist of this invention is compound 10l, listed in Table 1. In another embodiment, ER-β agonist of this invention is compound 10w, listed in Table 1, or any combination thereof.

In some embodiments, the colon cancer is caused by a gastrointestinal disorder, disease or condition. In one embodiment, the gastrointestinal disorder, disease or condition may comprise colitis, Crohn's disease, irritable bowel syndrome, indeterminant colitis, infectious colitis, irritable bowel diseases, ulcerative colitis, ulcerative proctitis or others as known to those skilled in the art.

In another embodiment, the invention provides a method of treating, preventing the recurrence, inhibiting, reducing the incidence of, delaying onset, reducing the recurrence of, or reducing the severity of gastrointestinal disorder, disease or condition in a subject, comprising administering a compound of formula (I)-(XI), which in some embodiments is a SERM, or its prodrug, analog, isomer, metabolite, derivative, pharmaceutically acceptable salt, pharmaceutical product, polymorph, crystal, impurity, N-oxide, ester, hydrate or any combination thereof, to the subject.

In some embodiments, treatment may comprise administration of other agents, which treat colon cancer, such as, for example, azetidinone-based cholesterol absorption inhibitors, or others, as known to those skilled in the art. In some embodiments, such treatment may precede, or follow that of the NRBAs of this invention, or be concurrent therewith. In some embodiments, such methods may comprise administration of a composition comprising the compound, or compounds, and optionally other agents, which are useful in this context.

In one embodiment, the invention provides a method of treating, preventing the recurrence, inhibiting, reducing the incidence of, delaying onset, reducing the recurrence of, or reducing the severity of head and neck cancer in a subject, comprising administering a compound of formula (I)-(XI), which in some embodiments is a SERM, or its prodrug, analog, isomer, metabolite, derivative, pharmaceutically acceptable salt, pharmaceutical product, polymorph, crystal, impurity, N-oxide, ester, hydrate or any combination thereof, to the subject.

In one embodiment, the invention provides a method of treating, preventing the recurrence, inhibiting, reducing the incidence of, delaying onset, reducing the recurrence of, or reducing the severity of liver cancer in a subject, comprising administering a compound of formula (I)-(XI), which in some embodiments is a SERM, or its prodrug, analog, isomer, metabolite, derivative, pharmaceutically acceptable salt, pharmaceutical product, polymorph, crystal, impurity, N-oxide, ester, hydrate or any combination thereof, to the subject.

In one embodiment, the invention provides a method of treating, preventing the recurrence, inhibiting, reducing the incidence of, delaying onset, reducing the recurrence of, or reducing the severity of thyroid cancer in a subject, comprising administering a compound of formula (I)-(XI), which in some embodiments is a SERM, or its prodrug, analog, isomer, metabolite, derivative, pharmaceutically acceptable salt, pharmaceutical product, polymorph, crystal, impurity, N-oxide, ester, hydrate or any combination thereof, to the subject.

In one embodiment, the invention provides a method of treating, preventing the recurrence, inhibiting, reducing the incidence of, delaying onset, reducing the recurrence of, or reducing the severity of kidney cancer in a subject, comprising administering a compound of formula (I)-(XI), which in some embodiments is a SERM, or its prodrug, analog, isomer, metabolite, derivative, pharmaceutically acceptable salt, pharmaceutical product, polymorph, crystal, impurity, N-oxide, ester, hydrate or any combination thereof, to the subject.

In one embodiment, the invention provides a method of treating, preventing the recurrence, inhibiting, reducing the incidence of, delaying onset, reducing the recurrence of, or reducing the severity of pancreatic cancer in a subject, comprising administering a compound of formula (I)-(XI), which in some embodiments is a SERM, or its prodrug, analog, isomer, metabolite, derivative, pharmaceutically acceptable salt, pharmaceutical product, polymorph, crystal, impurity, N-oxide, ester, hydrate or any combination thereof, to the subject.

Melanomas are aggressive, frequently metastatic tumors derived from either melanocytes or melanocyte related nevus cells ("Cellular and Molecular Immunology" (1991) (eds) Abbas A. K., Lechtman, A. H., Pober, J. S.; W. B. Saunders Company, Philadelphia: pages 340-341). Melanomas make up approximately three percent of all skin cancers and the worldwide increase in melanoma is unsurpassed by any other neoplasm with the exception of lung cancer in women ("Cellular and Molecular Immunology" (1991) (eds) Abbas, A. K., Lechtiman, A. H., Pober, J. S.; W. B. Saunders Company Philadelphia pages: 340-342; Kirkwood and Agarwala (1993) *Principles and Practice of Oncology* 7:1-16). Even when melanoma is apparently localized to the skin, up to 30% of the patients will develop systemic metastasis and the majority will die (Kirkwood and Agarwala (1993) *Principles and Practice of Oncology* 7:1-16). Classic modalities of treating melanoma include surgery, radiation and chemotherapy. In the past decade immunotherapy and gene therapy have emerged as new and promising methods for treating melanoma.

In one embodiment, the invention provides a method of treating, preventing the recurrence, inhibiting, reducing the incidence of, delaying onset, reducing the recurrence of, or reducing the severity of melanoma in a subject, comprising administering a compound of formula (I)-(XI), which in some embodiments is a SERM, or its prodrug, analog, isomer, metabolite, derivative, pharmaceutically acceptable salt, pharmaceutical product, polymorph, crystal, impurity, N-oxide, ester, hydrate or any combination thereof, to the subject.

In one embodiment, the invention provides a method of treating, preventing the recurrence, inhibiting, reducing the incidence of, delaying onset, reducing the recurrence of, or reducing the severity of skin disorder, disease or condition in a subject, comprising administering a compound of formula (I)-(XI), which in some embodiments is a SERM, or its prodrug, analog, isomer, metabolite, derivative, pharmaceutically acceptable salt, pharmaceutical product, polymorph, crystal, impurity, N-oxide, ester, hydrate or any combination thereof, to the subject.

In one embodiment, skin disorder, disease or condition may comprise, dermatitis, melanoma, pruritis, psoriasis, skin atrophy.

In one embodiment, this invention provides methods of 1) improving the lipid profile of a subject; 2) reducing the circulating lipid levels in a subject; 3) increasing high density lipoprotein (HDL) cholesterol levels in a subject; 4) altering ratios of low density lipoprotein to high density lipoprotein levels in a subject; wherein said subject has prostate cancer and is undergoing or has undergone ADT, wherein said method comprises administering to said subject a compound of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof. In another embodiment, the method comprises administering a composition comprising the compound.

In another embodiment, the subject is undergoing or has undergone ADT. The terms "has undergone," "undergoing", and the like refer, in one embodiment, to subjects that have recently (within the last 6 months) or are currently receiving any treatment or therapy known in the art that reduces androgen levels in general or testosterone levels in particular. In another embodiment, the terms refer to a subject that received such a treatment or therapy more than 6 months previously. In one embodiment, the treatment or therapy is surgical. In another embodiment, the treatment or therapy is medical. In another embodiment, the treatment or therapy eliminates an androgen or a testosterone entirely, or below detectable levels. In another embodiment, the ADT is a side effect of a treatment or therapy not intended to reduce androgen or testosterone levels. Each of these possibilities represents a separate embodiment of the present invention.

In another embodiment, ADT is used for treating prostate cancer, for delaying the progression of prostate cancer, and for preventing and/or treating the recurrence of prostate cancer, which comprise administering LHRH analogs, reversible anti-androgens (such as bicalutamide or flutamide), anti-estrogens, anticancer drugs, 5-alpha reductase inhibitors, aromatase inhibitors, progestins, selective androgen receptor modulators (SARMS) or agents acting through other nuclear hormone receptors. In another embodiment, ADT is administered monthly, or every 3, 4, 6 or 12 months. In another embodiment, ADT is administered every two weeks in the first month, then every four weeks.

In some embodiments, according to this aspect, such methods comprise administering a compound of this invention to a subject that has prostate cancer and is undergoing or has undergone ADT. In one embodiment, the compound can be administered prior to the ADT. In another embodiment, the compound can be administered concurrent with ADT. In another embodiment, the compound can be administered following ADT.

In some embodiments, the methods of this invention comprise administering a compound of this invention in combination with the ADT, prior to the ADT or after the ADT as a preventive for all diseases in this invention. In some embodiments, such compounds are SERMs. In one embodiment the SERM is administered between 1-2 weeks before ADT. In another embodiment the SERM is administered between 2-4 weeks prior to ADT. In another embodiment the SERM is administered between 1-2 months before ADT. In another embodiment the SERM is administered between 2-4 months before ADT. In another embodiment the SERM is administered between 4-6 months before ADT. In one embodiment the SERM is administered between 1-2 weeks after ADT. In another embodiment the SERM is administered between 2-4 weeks after ADT. In another embodiment the SERM is administered between 1-2 months after ADT. In another embodiment the SERM is administered between 2-4 months after ADT. In another embodiment the SERM is administered between 4-6 months after ADT.

In other embodiments, the present invention provides a method of treating any disease, disorder, or symptom associated with ADT. In other embodiments, the present invention provides a method of treating any disease, disorder, or symptom associated with testosterone deprivation. Each disease, disorder, or symptom represents a separate embodiment of the present invention.

Papilloma viruses are non-enveloped DNA viruses that induce hyperproliferative lesions of the epithelia. The papilloma viruses are widespread in nature and have been identified in higher vertebrates. Viruses have been characterized, amongst others, from humans, cattle, rabbits, horses, and dogs. Human papilloma viruses (HPV) have been classified into more than 80 types (Epidemiology and Biology of Cervical Cancer. Seminars in Surgical Oncology 1999 16:203-211).

In one embodiment, the invention provides a method of treating, preventing the recurrence, inhibiting, reducing the incidence of, delaying onset, reducing the recurrence of, or reducing the severity of papilloma in a subject, comprising administering a compound of formula (I)-(XI), which in some embodiments is a SERM, or its prodrug, analog, isomer, metabolite, derivative, pharmaceutically acceptable salt, pharmaceutical product, polymorph, crystal, impurity, N-oxide, ester, hydrate or any combination thereof, to the subject.

Cross-talk has been shown to occur between endocrine-disrupting chemicals and cytokine signaling through estrogen receptors, suggesting a role for SERMs and/or other nuclear hormone binding agents in the modulation of the immune system and/or diseases thereof.

For example, tamoxifen, clomiphene and nafoxidine cause a decrease in viability of the estrogen receptor-negative T-lymphoblastic leukemia cell line CCRF/CEM, suggesting a role for antiestrogens in the clinical treatment of leukemia.

Leukemia is a malignant cancer of the bone marrow and blood and comprises acute or chronic myelogenous, or acute or chronic lymphocytic type disease.

Standard treatment for leukemia usually involves chemotherapy and/or bone marrow transplantation and/or radiation therapy. Chemotherapy usually involves a combination of two or more anti-cancer drugs, with common combinations including cytarabine with either doxorubicin or daunorubicin or mitoxantrone or thioguanine, mercaptopurine with methotrexate, mitroxantrone with etoposide, asparaginase with vincristine, daunorubicin and prednisone, cyclophosphamide with vincristine, cytarabine and prednisone, cyclophosphamide with vincristine and prednisone, daunorubicin with cytarabine and thioguanine and daunorubicin with vincristine and prednisone.

In one embodiment, the invention provides a method of treating, preventing the recurrence, inhibiting, reducing the incidence of, delaying onset or reducing the severity of leukemia in a subject, comprising administering a compound of formula (I)-(XI) or its prodrug, analog, isomer, metabolite, derivative, pharmaceutically acceptable salt, pharmaceutical product, polymorph, crystal, impurity, N-oxide, ester, hydrate or any combination thereof, to the subject.

In some embodiments, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, or reducing pathogenesis of cancer. In another embodiment, the cancer comprises androgen AR dependent tumors (malignant or benign) such as prostate cancer, breast cancer (male or female, operable or inoperable). In another embodiment the compounds adjunct to ADT for treating prostate cancer; bladder cancers; brain cancers; bone tumors, colon cancer, endometrial cancer, liver cancer, lung cancer, lymphatic cancer, kidney cancer, osteosarcoma cancer, ovarian cancer, pancreas cancer, penis cancer, skin cancer, thyroid cancer; and/or hormone-dependent cancers.

In some embodiments this invention provides a method of treating, suppressing, reducing the incidence or severity of, or prolonging remission of bladder cancer in a subject, the method comprising administering a NRBA or SERM of formula (I)-(XI) or its prodrug, analog, isomer, metabolite, derivative, pharmaceutically acceptable salt, pharmaceutical product, polymorph, crystal, impurity, N-oxide, ester, hydrate or any combination thereof to the subject.

Existing therapies for bladder cancer may be combined with the therapies provided herein, including, cystectomy with or without administration of methotrexate, vinbiastine, doxorubicin, or cisplatin (M-VAC), or others as known in the art.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for a) treating a bone related disorder; b) preventing a bone related disorder; c) suppressing a bone related disorder; d) inhibiting a bone related disorder; e) increasing a strength of a bone of a subject; f) increasing a bone mass in a subject; g) use for osteoclastogenesis inhibition.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for a) Accelerate bone repair; b) treating bone disorders; c) treating bone density loss; d) treating low bone mineral density (BMD); e) treating reduced bone mass; f) treating metabolic bone disease; g) promoting bone growth or regrowth; h) promoting bone restoration; i) promoting bone fracture repair; j) promoting bone remodeling; k) treating bone damage following reconstructive surgery including of the face, hip, or joints; l) enhancing of bone strength and function; m) increasing cortical bone mass; n) increasing trabecular connectivity.

In one embodiment, the invention provides a method of treating, preventing, reducing the severity of, delaying onset, reducing the recurrence of a bone-related disease or disorder in a subject, comprising administering a NRBA, which in some embodiments is a SERM, of this invention to the subject. In one embodiment, the subject is administered a NRBA/SERM or composition comprising the same, wherein the NRBA/SERM is a of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof. In some embodiments ER-β agonists are useful in treating, preventing, reducing the severity of, delaying onset, reducing the recurrence of a bone-related disease or disorder in a subject. In another embodiment, ER-β agonist of this invention is compound 3a, listed in Table 1. In another embodiment, ER-β agonist of this invention is compound 3d, listed in Table 1. In another embodiment, ER-β agonist of this invention is compound 3e, listed in Table 1. In another embodiment, ER-β agonist of this invention is compound 3l, listed in Table 1. In another embodiment, ER-β agonist of this invention is compound 3g, listed in Table 1. In another embodiment, ER-β agonist of this invention is compound 3j, listed in Table 1. In another embodiment, ER-β agonist of this invention is compound 3i, listed in Table 1, or any combination thereof. In another embodiment, ER-β agonist of this invention is compound 4a, listed in Table 1. In another embodiment, ER-β agonist of this invention is compound 4h, listed in Table 1. In another embodiment, ER-β agonist of this invention is compound 4u, listed in Table 1. In another embodiment, ER-β agonist of this invention is compound 10o, listed in Table 1. In another embodiment, ER-β agonist of this invention is compound 10d, listed in Table 1. In another embodiment, ER-β agonist of this invention is compound 10f, listed in Table 1. In another embodiment, ER-β agonist of this invention is compound 10l, listed in Table 1. In another embodiment, ER-β agonist of this invention is compound 10w, listed in Table 1, or any combination thereof.

In one embodiment, the bone related disorder is a genetic disorder, or in another embodiment, is induced as a result of a treatment regimen for a given disease. For example, and in one embodiment, the compounds as herein described are useful in treating a bone-related disorder that arises as a result of cancer metastasis to bone, or in another embodiment, as a result of androgen-deprivation therapy, for example, given in response to prostate carcinogenesis in the subject.

In one embodiment, the bone-related disorder is osteoporosis. In another embodiment, the bone-related disorder is osteopenia. In another embodiment, the bone-related disorder is increased bone resorption. In another embodiment, the bone-related disorder is bone fracture. In another embodiment, the bone-related disorder is bone frailty.

In another embodiment, the bone-related disorder is a loss of bone mineral density (BMD). In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures can also occur in other skeletal areas.

Unchecked osteoporosis can lead, in another embodiment, to changes in posture, physical abnormality, and decreased mobility.

In one embodiment, the osteoporosis results from androgen deprivation. In another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

In another embodiment, the primary osteoporosis is Type I primary osteoporosis. In another embodiment, the primary osteoporosis is Type II primary osteoporosis. Each type of osteoporosis represents a separate embodiment of the present invention.

According to this aspect of the invention and in one embodiment, the bone-related disorder is treated with a compound as herein described, or a combination thereof. In another embodiment, other bone-stimulating compounds can be provided to the subject, prior to, concurrent with or following administration of a compound or compounds as herein described. In one embodiment, such a bone stimulating compound may comprise natural or synthetic materials.

In another embodiment, the invention provides, a method of reducing the incidence, inhibiting, suppressing, and treating osteoporosis, bone fractures and/or loss of bone mineral density (BMD) in a subject, comprising administering a NRBA/SERM of formula (I)-(XI), or its prodrug, ester, analog, isomer, metabolite, derivative, pharmaceutically acceptable salt, pharmaceutical product, polymorph, crystal, impurity, N-oxide, hydrate or any combination thereof, or a composition comprising the same, thereby reducing the incidence, inhibiting, suppressing, and treating osteoporosis, bone fractures and/or loss of bone mineral density (BMD) in the subject. In some embodiments ER-β agonists are useful in reducing the incidence, inhibiting, suppressing, and treating osteoporosis, bone fractures and/or loss of bone mineral density (BMD) in a subject In another embodiment, ER-β agonist of this invention is compound 3a, listed in Table 1. In another embodiment, ER-β agonist of this invention is compound 3d, listed in Table 1. In another embodiment, ER-β agonist of this invention is compound 3e, listed in Table 1. In another embodiment, ER-β agonist of this invention is compound 3l, listed in Table 1. In another embodiment, ER-β agonist of this invention is compound 3g, listed in Table 1. In another embodiment, ER-β agonist of this invention is compound 3j, listed in Table 1. In another embodiment, ER-β agonist of this invention is compound 3i, listed in Table 1, or any combination thereof. In another embodiment, ER-β agonist of this invention is compound 4a, listed in Table 1. In another embodiment, ER-β agonist of this invention is compound 4h, listed in Table 1. In another embodiment, ER-β agonist of this invention is compound 4u, listed in Table 1. In another embodiment, ER-β agonist of this invention is compound 10o, listed in Table 1. In another embodiment, ER-β agonist of this invention is compound 10d, listed in Table 1. In another embodiment, ER-β agonist of this invention is compound 10f, listed in Table 1. In another embodiment, ER-β agonist of this invention is compound 10, listed in Table 1. In another embodiment, ER-β agonist of this invention is compound 10w, listed in Table 1, or any combination thereof.

In one embodiment, the bone stimulating compound may comprise a bone morphogenetic protein (BMP), a growth factor, such as epidermal growth factor (EGF), a fibroblast growth factor (FGF), a transforming growth factor (TGF, an insulin growth factor (IGF), a platelet-derived growth factor (PDGF) hedgehog proteins such as sonic, indian and desert hedgehog, a hormone such as follicle stimulating hormone, parathyroid hormone, parathyroid hormone related peptide, activins, inhibins, follistatin, frizzled, frzb or frazzled proteins, BMP binding proteins such as chordin and fetuin, a cytokine such as IL-3, IL-7, GM-CSF, a chemokine, such as eotaxin, a collagen, osteocalcin, osteonectin and others, as will be appreciated by one skilled in the art.

In another embodiment, the compositions for use in treating a bone disorder of this invention may comprise a compound or compounds as herein described, an additional bone stimulating compound, or compounds, and osteogenic cells. In one embodiment, an osteogenic cell may be a stem cell or progenitor cell, which may be induced to differentiate into an osteoblast. In another embodiment, the cell may be an osteoblast. In another embodiment, nucleic acids which encode bone-stimulating compounds may be administered to the subject, which is to be considered as part of this invention.

In one embodiment, the methods of the present invention comprise administering the compound for treating osteoporosis. In another embodiment, the methods of this invention comprise administering a compound in combination with SERMs for treating osteoporosis. In another embodiment, the SERMs are tamoxifene, 4-hydroxytamoxifene, idoxifene, toremifene, ospemifene, droloxifene, raloxifene, arzoxifene, bazedoxifene, PPT (1,3,5-Tris(4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstibestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, Ban zhi lian, CT-101, CT-102, or VG-101.

In another embodiment, the methods of the present invention comprise administering the compounds of this invention, in combination with bisphosphonates such as alendronate, tiludroate, clodroniate, pamidronate, etidronate, alendronate, zolendronate, cimadronate, neridronate, minodronic acid, ibandronate, risedronate, or homoresidronate for treating osteoporosis.

In another embodiment, the methods of the present invention comprise administering the compound, in combination with Calcitonin such as salmon, Elcatonin, SUN-8577 or TJN-135 for treating osteoporosis.

In another embodiment, the methods of treating osteoporosis of the present invention comprise administering the compound of this invention, in combination with a) vitamin D or derivative such as ZK-156979; b) vitamin D receptor ligand and analogues such as calcitriol, topitriol, ZK-150123, TEI-9647, BXL-628, Ro-26-9228, BAL-2299, Ro-65-2299 or DP-035; c) estrogen, estrogen derivative, or conjugated estrogens; d) antiestrogen, progestins, or synthetic estrogen/progestins; e) RANK ligand mAb such as denosumab formerly AMG162 (Amgen); f) αvβ3 Integrin receptor antagonist; g) osteoclast vacuolar ATPase inhibitor; h) antagonist of VEGF binding to osteoclast receptors; i) calcium receptor antagonist; j) PTh (parathyroid hormone) and analogues, PTHrP analogues (parathyroid hormone-related peptide); k) Cathepsin K inhibitors (AAE581, etc.); l) strontium ranelate; m) tibolone; n) HCT-1026, PSK3471; o) gallium maltolate; p) nutropin AQ; q) prostaglandins (for osteo); r) p38 protein kinase inhibitor; s) bone morphogenetic protein; t) inhibitor of BMP antagonism; u) HMG-CoA reductase inhibitor; v) vitamin K or derivative; w) ipriflavone; x) fluoride salts; y) dietary calcium supplement, and z) osteoprotegerin.

In one embodiment, the methods of this invention are useful in treating diseases or disorders caused by, or associated with a hormonal disorder, disruption or imbalance. In one embodiment, the hormonal disorder, disruption or imbalance comprises an excess of a hormone. In another embodiment, the hormonal disorder, disruption or imbalance comprises a deficiency of a hormone. In one embodiment, the hormone is a steroid hormone. In another embodiment, the hormone is an estrogen. In another embodiment, the hormone is an androgen. In another embodiment, the hormone is a glucocorticoid. In another embodiment, the hormone is a cortico-steroid. In another embodiment, the hormone is Luteinizing Hormone (LH). In another embodiment, the hormone is Follicle Stimulating Hormone (FSH). In another embodiment, the hormone is any other hormone known in the art. In another embodiment, the hormonal disorder, disruption or imbalance is associated with menopause. In another embodiment, the hormonal disorder, disruption or imbalance is associated with andropause, andropausal vasomotor symptoms, andropausal gynecomastia, muscle strength and/or function, bone strength and/or function and anger. In another embodiment, hormone deficiency is a result of specific manipulation, as a byproduct of treating a disease or disorder in the subject. For example, the hormone deficiency may be a result of androgen depletion in a subject, as a therapy for prostate cancer in the subject. Each possibility represents a separate embodiment of the present invention.

In another embodiment the invention is directed to treating sarcopenia or cachexia, and associated conditions related thereto, for example diseases or disorders of the bone.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder; and/or treating, preventing, inhibiting, reducing or suppressing end stage renal disease; and/or 6) treating, preventing, inhibiting, reducing or suppressing fraility.

In another embodiment, the use of a compound for treating a subject having a muscle wasting disorder, or any of the disorders described herein, includes administering a pharmaceutical composition including a compound as herein described. In another embodiment, the administering step includes intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

A muscle is a tissue of the body that primarily functions as a source of power. There are three types of muscles in the body: a) skeletal muscle—the muscle responsible for moving extremities and external areas of the bodies; b) cardiac muscle—the heart muscle; and c) smooth muscle—the muscle that is in the walls of arteries and bowel.

A wasting condition or disorder is defined herein as a condition or disorder that is characterized, at least in part, by an abnormal, progressive loss of body, organ or tissue mass. A wasting condition can occur as a result of a pathology such as, for example, cancer, or an infection, or it can be due to a physiologic or metabolic state, such as disuse deconditioning that can occur, for example, due to prolonged bed rest or when a limb is immobilized, such as in a cast. A wasting condition can also be age associated. The loss of body mass that occurs during a wasting condition can be characterized by a loss of total body weight, or a loss of organ weight such as a loss of bone or muscle mass due to a decrease in tissue protein.

In one embodiment, "muscle wasting" or "muscular wasting", used herein interchangeably, refer to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of a pathology, disease, condition or disorder. In one embodiment, the pathology, illness, disease or condition is chronic. In another embodiment, the pathology, illness, disease or condition is genetic. In another embodiment, the pathology, illness, disease or condition is neurological. In another embodiment, the pathology, illness, disease or condition is infectious. As described herein, the pathologies, diseases, conditions or disorders for which the compounds and compositions of the present invention are administered are those that directly or indirectly produce a wasting (i.e. loss) of muscle mass, that is a muscle wasting disorder.

In one embodiment, muscle wasting in a subject is a result of the subject having a muscular dystrophie; muscle atrophy; X-linked spinal-bulbar muscular atrophy (SBMA).

The muscular dystrophies are genetic diseases characterized by progressive weakness and degeneration of the skeletal or voluntary muscles that control movement. The muscles of the heart and some other involuntary muscles are also affected in some forms of muscular dystrophy. The major forms of muscular dystrophy (MD) are: duchenne muscular dystrophy, myotonic dystrophy, duchenne muscular dystrophy, becker muscular dystrophy, limb-girdle muscular dystrophy, facioscapulhumeral muscular dystrophy, congenital muscular dystrophy, oculopharyngeal muscular dystrophy, distal muscular dystrophy and emery-dreifuss muscular dystrophy.

Muscular dystrophy can affect people of all ages. Although some forms first become apparent in infancy or childhood, others may not appear until middle age or later. Duchenne MD is the most common form, typically affecting children. Myotonic dystrophy is the most common of these diseases in adults.

Muscle atrophy (MA) is characterized by wasting away or diminution of muscle and a decrease in muscle mass. For example, Post-Polio MA is a muscle wasting that occurs as part of the post-polio syndrome (PPS). The atrophy includes weakness, muscle fatigue, and pain.

Another type of MA is X-linked spinal-bulbar muscular atrophy (SBMA—also known as Kennedy's Disease). This disease arises from a defect in the androgen receptor gene on the X chromosome, affects only males, and its onset is in adulthood. Because the primary disease cause is an androgen receptor mutation, androgen replacement is not a current therapeutic strategy. There are some investigational studies where exogenous testosterone propionate is being given to boost the levels of androgen with hopes of overcoming androgen insensitivity and perhaps provide an anabolic effect. Still, use of supraphysiological levels of testosterone for supplementation will have limitations and other potentially serious complications.

Sarcopenia is a debilitating disease that afflicts the elderly and chronically ill patients and is characterized by loss of muscle mass and function. Further, increased lean body mass is associated with decreased morbidity and mortality for certain muscle-wasting disorders. In addition, other circumstances and conditions are linked to, and can cause muscle wasting disorders. For example, studies have shown that in severe cases of chronic lower back pain, there is paraspinal muscle wasting.

Muscle wasting and other tissue wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance.

Long term hospitalization due to illness or injury, or disuse deconditioning that occurs, for example, when a limb is immobilized, can also lead to muscle wasting, or wasting of other tissue. Studies have shown that in patients suffering injuries, chronic illnesses, burns, trauma or cancer, who are hospitalized for long periods of time, there is a long-lasting unilateral muscle wasting, and a decrease in body mass.

Injuries or damage to the central nervous system (CNS) are also associated with muscle wasting and other wasting disorders. Injuries or damage to the CNS can be, for example, caused by diseases, trauma or chemicals. Examples are central nerve injury or damage, peripheral nerve injury or damage and spinal cord injury or damage. In one embodiment CNS damage or injury comprise Alzheimer's diseases (AD); anger (mood); anorexia, anorexia nervosa, anorexia associated with aging and/or assertiveness (mood).

In another embodiment, muscle wasting or other tissue wasting may be a result of alcoholism, and may be treated with the compounds and compositions of the invention, representing embodiments thereof.

In one embodiment, the invention provides a use of a compound as described herein or its prodrug, analog, isomer, metabolite, derivative, pharmaceutically acceptable salt, pharmaceutical product, polymorph, crystal, impurity, N-oxide, hydrate or any combination thereof for the treatment of a wasting disease, disorder or condition in a subject.

In one embodiment, the wasting disease, disorder or condition being treated is associated with chronic illness This invention is directed to treating, in some embodiments, any wasting disorder, which may be reflected in muscle wasting, weight loss, malnutrition, starvation, or any wasting or loss of functioning due to a loss of tissue mass.

In some embodiments, wasting diseases or disorders, such as cachexia; malnutrition, tuberculosis, leprosy, diabetes, renal disease, chronic obstructive pulmonary disease (COPD), cancer, end stage renal failure, sarcopenia, emphysema, osteomalacia, or cardiomyopathy, may be treated by the methods of this invention, via the administration of a SARM compound as herein described, compositions comprising the same, with or without additional drugs, compounds, or agents, which provide a therapeutic effect for the condition being treated.

In some embodiments, wasting is due to infection with enterovirus, Epstein-Ban virus, herpes zoster, HIV, trypanosomes, influenze, coxsackie, *rickettsia, trichinella, schistosoma* or mycobacteria, and this invention, in some embodiments, provides methods of treatment thereof.

Cachexia is weakness and a loss of weight caused by a disease or as a side effect of illness. Cardiac cachexia, i.e. a muscle protein wasting of both the cardiac and skeletal muscle, is a characteristic of congestive heart failure. Cancer cachexia is a syndrome that occurs in patients with solid tumors and hematological malignancies and is manifested by weight loss with massive depletion of both adipose tissue and lean muscle mass.

Cachexia is also seen in acquired immunodeficiency syndrome (AIDS), human immunodeficiency virus (HIV)-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

In some embodiments, the present invention provides a method for treating, reducing the incidence, delaying the onset or progression, or reducing and/or abrogating the symptoms associated with an infection in a subject. In one embodiment, the method comprises administering to a subject a composition comprising a compound and an immunomodulating agent, an anti-infective agent, a gene therapy agent, or a combination thereof. In some embodiments, infections comprise actinomycosis, anaplasmosis, anthrax, aspergillosis, bacteremia, bacterial mycoses, *bartonella* infections, botulism, brucellosis, *burkholderia* infections, *campylobacter* infections, candidiasis, cat-scratch disease, chlamydia infections, cholera, *clostridium* infections, coccidioidomycosis, cross infection, cryptococcosis, dermatomycoses, diphtheria, ehrlichiosis, *Escherichia coli* infections, fasciitis, necrotizing, *Fusobacterium* infections, gas gangrene, gram-negative bacterial infections, gram-positive bacterial infections, histoplasmosis, impetigo, *Klebsiella* infections, legionellosis, leprosy, leptospirosis, *Listeria* infections, lyme disease, maduromycosis, melioidosis, *mycobacterium* infections, mycoplasma infections, mycoses, *nocardia* infections, onychomycosis, plague, pneumococcal infections, pseudomonas infections, psittacosis, q fever, rat-bite fever, relapsing fever, rheumatic fever, *Rickettsia* infections, rocky mountain spotted fever, *salmonella* infections, scarlet fever, scrub typhus, sepsis, sexually transmitted diseases, Staphylococcal infections, Streptococcal infections, tetanus, tick-borne diseases, tuberculosis, tularemia, typhoid fever, typhus, louse-borne, *vibrio* infections, yaws, *yersinia* infections, zoonoses, zygomycosis, acquired immunodeficiency syndrome, adenoviridae infections, alphavirus infections, arbovirus infections, borna disease, bunyaviridae infections, caliciviridae infections, chickenpox, coronaviridae infections, coxsackievirus infections, cytomegalovirus infections, dengue, DNA virus infections, ecthyma, contagious, encephalitis, arbovirus, Epstein-ban virus infections, erythema infectiosum, hantavirus infections, hemorrhagic fevers, viral hepatitis, viral human herpes simplex, herpes zoster, herpes zoster oticus, herpesviridae infections, infectious mononucleosis, human-lassa fever, measles, molluscum, contagiosum, mumps, paramyxoviridae infections, phlebotomus fever, polyomavirus infections, rabies, respiratory syncytial virus infections, rift valley fever, RNA virus infections, rubella, slow virus diseases, smallpox, subacute sclerosing panencephalitis, tumor virus infections, warts, west nile fever, virus diseases, yellow fever, amebiasis, anisakiasis, ascariasis, babesiosis, blastocystis hominis infections, bug bite, cestode infections, chagas disease, cryptosporidiosis, cyclosporiasis, cysticercosis, dientamoebiasis, diphyllobothriasis, dracunculiasis, echinococcosis, ectoparasitic infestations, filariasis, giardiasis, helminthiasis, hookworm infections, larva migrans, leishmaniasis, lice infestations, loiasis, malaria, mite infestations, myiasis, onchocerciasis, protozoan infections, scabies, schistosomiasis, skin diseases, parasitic, strongyloidiasis, taeniasis, toxocariasis, toxoplasmosis, trichinosis, trichomonas infections, trypanosomiasis, trypanosomiasis, african, or whipworm infections.

In some embodiments, the present invention provides a method for treating, reducing the incidence, delaying the onset or progression, or reducing and/or abrogating the symptoms associated with a musculoskeletal disease in a subject. In one embodiment, the method comprises administering to a subject a composition comprising a compound and an anti-cancer agent, an immunomodulating agent, an antidiabetic agent, an agent treating the central nervous system, an agent treating a metabolic disease, an agent treating a wasting disease, a gene therapy agent, an agent treating the endocrine system, vitamins, or a combination thereof. In some embodiments, musculoskeletal diseases comprise achondroplasia, acquired hyperostosis syndrome, acrocephalosyndactylia, arthritis, arthrogryposis, arthropathy, neurogenic bursitis, cartilage diseases, cleidocranial dysplasia, clubfoot, compartment syndromes, craniofacial dysostosis, craniosynostoses, dermatomyositis, Dupuytren's contracture, dwarfism, Ellis Van Creveld syndrome, enchondromatosis, eosinophilia-myalgia syndrome, exostoses, fasciitis, fatigue syndrome, fibromyalgia, fibrous dysplasia of bone, fibrous dysplasia, polyostotic, flatfoot, foot deformities, Freiberg's disease, funnel chest, Goldenhar syndrome, gout, hallux valgus, hip dislocation, hyperostosis, intervertebral disk displacement, kabuki make-up syndrome, Klippel-Feil syndrome, Langer-Giedion syndrome, Legg-Perthes disease, lordosis, mandibulofacial dysostosis, melorheostosis, mitochondrial myopathies, muscle cramp, muscle spasticity, muscular dystrophies, musculoskeletal abnormalities, musculoskeletal diseases, myositis, myositis ossificans, myotubular myopathy, osteitis deformans, osteoarthritis, osteochondritis, osteogenesis imperfecta, osteomyelitis, osteonecrosis, osteopetrosis, osteoporosis, poland syndrome, polychondritis, relapsing, polymyalgia rheumatica, polymyositis, rhabdomyolysis, rheumatic diseases, Russell silver syndrome, Scheuermann's disease, scoliosis, Sever's disease/calceneal apophysitis, spinal diseases, spinal osteophytosis, spinal stenosis, spondylitis, ankylosing, spondylolisthesis, sprengel's deformity, synovitis, tendinopathy, tennis elbow, tenosynovitis, thanatophoric dysplasia, or Tietze's syndrome.

In some embodiments, the present invention provides a method for treating, reducing the incidence, delaying the onset or progression, or reducing and/or abrogating the symptoms associated with a digestive system disease in a subject. In one embodiment, the method comprises administering to a subject a composition comprising a compound and an anti-cancer agent, an immunomodulating agent, an antidiabetic agent, an agent treating the central nervous system, an agent treating the gastrointestinal system, an anti-infective agent, an agent treating a metabolic disease, a gene therapy agent, an agent treating the endocrine system, vitamins, or a combination thereof. In some embodiments, gastrointestinal diseases comprise adenomatous polyposis coli, Alagille syndrome, anus diseases, appendicitis, barrett esophagus, biliary atresia, biliary tract diseases, Caroli disease, celiac disease, cholangitis, cholecystitis, cholelithiasis, colitis, ulcerative, Crohn's disease, deglutition disorders, duodenal ulcer, dysentery, enterocolitis, pseudomembranous, esophageal achalasia, esophageal atresia, esophagitis, exocrine pancreatic insufficiency, fatty liver, fecal incontinence, gastritis, gastritis, hypertrophic, gastroenteritis, gastroesophageal reflux, gastroparesis, hemorrhoids, hepatic vein thrombosis, hepatitis, hepatitis, chronic, hernia, diaphragmatic, hernia, hiatal, Hirschsprung disease, hypertension (HTN), portal, inflammatory bowel diseases, intestinal diseases, intestinal neoplasms, intestinal neuronal dysplasia, intestinal obstruction, irritable bowel syndrome, lactose intolerance, liver cirrhosis, liver diseases, meckel diverticulum, pancreatic diseases, pancreatic neoplasms, pancreatitis, peptic ulcer, Peutz-Jeghers syndrome, proctitis, rectal diseases, rectal prolapse, short bowel syndrome, tracheoesophageal fistula, whipple disease, or Zollinger-Ellison syndrome.

In some embodiments, the present invention provides a method for treating, reducing the incidence, delaying the onset or progression, or reducing and/or abrogating the symptoms associated with a stomatognathic disease in a subject. In one embodiment, the method comprises administering to a subject a composition comprising a compound and an anti-cancer agent, an immunomodulating agent, an anti-infective agent, an agent treating a wasting disease, a gene therapy agent, an agent treating the endocrine system, vitamins, or a combination thereof. In some embodiments, stomatognathic diseases comprise ankyloglossia, bruxism, burning mouth syndrome, cheilitis, cherubism, cleft lip, dentigerous cyst, gingivitis, glossitis, benign migratory, herpes labialis, Ludwig's angina, macroglossia, Melkersson-Rosenthal syndrome, periodontal diseases, Pierre Robin syndrome, prognathism, salivary gland diseases, sialorrhea, stomatitis, aphthous, temporomandibular joint disorders, temporomandibular joint dysfunction syndrome, or xerostomia.

In some embodiments, the present invention provides a method for treating, reducing the incidence, delaying the onset or progression, or reducing and/or abrogating the symptoms associated with a respiratory tract disease in a subject. In one embodiment, the method comprises administering to a subject a composition comprising a compound and an anti-cancer agent, an immunomodulating agent, an agent treating the central nervous system, an agent treating the cardiovascular system, an anti-infective agent, an agent treating a wasting disease, a gene therapy agent, an agent treating the endocrine system, vitamins, or a combination thereof. In some embodiments, respiratory tract diseases comprise airway obstruction, apnea, asbestosis, asthma, asthma-induced muscle weakness or bone weakness, atelectasis, berylliosis, bronchial diseases, bronchiectasis, bronchiolitis, bronchiolitis obliterans organizing pneumonia, bronchitis, bronchopulmonary dysplasia, chronic obstructive pulmonary disease (COPD), common cold, cough, empyema, pleural, epiglottitis, glucocorticoid (GC)-induced myopathy or osteopenia hemoptysis, hypertension, pulmonary, hyperventilation, kartagener syndrome, lung abscess, lung diseases, meconium aspiration syndrome, pleural effusion, pleurisy, pneumonia, pneumothorax, pulmonary alveolar proteinosis, pulmonary disease, chronic obstructive, pulmonary edema, pulmonary embolism, pulmonary emphysema, pulmonary fibrosis, respiratory distress syndrome, newborn-respiratory hypersensitivity, respiratory tract infections, rhinoscleroma, scimitar syndrome, severe acute respiratory syndrome, silicosis, sleep apnea, central stridor, tracheal stenosis, decreased muscle mass or bone mass due to asthma, wasting in chronic obstructive pulmonary disease (COPD), Wegener's granulomatosis, or whooping cough.

Lung diseases include diseases such as chronic obstructive pulmonary disease (COPD), cystic fibrosis and interstitial lung disease. A common characteristic of these diseases is the decreased capacity of lungs to exchange oxygen and carbon dioxide. This causes the patient to breathe faster which increases the energy the patient must expend in order to obtain enough oxygen. Various respiratory syndromes interfere with the ability of the lungs to adequately exchange gas with the atmosphere. These respiratory problems are a major cause of mortality and morbidity.

In another embodiment, the invention provides a method of treating, preventing, inhibiting reducing the incidence of lung diseases, disorders or conditions in a subject, comprising administering a pharmaceutical composition comprising a SERM of formula (I)-(XI) or its prodrug, analog, isomer, metabolite, derivative, pharmaceutically acceptable salt, pharmaceutical product, polymorph, crystal, impurity, N-oxide, ester, hydrate or any combination thereof, thereby treating, preventing, inhibiting reducing the incidence of inflammatory conditions in a subject.

In some embodiments, the lung diseases, disorders or conditions may comprise asthma, chronic obstructive pulmonary disease (COPD), cystic fibrosis, hemorrhagic shock, lung cancer or pleurisy.

In some embodiments, the present invention provides a method for treating, reducing the incidence, delaying the onset or progression, or reducing and/or abrogating the symptoms associated with an otorhinolaryngologic disease in a subject. In one embodiment, the method comprises administering to a subject a composition comprising a compound and an anti-cancer agent, an immunomodulating agent, an anti-infective agent, an agent treating a wasting disease, a gene therapy agent, an agent treating the endocrine system, vitamins, or a combination thereof. In some embodiments, otorhinolaryngologic diseases comprise cholesteatoma, middle ear, croup, deafness, epistaxis, hearing loss, hyperacusis, labyrinthitis, laryngitis, laryngomalacia, laryngostenosis, mastoiditis, Meniere's disease, nasal obstruction, nasal polyps, otitis, otorhinolaryngologic diseases, otosclerosis, pharyngitis, presbycusis, retropharyngeal abscess, rhinitis, sinusitis, tinnitus, tonsillitis, tympanic membrane perforation, vestibular neuronitis, vocal cord paralysis, or voice disorders.

In some embodiments, the present invention provides a method for treating, reducing the incidence, delaying the onset or progression, or reducing and/or abrogating the symptoms associated with a nervous system disease in a subject. In one embodiment, the method comprises administering to a subject a composition comprising a compound and an anti-cancer agent, an immunomodulating agent, an agent treating the central nervous system, an anti-infective agent, an agent treating a metabolic disease, an agent treating a wasting disease, a gene therapy agent, an agent treating the endocrine system, vitamins, or a combination thereof. In some embodiments, nervous system diseases comprise autonomic nervous system diseases, central nervous system diseases, cranial nerve diseases, demyelinating diseases, nervous system malformations, neurologic manifestations, or neuromuscular diseases.

In some embodiments, autonomic nervous system diseases comprise causalgia, or reflex sympathetic dystrophy.

In some embodiments, central nervous system diseases comprise Alzheimer's disease, arachnoiditis, brain abscess, brain ischemia, central nervous system infections, cerebral palsy, cerebrovascular disorders, corticobasal ganglionic degeneration (CBGD), Creutzfeldt-Jakob syndrome, Dandy-Walker syndrome, dementia, encephalitis, encephalomyelitis, epilepsy, epilepsy induced hypogonadal and/or hypermetabolic state, essential tremor, Friedreich ataxia, Gerstmann-Straussler-Scheinker disease, Hallervorden-Spatz syndrome, Huntington disease, hydrocephalus, hypoxia, insomnia, ischemic attack, kuru, Landau-Kleffner syndrome, Lewy Body disease, Machado-Joseph disease, meige syndrome, meningitis, bacterial meningitis, viral, migraine disorders, movement disorders, multiple system atrophy, myelitis, olivopontocerebellar atrophies, Parkinson's disease, parkinsonian disorders, poliomyelitis, postpoliomyelitis syndrome, prion diseases, pseudotumor cerebri, Shy-Drager syndrome, spasms, infantile, spinal cord diseases, supranuclear palsy, syringomyelia, thalamic diseases, tic disorders, tourette syndrome, or uveomeningoencephalitic syndrome. In some embodiments, the central nervous system disease is cystic fibrosis induced hypogonadal state.

In some embodiments, cranial nerve diseases comprise bell palsy, cranial nerve diseases, facial hemiatrophy, facial neuralgia, glossopharyngeal nerve diseases, Moebius syndrome, or trigeminal neuralgia.

In some embodiments, central nervous system diseases comprise injuries or damage to the central nervous system (CNS). In some embodiments, injuries or damage to the CNS may be associated with muscle wasting disorders. Injuries or damage to the CNS can be, for example, caused by diseases, trauma or chemicals. Examples are central nerve injury or damage, peripheral nerve injury or damage and spinal cord injury or damage.

Studies involving patients with spinal cord injuries (SCI) have shown that central neurotransmitters may be altered after SCI causing hypothalamus-pituitary-adrenal axis dysfunction, whose disruption led to a significant decrease in testosterone and other hormone levels. SCI or other acute illness or trauma characteristically includes heightened catabolism in conjunction with the lowered anabolic activity resulting in a condition that is prone to loss of lean body tissue, which is often accompanied by disturbed nutrient utilization. The effects of the loss of lean body mass include the development of wounds and impaired healing mechanisms, further compounding the problem. Because of poor nutrition and protein combined with immobilization, patients with spinal cord injury are at high risk for bed sores.

In one embodiment, a wide variety of injuries of the CNS may be treated by the methods of the present invention. CNS injury may refer, in one embodiment, to a breakdown of the membrane of a nerve cell, or, in another embodiment, to the inability of the nerve to produce and propagate nerve impulses, or in another embodiment, to the death of the cell. An injury includes damage that directly or indirectly affects the normal functioning of the CNS. The injury may be a structural, physical, or mechanical impairment and may be caused by physical impact, as in the case of a crushing, compression, or stretching of nerve fibers. Alternatively, the cell membrane may be destroyed by or degraded by an illness, a chemical imbalance, or a physiological malfunction such as anoxia (e.g., stroke), aneurysm, or reperfusion. A CNS injury includes, for example and without limitation, damage to retinal ganglion cells, a traumatic brain injury, a stroke-related injury, a cerebral aneurism-related injury, a spinal cord injury, including monoplegia, diplegia, paraplegia, hemiplegia and quadriplegia, a neuroproliferative disorder, or neuropathic pain syndrome.

In another embodiment, the invention provides a method of treating, preventing, suppressing, inhibiting, or reducing the incidence of central nervous system (CNS) disorder, disease or condition in a mammalian subject comprising administering a compound of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof to the subject.

With injury to the spinal cord of a mammal, connections between nerves in the spinal cord are broken. Such injuries block the flow of nerve impulses for the nerve tracts affected by the injury, with a resulting impairment to both sensory and motor function. Injuries to the spinal cord may arise from compression or other contusion of the spinal cord, or a crushing or severing of the spinal cord. A severing of the spinal cord, also referred to herein as a "transection," may be a complete severing or, may be an incomplete severing of the spinal cord.

In some embodiments, the methods of treating a subject suffering form a CNS injury or, in other embodiments, spinal cord injury, may be accompanied by treatment of the subject with electrical stimulation of the injured site and the administration of a purine nucleoside, or analog thereof, for example as described in United States Patent Application Publication Number 20040214790A1.

In some embodiments, demyelinating diseases comprise adrenoleukodystrophy, alexander disease, canavan disease, demyelinating disease, diffuse cerebral sclerosis of schilder, leukodystrophy-globoid cell, leukodystrophy-metachromatic, multiple sclerosis, or neuromyelitis optica.

In some embodiments, nervous system malformations comprise Arnold-Chiari malformation, Charcot-Marie-Tooth disease, encephalocele, hereditary motor and sensory neuropathies, septo-optic dysplasia, spina bifida occulta, or spinal dysraphism.

In some embodiments, neurologic manifestations comprise agnosia, amnesia, anomia, aphasia, apraxias, back pain, Brown-Sequard syndrome, cerebellar ataxia, chorea, communication disorders, confusion, dizziness, dyslexia, dystonia, facial paralysis, fasciculation, gait disorders, neurologic-headache, hemiplegia, memory disorders, mental retardation, mutism, myoclonus, neck pain, nonverbal learning disorder, olfaction disorders, pain, paralysis, phantom limb, prosopagnosia, quadriplegia, seizures, spasm, speech disorders, synesthesia tardive dyskinesia, taste disorders, torticollis, tremor, trismus, unconsciousness, or vertigo.

In some embodiments, neuromuscular diseases comprise. amyotrophic lateral sclerosis, brachial plexus neuritis, brachial plexus neuropathies, bulbar palsy, carpal tunnel syndrome, cubital tunnel syndrome, diabetic neuropathies, dysautonomia, guillain, barre syndrome, hereditary sensory and autonomic neuropathies, miller fisher syndrome, motor neuron disease, muscular atrophy, spinal, myasthenia gravis, myopathies, structural, congenital, nerve compression syndromes, neuralgia, neuromuscular diseases, paralyses, familial periodic, peripheral nervous system diseases, poems syndrome, polyneuropathies, polyradiculopathy, refsum disease, sciatica, spinal muscular atrophies of childhood, stiff-person syndrome, thoracic outlet syndrome, or ulnar nerve compression syndromes.

In one embodiment, methods of treating a subject with a nervous system disease encompass treating any secondary conditions in the subject, which arise due to the subject having a nervous system disease, some of which are described herein.

The compounds of this invention may be useful for the treatment or amelioration of conditions affecting the neural retina. Estrogen may have neuroprotective effects in the retina (see for example Invest Ophthal Vis Sci 38:1193-1202 (1997) and Invest Ophthal Vis Sci 44(7):3155-3162 (2003)), and estrogen receptors are found in the inner retina as well as the choroid (Br J Ophthalmol 85:877-882 (2001). The NRBAs of the present invention may be useful in treating the eye for, or protecting against local ischemia or degenerative events that include, but are not limited to, macular degeneration, glaucoma, diabetic retinopathy, retinitis pigmentosa and other retinal degeneration resulting from genetic defects, trauma or environmental exposure.

In some embodiments, the present invention provides a method for treating, reducing the incidence, delaying the onset or progression, or reducing and/or abrogating the symptoms associated with an ophthalmic disease in a subject. In one embodiment, the method comprises administering to a subject a composition comprising a NRBA/SERM compound and an anti-cancer agent, an immunomodulating agent, an agent treating the cardiovascular system, an anti-infective agent, an agent treating a wasting disease, a gene therapy agent, an agent treating the endocrine system, vitamins, or a combination thereof. In some embodiments ophthalmic disease comprise acute zonal occult outer retinopathy, abnormal color vision, Adie syndrome, albinism, ocular-amaurosis, fugax, amblyopia, aniridia, anisocoria, anterior ischemic optic neuropathy, anophthalmos, aphakia, astheno-pia astigmatism, autoimmune disease blepharitis, blepharoptosis, blepharospasm, blindness, cataract, senile cataract central chorioretinopathy chalazion, chorioretinitis, chorioretinal hemorrhage, choroideremia, coloboma, color vision defects, conjunctivitis, corneal diseases, corneal dystrophies, corneal edema, corneal ulcer, corneal opacity, corneal erosion, corneal endothelial cell degeneration and dystrophy or loss of endothelial cell, corneal dystrophy or degeneration, detachment of corneal epithelium, epidemic keratoconjunctivitis, chalazion, central nerve diseases, central retinal artery or vein occlusion, arteriosclerosis of retinal artery, photopsia, diabetic retinopathy, chorioretinal atrophy, diabetic retinopathy, diplopia, distichiasis, dry eye syndromes, Duane retraction syndrome, ectropion, entropion, esotropia, exfoliation syndrome, exotropia, eye hemorrhage, eye neoplasms, eyelid diseases, floaters, general fibrosis syndrome, glaucoma, high tension glaucoma, normal tension glaucoma, gyrate atrophy, hemianopsia, Hermanski-Pudlak syndrome, hordeolum, Horner syndrome, hysteria hyperopia, hyphema, iridocyclitis iritis, Kearns-Sayer syndrome, keratitis, keratoconus, lacrimal apparatus diseases, lacrimal duct obstruction, lens diseases, lowering in dynamic visual activity, macular degeneration, macular hole microphthalmos, myopia, nystagmus, narrowing of visual field due to various kinds of diseases pathologic, ocular motility disorders, oculomotor nerve diseases, ophthalmoplegia, optic atrophies, optic nerve diseases, optic neuritis, optic neuropathy, optic nerve atrophy orbital cellulitis, papilledema, peters anomaly, presbyopia, psychosis pterygium, pupil disorders, refractive errors, retinal detachment, retinal diseases, retinal vein occlusion, retinal and choroidal neovascular diseases, cataract due to removal of ovary, cataract due to TGFβ, macular fibrosis, macular epiretinal membrane, refractive error retinal tear, retinitis proliferans, pigmentary retinal degeneration retinitis pigmentosa, retinopathy of prematurity, retinoschisis, scleritis, senile macular degeneration scotoma, strabismus, Thygeson's superficial punctate keratitis, trachoma, uveitis, white dot syndrome, vision disorders, or vitreous disorders, diseases due to cerebral pituitary gland disorder and imbalance of hormones, diseases due to gene disorder and diseases due to immune disorder, the method comprising administering a NRBA or SERM of formula (I)-(XI) or its prodrug, analog, isomer, metabolite, derivative, pharmaceutically acceptable salt, pharmaceutical product, polymorph, crystal, impurity, N-oxide, ester, hydrate or any combination thereof to the subject.

In some embodiments ER-β agonists are useful in treating, reducing the incidence, delaying the onset or progression, or reducing and/or abrogating the symptoms associated with an ophthalmic disease in a subject. In another embodiment, ER-β agonist of this invention is compound 3a, listed in Table 1. In another embodiment, ER-β agonist of this invention is compound 3d, listed in Table 1. In another embodiment, ER-β agonist of this invention is compound 3e, listed in Table 1. In another embodiment, ER-β agonist of this invention is compound 3l, listed in Table 1. In another embodiment, ER-β agonist of this invention is compound 3g, listed in Table 1. In another embodiment, ER-β agonist of this invention is compound 3j, listed in Table 1. In another embodiment, ER-β agonist of this invention is compound 3i, listed in Table 1, or any combination thereof. In another embodiment, ER-β agonist of this invention is compound 4a, listed in Table 1. In another embodiment, ER-β agonist of this invention is compound 4h, listed in Table 1. In another embodiment, ER-β agonist of this invention is compound 4u, listed in Table 1. In another embodiment, ER-β agonist of this invention is compound 10o, listed in Table 1. In another embodiment, ER-β agonist of this invention is compound 10d, listed in Table 1. In another embodiment, ER-β agonist of this invention is compound 10f, listed in Table 1. In another embodiment, ER-β agonist of this invention is compound 10l, listed in Table 1. In another embodiment, ER-β agonist of this invention is compound 10w, listed in Table 1, or any combination thereof.

In another embodiment, the methods of treating eye diseases comprise administering a composition comprising the compounds of this invention to the subject, wherein the composition is in the form of eye drops, eye wash, ointments, conjunctival injections, or contact lens adsorbents. In another embodiment, the methods of treating eye diseases comprises administering a composition comprising the compounds of this invention in the form of a tablet, capsule, liquid, syrup, injection, hap, ointment, eye drops, suppository, and the like, and administered orally, or non-orally such as injection, locally such as dropping to eye, etc. The effective ingredient may be vaporized and inhaled, for example through the nose, mouth or trachea.

In some embodiment, the methods of treating eye diseases comprise administering a composition comprising the compounds of this invention and any other compound, which is useful in treating the indicated conditions, as known in the art.

In some embodiment, eye drops and eye wash comprise water-solubilized compounds (I)-(XI) of this invention, which are, in one embodiment, dissolved in sterilized distilled water, BSS Plus, and/or physiological saline. In another embodiment, additives are added comprising excipients, carriers, pH controllers, isotonic agents, preservatives, glutathione, glucose, various kind of salt(s), stabilizers, refrigerants, antioxidants, antiseptic agents, or any combination thereof. In another embodiment, the eye drops and eye wash comprise hydroxypropylmethyl cellulose, carboxymethyl cellulose or its sodium salt, polypyrrolidone, polyvinylpyrrolidone (this is added and heated), or any combination thereof.

In some embodiments, the compounds of this invention have low solubility in water. In one embodiment, the compounds may be water solubilized by using cyclodextrin. In another embodiment α-cyclodextrin is used. In another embodiment β cyclodextrin is used. In another embodiment, δ cyclodextrin is used. In another embodiment, hydroxyalkylated β cyclodextrin is used.

In some embodiments, the present invention provides a method for treating, reducing the incidence, delaying the onset or progression, or reducing and/or abrogating the symptoms associated with a dermatological disorder in a subject. In one embodiment, the method comprises administering to a subject a composition comprising a compound and anti-cancer agent, an immunomodulating agent, an agent treating a dermatological disorder, an anti-infective agent, a gene therapy agent, an agent treating the endocrine system, vitamins, or a combination thereof. In some embodiments, dermatological disorders comprise acne, actinic keratosis, alopecia, androgenic alopecia, alopecia areata, alopecia secondary to chemotherapy, alopecia secondary to radiation therapy, alopecia induced by scarring, alopecia induced by stress, angioma, athlete's foot, aquagenic pruritus, atopic dermatitis, baldness, premature baldness, male pattern baldness, androgenic baldness, basal cell carcinoma, burns, bed sore, Behcet's disease, blepharitis, boil, Bowen's disease, bullous pemphigoid, canker sore, carbuncles, cellulitis, chloracne, chronic dermatitis of the hands and feet, dyshidrosis, cold sores, contact dermatitis, creeping eruption, dandruff, dermatitis, dermatitis herpetiformis, dermatofibroma, diaper rash, eczema, epidermolysis bullosa, erysipelas, erythroderma, friction blister, genital wart, hidradenitis, suppurativa, hives, hyperhidrosis, ichthyosis, impetigo, jock itch, Kaposi's sarcoma, keloid, keratoacanthoma, keratosis pilaris, lice infection, lichen planus, lichen simplex chronicus, lipoma, lymphadenitis, malignant melanoma, melasma, miliaria, molluscum contagiosum, nummular dermatitis, paget's disease of the nipple, pediculosis, pemphigus, perioral dermatitis, photoallergy, photosensitivity, pityriasis rosea, pityriasis rubra pilaris, psoriasis, raynaud's disease, ring worm, rosacea, scabies, scleroderma, sebaceous cyst, seborrheic keratosis, seborrhoeic dermatitis, shingles, skin cancer, skin tags, spider veins, squamous cell carcinoma, stasis dermatitis, tick bite, tinea barbae, tinea capitis, tinea corporis, tinea cruris, tinea pedis, tinea unguium, tinea versicolor, tinea, tungiasis, vitiligo, or warts.

In one embodiment, the dermatological disorder is a wound or a burn. In some embodiments, wounds and/or ulcers are found protruding from the skin or on a mucosal surface or as a result of an infarction in an organ. A wound may be a result of a soft tissue defect or a lesion or of an underlying condition. In one embodiment, the term "wound" denotes a bodily injury with disruption of the normal integrity of tissue structures. The term is also intended to encompass the terms "sore", "lesion", "necrosis" and "ulcer". In one embodiment, the term "sore" refers to any lesion of the skin or mucous membranes and the term "ulcer" refers to a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions. All of these are encompassed by the term "wound", which denotes any wound at any particular stage in the healing process including the stage before any healing has initiated or even before a specific wound like a surgical incision is made (prophylactic treatment).

Examples of wounds which can be prevented and/or treated in accordance with the present invention are, e.g., aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores etc. Examples of ulcers are, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g. caused by gonorrhoea (including urethritis, endocervicitis and proctitis). Conditions related to wounds or sores which may be successfully treated according to the invention are burns, anthrax, tetanus, gas gangrene, scalatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore as mentioned above, in the present context the term "wounds" encompasses the term "ulcer", "lesion", "sore" and "infarction", and the terms are indiscriminately used unless otherwise indicated.

The kinds of wounds to be treated according to the invention include also i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is as i) small tissue loss due to surgical incisions, minor abrasions and minor bites, or as ii) significant tissue loss. The latter group includes ischemic ulcers, pressure sores, fistulae, lacerations, severe bites, thermal burns and donor site wounds (in soft and hard tissues) and infarctions.

In other aspects of the invention, the wound to be prevented and/or treated is selected from the group consisting of aseptic wounds, infarctions, contused wounds, incised wounds, lacerated wounds, non-penetrating wounds, open wounds, penetrating wounds, perforating wounds, puncture wounds, septic wounds and subcutaneous wounds.

Other wounds which are of importance in connection with the present invention are wounds like ischemic ulcers, pressure sores, fistulae, severe bites, thermal burns and donor site wounds.

In one embodiment, the compound as described herein is useful in wound healing as an adjunct to physical therapy/rehabilitation, as an anabolic agent. In another embodiment, the compound as described herein is useful in promoting healing of anterior cruciate ligament (ACL) or medial cruciate ligament (MCL) injuries, or accelerating recovery after ACL or MCL surgery. In another embodiment, the compound as described herein is useful in enhancing athletic performance. In another embodiment, the compound as described herein is useful in treating burns. In another embodiment, the compound as described herein is useful in stimulating cartilage regrowth. In another embodiment, the compound as described herein is useful in preventing, treating, or reversing of catabolism associated with prolonged critical illness, pulmonary dysfunction, ventilator dependency, aging, AIDS, trauma, surgery, congestive heart failure, cardiac myopathy, burns, cancer, COPD. In another embodiment, the compound as described herein is useful in preventing or reversing protein catabolism due to trauma. In another embodiment, the compound as described herein is useful as a) adjunct to cauterization therapy (laser or radio) as is used in surgery to promote wound healing, b) adjunct to cryotherapy to promote wound healing, c) adjunct to chemotherapy to prevent side effects such as alopecia, hypogonadism, muscle wasting, osteopenia, osteoporosis, sarcopenia, increased LDL, TG or total cholesterol, decreased HDL. In another embodiment, the compound as described herein is useful in chronic catabolic state (coma, wasting conditions, starvation, eating disorders); concomitant bone fracture and muscle damage;

critical illness in which muscle or bone wasting are apparent; and/or connective tissue diseases and disorders.

Ischemic ulcers and pressure sores are wounds, which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

In some embodiments, burns are associated with reduced testosterone levels, and hypgonadism is associated with delayed wound healing. In one embodiment, the methods of this invention, provide for treating a subject suffering from a wound or a burn.

In some embodiments, the present invention provides a method for promoting healing of anterior cruciate ligament (ACL) or medial cruciate ligament (MCL) injuries, or accelerating recovery after ACL or MCL surgery.

In some embodiments, the present invention provides a method for treating, reducing the incidence, delaying the onset or progression, or reducing and/or abrogating the symptoms associated with an endocrine disorder in a subject. In one embodiment, the method comprises administering to a subject a composition comprising a compound and anti-cancer agent, an immunomodulating agent, an antidiabetic agent, an agent treating the cardiovascular system, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, endocrine disorders comprise acromegaly, Addison disease, adrenal gland diseases, adrenal hyperplasia, congenital, androgen-insensitivity syndrome, congenital hypothyroidism, Cushing syndrome, diabetes insipidus, diabetes mellitus, diabetes mellitus-type 1, diabetes mellitus-type 2, diabetic, ketoacidosis, empty Sella syndrome, endocrine gland neoplasms, endocrine system diseases, gigantism, gonadal disorders, graves disease, hermaphroditism, hyperaldosteronism, hyperglycemic hyperosmolar nonketotic coma, hyperpituitarism, hyperprolactinemia, hyperthyroidism, hypogonadism, hypopituitarism, hypothyroidism, Kallmann syndrome, Nelson syndrome, parathyroid diseases, pituitary diseases, polyendocrinopathies, autoimmune, puberty, delayed, puberty, precocious, renal osteodystrophy, thyroid diseases, thyroid hormone resistance syndrome, thyroid neoplasms, thyroid nodule, thyroiditis, thyroiditis, autoimmune, thyroiditis, subacute, or Wolfram syndrome.

In one embodiment, "Hypogonadism" is a condition resulting from or characterised by abnormally decreased functional activity of the gonads, with retardation of growth and sexual development.

In some embodiments, the present invention provides a method for treating, reducing the incidence, delaying the onset or progression, or reducing and/or abrogating the symptoms associated with urogenital disease and/or fertility in a subject. In one embodiment, the method comprises administering to a subject a composition comprising a compound of this invention and anti-cancer agent, an immunomodulating agent, an anti-infective agent, an agent treating the kidney, gene therapy agent, an agent treating the endocrine system, vitamins, or a combination thereof. In some embodiments, urogenital diseases and/or fertility diseases comprise abortion, spontaneous-adhesions-pelvic, candidiasis, vulvovaginal, depression-postpartum, diabetes, gestational, dyspareunia, dystocia, eclampsia, endometriosis, fetal death, fetal growth retardation, fetal membranes, premature rupture, genital diseases, female, genital neoplasms, female, hydatidiform mole, hyperemesis gravidarum, infertility, ovarian cysts, ovarian torsion, pelvic inflammatory disease, placenta diseases, placental insufficiency, polycystic ovary syndrome, polyhydramnios, postpartum hemorrhage, pregnancy complications, pregnancy, ectopic, pruritus vulvae, puerperal disorders, puerperal infection, salpingitis, trophoblastic neoplasms, uterine cervix incompetence, uterine inversion, uterine prolapse, vaginal diseases, vulvar diseases, vulvar lichen sclerosis.

In some embodiments, the present invention provides a method for treating, reducing the incidence, delaying the onset or progression, or reducing and/or abrogating the symptoms associated with hemic and/or lymphatic disease in a subject. In one embodiment, the method comprises administering to a subject a composition comprising a compound of this invention and an anti-cancer agent, an immunomodulating agent, an antidiabetic agent, an agent treating the cardiovascular system, an anti-infective agent, an agent treating the liver, an agent treating the kidney, an agent treating a metabolic disease, a gene therapy agent, an agent treating the endocrine system, vitamins, or a combination thereof. In some embodiments, hemic and/or lymphatic diseases comprise afibrinogenemia, anemia, aplastic anemia, hemolytic anemia, congenital nonspherocytic anemia, megaloblastic anemia, pernicious anemia, sickle cell anemia, renal anemia, angiolymphoid hyperplasia with eosinophilia, antithrombin III deficiency, Bernard-Soulier syndrome, blood coagulation disorders, blood platelet disorders, blue rubber bleb nevus syndrome, Chediak-Higashi syndrome, cryoglobulinemia, disseminated intravascular coagulation, eosinophilia, Erdheim-Chester disease, erythroblastosis, fetal, evans syndrome, factor V deficiency, factor VII deficiency, factor X deficiency, factor XI deficiency, factor XII deficiency, fanconi anemia, giant lymph node hyperplasia, hematologic diseases, hemoglobinopathies, hemoglobinuria, paroxysmal, hemophilia a, hemophilia b, hemorrhagic disease of newborn, histiocytosis, histiocytosis, langerhans-cell, histiocytosis, non-langerhans-cell, job's syndrome, leukopenia, lymphadenitis, lymphangioleiomyomatosis, lymphedema, methemoglobinemia, myelodysplastic syndromes, myelofibrosis, myeloid metaplasia, myeloproliferative disorders, neutropenia, paraproteinemias, platelet storage pool deficiency, polycythemia vera, protein c deficiency, protein s deficiency, purpura, thrombocytopenic, purpura, thrombotic thrombocytopenic, RH-isoimmunization, sarcoidosis, sarcoidosis, spherocytosis, splenic rupture, thalassemia, thrombasthenia, thrombocytopenia, Waldenstrom macroglobulinemia, or Von Willebrand disease.

In some embodiments, the present invention provides a method for treating, reducing the incidence, delaying the onset or progression, or reducing and/or abrogating the symptoms associated with a congenital, hereditary, or neonatal disease in a subject. In one embodiment, the method comprises administering to a subject a composition comprising a compound of this invention and anti-cancer agent, an immunomodulating agent, an antidiabetic agent, an agent treating the cardiovascular system, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, congenital, hereditary, and neonatal diseases comprise Aicardi syndrome, amniotic band syndrome, anencephaly, Angelman syndrome, ataxia telangiectasia, Bannayan-Zonana syndrome, Barth syndrome, basal cell nevus syndrome, Beckwith-Wiedemann syndrome, bloom syndrome, branchio-oto-renal syndrome, cat eye syndrome, cerebral gigantism-charge syndrome, chromosome 16 abnormalities, chromosome 18 abnormalities, chromosome 20 abnormalities, chromosome 22 abnormalities, Costello syndrome, cri-du-chat syndrome, Currarino syndrome, cystic fibrosis, de-Lange syndrome, distal trisomy 10q, down syndrome, ectodermal dysplasia, fetal alcohol syndrome, fetal diseases, fetofetal transfusion, fragile x syndrome, Freeman-Sheldon syndrome, gastroschisis, genetic diseases, inborn, hernia, umbilical, holoprosencephaly, incontinentia pigmenti, Ivemark syndrome, Jacobsen syndrome, jaundice, Klinefelter syndrome, Larsen syndrome, Laurence-moon syndrome, lissencephaly, microcephaly, monosomy 9p, nail-patella syndrome, neurofibromatoses, neuronal ceroid-lipofuscinosis, Noonan syndrome, ochoa syndrome (urofacial syndrome, hydronephrosis with peculiar facial expression), oculocerebrorenal syndrome, Pallister-Killian syndrome, Prader-Willi syndrome, proteus syndrome, prune belly syndrome, Rett syndrome, Robinow syndrome, Rubinstein-Taybi syndrome, schizencephaly, situs inversus, Smith-Lemli-Opitz syndrome, Smith-Magenis syndrome, Sturge-Weber syndrome, syphilis, congenital, trichothiodystrophy, triple-x females, trisomy 13 (Patau syndrome), trisomy 9, turner syndrome, twins, conjoined, Usher syndrome, Waardenburg's syndrome, Werner syndrome, or Wolf-Hirschhorn syndrome.

In some embodiments, the present invention provides a method for treating, reducing the incidence, delaying the onset or progression, or reducing and/or abrogating the symptoms associated with a connective tissue disease in a subject. In one embodiment, the method comprises administering to a subject a composition comprising a compound of this invention and anti-cancer agent, an immunomodulating agent, an agent treating a dermatological disorder, an anti-infective agent, an agent treating a metabolic disease, an agent treating a wasting disease, a gene therapy agent, an agent treating the endocrine system, vitamins, or a combination thereof. In some embodiments, connective tissue diseases comprise ankylosing spondylitis, Ehlers-Danlos syndrome, Henoch-Schonlein purpura, Kawasaki disease, Marfan syndrome, polyarteritis nodosa, polymyositis, psoriatic arthritis, reactive arthritis, rheumatoid arthritis, scleroderma, Sjogren's syndrome, xerophthalmia, Still's disease, systemic lupus erythematosus, Takayasu disease, or Wegener's granulomatosis.

In some embodiments, the present invention provides a method for treating, reducing the incidence, delaying the onset or progression, or reducing and/or abrogating the symptoms associated with a metabolic disease in a subject. In one embodiment, the method comprises administering to a subject a composition comprising a compound of this invention and antidiabetic agent, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, metabolic diseases comprise acid-base imbalance, acidosis, alkalosis, alkaptonuria, alpha-mannosidosis, amino acid metabolism inborn errors, amyloidosis, iron-deficiency anemia, ascorbic acid deficiency, avitaminosis, beriberi, biotinidase deficiency, carbohydrate-deficient glycoprotein syndrome, carnitine disorders, cystinosis, cystinuria, dehydration, fabry disease, fatty acid oxidation disorders, fucosidosis, galactosemias, Gaucher disease, Gilbert disease, glucosephosphate dehydrogenase deficiency, glutaric acidemia, glycogen storage disease, Hartnup disease, hemochromatosis, hemosiderosis, hepatolenticular degeneration, histidinemia, homocystinuria, hyperbilirubinemia, hypercalcemia, hyperinsulinism, hyperkalemia, hyperlipidemia, hyperoxaluria, hypervitaminosis A, hypocalcemia, hypoglycemia, hypokalemia, hyponatremia, hypophosphatasia, insulin resistance, iodine deficiency, iron overload, jaundice, chronic idiopathic, leigh disease, lesch-nyhan syndrome, leucine metabolism disorders, lysosomal storage diseases, magnesium deficiency, maple syrup urine disease, Melas syndrome, Menkes kinky hair syndrome, metabolic diseases, metabolic syndrome x, metabolism, inborn errors, mitochondrial diseases, mucolipidoses, mucopolysaccharidoses, Niemann-Pick diseases, obesity, ornithine carbamoyltransferase deficiency disease, osteomalacia, pellagra, peroxisomal disorders, phenylketonurias, porphyria, erythropoietic, porphyrias, progeria, pseudo, gaucher disease, refsum disease, Reye syndrome, rickets, Sandhoff disease, starvation, tangier disease, Tay-Sachs disease, tetrahydrobiopterin deficiency, trimethylaminuria, tyrosinemias, urea cycle disorders, water-electrolyte imbalance, Wernicke encephalopathy, vitamin A deficiency, vitamin B12 deficiency, vitamin B deficiency, Wolman disease, or Zellweger syndrome.

In some embodiments, the present invention provides a method for treating, reducing the incidence, delaying the onset or progression, or reducing and/or abrogating the symptoms associated with a disorder of environmental origin in a subject. In one embodiment, the method comprises administering to a subject a composition comprising a compound of this invention and anti-cancer agent, an immunomodulating agent, an antidiabetic agent, an agent treating the cardiovascular system, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, disorders of environmental origin comprise barotrauma, bites and stings, brain concussion, burns, central cord syndrome, craniocerebral trauma, electric injuries, fractures, bone, frostbite, heat stress disorders, motion sickness, occupational diseases, poisoning, shaken baby syndrome, shoulder injuries, space motion sickness, spinal cord injuries, tick paralysis, or wounds (penetrating and non-penetrating).

In some embodiments, the present invention provides a method for treating, reducing the incidence, delaying the onset or progression, or reducing and/or abrogating the symptoms associated with a behavior mechanism in a subject. In one embodiment, the method comprises administering to a subject a composition comprising a compound of this invention and an agent treating the cardiovascular system, an agent treating the central nervous system, a gene therapy agent, an agent treating the endocrine system, vitamins, or a combination thereof. In some embodiments, behavior mechanisms comprise aggression, attitude to death, codependency, self-injurious behavior, sexual behavior, or social behavior.

In some embodiments, the present invention provides a method for treating, reducing the incidence, delaying the onset or progression, or reducing and/or abrogating the symptoms associated with a mental disorder in a subject. In one embodiment, the method comprises administering to a subject a composition comprising a compound of this invention and an agent treating the central nervous system, a gene therapy agent, an agent treating the endocrine system, vitamins, or a combination thereof. In some embodiments, mental disorders comprise Asperger syndrome, attention deficit disorder with hyperactivity, autistic disorder, bipolar disorder, borderline personality disorder, capgras syndrome, child behavior disorders, combat disorders, cyclothymic disorder, dependent personality disorder, depressive disorder, dissociative disorders, dysthymic disorder, eating disorders, firesetting behavior, hypochondriasis, impulse control disorders, Kleine-Levin syndrome, mental disorders, mental disorders diagnosed in childhood, multiple personality disorder, Munchausen syndrome, Munchhausen syndrome, narcissistic personality disorder, narcolepsy, obsessive-compulsive disorder, paraphilias, phobic disorders, psychotic disorders, restless legs syndrome, schizophrenia, seasonal affective disorder, sexual and gender disorders, sexual dysfunctions, psychological, sleep disorders, somatoform disorders, stress disorders, post-traumatic, substance-related disorders, suicidal behavior, or trichotillomania.

In one embodiment, "depression" refers to an illness that involves the body, mood and thoughts that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

In one embodiment, "cognition" refers to the process of knowing, specifically the process of being aware, knowing, thinking, learning and judging. Cognition is related to the fields of psychology, linguistics, computer science, neuroscience, mathematics, ethology and philosophy. In one embodiment, "mood" refers to a temper or state of the mind As contemplated herein, alterations mean any change for the positive or negative, in cognition and/or mood.

In some embodiments, the present invention provides a method for treating, reducing the incidence, delaying the onset or progression, or reducing and/or abrogating the symptoms associated with a liver disease in a subject. In one embodiment, the method comprises administering to a subject a composition comprising a compound of this invention and anti-cancer agent, an immunomodulating agent, an agent treating the gastrointestinal system, an anti-infective agent, an agent treating the liver, an agent treating a metabolic disease, an agent treating a wasting disease, a gene therapy agent, an agent treating the endocrine system, vitamins, or a combination thereof. In some embodiments, liver diseases comprise liver cancer, primary biliary cirrhosis, autoimmune hepatitis, chronic liver disease, cirrhosis of the liver, hepatitis, viral hepatitis (hepatitis a, hepatitis b, chronic hepatitis b, hepatitis c, chronic hepatitis c, hepatitis d, hepatitis e, hepatitis x), liver failure, jaundice, neonatal jaundice, hepatoma, liver cancer, liver abscess, alcoholic liver disease, hemochromatosis, Wilson's disease, portal hypertension, primary sclerosing cholangitis, sarcoidosis, tapeworms, alveolar hydatid disease, fascioliasis, schistosomiasis, gaucher disease, Zellweger syndrome, alcoholism, food poisoning, pneumococcal pneumonia' or *vibrio vulnificus*.

In some embodiments, the present invention provides a method for treating, reducing the incidence, delaying the onset or progression, or reducing and/or abrogating the symptoms associated with a kidney disease in a subject. In one embodiment, the method comprises administering to a subject a composition comprising a compound of this invention and anti-cancer agent, an immunomodulating agent, an antidiabetic agent, an agent treating the gastrointestinal system, an anti-infective agent, an agent treating the kidney, an agent treating a metabolic disease, a gene therapy agent, an agent treating the endocrine system, vitamins, or a combination thereof. In some embodiments, kidney diseases comprise acromegaly, acute renal failure (ARF) amyloidosis, autosomal dominant polycystic kidney disease, kidney stones, kidney cysts, autosomal recessive polycystic kidney disease, chronic renal failure (CRF), chronic renal disease, coffin-Lowry syndrome, cor pulmonale, cryoglobulinemia, diabetic nephropathy, dyslipidemia, Gaucher disease, glomerulonephritis, goodpasture syndrome, hemolytic uremic syndrome, hepatitis, kidney cancer, kidney stones, leukemia, lipoproteinemia, lupus, multiple myeloma, nephritis, polyartekidney cysts, post streptococcal glomerulonephritis, glomerulonephritis, kidney pain, preeclampsia, renal tuberculosis, pyelonephritis, renal tubular acidosis kidney disease, streptococcal toxic shock syndrome, thromboembolism, toxoplasmosis, urinary tract infections, vesicoureteral reflux, or williams syndrome.

In one embodiment, the kidney disease or disorder is acute, or in another embodiment, chronic. In one embodiment, clinical indications of a kidney disease or disorder, wherein the methods of treatment may be useful include urinary casts, measured GFR, or other markers of renal function.

In one embodiment, the methods of this invention are useful in subjects predisposed to kidney diseases or disorders. In one embodiment, the phrase "predisposed to a kidney disease or disorder" with respect to a subject is synonymous with the phrase "subject at risk", and includes a subject at risk of acute or chronic renal failure, or at risk of the need for renal replacement therapy, if the subject is reasonably expected to suffer a progressive loss of renal function associated with progressive loss of functioning nephron units. Whether a particular subject is at risk is a determination which may routinely be made by one of ordinary skill in the relevant medical or veterinary art.

In one embodiment, subjects with kidney disease, in particular male subjects with end-stage renal disease (ESRD) suffer from hypogonadism, with some having concomitant moderate to severe protein-energy malnutrition (PEM), which leads to higher required doses of EPO, lower QOL scores, and higher mortality. Many have other symptoms associated with hypogonadism, including fatigue, lack of apetite, muscle weakness, etc. In some embodiments, the treatment methods of this invention are useful in treating symptoms associated with hypogonadism, brought about in the subject by androgen deficiency in a female (ADIF); androgen deficiency in aging male (ADAM) to include fatigue, depression, decreased libido, erectile dysfunction, decreased cognition, decreased mood; androgen insufficiency (male or female), androgen deficiency (male or female).

In one embodiment, diabetic nephropathy is a complication of diabetes that evolves early, typically before clinical diagnosis of diabetes is made. The earliest clinical evidence of nephropathy is the appearance of low but abnormal levels (>30 mg/day or 20 µg/min) of albumin in the urine (microalbuminuria), followed by albuminuria (>300 mg/24 h or 200 µg/min) that develops over a period of 10-15 years. In patients with type 1 diabetes, diabetic hypertension typically becomes manifest early on, by the time that patients develop microalbuminuria. Once overt nephropathy occurs, the glomerular filtration rate (GFR) falls over a course of times, which may be several years, resulting in End Stage Renal Disease (ESRD) in diabetic individuals.

Hypertension is another comorbid factor for renal disease. In some embodiments, treatment of renal disease according to the present invention may comprise concomitant treatment with a compound of this invention and an agent which treats hypertension.

In some embodiments, the present invention provides a method for treating, reducing the incidence, delaying the onset or progression, or reducing and/or abrogating the symptoms associated with a wasting disease in a subject. In one embodiment, the method comprises administering to a subject a composition comprising a compound of this invention and anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, vitamins, or a combination thereof. In some embodiments, wasting diseases comprise muscle injury, bed rest, immobility, nerve injury, neuropathy, diabetic neuropathy, alcoholic neuropathy, subacute combined degeneration of the spinal cord, diabetes, rheumatoid arthritis, motor neurone diseases, Duchenne muscular dystrophy, carpal tunnel syndrome, chronic infection, tuberculosis, Addison's disease, adult sma, limb muscle atrophy, alcoholic neuropathy, anorexia, anorexia nervosa, anorexia associated with cachexia, anorexia associated with aging, back tumour, dermatomyositis, hip cancer, inclusion body myositis, incontinentia pigmenti, intercostal neuralgia, juvenile rheumatoid arthritis, Legg-Calve-Perthes disease, muscle atrophy, multifocal motor neuropathy, nephrotic syndrome, osteogenesis imperfecta, post-polio syndrome, rib tumor, spinal muscular atrophy, reflex sympathetic dystrophy syndrome, or Tay-Sachs.

A wasting condition or disorder is defined herein as a condition or disorder that is characterized, at least in part, by an abnormal, progressive loss of body, organ or tissue mass. A wasting condition can occur as a result of a pathology such as, for example, cancer, or it can be due to a physiologic or metabolic state, such as disuse deconditioning that can occur, for example, due to prolonged bed rest or when a limb is immobilized, such as in a cast, or with the occurrence of multiple wounds, including, for example, amputation, as occurs in diabetics, and other conditions, as will be appreciated by one skilled in the art. A wasting condition can also be age associated. The loss of body mass that occurs during a wasting condition can be characterized by a loss of total body weight, or a loss of organ weight such as a loss of bone or muscle mass due to a decrease in tissue protein.

In one embodiment, the terms "muscle wasting" or "muscular wasting", refer to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of pathology, disease, condition or disorders, including disorders for treatment via the methods of this invention, such as, for example, end stage renal failure.

In some embodiments, the present invention provides a method for prevention of statin induced rhabdomyolysis. In some embodiments, the present invention provides a method for prevention of statin induced rhabdomyolysis, organ failure or insufficiency. In some embodiments, the present invention provides a method for prevention of statin induced kidney or liver failure or insufficiency. In one embodiment, the method comprises administering to a subject a composition comprising a compound of this invention and a statin.

In one embodiment, the wasting disease is cachexia or involuntary weight loss in a subject. In another embodiment, the present invention provides a method of treating, preventing, inhibiting, reducing or suppressing muscle wasting in a subject suffering from a kidney disease. In one embodiment, the present invention provides a method of treating, preventing, inhibiting, reducing or suppressing protein catabolism in a subject suffering from a kidney disease or disorder, Cachexia is weakness and a loss of weight caused by a disease or as a side effect of illness. Long term hospitalization due to illness or injury, or disuse deconditioning that occurs, for example, when a limb is immobilized, can also lead to muscle wasting. Studies have shown that in patients suffering injuries, chronic illnesses, burns, trauma or cancer, who are hospitalized for long periods of time, there is a long-lasting unilateral muscle wasting, with a consequent decrease in body mass. Nervous system injury, for example, spinal cord injury, as described further herein, may be a contributory factor, as well.

In some embodiments, the present invention provides a method for treating, reducing the incidence, delaying the onset or progression, or reducing and/or abrogating the symptoms associated with a wasting diseases or disorders in a subject. In another embodiment, the wasting diseases and disorders include inter-alia: a) acquired immunodeficiency syndrome (AIDS) wasting; b) wasting associated with bed rest; c) bulimia, and/or wasting associated with bulimia; c) cachexia; d) cancer cachexia; e) HIV wasting; f) reduce cachexia and protein loss due to prolonged critical illness, pulmonary dysfunction, ventilator dependency, aging, AIDS, trauma, surgery, congestive heart failure, cardiac myopathy, burns, cancer, chronic obstructive pulmonary disease (COPD), eating disorders such bulimia, anorexia nervosa, loss of appetite, starvation, and/or depression.

In some embodiments, the present invention provides a method for treating, reducing the incidence, delaying the onset or progression, or reducing and/or abrogating the symptoms associated with invalid states in a subject. In one embodiment, the invalid state is post-polio syndrome. In one embodiment, the method comprises administering to a subject a composition comprising a compound of this invention and an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, vitamins, or a combination thereof.

In some embodiments, the present invention provides a method for treating, reducing the incidence, delaying the onset or progression, or reducing and/or abrogating the symptoms associated with a hypogonadal state in a subject. In one embodiment, the present invention provides a method for treating, reducing the incidence, delaying the onset or progression, or reducing and/or abrogating the symptoms associated with a pharmacotherapy induced hypogonadal state in a subject. In some embodiments, hypogonadism is caused by treatments which alter the secretion of hormones from the sex glands in both women and men. In some embodiments, hypogonadism may be "primary" or "central". In primary hypogonadism, the ovaries or testes themselves do not function properly. In some embodiments, hypogonadism may be induced by surgery, radiation, genetic and developmental disorders, liver and kidney disease, infection, or certain autoimmune disorders. In some embodiments, menopause is a form of hypogonadism. Menopause may cause, in some embodiments, amenorrhea, hot flashes, vaginal dryness, or irritability due to woman's estrogen levels fall. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

In another embodiment, the invention provides a contraceptive, and/or a method of use thereof, the contraceptive comprising a composition comprising a NRBA, which in one embodiment is a SERM of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof. In one embodiment, the invention provides a method for providing post-coital contraception by administering the composition comprising a NRBA, which in one embodiment is a SERM of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof.

In one embodiment this invention provides a method of treating a subject suffering from post menopausal conditions, said method comprising the step of administering to said subject a NRBA, which in one embodiment is a SERM and/or its pharmaceutically acceptable salt, hydrate, N-oxide, or any combination thereof.

In another embodiment this invention provides a method of suppressing, inhibiting or reducing the risk of post menopausal conditions, said method comprising the step of administering to said subject a NRBA, which in one embodiment is a SERMs and/or its pharmaceutically acceptable salt, hydrate, N-oxide, or any combination thereof.

In another embodiment, the invention provides a method of treating, preventing, suppressing, inhibiting, or reducing the incidence of hot flashes, gynecomastia, and/or hair loss in female subjects, or in another embodiment, in male human subjects. In one embodiment, invention provides a method of treating, preventing, suppressing, inhibiting, or reducing the incidence of hot flashes, gynecomastia, and/or hair loss in a male subject having prostate cancer, comprising administering a NRBA, which in one embodiment is a SERM of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof, or a composition comprising the same, thereby treating, preventing, suppressing, inhibiting, or reducing the incidence of hot flashes, gynecomastia, and/or hair loss in said male human subjects.

In one embodiment, the term "hot flashes" refers to the following: sudden feeling of heat in the upper part or all of the body, face and neck flush, red blotches appearing on the chest, back and arms, heavy sweating, cold shivering, etc.

It is to be understood that any sex hormone-dependent disease, disorder or condition may be treated via the methods of this invention, using the SERMs/compositions of this invention.

In one embodiment, hot flashes can be treated with any SERM, which has a structure characterized by any of the formulas, as described herein. In one embodiment, hot flashes may be treated, prevented, alleviated with the following SERMs chosen based on their pharmacologic activity as demonstrated in receptor binding studies, estrogen receptor transactivation, in vitro studies of osteoblast and osteoclast activity, and in vivo studies Hot flash is mediated by both ER-α and ER-β. In some embodiments, to overcome this, tissue selective agonists of both the isoforms can be used. In some embodiments, side effects associated with some ER-α agonists such as thromboembolism, mammary carcinogenesis and uterine cancer, may be avoided via selection of specific ER-β agonists for this indication.

In some embodiments, the present invention provides a method for treating, reducing the incidence, delaying the onset or progression, or reducing and/or abrogating the symptoms associated with osteopenic state in a subject. In one embodiment, the present invention provides a method for treating, reducing the incidence, delaying the onset or progression, or reducing and/or abrogating the symptoms associated with a pharmacotherapy induced osteopenic state in a subject. In some embodiments, osteopenia is a mild thinning of the bone mass. In some embodiments, osteopenia is a precursor to osteoporosis. In some embodiments osteopenia is defined as a bone density between one standard deviation (SD) and 2.5 SD below the bone density of a normal young adult. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

In some embodiments, the present invention provides a method for treating, reducing the incidence, delaying the onset or progression, or reducing and/or abrogating the symptoms associated with a sarcopenic state in a subject. In one embodiment, the present invention provides a method for treating, reducing the incidence, delaying the onset or progression, or reducing and/or abrogating the symptoms associated with a pharmacotherapy induced sarcopenic state in a subject. In some embodiments, sarcopenia is a significant loss of muscle mass. In one embodiment, sarcopenia definition is having a lean body mass less than two standard deviation below the mean for normal young adults. In some embodiments, sarcopenia is caused by genetic factors, altered circulation, decrease in the capillary:muscle fiber ratio, altered motor neurons, denervation, deterioration of motor end plates, selective reinnervation of Type I fibers, inflammatory responses causing muscle damage, reduced exercise, malnutrition, low dietary protein intake, vitamin D deficiency, age-related decline in vitamin D, oxidative stress, muscle mitochondrial mutations, changes in specific types of muscle fibers, decline in muscle protein, disabling disease, strokes, Alzheimer's disease, Parkinson's disease, osteoporosis, atherosclerosis, diabetes mellitus, hyperinsulinemia, renal failure, or hypogonadism. In one embodiment, the method comprises administering to a subject a composition comprising a SARM compound and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

In some embodiments, the present invention provides a method for treating, reducing the incidence, delaying the onset or progression, or reducing and/or abrogating the symptoms associated with a combination of diseases and/or disorders in a subject as described hereinabove. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

It is to be understood that any method of this invention, as herein described, encompasses the administration of a compound as herein described, or a composition comprising the same, to the subject, in order to treat the indicated disease, disorder or condition. The methods as herein described each and/or all may further comprise administration of an additional therapeutic agent as herein described, and as will be appreciated by one skilled in the art.

In some embodiments, the present invention provides a method for enhanced production such as milk, sperm, or egg. In some embodiments, the present invention provides a method for enhanced production of lean meats or eggs. In some embodiments, the present invention provides a method for increased productivity of feeds or stud livestock, for example, increased sperm count, improved morphology of sperm, etc. In some embodiments, the present invention provides a method for expanding the productive life of farm animals, for example, egg-laying hens, milk-producing cows, etc, and/or enhanced herd health, for example, improved immune clearance, stronger animals.

In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, nutritional additives, hormones, each and/or all as herein described, or any other therapeutic agent as herein described, or a combination thereof.

In another embodiment, this invention provides methods of treatment of cystic fibrosis and induced hypogonadal states as a result of the same, epilepsy and induced hypogonadal and/or hypermetabolic states as a result of the same, hereditary angioedema, lupus erythematosus and decreased BMD as a result of the same, alcohol and smoking induced osteoporosis, in a subject the methods comprising administering a compound as herein described to the subject.

In another embodiment, this invention provides methods of treatment of polio and post-polio syndrome and other invalid states, statin induced rhabdomyolysis, statin-induced muscle weakness, statin-induced organ failure or insufficiency, in a subject, the methods comprising the administration of a compound as herein described, optionally with a statin, as appropriate, as will be appreciated by one skilled in the art, and/or with any therapeutic agent.

In another embodiment, this invention provides a method of treating Opioid Induced Androgen Deficiency (OPIAD), the method comprising administering to the subject a compound as herein described, and optionally opiates, opioids, narcotics, etc. methadone, long-acting opiates/opioids such as Kadian, extended release morphines, all opiates/opioids/narcotics agents approved by FDA, opiates/opioids used in treatment of heroin addiction, opiates/opioids used in the treatment of chronic pain of malignancy, opiates/opioids used in the treatment non-malignant of chronic pain syndromes.

In another embodiment, this invention provides a method of treating a nervous system disease, disorder or condition, the method comprising administering to the subject a compound as herein described, and optionally anti-psychotics, such as, for example, zotepine, haloperidol, amisulpride, risperidone, other D2 dopamine receptor antagonists; anti-epileptics, such as valproic acid, carbamazepine, oxcarbamazepine, etc. or combinations thereof.

In another embodiment, this invention provides a method of treating a hormone dependent disease, disorder or condition, the method comprising administering to the subject a compound as herein described, and optionally chemotherapeutics agents and therapies (methotrexate, cyclophosphamide, ifosfamide, adriamycin, doxorubicin, glucocorticoids, cyclosporine, L-thyroxine, SERMs, AI, fulvestrant, GnRH agents, ADT, discontinuation of hormone replacement therapy, cranial irradiation, peripheral irradiation, etc.; prolactinemia-inducing pharmacotherapeutics (serotonergic antidepressants acting through 5HT2 receptors, selective serotonin reuptake inhibitors, monoamine oxidase inhibitors, tricyclic antidepressants, antihypertensives such as methyldopa, reserpine, clonidine, and verapamil; antidopaminergic anti-emetics such as metoclopramide, H2 receptor antagonists such as cimetidine and ranitidine, estrogens, amphetamines, AR partial antagonists (ketoconazole, spironolactone, eplerenone)

In another embodiment, the compounds of this invention and compositions as described herein are useful in promoting or speeding recovery following a surgical procedure.

In one embodiment, the present invention provides a use of a compound as described herein for reducing a fat mass in a subject. In another embodiment the invention provides such methods for use of the compound as described herein or its prodrug, analog, isomer, metabolite, derivative, pharmaceutically acceptable salt, pharmaceutical product, polymorph, crystal, impurity, N-oxide, hydrate or any combination thereof, or a composition comprising the same.

In another embodiment, this invention provides for the use of a compound as described herein or its prodrug, analog, isomer, metabolite, derivative, pharmaceutically acceptable salt, pharmaceutical product, polymorph, crystal, impurity, N-oxide, hydrate or any combination thereof, or a composition comprising the same, in treating abdominal fat accumulation; improving body composition; lowering body fat content; lowering fat mass; improving blood lipid profile, increasing muscle mass/strength/function; increasing bone mass/BMD/strength/function; lowering body fat; congenital hyperinsulinemia; cushing's disease (hypercortisolemia); obesity or diabetes associated with a metabolic syndrome in a subject.

In another embodiment, the subject has a hormonal imbalance, disorder, or disease. In another embodiment the subject has menopause.

In one embodiment, the present invention provides a use of a compound as described herein for increasing a lean mass in a subject. In another embodiment such use comprises administration of a compound as described herein or its prodrug, analog, isomer, metabolite, derivative, pharmaceutically acceptable salt, pharmaceutical product, polymorph, crystal, impurity, N-oxide, hydrate or any combination thereof.

In one embodiment the subject has a hormonal imbalance, disorder, or disease. In another embodiment the subject has menopause.

In one embodiment, the compounds as herein described alter the levels of leptin in a subject. In another embodiment, the compounds as herein described decrease the levels of leptin. In another embodiment, the compounds as herein described increase the levels of leptin in a subject. Leptin is known to have an effect on appetite on weight loss in obese mice, and thus has been implicated in obesity.

The compounds as herein described, in one embodiment, affect circulating, or in another embodiment, tissue levels of leptin. In one embodiment, the term 'level's of leptin' refers to the serum level of leptin. As contemplated herein, the compounds of the present invention have an effect on leptin in-vitro and in-vivo. Leptin levels can be measured by methods known to one skilled in the art, for example by commercially available ELISA kits. In addition, Leptin levels may be determined in in-vitro assays, or in in-vivo assays, by any method known to a person skilled in the art.

Since leptin is implicated in controlling appetite, weight loss, food intake, and energy expenditure, modulating and/or controlling the levels of leptin is a useful therapeutic approach in treating preventing, inhibiting or reducing the incidence of obesity in subjects suffering from obesity. Modulating the level of leptin can result in a loss of appetite, a reduction of food intake, and an increase in energy expenditure in the subject, and thus may contribute to the control and treatment of obesity.

The term "obesity" is defined, in one embodiment, as an increase in body weight beyond the limitation of skeletal and physical requirement, as the result of excessive accumulation of fat in the body.

The term "obesity-associated metabolic disorder" refers, in one embodiment, to a disorder which results from, is a consequence of, is exacerbated by or is secondary to obesity. Non-limiting examples of such a disorder are osteoarthritis, Type II diabetes mellitus, increased blood pressure, stroke, and heart disease.

Cholesterol, triacylglycerol and other lipids are transported in body fluids by lipoproteins which may be classified according to their density, for example, the very low density lipoproteins (VLDL), intermediate density lipoproteins (IDL), low density lipoproteins (LDL) and high density lipoproteins (HDL).

It has been shown that high levels of LDL-Cholesterol in the blood correlate with atherosclerosis which is a progressive disease characterized in part by sedimentation of lipids in inner walls of arteries, particularly of coronary arteries. It has also been shown that a high blood level of LDL-Cholesterol correlates with coronary heart disease. Also, a negative correlation exists between blood levels of HDL cholesterol and coronary heart disease.

The level of total cholesterol in blood, which is the sum of HDL-Cholesterol, LDL-Cholesterol, VLDL-Cholesterol and chylomicron-Cholesterol, is not necessarily predictive of the risk of coronary heart disease and atherosclerosis.

The correlation between atherosclerosis and LDL cholesterol levels, however, is much higher than a similar correlation between atherosclerosis and total serum cholesterol levels.

In one embodiment, this invention provides methods of use of the compounds as herein described for improving the lipid profile and/or reducing the circulating lipid levels in a subject. In some embodiments, according to this aspect of the invention, the subject suffers from one or more conditions selected from the group consisting of: atherosclerosis and its associated diseases, premature aging, Alzheimer's disease, stroke, toxic hepatitis, viral hepatitis, peripheral vascular insufficiency, renal disease, and hyperglycemia, and the invention provides for the administration of a compound or composition comprising the same, as herein described, which in some embodiments positively affects a lipid profile in the subject, which is one means by which the method is useful in treating the indicated diseases, disorders and conditions.

In one embodiment the invention provides for the treatment of atherosclerosis and its associated diseases, such as for example, cardiovascular disorders, cerebrovascular disorders, peripheral vascular disorders, intestinal vascular disorders, or combinations thereof.

In one embodiment cardiovascular disorders comprise of hypertension (HTN), coronary artery disease (CAD) or myocardial perfusion. In another embodiment this invention provides methods of use of the SARM compounds as herein described for promoting aortic smooth muscle cell proliferation. In another embodiment this invention provides methods of use of the compounds as herein described for treating arteriosclerosis. In another embodiment this invention provides methods of use of the compounds as herein described for lowering blood pressure. In another embodiment this invention provides methods of use of the compounds as herein described for treating cardiac diseases and disorders comprising cardiomyopathy, cardiac dysfunctions such as, myocardial infarction, cardiac hypertrophy and cognitive heart failure. In another embodiment this invention provides methods of use of the compounds as herein described for cardioprotection comprising cardioprotection in insulin resistance; treating diabetes type I and II, metabolic syndrome, syndrome X and/or high blood pressure.

In one embodiment, the invention provides a method of treating, preventing, reducing the risk of mortality from cardiovascular and/or cerebrovascular disease in a subject, comprising administering a compound of this invention or its prodrug, ester, analog, isomer, metabolite, derivative, pharmaceutically acceptable salt, pharmaceutical product, polymorph, crystal, impurity, N-oxide, hydrate or any combination thereof, or a pharmaceutical composition comprising the same.

In one embodiment, compounds of this invention reduce LDL and total cholesterol levels. In another embodiment the compound of this invention reduces LDL and total cholesterol levels in a subject.

In another embodiment, compounds of this invention are co-administered with HDL-elevating agents. In another embodiment, a compound of this invention is co-administered with an HDL-elevating agents. In another embodiment, HDL-elevating agents include niacin. In another embodiment the HDL-elevating agents include fibrates including gemfibrozil (Lopid), thiourea based gemfibrozil analogues, and fenofibrate (TriCor). In another embodiment, HDL-elevating agents include statins. In another embodiment, HDL-elevating agents include 1-hydroxyalkyl-3-phenylthiourea, and analogs thereof.

In one embodiment, this invention provides a method of reducing circulating lipid levels in a subject, said method comprising administering a compound of this invention or its pharmaceutically acceptable salt, hydrate, N-oxide, or any combination thereof, or a composition comprising the same. In one embodiment, the subject suffers from atherosclerosis and its associated diseases, premature aging, Alzheimer's disease, stroke, toxic hepatitis, viral hepatitis, peripheral vascular insufficiency, renal disease, hyperglycemia, or any combination thereof.

In one embodiment, this invention provides a method of treating atherosclerosis and its associated diseases, such as, for example, cardiovascular disorders, cerebrovascular disorders, peripheral vascular disorders, or intestinal vascular disorders in a subject, the method comprising the step of administering to the subject compound of this invention or its pharmaceutically acceptable salt, hydrate, N-oxide, or any combination thereof, or a composition comprising the same. The method may further comprise co-administration, subsequent or prior administration with an agent or agents, which are known to be useful in treating cardiovascular disorders, cerebrovascular disorders, peripheral vascular disorders, or intestinal vascular disorders.

Cardiovascular cells, as well as reproductive tissues, bone, liver, and brain, express both of the known estrogen receptors, estrogen receptor-α (ER-α) and estrogen receptor-β (ER-β). These receptors are important targets for endogenous estrogen, estrogen replacement therapy (ERT), and pharmacological estrogen agonists. Estrogen—estrogen receptor complexes serve as transcription factors that promote gene expression with a wide range of vascular effects, including regulation of vasomotor tone and response to injury, which may be protective against development of atherosclerosis and ischemic diseases. Estrogen receptors in other tissues, such as the liver, may mediate both beneficial effects (e.g., changes in apoprotein gene expression that improve lipid profiles) and adverse effects (e.g., increases in gene expression of coagulation proteins and/or decreases in fibrinolytic proteins). Two general estrogen-mediated vascular effects are recognized. Rapid, transient vasodilation occurs within a few minutes after estrogen exposure, independently of changes in gene expression. Longer-term effects of estrogen on the vasculature, such as those related to limiting the development of atherosclerotic lesions or vascular injury, occur over hours to days after estrogen treatment and have as their hallmark alterations in vascular gene expression. Progesterone and other hormonal receptors are also expressed in the vasculature.

In another embodiment, the invention provides a method of improving a lipid profile in a subject, comprising administering a NRBA, which in one embodiment is a SERM of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof, or a composition comprising the same, thereby improving the lipid profile in said subject. In some embodiments ER-β agonists are useful in improving a lipid profile in a subject In another embodiment, ER-β agonist of this invention is compound 3a, listed in Table 1. In another embodiment, ER-β agonist of this invention is compound 3d, listed in Table 1. In another embodiment, ER-β agonist of this invention is compound 3e, listed in Table 1. In another embodiment, ER-β agonist of this invention is compound 3l, listed in Table 1. In another embodiment, ER-β agonist of this invention is compound 3g, listed in Table 1. In another embodiment, ER-β agonist of this invention is compound 3j, listed in Table 1. In another embodiment, ER-β agonist of this invention is compound 3i, listed in Table 1, or any combination thereof. In another embodiment, ER-β agonist of this invention is compound 4a, listed in Table 1. In another embodiment, ER-β agonist of this invention is compound 4h, listed in Table 1. In another embodiment, ER-β agonist of this invention is compound 4u, listed in Table 1. In another embodiment, ER-β agonist of this invention is compound 10o, listed in Table 1. In another embodiment, ER-β agonist of this invention is compound 10d, listed in Table 1. In another embodiment, ER-β agonist of this invention is compound 10f, listed in Table 1. In another embodiment, ER-β agonist of this invention is compound 10l, listed in Table 1. In another embodiment, ER-β agonist of this invention is compound 10w, listed in Table 1, or any combination thereof.

In some embodiments, the phrase "improving a lipid profile" may refer to lowering pathogenic circulating lipid levels, lowering plaque formation in vasculature, altering circulating HDL/LDL ratios, ratios reducing the ratio of LDL levels to HDL levels, lowering circulating cholesterol levels, preventing lipid accumulation in vasculature, or any combination thereof, or other therapeutic effects related thereto, as will be appreciated by one skilled in the art.

In one embodiment, the invention provides a method of treating, preventing, reducing the risk of mortality from vasculature disease disorder or condition in a subject, comprising administering a NRBA, which in one embodiment is a SERM, of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof, or a composition comprising the same.

In one embodiment, vasculature disease disorder or condition may comprise, inter alia, aortic smooth cell proliferation, restenosis, repurfusion injury, vascular smooth muscle cell proliferation or vasospasm.

In one embodiment, the invention provides a method of treating, preventing, reducing the risk of mortality from cardiovascular and/or cerebrovascular disease in a subject, comprising administering a NRBA, which in one embodiment is a SERM, of formula (I)-(XI) or its prodrug, ester, analog, isomer, metabolite, derivative, pharmaceutically acceptable salt, pharmaceutical product, polymorph, crystal, impurity, N-oxide, hydrate or any combination thereof, or a composition comprising the same. In some embodiments ER-β agonists are useful in treating, preventing, reducing the risk of mortality from cardiovascular and/or cerebrovascular disease in a subject. In another embodiment, ER-β agonist of this invention is compound 3a, listed in Table 1. In another embodiment, ER-β agonist of this invention is compound 3d, listed in Table 1. In another embodiment, ER-β agonist of this invention is compound 3e, listed in Table 1. In another embodiment, ER-β agonist of this invention is compound 3l, listed in Table 1. In another embodiment, ER-β agonist of this invention is compound 3g, listed in Table 1. In another embodiment, ER-β agonist of this invention is compound 3j, listed in Table 1. In another embodiment, ER-β agonist of this invention is compound 3i, listed in Table 1, or any combination thereof. In another embodiment, ER-β agonist of this invention is compound 4a, listed in Table 1. In another embodiment, ER-β agonist of this invention is compound 4h, listed in Table 1. In another embodiment, ER-β agonist of this invention is compound 4u, listed in Table 1. In another embodiment, ER-β agonist of this invention is compound 10o, listed in Table 1. In another embodiment, ER-β agonist of this invention is compound 10d, listed in Table 1. In another embodiment, ER-β agonist of this invention is compound 10f, listed in Table 1. In another embodiment, ER-β agonist of this invention is compound 10l, listed in Table 1. In another embodiment, ER-β agonist of this invention is compound 10w, listed in Table 1, or any combination thereof.

In one embodiment, cardiovascular disease comprises, inter alia, atherosclerosis of the coronary arteries, angina pectoris, and myocardial infarction. In one embodiment, cerebrovascular disease comprises, inter alia, atherosclerosis of the intracranial or extracranial arteries, stroke, syncope, and transient ischemic attacks.

In one embodiment, this invention provides a method of improving the dexterity and movement in a subject, for example, by treating arthritis in the subject.

The term "arthritis" refers, in another embodiment, to a non-inflammatory degenerative joint disease occurring chiefly in older people, characterized by degeneration of the articular cartilage, hypertrophy of bones and the margins, changes in the synovial membrane, etc. It is accompanied, in other embodiments, by pain and stiffness, particularly after prolonged activity.

The term "diabetes", in one embodiment, refers to a relative or absolute lack of insulin leading to uncontrolled carbohydrate metabolism. Most patients can be clinically classified as having either insulin-dependent diabetes mellitus (IDDM or Type-I diabetes) or non-insulin-dependent diabetes mellitus (NIDDM or Type-II diabetes).

The term "increased blood pressure" or "hypertension" refers, in other embodiments, to a repeatedly high blood pressure above 140 over 90 mmHg. Chronically-elevated blood pressure can cause blood vessel changes in the back of the eye, thickening of the heart muscle, kidney failure, and brain damage.

The term "stroke" refers, in other embodiments, to damage to nerve cells in the brain due to insufficient blood supply often caused by a bursting blood vessel or a blood clot. The term "heart disease", in other embodiments, refers to a malfunction in the heart normal function and activity, including heart failure.

In addition, androgens have recently been shown to be involved in commitment of mesenchymal pluripotent cells into myogenic lineage and to block differentiation into adipogenic lineage (Singh et al., Endocrinology, 2003, Jul. 24). Accordingly, the compounds can be useful in methods of blocking adipogenesis, and/or altering stem cell differentiation, as described herein.

In another embodiment, this invention relates to a method of promoting, increasing or facilitating weight loss in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to promote, increase or facilitate weight loss in the subject.

In another embodiment, this invention relates to a method of decreasing, suppressing, inhibiting or reducing appetite of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce the appetite of the subject.

In another embodiment, this invention relates to a method of altering the body composition of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the body composition of the subject. In one embodiment, altering the body composition comprises altering the lean body mass, the fat free body mass of the subject, or a combination thereof.

In another embodiment, this invention relates to a method of altering lean body mass or fat free body mass of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the lean body mass or fat free body mass of the subject.

In another embodiment, this invention relates to a method of converting fat to lean muscle in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to convert fat to lean muscle in the subject.

In another embodiment, this invention relates to a method of treating an obesity-associated metabolic disorder in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to treat the obesity-associated metabolic disorder in the subject.

In another embodiment, this invention relates to a method of preventing, suppressing, inhibiting or reducing an obesity-associated metabolic disorder in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to prevent, suppress, inhibit or reduce the obesity-associated metabolic disorder in the subject.

In one embodiment, the obesity-associated metabolic disorder is hypertension. In another embodiment, the disorder is osteoarthritis. In another embodiment, the disorder is Type II diabetes mellitus. In another embodiment, the disorder is increased blood pressure. In another embodiment, the disorder is stroke. In another embodiment, the disorder is heart disease.

In another embodiment, this invention relates to a method of decreasing, suppressing, inhibiting or reducing adipogenesis in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof.

In another embodiment, this invention relates to a method of altering stem cell differentiation in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter stem cell differentiation in the subject.

In one embodiment, the compounds as herein described are useful in a) treating, preventing, suppressing, inhibiting, or reducing obesity; b) promoting, increasing or facilitating weight loss; c) decreasing, suppressing, inhibiting or reducing appetite; d) altering the body composition; e) altering lean body mass or fat free body mass; converting fat to lean muscle; f) g) treating, preventing, suppressing, inhibiting, or reducing an obesity-associated metabolic disorder, for example hypertension, osteoarthritis, diabetes mellitus, MODY, increased blood pressure, stroke, or heart disease; h) decreasing, suppressing, inhibiting or reducing adipogenesis; i) altering stem cell differentiation; and/or j) altering the level of leptin.

In one embodiment, the compounds as herein described find utility in treating or halting the progression of, or treating symptoms of diabetes. In another embodiment, the compounds as herein described are useful in treating co-morbidities related to diabetes. These conditions include: hypertension (HTN), cerebrovascular disease, atherosclerotic coronary artery disease, macular degeneration, diabetic retinopathy (eye disease) and blindness, cataracts-systemic inflammation (characterized by elevation of inflammatory markers such as erythrocyte sedimentation rate or C-reactive protein), birth defects, pregnancy related diabetes, pre-eclampsia and hypertension in pregnancy, kidney disease (renal insufficiency, renal failure etc.), nerve disease (diabetic neuropathy), superficial and systemic fungal infections, congestive heart failure, gout/hyperuricemia, obesity, hypertriglyceridemia, hypercholesterolemia, fatty liver disease (non-alcoholic steatohepatitis, or NASH), and diabetes-related skin diseases such as Necrobiosis Lipoidica Diabeticorum (NLD), Blisters of diabetes (Bullosis Diabeticorum), Eruptive Xanthomatosis, Digital Sclerosis, Disseminated Granuloma Annulare, and Acanthosis Nigricans.

In one embodiment this invention provides a method of treating, suppressing, inhibiting or reducing the incidence of (a) diabetes type I; (b) diabetes type II; (c) glucose intolerance; (d) hyperinsulinemia; (e) insulin resistance (f) nephropathy; (g) diabetic neuropathy; (h) diabetic retinopathy (i) fatty liver conditions (j) MODY and (k) cardiovascular disease in a human subject, comprising the step of administering to said subject a compound of this invention.

In some embodiments, the compounds as herein described and/or compositions comprising the same may be used for applications in, or treating diseases or conditions associated with a subject having diabetes. In one embodiment, the subject for whom treatment is sought via the methods of this invention is one with diabetic I. Type I diabetes is characterized by autoimmune destruction of pancreatic beta-cells. Markers of immune destruction of the beta-cell are present at the time of diagnosis in 90% of individuals and include antibodies to the islet cell (ICAs), to glutamic acid decarboxylase (GAD), and to insulin (IAAs). While this form of diabetes usually occurs in children and adolescents, it can occur at any age. Younger individuals typically have a rapid rate of beta-cell destruction and present with ketoacidosis, while adults often maintain sufficient insulin secretion to prevent ketoacidosis for many years. Eventually, all type I diabetic patients require insulin therapy to maintain normglycemia.

In one embodiment, this invention provides a method of treating diabetes type II. Type II diabetes is characterized by insulin resistance and at some stage in pathogenesis of the disease, a relative deficiency of insulin secretion. In absolute terms, the plasma insulin concentration (both fasting and meal-stimulated) usually is increased, although "relative" to the severity of insulin resistance, the plasma insulin concentration is insufficient to maintain normal glucose homeostasis. With time, however, there is progressive beta cell failure and absolute insulin deficiency ensues. Most individuals with type II diabetes exhibit intra abdominal (visceral) obesity, fatty liver, which is closely related to the presence of insulin resistance. The patient's liver becomes insulin resistant and glycogen breakdown is uncontrolled and the result is increased and unphysiological glucose delivery to the bloodstream. The liver generated cholesterol and VLDL particles is also uncontrolled. In addition, hypertension, dyslipidemia (high triglyceride and low HDL-cholesterol levels; postprandial hyperlipemia), and elevated PAI-1 levels often are present in these individuals. This clustering of abnormalities is referred to as the "insulin resistance syndrome", or the "metabolic syndrome" or obesity related disorders. Because of these abnormalities, patients with type II diabetes are at increased risk of developing macrovascular complications such as myocardial infarction and stroke.

In one embodiment, this invention provides a method of treating diabetic nephropathy. Diabetic nephropathy is a complication of diabetes that evolves early, typically before clinical diagnosis of diabetes is made. The earliest clinical evidence of nephropathy is the appearance of low but abnormal levels (>30 mg/day or 20 µg/min) of albumin in the urine (microalbuminuria), followed by albuminuria (>300 mg/24 h or 200 µg/min) that develops over a period of 10-15 years. In patients with type 1 diabetes, diabetic hypertension typically becomes manifest early on, by the time that patients develop microalbuminuria. Once overt nephropathy occurs, the glomerular filtration rate (GFR) falls over a course of times, which may be several years, resulting in End Stage Renal Disease (ESRD) in diabetic individuals.

In one embodiment, this invention provides a method of treating diabetic neuropathy. Diabetic neuropathy is a family of nerve disorders caused by diabetes. Diabetic neuropathies cause numbness and sometimes pain and weakness in the hands, arms, feet, and legs. Neurologic problems in diabetes may occur in every organ system, including the digestive tract, heart, and genitalia. Diabetic neuropathies are classified as peripheral, autonomic, proximal, and focal. Peripheral neuropathy causes pain or loss of feeling in the toes, feet, legs, hands, and arms. Autonomic neuropathy causes changes in digestion, bowel and bladder function, sexual response, and perspiration and can also affect the nerves that serve the heart and control blood pressure. Proximal neuropathy causes pain in the thighs, hips, or buttocks and leads to weakness in the legs. Focal neuropathy results in the sudden weakness of one nerve, or a group of nerves, causing muscle weakness or pain. Any nerve in the body may be affected.

In one embodiment, this invention provides a method of treating diabetic retinopathy. The effect of diabetes on the eye is called diabetic retinopathy. Patients with diabetes are more likely to develop eye problems such as cataracts and glaucoma. The affect of diabetic retinopathy on vision varies widely, depending on the stage of the disease. Some common symptoms of diabetic retinopathy are blurred vision (this is often linked to blood sugar levels), floaters and flashes and sudden loss of vision.

In one embodiment, the subject for whom treatment is sought via the methods of this invention is one with glucose intolerance. Glucose intolerance is a pre-diabetic state in which the blood glucose is higher than normal but not high enough to warrant the diagnosis of diabetes.

In one embodiment, the subject for whom treatment is sought via the methods of this invention is one with hyperinsulinemia. Hyperinsulinemia is a sign of an underlying problem that is causing the pancreas to secrete excessive amounts of insulin. The most common cause of hyperinsulinemia is insulin resistance, a condition in which your body is resistant to the effects of insulin and the pancreas tries to compensate by making more insulin. hyperinsulinemia is associated with type II diabetes In one embodiment, the subject for whom treatment is sought via the methods of this invention is one with insulin resistance. Insulin resistance is a condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to the metabolic syndrome and type II diabetes.

Diabetes and the liver obesity is typically associated with elevated levels of free fatty acid (FFAs) that promote lipid accumulation and insulin resistance in target tissues, i.e. reduced action of insulin primarily in skeletal muscle and liver. A prominent role of insulin is to reduce glucose output from the liver. FFAs stimulate hepatic gluconeogenesis which per se does not lead to increased hepatic glucose output as long as it is paralleled by a decrease in hepatic glycogenolysis, a compensatory process referred to as "hepatic autoregulation". FFAs stimulate insulin secretion and insulin blocks glycogenolysis in part by inhibiting secretion of glucagon, an inducer of glycogenolysis. However, long-term elevated levels of FFAs leads to hepatic insulin resistance and thus breakdown of hepatic autoregulation, resulting in increased hepatic glucose production and development of type II diabetes. Fatty liver and hepatic insulin resistance is a major driving force behind hyperglycemia and type II diabetes.

In one embodiment, this invention provides methods that inhibit (improve) the fatty liver, resulting in that the insulin resistance in the liver is inhibited (improved) and thereby solving the basic problem in type II diabetes.

In another embodiment, the diabetes is a type I diabetes. In another embodiment, the diabetes is a type II diabetes.

In one embodiment, this invention provides a method of treating suppressing, inhibiting or reducing the incidence of diabetes is a human subject, comprising the step of administering to said subject a compound of this invention or its isomer, pharmaceutically acceptable salt, pharmaceutical product, hydrate, N-oxide, or any combination thereof.

In another embodiment, the diabetes is a Type I diabetes. In another embodiment, the diabetes is a type II diabetes.

In one embodiment, this invention provides a method of treating a human subject having glucose intolerance, comprising the step of administering to said subject compound of this invention or its isomer, pharmaceutically acceptable salt, pharmaceutical product, hydrate, N-oxide, or any combination thereof.

In one embodiment, this invention provides a method of treating hyperinsulinemia in a human subject, comprising the step of administering to said subject a compound of this invention or its isomer, pharmaceutically acceptable salt, pharmaceutical product, hydrate, N-oxide, or any combination thereof.

In one embodiment, this invention provides a method of treating insulin resistance in a human subject, comprising the step of administering to said subject the compound of this invention or its isomer, pharmaceutically acceptable salt, pharmaceutical product, hydrate, N-oxide, or any combination thereof.

In one embodiment, this invention provides a method of treating diabetic nephropathy in a human subject, comprising the step of administering to said subject a compound of this invention or its isomer, pharmaceutically acceptable salt, pharmaceutical product, hydrate, N-oxide, or any combination thereof.

In one embodiment, this invention provides a method of treating diabetic neuropathy in a human subject, comprising the step of administering to said subject compound of this invention or its isomer, pharmaceutically acceptable salt, pharmaceutical product, hydrate, N-oxide, or any combination thereof.

In one embodiment, this invention provides a method of treating diabetic retinopathy in a human subject, comprising the step of administering to said subject a compound of this invention or its isomer, pharmaceutically acceptable salt, pharmaceutical product, hydrate, N-oxide, or any combination thereof.

In one embodiment, this invention provides a method of treating fatty liver conditions in a human subject, comprising the step of administering to said subject a selective androgen receptor modulator compound of this invention or its isomer, pharmaceutically acceptable salt, pharmaceutical product, hydrate, N-oxide, or any combination thereof.

In one embodiment, this invention provides a method of treating ovascular disease in a human subject, comprising the step of administering to said subject a compound of this invention or its isomer, pharmaceutically acceptable salt, pharmaceutical product, hydrate, N-oxide, or any combination thereof.

In one embodiment this invention provides a method for a) treating, preventing, suppressing inhibiting atherosclerosis b) treating, preventing, suppressing inhibiting liver damage due to fat deposits comprising the step of administering to the subject a compound as described herein and/or its analog, derivative, isomer, metabolite, pharmaceutically acceptable salt, pharmaceutical product, hydrate, N-oxide, prodrug, polymorph, crystal, or any combination thereof, or a composition comprising the same, in an amount effective to treat, prevent or inhibit atherosclerosis and liver damage due to fat deposit.

In one embodiment, the compound as described herein is useful in a) treating, preventing, suppressing, inhibiting, or reducing atherosclerosis; b) treating, preventing, suppressing inhibiting liver damage due to fat deposits.

In one embodiment atherosclerosis refers to a slow, complex disease that may begin with damage to the innermost layer of the artery. In another embodiment the causes of damage to the arterial wall may include a) elevated levels of cholesterol and in the blood; b) high blood pressure; c) tobacco smoke d) diabetes. In another embodiment, the condition is treatable in a smoker, despite the fact that tobacco smoke may greatly worsen atherosclerosis and speed its growth in the coronary arteries, the aorta and arteries in the legs. Similarly, in another embodiment, the methods of this invention may be useful in treating subjects with a family history of premature cardiovascular disease who have an increased risk of atherosclerosis.

In one embodiment, liver damage due to fat deposits refer to the build-up of fat in the liver cells forming a Fatty Liver which may be associated with or may lead to inflammation of the liver. This can cause scarring and hardening of the liver. When scarring becomes extensive, it is called cirrhosis.

In another embodiment the fat accumulates in the liver as obesity. In another embodiment fatty liver is also associated with diabetes mellitus, high blood triglycerides, and the heavy use of alcohol. In another embodiment fatty Liver may occur with certain illnesses such as tuberculosis and malnutrition, intestinal bypass surgery for obesity, excess vitamin A in the body, or the use of certain drugs such as valproic acid (trade names: Depakene/Depakote) and corticosteroids (cortisone, prednisone). Sometimes fatty liver occurs as a complication of pregnancy.

In one embodiment, subjects with kidney disease, in particular male subjects with end-stage renal disease (ESRD) suffer from hypogonadism, with some having concomitant moderate to severe protein-energy malnutrition (PEM), which leads to higher required doses of EPO, lower QOL scores, and higher mortality. Many have other symptoms associated with hypogonadism, including fatigue, lack of apetite, muscle weakness, etc. In some embodiments, the treatment methods of this invention are useful in treating symptoms associated with hypogonadism, brought about in the subject by the kidney disease or disorder.

In one embodiment, diabetic nephropathy is a complication of diabetes that evolves early, typically before clinical diagnosis of diabetes is made. The earliest clinical evidence of nephropathy is the appearance of low but abnormal levels (>30 mg/day or 20 µg/min) of albumin in the urine (microalbuminuria), followed by albuminuria (>300 mg/24 h or 200 µg/min) that develops over a period of 10-15 years. In patients with type 1 diabetes, diabetic hypertension typically becomes manifest early on, by the time that patients develop microalbuminuria. Once overt nephropathy occurs, the glomerular filtration rate (GFR) falls over a course of times, which may be several years, resulting in End Stage Renal Disease (ESRD) in diabetic individuals.

Hypertension is another comorbid factor for renal disease. In some embodiments, treatment of renal disease according to the present invention may comprise concomitant treatment with a compound of this invention and an agent which treats hypertension.

Androgen-dependent conditions which may be treated with the compounds and/or compositions as herein described, comprising the methods of the present invention include those conditions which are associated with aging. In one embodiment, the compound as described herein is useful in a) Age-related functional decline (ARFD); b) reversal or prevention of ARFD; c) reversal or prevention of ARFD in elderly d) reversal or prevention of ARFD-induced sarcopenia or osteopenia; e) Andropause, andropausal vasomotor symptoms, f) andropausal gynecomastia, muscle strength/function; g) bone strength/function; h) Anger; i) Asthenia; j) Chronic fatigue syndrome; k) Cognitive impairment; and/or l) improving cognitive function.

In one embodiment, the compound as described herein is useful in treating inflammation and related disorders such as: a) prevention, treatment, or reversal of arthritis; b) prevention, treatment, or reveral of an arthritic condition such as Behcet's disease (autoimmune vasculitis), bursitis, calcium pyrophosphate dihydrate crystal (CPPD), deposition disease (or pseudogout), carpal tunnel syndrome, connective tissue disorders, Crohn's diseases, Ehlers-Danlos syndrome (EDS), fibromyalgia, gout, infectious arthritis, inflammatory bowel disease (IBD), juvenile arthritis, systemic lupus erythematosus (SLE), Lyme's disease, Marfan syndrome, myositis, osteoarthritis, polyarteritis nodosa, polymyalgia rheumatica, psoriasis, psoriatic arthritis, Raynaud's phenomenon, reflex sympathetic dystrophy syndrome, Reiter's syndrome, rheumatoid arthritis, scleroderma, Sjögrens' syndrome, tendonitis or ulcerative colitis; c) preventing, treatment, or reversing an autoimmune disease.

In one embodiment, the compound as described herein is useful in prevention of iatrogenic effects comprising acute fatigue syndrome (post-surgical) or androgen-deprivation therapy (ADT) induced side effects such as reduced muscle mass, reduced muscle strength, frailty, hypogonadism, osteoporosis, osteopenia, decreased BMD and/or decreased bone mass.

In one embodiment, the compounds and/or compositions and/or methods of use thereof are for the treatment of human subjects, wherein, in one embodiment, the subject is male, or in another embodiment, the subject is female.

In one embodiment, the methods of the present invention comprise administering a compound of this invention as the sole active ingredient. However, also encompassed within the scope of the present invention are methods for diabetes and related disorders, hormone therapy, dry eye, obesity, treating prostate cancer, delaying the progression of prostate cancer, and for preventing and/or treating the recurrence of prostate cancer, male contraception; treatment of osteoporosis, treatment of conditions associated with ADIF and for treatment and/or prevention of chronic muscular wasting which comprise administering the compounds in combination with one or more therapeutic agents. These agents include, but are not limited to: LHRH analogs, reversible antiandrogens, antiestrogens, anticancer drugs, 5-alpha reductase inhibitors, aromatase inhibitors, progestins, agents acting through other nuclear hormone receptors, selective estrogen receptor modulators (SERM), progesterone, estrogen, PDE5 inhibitors, apomorphine, bisphosphonate, and one or more additional SARMs.

Thus, in one embodiment, the methods of the present invention comprise administering the compound of this invention in combination with diabetes drug such as Troglitazone, Rosiglitazone, and Pioglitazone. In another embodiment, the methods of the present invention comprise administering the compound in combination with an LHRH analog. In another embodiment, the methods of the present invention comprise administering the compound, in combination with a reversible antiandrogen. In another embodiment, the methods of the present invention comprise administering the compound, in combination with an antiestrogen. In another embodiment, the methods of the present invention comprise administering the compound, in combination with an anticancer drug. In another embodiment, the methods of the present invention comprise administering the compound, in combination with a 5-alpha reductase inhibitor. In another embodiment, the methods of the present invention comprise administering the compound, in combination with an aromatase inhibitor. In another embodiment, the methods of the present invention comprise administering the compound, in combination with a progestin. In another embodiment, the methods of the present invention comprise administering the compound, in combination with an agent acting through other nuclear hormone receptors. In another embodiment, the methods of the present invention comprise administering the compound, in combination with a selective estrogen receptor modulators (SERM). In another embodiment, the methods of the present invention comprise administering the compound, in combination with a progesterone. In another embodiment, the methods of the present invention comprise administering the compound, in combination with an estrogen. In another embodiment, the methods of the present invention comprise administering the compound, in combination with a PDE5 inhibitor. In another embodiment, the methods of the present invention comprise administering the compound, in combination with apomorphine. In another embodiment, the methods of the present invention comprise administering the compound, in combination with a bisphosphonate. In another embodiment, the methods of the present invention comprise administering the compound, in combination with one or more additional SARMs. In some embodiments, the methods of the present invention comprise combined preparations comprising the compound and an agent as described hereinabove. In some embodiments, the combined preparations can be varied, e.g., in order to cope with the needs of a patient subpopulation to be treated or the needs of the single patient which different needs can be due to the particular disease, severity of the disease, age, sex, or body weight as can be readily determined by a person skilled in the art. In some embodiments, the methods of the present invention comprise personalized medicine methods which treat the needs of a single patient. In one embodiment, different needs can be due to the particular disease, severity of the disease, the overall medical state of a patient, or the age of the patient. In some embodiments, personalized medicine is the application of genomic data to better target the delivery of medical interventions. Methods of personalized medicine, in some embodiments, serve as a tool in the discovery and clinical testing of new products of the present invention. In one embodiment, personalized medicine involves the application of clinically useful diagnostic tools that may help determine a patient's predisposition to a particular disease or condition. In some embodiments, personalized medicine is a comprehensive approach utilizing molecular analysis of both patients and healthy individuals to guide decisions throughout all stages of the discovery and development of pharmaceuticals and diagnostics; and applying this knowledge in clinical practice for a more efficient delivery of accurate and quality healthcare through improved prevention, diagnosis, treatment, and monitoring methods.

Oxidative damage can comprise damage to cells and tissue, caused by oxidation of various cellular products, which through the production of peroxides and free radicals damage components of the cell and tissue, for example, damaging cell integrity, cell membranes, DNA, etc.

In another embodiment, the invention provides a method of treating, preventing, inhibiting reducing the incidence of oxidative damage-related diseases, disorders or conditions in a subject, comprising administering a pharmaceutical composition comprising a SERM of formula (I)-(XI) or its prodrug, analog, isomer, metabolite, derivative, pharmaceutically acceptable salt, pharmaceutical product, polymorph, crystal, impurity, N-oxide, ester, hydrate or any combination thereof, thereby treating, preventing, inhibiting reducing the incidence of oxidative damage-related diseases in a subject.

In some embodiments, the oxidative damage-related diseases, disorders or conditions may comprise cancers; skin disorders; neurodegenerative diseases such as Alzheimer's disease, Parkinson's disease, Huntington's disease, multiple sclerosis, and amyotrophic lateral sclerosis; vascular diseases such as stroke and various age-related dementias, and atherosclerosis; or age-related macular degeneration.

Inflammation is a common and potentially debilitating condition that occurs when the white blood cells and endogenous chemicals that can protect us from infection and foreign substances such as bacteria and viruses act on tissue surrounding a wound or infection. In some diseases, however, the body's defense system (immune system) triggers an inflammatory response when there are no foreign substances to fight off. In these diseases, called autoimmune diseases, the body's normally protective immune system causes damage to its own tissues. The body responds as if normal tissues are infected or somehow abnormal. Some, but not all types of arthritis are the result of misdirected inflammation. Arthritis is a general term that describes inflammation in joints and affects more than 2-4% of the world's population. There are many medications available to decrease swelling and inflammation and hopefully prevent or minimize the progression of the inflammatory disease. The medications include non-steroidal anti-inflammatory drugs (NSAIDs—such as aspirin, ibuprofen or naproxen), corticosteroids (such as prednisone), anti-malarial medications (such as hydroxychloroquine), and other medications including gold, methotrexate, sulfasalazine, penicillamine, cyclophosphamide and cyclosporine.

The role of estrogen receptor and its ligands as therapy for inflammation has been under consideration. The effects are regarded to be mediated by the isoform ER-β. Treatment of rats with estradiol or SERMs such as raloxifene and tamoxifen has been shown to reduce the incidence of lipo-polysacharride induced inflammatory responses. One of the pathways through which inflammatory responses are mediated is through the activation of NFκB pathway. Nuclear receptor ligands inhibit the NFκB activity through protein interaction. Recently it was shown that SERMs inhibit the inflammatory responses by inhibiting the NFκB function without having estrogenic effects on other reproductive tissues.

In one embodiment, the NRBA or SERM compounds as described herein are useful in treating inflammation and related disorders such as: a) prevention, treatment, or reversal of arthritis; b) prevention, treatment, or reveral of an arthritic condition such as Behcet's disease (autoimmune vasculitis), bursitis, calcium pyrophosphate dihydrate crystal (CPPD), deposition disease (or pseudogout), carpal tunnel syndrome, connective tissue disorders, Crohn's diseases, Ehlers-Danlos syndrome (EDS), fibromyalgia, gout, infectious arthritis, inflammatory bowel disease (IBD), juvenile arthritis, systemic lupus erythematosus (SLE), Lyme's disease, Marfan syndrome, myositis, osteoarthritis, polyarteritis nodosa, polymyalgia rheumatica, psoriasis, psoriatic arthritis, Raynaud's phenomenon, reflex sympathetic dystrophy syndrome, Reiter's syndrome, rheumatoid arthritis, scleroderma, Sjögrens' syndrome, tendonitis or ulcerative colitis; c) preventing, treatment, or reversing an autoimmune disease; d) chronic kidney disease (CKD).

In another embodiment, the invention provides a method of treating, preventing, inhibiting reducing the incidence of inflammatory diseases, disorders or conditions in a subject, comprising administering a pharmaceutical composition comprising a SERM of formula (I)-(XI) or its prodrug, analog, isomer, metabolite, derivative, pharmaceutically acceptable salt, pharmaceutical product, polymorph, crystal, impurity, N-oxide, ester, hydrate or any combination thereof, thereby treating, preventing, inhibiting reducing the incidence of inflammatory conditions in a subject. In some embodiments ER-β agonists are useful in treating, preventing, inhibiting reducing the incidence of inflammatory diseases, disorders or conditions in a subject. In another embodiment, ER-β agonist of this invention is compound 3a, listed in Table 1. In another embodiment, ER-β agonist of this invention is compound 3d, listed in Table 1. In another embodiment, ER-β agonist of this invention is compound 3e, listed in Table 1. In another embodiment, ER-β agonist of this invention is compound 3l, listed in Table 1. In another embodiment, ER-β agonist of this invention is compound 3g, listed in Table 1. In another embodiment, ER-β agonist of this invention is compound 3j, listed in Table 1. In another embodiment, ER-β agonist of this invention is compound 3i, listed in Table 1, or any combination thereof. In another embodiment, ER-β agonist of this invention is compound 4a, listed in Table 1. In another embodiment, ER-β agonist of this invention is compound 4h, listed in Table 1. In another embodiment, ER-β agonist of this invention is compound 4u, listed in Table 1. In another embodiment, ER-β agonist of this invention is compound 10o, listed in Table 1. In another embodiment, ER-β agonist of this invention is compound 10d, listed in Table 1. In another embodiment, ER-β agonist of this invention is compound 10f, listed in Table 1. In another embodiment, ER-β agonist of this invention is compound 10l, listed in Table 1. In another embodiment, ER-β agonist of this invention is compound 10w, listed in Table 1, or any combination thereof.

In some embodiments, ER-β agonists of this invention inhibit stroma-epithelial proliferation (FIG. 3, Example 4) which can affect the development of anatomic obstruction, which can reduce inflammation and thereby, treat inflammation. In one embodiment, ER-β agonists of this invention relax smooth muscle which can lower urinary tract symptoms, affect the development of BPH, which can reduce inflammation and thereby, treat inflammation.

In some embodiments, the inflammatory diseases disorders or conditions which may comprise acute inflammation, arthropathies (in general), rheumatoid arthritis, systemic lupus erythema, asthma, acute inflammation, chronic inflammation, joint damage, joint swelling, joint erosion, sepsis, or any combination thereof.

In one embodiment, joint inflammation is one of the most common causes of pain, lameness, and loss of physical activity, not only in humans but in animals, particularly horses. This debilitating condition is marked by edema, redness, heat and pain. If left untreated, joint inflammation also can lead to destruction of the joint synovium and the articular cartilage producing a permanent debilitating condition. The edema, redness, and pain that occur during inflammation are the result of physiological changes in the joint. For example, the permeability of the synovial membrane increases during inflammation allowing synovial fluid to leak into the tissues of the joint. Alterations in blood flow and pressure in the vascular system of the joint also occur during inflammation.

In addition, the metabolic activity of the cells of the joint increases during inflammation.

In another embodiment, the invention provides a method of treating, preventing, inhibiting reducing the incidence of joint inflammation in a subject, comprising administering a pharmaceutical composition comprising a SERM of formula (I)-(XI) or its prodrug, analog, isomer, metabolite, derivative, pharmaceutically acceptable salt, pharmaceutical product, polymorph, crystal, impurity, N-oxide, ester, hydrate or any combination thereof, thereby treating, preventing, inhibiting reducing the incidence of joint inflammation in a subject.

In one embodiment, the NRBAs or SERMs of this invention bind their cognate receptor at the cell surface, translocate to the cell's nucleus, and exerts their effects. In one embodiment, such effects may comprise, inter alia, regulation of particular gene expression, and may in turn play a role in the inhibition of apoptosis, activation of protein kinase pathways, and others.

In another embodiment, the NRBAs or SERMs of this invention bind cognate receptors and translocate within the mitochondria, whereupon they associate with mitochondrial DNA, and in turn play a role in the increased respiratory chain activity, inhibition of TGFβ-induced apoptosis and/or activation of manganese superoxide dismutase, and others.

Superoxide dismutases (SODs) are key enzymes in the cellular defense against free radical oxidation. By catalyzing the degradation of the superoxide free radical to water and hydrogen peroxide, SODs, play an important role in reducing the damage associated with, for example ischemic injury, chronic lung disease, Alzheimer's disease, Down syndrome, inflammatory disorders, cardiovascular disease, immune-system decline, brain disfunction, cataracts, and other aspects of aging and degenerative disease.

In one embodiment, this invention provides a method of treating, ameliorating and/or preventing reactive species-mediated damage in a subject, comprising the step of administering a NRBA or SERM of formula (I)-(XI) or its prodrug, analog, isomer, metabolite, derivative, pharmaceutically acceptable salt, pharmaceutical product, polymorph, crystal, impurity, N-oxide, ester, hydrate or any combination thereof to the subject. In one embodiment, the reactive species comprises reactive oxygen intermediates and the NRBA promotes or enhances the activity of cellular superoxide dismutase. In one embodiment, the reactive species comprises reactive nitrogen intermediates and the NRBA promotes or enhances the activity of cellular nitric oxide synthase.

In some embodiments, such damage is associated with a variety of diseases, such as, but not limited to cardiovascular disease, such as coronary heart disease and atherosclerosis, neurodegenerative disease, such as Alzheimer's disease and/or multiple sclerosis, infection, for example, HCV infection and complications thereof, autoimmune disease, such as lupus, cancer, and others, as appreciated by one skilled in the art.

In some embodiments, such activity results in suppression of pathogenic apoptosis, for example, as occurs in various disease states, such as neurodegenerative diseases or disorders, glaucoma, autoimmune disease, and others as will be appreciated by one skilled in the art.

In some embodiments, the compounds of this invention, characterized by the structures of formulae I-XI, and including any embodiment thereof, localize within the cytosol of a cell, or within cytosolic organelles, such as mitochondrion, wherein such compounds may affect cellular signaling pathways, and thereby effect the methods as described herein. For example, and in one embodiment, the compounds may interact with cellular proteins and thereby synergize a desired effect, in some embodiments, in signaling pathways within the cell, producing the desired effect. In other embodiments, the compounds of formulae I-XI antagonize a particular response or pathway in the cell, which otherwise produces an undesired effect, for example, exacerbating disease, and thus the compounds as described herein are effective in such methods by their ability to disrupt or interfere or antagonize pathogenic mechanisms in a cell or in a subject.

In some embodiments, the agents of this invention, may alter intracellular signaling pathways or responsiveness to such pathways or cascades.

In some embodiments, downstream effects of the compounds of this invention, characterized by the structures of formulae I-XI, and including any embodiment thereof, may be controlled by intracellular kinase signaling pathways activated by growth factors. In some embodiments, the compounds may affect signaling downstream of binding of a hormone to its receptor, for example, with the case of glycogen synthase kinase 3 (GSK3), an effector kinase of the phosphatidylinositol 3-kinase (PI3K) pathway, may be activated by administration of a compound of this invention and in turn affect ERalpha activity in specific cells, for example in neuroblastoma cells, and thereby effect some of the methods of this invention. In some embodiments, the compounds of this invention may result in greater expression of GSK3, which in turn stimulates or increases ER-dependent gene expression.

It is to be understood that any use of any of the compounds as herein described may be used in the treatment of any disease, disorder or condition as described herein, and represents an embodiment of this invention.

The following examples are presented in order to more fully illustrate the preferred embodiments of the invention. They should in no way, however, be construed as limiting the broad scope of the invention.

EXAMPLES

Example 1

Novel SERMs and their Estrogen Receptor Binding Affinities, Agonist and Antagonist Activity Materials and Methods ER binding affinity was determined via one of the following methods:
Method 1:
Human recombinant ER was expressed in insect Sf9 cells and performed a radioactive competitive binding assay with tritiated estradiol. If the NRBA compounds tested showed a ≥50% inhibition of [$^3$H] estradiol binding at 1 μM (1000 nM) concentration, they were tested using four concentrations of the compound to give an estimated $IC_{50}$ and $K_i$ value.
Method 2:
Estrogen receptor (ER) binding affinity of NRBA compounds was also determined using an in vitro competitive radioligand-binding assay with [$^3$H]-estradiol ([$^3$H]-$E_2$, PerkinElmer), a high affinity ligand for both ERα and ERβ. The equilibrium dissociation constant ($K_d$) of [$^3$H]-$E_2$ was determined by incubating increasing concentrations of [$^3$H]-$E_2$ (0.01 to 10 nM) with bacterial expressed ERα or β ligand binding domain (LBD) at 4° C. for 18 h. Non-specific binding was determined by adding 1000 nM $E_2$ to the incubation mixture. It was determined that the minimum concentration of [$^3$H]-$E_2$ required to saturate ERα and ERβ binding sites in the incubation mixture was 1 nM, respectively. The binding affinity of the NRBA compounds was determined under identical conditions by incubating increasing concentrations ($3\times10^{-2}$ to 1,000 nM) of ligand with isolated ER LBD and 1 nM [$^3$H]-$E_2$. Following incubation, bound and free [$^3$H]-$E_2$ was separated by using vacuum filtration with the Harvester (PerkinElmer). Briefly, the incubation mixture was filtered through a high affinity protein binding filter, and washed several times to remove any unbound radioactivity. The filter plate was air dried and sealed on the bottom. Scintillation cocktail was added to each well and the top of the plate was sealed. Radioactivity was counted in a TopCount NXT Microplate Scintillation Counter.

Specific binding of [$^3$H]-E$_2$ (B) at each concentration of SERM was obtained by subtracting the nonspecific binding of [$^3$H]-E$_2$, and expressed as a percentage of the specific binding of [$^3$H]-E$_2$ in the absence of SERM (B$_0$). The concentration of SERM that reduced the specific binding of [$^3$H]-E$_2$ by 50% (IC$_{50}$) was determined by computer-fitting the data by nonlinear regression analysis using SigmaPlot (SPSS Inc., Chicago, Ill.) to the following equation:

$$B = B_0 * [1 - C/(IC_{50} + C)]$$

where C is the concentration of SERM.

The equilibrium dissociation constant (K$_i$) of SERM was calculated by:

$$K_i = K_d * IC_{50}/(K_d + L)$$

where K$_d$ is the equilibrium dissociation constant of [$^3$H]-E$_2$ (ERα=0.65 nM, ERβ=1.83 nM), and L is the concentration of [$^3$H]-E$_2$ (1 nM).

Table 1 presents a series of NRBA compounds. Representative NRBAs are described hereinbelow, whose activity under specific experimental conditions is provided. It is to be understood that while the indicated compounds may exhibit a particular activity (for example, compound 3v is an agonist) under the experimental conditions employed, as a function, in some embodiments of the particular cells utilized, etc., such compounds may possess alternate or varied activity in different experimental settings.

Representative examples of the NRBAs of this invention and their activity under the indicated conditions are as follows:

ER alpha agonists: 3v (ER-α: K$_i$=20 nM; EC$_{50}$=22.4 nM), 3b (ER-α: K$_i$=14 nM; EC$_{50}$=10 nM), 3k (ER-α: K$_i$=129 nM; EC$_{50}$=12 nM), 10x (ER-α: K$_i$=13 nM; EC$_{50}$=16 nM).

ER alpha antagonists: 10m (ER-α: K$_i$=221 nM; IC$_{50}$=<10 nM), 4a (ER-α: K$_i$=111 nM; IC$_{50}$=35 nM), 11f (ER-α: K$_i$=60 nM; IC$_{50}$=69 nM), and 11g (ER-α: K$_i$=79 nM; IC$_{50}$=16 nM)

ER beta agonists: 10d (ER-β: K$_i$=61 nM; EC$_{50}$=85 nM), 10f (ER-β: K$_i$=57 nM; EC$_{50}$=42 nM), 10l (ER-β: K$_i$=82 nM; EC$_{50}$=27 nM), 11p (ER-β: K$_i$=108 nM; EC$_{50}$=<10 nM)

ER beta antagonist: 10j (ER-β: K$_i$=36 nM; IC$_{50}$=20 nM), 10n (ER-β: K$_i$=92 nM; IC$_{50}$=47 nM), 10t (ER-β: K$_i$=<10 nM; IC$_{50}$=17 nM)

TABLE 1

| Compound # and IUPAC NAME | PHYSICAL CHARACTERIZATION |
|---|---|
| Estradiol (E2) | |
| Propyl pyrazole triol (PPT) | |
| Dipropionitrile (DPN) | |
| ICI-182780 | |
| 5d<br>4-Hydroxy-N-(4-hydroxyphenyl)-N-(4-methoxyphenyl)-benzamide | tan solid. 95% yield. M.p. 239-241° C. $^1$H NMR (DMSO-d$_6$, 300 MHz) δ 9.80 (bs, 1H), 9.46 (bs, 1H), 7.23-7.21 (m, 2H), 7.08-7.05 (m, 2H), 6.96-6.93 (m, 2H), 6.87-6.84 (m, 2H), 6.68-6.65 (m, 2H), 6.60-6.57 (m, 2H), 3.72 (s, 3H). MS m/z 334 (M − H)$^-$. |
| 5e<br>N-(4-Hydroxyphenyl)-4-methoxy-N-(4-methoxyphenyl)-benzamide | tan solid. 90% yield. M.p. 205-206° C. $^1$H NMR (DMSO-d$_6$, 300 MHz) δ 9.48 (bs, 1H), 7.35-7.32 (m, 2H), 6.99-6.97 (m, 2H), 6.87-6.85 (m, 2H), 6.81-6.77 (m, 2H), 6.68-6.66 (m, 2H), 3.72 (s, 6H). MS m/z 348 (M − H)$^-$. |
| 4n<br>4-Methoxy-N-(4-methoxyphenyl)-N-[4-(2-piperidin-1-ylethoxy)phenyl]-benzamide | white solid. 88% yield. M.p. 163-165° C. $^1$H NMR (DMSO-d$_6$, 300 MHz) δ 7.36 (d, 2H, J = 8.69 Hz), 7.16-7.07 (m, 4H), 6.94 (d, 2H, J = 8.82 Hz), 6.87 (d, 2H, J = 8.82 Hz), 6.80 (d, 2H, J = 8.75 Hz), 4.38-4.35 (m, 2H), 3.69 (s, 6H), 3.48-3.44 (m, 4H), 2.51-2.50 (m, 2H), 1.78-1.66 (m, 4H), 1.41-1.37 (m, 2H). MS m/z 461 (M + H)$^+$. |
| 3u<br>N-Biphenyl-4-yl-N-(4-hydroxyphenyl)-4-methoxybenzamide | tan solid. 21% yield. M.p. 232-234° C. $^1$H NMR (DMSO-d$_6$, 300 MHz) δ 9.55 (s, 1H). 7.65-7.62 (m, 4H), 7.45 (t, 1H, J = 7.69 Hz), 7.40-7.34 (m, 4H), 7.23 (d, 2H, J = 8.55 Hz), 7.03-7.02 (m, 2H), 6.82-6.80 (m, 2H), 6.71-6.69 (m, 2H), 3.73 (s, 3H),. MS m/z 418 (M + Na)$^+$. |
| 3v<br>N-Biphenyl-4-yl-4-hydroxy-N-(4-hydroxyphenyl)-benzamide | white solid. 49% yield. M.p. 253-255° C. $^1$H NMR (DMSO-d$_6$, 300 MHz) δ 7.65-7.61 (m, 4H), 7.45 (t, 2H, J = 7.69 Hz), 7.36-7.33 (m, 1H), 7.28-7.26 (m, 2H), 7.21-7.19 (m, 2H), 7.01-6.98 (m, 2H), 6.71-6.68 (m, 2H), 6.62-6.60 (m, 2H). MS m/z 404 (M + Na)$^+$. |
| 3w<br>4-Hydroxy-N-(4-hydroxyphenyl)-N-[4-(2-piperidin-1-ylethoxy)phenyl]-benzamide | tan solid. 46% yield. M.p. 233-235° C. $^1$H NMR (DMSO-d$_6$, 300 MHz) δ 9.81 (bs, 1H), 9.47 (bs, 1H), 7.24-7.20 (m, 2H), 7.05-7.03 (m, 2H), 6.96-6.93 (m, 2H), 6.87-6.84 (m, 2H), 6.68-6.65 (m, 2H), 6.60-6.57 (m, 2H), 4.02-3.99 (m, 2H), 2.63-2.60 (m, 2H), 2.09-2.08 (m, 4H), 1.48-1.36 (m, 6H). MS m/z 433 (M + H)$^+$. |
| 2w<br>4-Cyano-N-(4-methoxyphenyl)-N-phenylbenzamide | pale-yellow solid. 96% yield. M.p. 125-128° C. $^1$H NMR (DMSO-d$_6$, 300 MHz) δ 7.77-7.74 (m, 2H), 7.61-7.58 (m, 2H), 7.34-7.21 (m, 7H), 6.88 (d, 2H, J = 7.92 Hz), 3.71 (s, 3H). MS m/z 351 (M + Na)$^+$. |
| 4o<br>N-Biphenyl-4-yl-N-(4-hydroxyphenyl)-4-(2-piperidin-1-ylethoxy)-benzamide | pale-yellow solid. 40% yield. M.p. 132-135° C. $^1$H NMR (DMSO-d$_6$, 300 MHz) δ 7.65-7.61 (m, 4H), 7.47-7.45 (m, 2H), 7.36-7.33 (m, 1H), 7.28-7.26 (m, 2H), 7.21-7.19 (m, 2H), 7.01-6.98 (m, 2H), 6.70-6.67 (m, 2H), 6.62-6.61 (m, 2H), 4.05 (bs, 2H), 2.66 (bs, 2H), 2.50-2.45 (m, 4H), 1.49-1.38 (m, 6H). MS m/z 493 (M + H)$^+$. |

TABLE 1-continued

| Compound # and IUPAC NAME | PHYSICAL CHARACTERIZATION |
|---|---|
| 3x<br>3-Hydroxy-N-(4-hydroxyphenyl)-N-phenyl-benzamide | tan solid. 78% yield. M.p. 221-222° C. $^1$H NMR ((DMSO-d$_6$, 300 MHz) δ 9.51 (bs, 2H), 7.33-7.29 (m, 2H), 7.19-7.15 (m, 3H), 7.04-6.98 (m, 3H), 6.82-6.66 (m, 5H). MS m/z 304 (M − H)$^−$. |
| 10a<br>4-cyano-N-(4-hydroxyphenyl)-N-phenylbenzamide | yellow solid, 74% yield, M.p. 243-244° C. $^1$H NMR (DMSO-d$_6$, 300 MHz) δ 7.76-7.74 (m, 1H), 7.58-7.56 (m, 2H), 7.33-7.21 (m, 5H), 7.09-7.08 (m, 2H), 6.67 (s, 2H). MS m/z 313 (M − H)$^−$. |
| 4p<br>4-Methoxy-N-phenyl-N-[4-(2-piperidin-1-ylethoxy)phenyl]-benzamide | yellow solid. 84% yield. M.p. 139-141° C. $^1$H NMR (DMSO-d$_6$, 300 MHz) δ 7.35-7.33 (m, 4H), 7.26-7.22 (m, 5H), 7.15-7.14 (m, 2H), 7.12-7.11 (m, 2H), 6.91-6.87 (m, 2H), 6.83-6.80 (m, 2H), 4.02 (t, 2H, J = 5.79 Hz), 3.72 (s, 3H), 2.63 (t, 2H, J = 5.79 Hz), 2.41 (bs, 4H), 1.48-1.46 (m, 4H), 1.38-1.36 (m, 2H). MS m/z 507 (M + H)$^+$. |
| 2y<br>4-Cyano-N-(3-methoxyphenyl)-N-phenylbenzamide | brown oil. 85% yield. $^1$H NMR (DMSO-d$_6$, 300 MHz) δ 7.77-7.75 (m, 2H). 7.63-7.61 (m, 2H), 7.35-7.30 (m, 4H), 7.25-7.22 (m, 2H), 6.91 (s, 1H), 6.83-6.80 (m, 2H), 3.67 (s, 3H). MS m/z 351 (M + Na)$^+$. |
| 2z<br>4-Cyano-N,N-diphenylbenzamide | tan solid. 85% yield. M.p.145-147° C. $^1$H NMR (DMSO-d$_6$, 300 MHz) δ7.76-7.74 (m, 2H), 7.61-7.59 (m, 2H), 7.34-7.22 (m, 10H). MS m/z 321 (M + Na)$^+$. |
| 4q<br>N-(4-Hydroxyphenyl)-N-phenyl-3-(2-piperidin-1-ylethoxy)-benzamide | tan solid. 64% yield. M.p. 93-95° C. $^1$H NMR (DMSO-d$_6$) δ 9.56 (d, 1H, J = 6.00 Hz), 7.35-7.30 (m, 2H), 7.23-7.14 (m, 4H), 7.05-6.76 (m, 5H), 6.69-6.67 (m, 2H), 4.20 (bs, 2H), 2.81-2.73 (m, 6H), 1.48 (bs, 4H), 1.46 (bs, 2H). MS m/z 417 (M + H)$^+$. |
| 3y<br>N-Biphenyl-4-yl-4-hydroxy-N-[4-(2-piperidin-1-ylethoxy)phenyl]-benzamide | pale-yellow solid. 46% yield. M.p.109-112° C. $^1$H NMR ((DMSO-d$_6$, 300 MHz) δ 9.89 (s, 1H), 7.65-7.61 (m, 4H), 7.46-7.43 (m, 2H), 7.37-7.33 (m, 1H), 7.31-7.28 (m, 2H), 7.22-7.19 (m, 2H), 7.12-7.09 (m, 2H), 6.91-6.89 (m, 2H), 6.63-6.60 (m, 2H), 4.04 (bs, 2H), 2.67-2.64 (m, 2H), 2.46 (bs, 4H), 1.50-1.49 (m, 4H), 1.37 (bs, 2H). MS m/z 493 (M + H)$^+$. |
| 10b<br>N-(biphenyl-4-yl)-4-cyano-N-(4-methoxyphenyl)-benzamide | yellow solid, 70% yield, M.p. 209-211° C. $^1$H NMR (DMSO-d$_6$, 300 MHz) δ 7.78-7.77 (m, 2H), 7.65-7.63 (m, 6H), 7.47-7.44 (m, 4H), 7.37-7.34 (m, 3H), 7.27-7.25 (m, 2H). 6.89 (bs, 2H), 3.72 (s, 3H). MS m/z 405 (M + H)$^+$. |
| 10c<br>N,N-bis(4-hydroxyphenyl)biphenyl-4-carboxamide | tan solid, 72% yield, M.p. > 250° C. $^1$H NMR (DMSO-d$_6$, 300 MHz) δ 9.49 (s, 2H), 7.66-7.64 (m, 2H), 7.58-7.56 (m, 6H), 7.46-7.42 (m, 4H), 7.38-7.35 (m, 1H), 7.05-7.03 (m, 4H). 6.69 (bs, 4H). MS m/z 382 (M + H)$^+$. |
| 10d<br>N,N-bis(4-hydroxyphenyl)-3,4-dimethylbenzamide | tan solid, 68% yield, M.p. > 250° C. $^1$H NMR (DMSO-d$_6$, 300 MHz) δ 9.46 (s, 3H), 7.20 (s, 1H), 7.03-6.95 (m, 6H), 6.68-6.65 (m, 4H), 2.14 (s, 3H), 2.12 (s, 4H). MS m/z 334 (M + H)$^+$. |
| 10e<br>N-(biphenyl-4-yl)-4-cyano-N-(4-hydroxyphenyl)-benzamide | yellow solid, 58% yield, M.p. 223-224° C. $^1$H NMR (DMSO-d$_6$, 300 MHz) δ 9.63 (s, 3H), 7.78-7.76 (m, 2H), 7.66-7.60 (m, 6H), 7.48-7.43 (m, 2H), 7.38-7.35 (m, 3H), 7.12 (d, 2H, J = 8.27 Hz), 6.69 (d, 2H, J = 8.27 Hz). MS m/z 334 (M + H)$^+$. |
| 10f<br>3-fluoro-4-hydroxy-N-(4-hydroxyphenyl)-N-phenylbenzamide | white solid, 66% yield, M.p. 223-225° C. $^1$H NMR (DMSO-d$_6$, 300 MHz) δ 10.11 (bs, 1H), 9.57 (bs, 1H), 7.34-7.29 (m, 2H), 7.20-7.10 (m, 4H), 7.06-6.97 (m, 3H), 6.81-6.75 (m, 1H), 6.70-6.67 (m, 2H). MS m/z 324 (M + H)$^+$. |
| 10g<br>4-fluoro-3-hydroxy-N,N-bis(4-hydroxyphenyl)-benzamide | tan solid, 71% yield, M.p. > 250° C. $^1$H NMR (DMSO-d$_6$, 300 MHz) δ 9.95 (bs, 1H), 9.47 (bs, 2H), 7.02-6.95 (m, 6H), 6.75-6.72 (m, 1H), 6.68-6.66 (m, 4H). MS m/z 340 (M + H)$^+$. |
| 10i<br>4-hydroxy-N,N-bis(4-hydroxyphenyl)-3,5-dimethylbenzamide | tan solid, 91% yield, M.p. > 250° C. $^1$H NMR (DMSO-d$_6$, 300 MHz) δ 9.41 (bs, 2H), 6.96-6.92 (m, 6H), 6.66 (d, 4H, J = 8.79 Hz), 2.02 (s, 6H). MS m/z 350 (M + H)$^+$. |
| 10j<br>N,N-bis(4-hydroxyphenyl)-2,3-dimethylbenzamide | peach-white solid, 68% yield, M.p. > 250° C. $^1$H NMR (DMSO-d$_6$, 300 MHz) δ 9.47 (bs, 2H), 7.18 (d, 2H, J = 8.30 Hz), 7.06 (d, 1H, J = 7.08 Hz), 7.00-6.92 (m, 4H), 6.78 (d, 2H, J = 8.30 Hz), 6.51 (d, 2H, J = 8.06 Hz), 2.22 (s, 3H), 2.15 (s, 3H). MS m/z 334 (M + H)$^+$. |
| 10k<br>3-fluoro-4-hydroxy-N,N-bis(4-hydroxyphenyl)-benzamide | tan solid, 71% yield, M.p. > 250° C. $^1$H NMR (DMSO-d$_6$, 300 MHz) δ 10.25 (bs, 1H), 9.48 (bs, 2H), 7.12-6.95 (m, 6H), 6.80-6.65 (m, 5H). MS m/z 338 (M − H)$^−$. |
| 10l<br>N,N-bis(4-hydroxyphenyl)-4-propylbenzamide | tan solid, 77% yield, M.p. 224-225° C. $^1$H NMR (DMSO-d$_6$, 300 MHz) δ 9.46 (s, 2H), 7.27-7.26 (m 2H), 7.06-7.04 (m, 2H), 6.99-6.97 (m, 4H), 6.66-6.65 (m, 4H), 2.50 (s, 2H), 1.53-1.52 (m, 2H), 0.82 (t, 3H, J = 7.33 Hz). MS m/z 346 (M − H)$^−$. |
| 10m<br>3,4-dihydroxy-N,N-bis(4-hydroxyphenyl)-benzamide | light-pink solid, 66% yield, M.p. > 250° C. $^1$H NMR (DMSO-d$_6$, 300 MHz) δ 9.39 (bs, 4H), 6.91 (d, 2H, J = 8.79 Hz), 6.84 (d, 1H, J = 1.95 Hz), 6.66 (d, 4H, J = 8.55 Hz), 6.62-6.60 (m, 1H), 6.51 (d, 1H, J = 8.30 Hz). MS m/z 336 (M − H)$^−$. |
| 10n<br>4-hydroxy-N,N-bis(4-hydroxyphenyl)-3- | tan solid, 78% yield, M.p. > 250° C. $^1$H NMR (DMSO-d$_6$, 300 MHz) δ 9.69 (bs, 1H), 9.44 (bs, 2H), 7.15 (d, 1H, J = 1.71 Hz), 6.97 (dd, 2H, J = 1.95, 8.30 Hz), 6.93 (d, 4H, J = 8.55 Hz), |

TABLE 1-continued

| Compound # and IUPAC NAME | PHYSICAL CHARACTERIZATION |
|---|---|
| methylbenzamide | 6.66 (d, 4H, J = 8.80 Hz), 6.55 (d, 1H, J = 8.55 Hz), 2.50 (s, 3H). MS m/z 334 (M − H)$^-$. |
| 10o<br>N-(4-hydroxyphenyl)-N-(4-(2-(piperidin-1-yl)ethoxy)phenyl)-4-propylbenzamide | yellow solid, 39% yield, M.p.168-171° C. $^1$H NMR (DMSO-d$_6$, 300 MHz) δ 9.49 (s, 1H), 7.28 (d, 2H, J = 7.28 Hz), 7.09 (d, 2H, J = 8.06 Hz), 7.06 (d, 2H, J = 8.30 Hz), 6.99 (d, 2H, J = 8.06 Hz), 6.86 (d, 2H, J = 7.82 Hz), 6.66 (d, 2H, J = 7.57 Hz), 4.00 (bs, 2H), 2.62 (bs, 2H), 2.51-2.50 (m, 2H), 2.40 (bs, 4H), 1.54-1.46 (m, 6H), 1.37-1.36 (m, 2H), 0.82 (t, 3H, J = 7.33 Hz). MS m/z 459 (M + H)$^+$. |
| 10p<br>N-(4-hydroxyphenyl)-2,3-dimethyl-N-(4-2-(piperidin-1-yl)ethoxy)phenyl)-benzamide | tan foam, 32% yield, M.p. 93-96° C. $^1$H NMR (DMSO-d$_6$, 300 MHz) δ 9.46 (s, 1H), 7.28 (d, 1H, J = 7.82 Hz), 7.18 (d, 1H, J = 7.08 Hz), 7.08 (d, 2H, J = 7.08 Hz), 6.99-6.91 (m, 4H), 6.77 (d, 1H, J = 7.33 Hz), 6.70 (d, 1H, J = 7.33 Hz), 6.51 (d, 1H, J = 7.57 Hz), 4.07 (bs, 1H), 3.91 (bs, 1H), 2.68-2.64 (m, 2H), 2.50-2.35 (m, 4H), 2.22 (s, 3H), 2.14 (s, 3H), 1.50-1.37 (m, 6H). MS m/z 445 (M + H)$^+$. |
| 10q<br>N,N-bis(4-hydroxyphenyl)-2,4-dimethylbenzamide | yellow solid, 80% yield, M.p. 227-228° C. $^1$H NMR (DMSO-d$_6$, 300 MHz) δ 9.45 (bs, 2H), 7.10-7.08 (m, 4H), 6.99-6.83 (m, 3H), 6.81-6.54 (m, 4H), 2.28 (s, 3H), 2.17 (s, 3H). MS m/z 334 (M + H)$^+$. |
| 10r<br>N,N-bis(4-hydroxyphenyl)-3,5-dimethylbenzamide | white solid, 61% yield, M.p. > 250° C. $^1$H NMR (DMSO-d$_6$, 300 MHz) δ 9.45 (bs, 2H), 7.10-7.08 (m, 4H), 6.98-6.83 (m, 3H), 6.81-6.54 (m, 4H), 2.28 (s, 3H), 2.17 (s, 3H). MS m/z 334 (M + H)$^+$. |
| 10s<br>N,N-bis(4-hydroxyphenyl)-4-methylbenzamide | tan solid, 32% yield, M.p. 223-225° C. $^1$H NMR (DMSO-d$_6$, 300 MHz) δ 9.47 (bs, 2H), 7.25 (d, 2H, J = 8.04 Hz), 7.05-6.97 (m, 6H), 6.66 (d, 4H, J = 8.33 Hz), 2.23 (s, 3H). MS m/z 320 (M + H)$^+$. |
| 10t<br>4,4'-(2,3-dimethyl-benzylazanediyl)diphenol | tan foam, 41% yield, M.p. 147-150° C. $^1$H NMR (DMSO-d$_6$, 300 MHz) δ 8.92 (s, 2H), 7.07 (d, 1H, J = 7.33 Hz), 7.00-6.94 (m, 2H), 6.76-6.72 (m, 4H), 6.63-6.59 (m, 4H), 4.72 (s. 2H), 2.23 (s, 3H), 2.16 (s, 3H). MS m/z 320 (M + H)$^+$. |
| 10u<br>4-formyl-N,N-bis(4-hydroxyphenyl)-benzamide | yellow foam, 50% yield, M.p. 117-122° C. $^1$H NMR (DMSO-d$_6$, 300 MHz) δ 9.98 (s, 1H), 9.52 (s, 2H), 7.78 (d, 2H, J = 8.13 Hz), 7.61 (d, 2H, J = 8.13 Hz), 7.06 (bs, 4H), 6.67 (bs, 4H). MS m/z 332 (M − H)$^-$. |
| 10v<br>4-hydroxy-N-(4-hydroxyphenyl)benzamide (10v) | |
| 11l<br>4-((hydroxyimino)methyl)-N,N-bis(4-hydroxyphenyl)benzamide | yellow solid, 67% yield, M.p. 146-148° C. $^1$H NMR (DMSO-d$_6$, 300 MHz) δ 11.36 (s, 1H), 9.49 (s, 2H), 8.07 (s, 1H), 7.45 (d, 2H, J = 8.28 Hz), 7.37 (d, 1H, J = 8.28 Hz), 7.01 (d, 4H, J = 7.52 Hz), 6.67 (d, 4H, J = 6.45 Hz). MS m/z 349 (M + H)$^+$. |
| 11m<br>N-(4-hydroxyphenyl)-2,4-dimethyl-N-(4-(2-(piperidin-1-yl)ethoxy)phenyl)benzamide | pale-yellow foam, 26% yield, M.p. 92-95° C. $^1$H NMR (DMSO-d$_6$, 300 MHz) δ 9.48 (s, 1H), 7.13-6.81 (m, 11H), 3.33 (bs, 2H), 2.65 (bs, 2H), 2.51-2.45 (m, 4H), 2.29 (s, 3H), 2.17 (s, 3H), 1.49 (bs, 4H), 1.38 (bs, 2H). MS m/z 446 (M + H)$^+$. |
| 11n<br>N-(4-hydroxyphenyl)-3,5-dimethyl-N-(4-(2-(piperidin-1-yl)ethoxy)phenyl)benzamide | pale-yellow foam, 26% yield, M.p. 94-100° C. $^1$H NMR (DMSO-d$_6$, 300 MHz) δ 9.50 (s, 1H), 7.11 (d, 2H, J = 8.67 Hz), 7.02-6.98 (m, 3H), 6.91-6.86 (m, 3H), 6.67 (d, 2H, J = 8.46 Hz), 4.03 (t, 2H, J = 5.10 Hz), 2.67 (bs, 2H), 2.51-2.46 (m, 4H), 2.15 (s, 6H), 1.50-1.49 (m, 4H), 1.39-1.37 (m, 2H). MS m/z 445. |
| 11o<br>4-((2,3-dimethylbenzyl)(4-(2-(piperidin-1-yl)ethoxy)phenyl)amino)phenol | purple foam, 38% yield, M.p. 65-70° C. $^1$H NMR (DMSO-d$_6$, 300 MHz) δ 9.08 (s, 1H), 7.08-6.86 (m, 5H), 6.78-6.65 (m, 6H), 4.75 (s, 2H), 3.96 (t, 2H, J = 5.83 Hz), 3.34 (bs, 2H), 2.65 (bs, 2H), 2.51 (bs, 2H), 2.27 (s, 3H), 2.16 (s, 3H), 1.51-1.48 (m, 4H), 1.38-1.37 (m, 2H). MS m/z 432. |
| 11p<br>N,N-bis(4-hydroxyphenyl)-4-pentylbenzamide | white solid, 68% yield, M.p. 201-202° C. $^1$H NMR (DMSO-d$_6$, 300 MHz) δ 9.46 (s, 2H), 7.26 (d, 2H, J = 8.10 Hz), 7.05 (d, 2H, J = 8.10 Hz), 6.98 (d, 4H, J = 8.42 Hz), 6.66 (d, 4H, J = 8.28 Hz), 2.52-2.47 (m, 2H), 1.52-1.48 (m, 2H), 1.28-1.21 (m, 4H), 0.83 (t, 3H, J = 7.00 Hz). MS m/z 376. |
| 11q<br>N-(4-hydroxyphenyl)-4-pentyl-N-(4-(2-(piperidin-1-yl)ethoxy)phenyl)benzamide | tan solid, 31% yield, M.p. 172-174° C. $^1$H NMR (DMSO-d$_6$, 300 MHz) δ 9.49 (s, 1H), 7.27 (d, 2H, J = 8.06 Hz), 7.09 (d, 2H, J = 7.82 Hz), 7.05 (d, 2H, J = 8.30 Hz), 6.99 (d, 2H, J = 7.82 Hz), 6.86 (d, 2H, J = 7.33 Hz), 6.66 (d, 2H, J = 7.33 Hz), 4.01 (bs, 2H), 3.33 (bs, 4H), 2.64-2.63 (m, 2H), 2.51-2.36 (m, 2H), 1.53-1.51 (m, 6H), 1.37 (bs, 2H), 1.27-1.23 (m, 4H), 0.83 (t, 3H, J = 7.20 Hz). MS m/z 488 (M + H)$^+$. |
| 11r<br>4-tert-butyl-N,N-bis(4-hydroxyphenyl)benzamide | tan solid, 80% yield, M.p. > 250° C. $^1$H NMR (DMSO-d$_6$, 300 MHz) δ 9.48 (bs, 2H), 7.32-7.24 (m, 4H), 6.99 (d, 4H, J = 8.56 Hz), 6.67 (d, 4H, J = 8.44 Hz), 1.21 (s, 9H). MS m/z 363. |
| 11s | tan solid, 39% yield, M.p. 208-210° C. $^1$H NMR (DMSO-d$_6$, |

TABLE 1-continued

| Compound # and IUPAC NAME | PHYSICAL CHARACTERIZATION |
|---|---|
| 4-tert-butyl-N-(4-hydroxyphenyl)-N-(4-(2-(piperidin-1-yl)ethoxy)phenyl)benzamide | 300 MHz) δ 9.50 (s, 1H), 7.34-7.25 (m, 4H), 7.10 (d, 2H, J = 8.71 Hz), 6.99 (d, 2H, J = 8.61 Hz), 6.87 (d, 2H, J = 8.71 Hz), 6.67 (d, 2H, J = 8.61 Hz), 4.02 (t, 2H, J = 5.70 Hz), 3.33 (bs, 2H), 2.64 (bs, 2H), 2.43 (bs 2H), 1.50-1.47 (m, 4H), 1.38-1.36 (m, 2H), 1.21 (s, 9H). MS m/z 473 (M + H)+. |
| 11t 3-{4-[Bis-(4-hydroxy-phenyl)-carbamoyl]-phenyl}-acrylic acid | yellow foam, M.p. 129-131° C. $^1$H NMR ((DMSO-d$_6$, 300 MHz) δ9.49 (s, 2H), 7.61-7.56 (m, 3H), 7.39 (d, J = 8.26 Hz, 2H), 7.04-7.02 (m, 4H), 6.66-6.61 (m, 5H), 3.71 (s, 3H), 1.53-1.52 (m, 2H, CH$_2$), 0.82tJ = 7.33 Hz, 3H, CH$_3$). MS m/z 388.1 (M − H)−. |
| 11u 3-{4-[Bis-(4-hydroxy-phenyl)-carbamoyl]-phenyl}-propionic acid | pale-yellow foam, M.p. 122-124° C. $^1$H NMR ((DMSO-d$_6$, 300 MHz) δ9.51 (bs, 1H), 7.29 (d, J = 8.23 Hz, 2H), 7.13-7.08 (m, 4H), 6.99 (d, J = 8.60 Hz, 2H), 6.85 (d, J = 8.60 Hz, 2H), 6.65 (d, J = 8.23 Hz, 2H), 3.99 (q, J = 7.10, 14.21 Hz, 2H), 3.71 (s, 3H), 2.78 (t, J = 7.44 Hz, 2H), 2.56 (t, J = 7.44 Hz, 2H), 1.11tJ = 7.06 Hz, 3H, CH$_3$). MS m/z 418.1 (M − H)−. |
| 11v N,N-Bis-(4-hydroxy-phenyl)-4-(3-hydroxy-propyl)-benzamide | pale-yellow foam, M.p. 122-124° C. $^1$H NMR ((DMSO-d$_6$, 300 MHz) δ9.51 (bs, 1H), 7.29 (d, J = 8.23 Hz, 2H), 7.13-7.08 (m, 4H), 6.99 (d, J = 8.60 Hz, 2H), 6.85 (d, J = 8.60 Hz, 2H), 6.65 (d, J = 8.23 Hz, 2H), 3.99 (q, J = 7.10, 14.21 Hz, 2H), 3.71 (s, 3H), 2.78 (t, J = 7.44 Hz, 2H), 2.56 (t, J = 7.44 Hz, 2H), 1.11tJ = 7.06 Hz, 3H CH$_3$). MS m/z 418.1 (M − H)−. |
| 6a 2-(N-(4-methoxyphenyl)-4-methylphenylsulfonamido)ethyl 4-methylbenzenesulfonate | white solid. 49% yield. $^1$H NMR (DMSO-d$_6$, 500 MHz) δ 7.69-7.68 (m, 2H), 7.46-7.45 (m, 2H), 7.41-7.40 (m, 2H), 7.37-7.35 (m, 2H), 6.79-6.77 (m, 2H), 6.72-6.70 (m, 2H), 3.91 (t, J = 5.0 Hz, 2H), 3.77 (t, J = 5.0 Hz, 2H), 3.72 (s, 3H), 2.43 (s, 3H), 2.39 (s, 3H). MS m/z 498 (M + Na)+. |
| 6b (R)-3-bromo-2-hydroxy-N-(4-methoxyphenyl)-2-methylpropanamide | white solid, 63% yield. M.p. 79.0-81.0° C. $^1$H NMR (DMSO-d$_6$, 500 MHz) δ 9.47 (s, 1H), 7.65 (d, 2H, J = 9.0 Hz), 6.89 (d, 2H, J = 9.0 Hz), 6.12 (s, 1H), 3.81 (d, 1H, J = 10.2 Hz), 3.71 (s, 3H), 3.56 (d, 1H, J = 10.2 Hz), 1.45 (s, 3H). MS m/z 288 (M + H)+. |
| 6c (S)-2-hydroxy-N,3-bis(4-methoxyphenyl)-2-methylpropanamide | colorless oil, 39% yield. $^1$H NMR (CDCl$_3$, 300 MHz) δ 8.34 (s, 1H), 7.40 (d, 2H, J = 9.0 Hz), 7.16 (d, 2H, J = 8.4 Hz), 6.86-6.83 (m, 4H), 3.79 (s, 3H), 3.78 (s, 3H), 3.38 (d, 1H, J = 13.6 Hz), 2.80 (d, 1H, J = 13.9 Hz), 1.53 (s, 3H). MS m/z 338 (M + Na)+. |
| 6d (S)-2-hydroxy-3-(4-methoxyphenoxy)-N-(4-methoxyphenyl)-2-methylpropanamide | white solid, 99% yield. M.p. 101.0-102.0° C. $^1$H NMR (CDCl$_3$, 300 MHz) δ 8.64 (s, 1H), 7.49 (d, 2H, J = 8.9 Hz), 6.89-6.79 (m, 6H), 4.35 (d, 1H, J = 8.9 Hz), 3.93 (d, 1H, J = 8.9 Hz), 3.79 (s, 3H), 3.76 (s, 3H), 1.56 (s, 3H). MS m/z 254 (M + Na)+. |
| 6e (R)-3-bromo-2-hydroxy-N-(4-hydroxyphenyl)-2-methylpropanamide | colorless oil, 98% yield. $^1$H NMR (DMSO-d$_6$, 500 MHz) δ 9.33 (s, 1H), 9.21 (s, 1H), 7.47 (d, 2H, J = 8.9 Hz), 6.68 (d, 2H, J = 9.0 Hz), 6.08 (s, 1H), 3.80 (d, 1H, J = 10.3 Hz), 3.55 (d, 1H, J = 10.5 Hz), 1.44 (s, 3H). MS m/z 297 (M + Na)+. |
| 6f (S)-2-hydroxy-3-(4-hydroxyphenoxy)-N-(4-hydroxyphenyl)-2-methylpropanamide | colorless oil, 67% yield. $^1$H NMR (DMSO-d$_6$, 500 MHz) δ 9.35 (s, 1H), 9.19 (s, 1H), 8.90 (s, 1H), 7.48 (d, 2H, J = 8.8 Hz), 6.73 (d, 2H, J = 9.0 Hz), 6.68 (d, 2H, J = 9.0 Hz), 6.63 (d, 2H, J = 9.0 Hz), 5.89 (s, 1H), 4.06 (d, 1H, J = 9.5 Hz), 3.81 (d, 1H, J = 9.3 Hz), 1.36 (s, 3H). MS m/z 326 (M + Na)+. |
| 6g (S)-2-hydroxy-N,3-bis(4-hydroxyphenyl)-2-methylpropanamide | colorless oil, 65% yield. $^1$H NMR (DMSO-d$_6$, 300 MHz) δ 9.15 (s, 1H), 9.08 (s, 1H), 9.03 (s, 1H), 7.34 (d, 2H, J = 9.0 Hz), 6.97 (d, 2H, J = 8.4 Hz), 6.64 (d, 2H, J = 8.9 Hz), 6.58 (d, 2H, J = 8.4 Hz), 5.50 (s, 1H), 2.90 (d, 1H, J = 13.5 Hz), 2.68 (d, 1H, J = 13.5 Hz), 1.29 (s, 3H). MS m/z 310 (M + Na)+. |
| 2a 4-Methoxy-N,N-bis-(4-methoxyphenyl)-benzamide | white solid, 98% yield. M.p. 119.5-120° C. $^1$H NMR (CDCl$_3$, 300 MHz) δ 7.42 (d, 2H, J = 8.9 Hz), 7.05 (d, 4H, J = 8.8 Hz), 6.81 (d, 4H, J = 8.9 Hz), 6.71 (d, 2H, J = 8.9 Hz), 3.77 (s, 9H). MS m/z 364 (M + H). |
| 3a 4-Hydroxy-N,N-bis-(4-hydroxyphenyl)-benzamide | white solid, 79% yield. M.p. 275-276° C. (decomposed). $^1$H NMR (DMSO-d$_6$, 300 MHz) δ 9.79 (s, 1H), 9.44 (s, 2H), 7.21 (d, 2H, J = 9.0 Hz), 6.93 (d, 4H, J = 8.7 Hz), 6.66 (d, 4H, J = 8.7 Hz), 6.58 (d, 2H, J = 9.0 Hz). MS m/z 344 (M + Na)+. |
| 2d N,N-Bis-(4-methoxyphenyl)-benzamide | white solid, 98% yield. M.p. 77-77.5° C. $^1$H NMR (CDCl$_3$, 300 MHz) δ 7.46-7.42 (m, 2H), 7.29-7.17 (m, 3H), 7.09-7.06 (m, 4H), 6.81-6.78 (m, 4H), 3.76 (s, 6H). MS m/z 356 (M + Na)+. |
| 3d N,N-Bis-(4-hydroxyphenyl)-benzamide | white solid, 98% yield. M.p. >265° C. (decomposed). $^1$H NMR (DMSO-d$_6$, 300 MHz) δ 9.48 (s, 2H), 7.37-7.20 (m, 5H), 7.01 (d, 4H, J = 8.9 Hz), 6.66 (d, 4H, J = 7.9 Hz), 6.58 (d, 2H, J = 7.3 Hz). MS m/e 304 (M − H)−. |
| 2g N,N-Diphenyl-benzamide | white solid, 89% yield. M.p. 178.4-179.3° C. $^1$H NMR (CDCl$_3$, 300 MHz) δ 7.46-7.44 (m, 2H), 7.28-7.23 (m, 5H), 7.21-7.14 (m, 8H). MS m/z 296 (M + Na)+. |

TABLE 1-continued

| Compound # and IUPAC NAME | PHYSICAL CHARACTERIZATION |
|---|---|
| 3e<br>4-Hydroxy-N,N-diphenyl-benzamide | white solid, 57% yield. M.p. 193.7.0-194.3° C. $^1$H NMR (DMSO-$d_6$, 300 MHz) δ 9.89 (s, 1H), 7.35-7.13 (m, 12H), 6.59 (d, 2H, J = 8.6 Hz). MS m/z 312 (M + Na)$^+$. |
| 2i<br>N-(3-methoxyphenyl)-N-phenyl-benzamide | white solid, 93% yield. M.p. 103-105.9° C. $^1$H NMR (CDCl$_3$, 300 MHz) δ 7.49-7.45 (m, 2H), 7.31-7.15 (m, 9H), 6.75-6.70 (m, 3H), 3.76 (s, 3H). MS m/z 326 (M + Na)$^+$. |
| 3h<br>N-(3-Hydroxyphenyl)-N-phenyl-benzamide | white solid, 56% yield. M.p. 199.0-202.0° C. $^1$H NMR (DMSO-$d_6$, 300 MHz) δ 9.55 (s, 1H), 7.44-7.06 (m, 12H), 6.62-6.59 (m, 2H). MS m/z 312 (M + Na)$^+$. |
| 2j<br>4-Methoxy-N-(4-methoxyphenyl)-N-phenyl-benzamide | white solid, 78% yield. $^1$H NMR (CDCl$_3$, 300 MHz) δ 7.44-7.41 (m, 2H), 7.28-7.26 (m, 2H), 7.15-7.05 (m, 5H), 6.83-6.80 (m, 2H), 6.72-6.70 (m, 2H), 3.77 (s, 6H). MS m/z 356 (M + Na)$^+$. |
| 3i<br>4-Hydroxy-N-(4-hydroxyphenyl)-N-phenyl-benzamide | white solid, 55% yield. M.p. 240.0-243.0° C. (decomposed). $^1$H NMR (DMSO-$d_6$, 300 MHz) δ 9.84 (s, 1H), 9.51 (s, 1H), 7.33-7.11 (m, 7H), 6.97-6.94 (m, 2H), 6.69-6.67 (m, 2H), 6.61-6.58 (m, 2H). MS m/e 304 (M − H)$^−$. |
| 2h<br>N-(4-methoxyphenyl)-N-phenyl-benzamide | white solid, 95% yield. M.p. 153-154.2° C. $^1$H NMR (CDCl$_3$, 300 MHz) δ 7.47-7.43 (m, 2H), 7.30-7.02 (m, 8H), 6.83-6.78 (m, 2H), 3.76 (s, 3H). MS m/z 326 (M + Na)$^+$. |
| 2k<br>4-Methoxy-N-(3-methoxyphenyl)-N-phenyl-benzamide | white solid, 84% yield. M.p. 119.0-119.5° C. $^1$H NMR (CDCl$_3$, 300 MHz) δ 7.47-7.43 (m, 2H), 7.31-7.13 (m, 7H), 6.75-6.68 (m, 4H), 3.77 (s, 3H), 3.71 (s, 3H). MS m/z 356 (M + Na)$^+$. |
| 3g<br>N-(4-Hydroxyphenyl)-N-phenyl-benzamide; | white solid, 70% yield. M.p. 255.0-256.0° C. $^1$H NMR (DMSO-$d_6$, 300 MHz) δ 9.53 (s, 1H), 7.40-7.15 (m, 10H), 7.02 (d, 2H, J = 8.7 Hz), 6.67 (d, 2H, J = 8.7 Hz). MS m/z 312 (M + Na)$^+$. |
| 3j<br>4-Hydroxy-N-(3-hydroxyphenyl)-N-phenyl-benzamide; | white solid, 73% yield. M.p. 245.0-247.5° C. (decomposed). $^1$H NMR (DMSO-$d_6$, 300 MHz) δ 9.90 (s, 1H), 9.53 (s, 1H), 7.35-7.06 (m, 8H), 6.63-6.52 (m, 5H). MS m/e 304 (M − H)$^−$. |
| 4a<br>N-(4-Hydroxyphenyl)-N-[4-(2-piperidin-1-ylethoxy)-phenyl]-benzamide | yellow solid. 45% yield. M.p. 164.5-165.0° C. $^1$H NMR (DMSO-$d_6$, 300 MHz) δ 9.49 (s, 1H), 7.38-7.36 (m, 2H), 7.26-7.24 (m, 3H), 7.12 (d, 2H, J = 8.5 Hz), 7.01 (d, 2H, J = 8.5 Hz), 6.87 (d, 2H, J = 8.3 Hz), 6.65 (d, 2H, J = 8.3 Hz), 4.01 (t, 2H, J = 5.1 Hz), 2.63 (br, 2H), 2.50-2.43 (m, 4H), 1.48 (br, 4H), 1.38-1.36 (m, 2H). MS m/z 417 (M + H)$^+$. |
| 3b<br>3-Hydroxy-N-bis-(4-hydroxyphenyl)-benzamide | white solid, 92% yield. M.p. 257.0-259.0° C. $^1$H NMR (DMSO-$d_6$, 300 MHz) δ 9.49 (s, 1H), 9.47 (s, 2H), 7.02-6.98 (m, 5H), 6.80-6.65 (m, 7H). MS m/e 320 (M − H)$^−$. |
| 3k<br>N,N-Bis(4-hydroxyphenyl)-4-fluoro-benzamide | off-white solid, 87% yield. M.p. 270.0-271.0° C. $^1$H NMR (DMSO-$d_6$, 300 MHz) δ 9.90 (s, 1H), 9.53 (s, 1H), 7.35-7.06 (m, 8H), 6.63-6.52 (m, 5H). MS m/e 304 (M − H)$^−$. |
| 3f<br>3-Hydroxy-N,N-diphenyl-benzamide | white solid, 85% yield. M.p. 152.5-153.2° C. $^1$H NMR (DMSO-$d_6$, 300 MHz) δ 9.89 (s, 1H), 7.35-7.13 (m, 12H), 6.59 (d, 2H, J = 8.6 Hz). MS m/z 312 (M + Na)$^+$. |
| 3c<br>4-Hydroxy-N-(4-hydroxyphenyl)-N-(3-hydroxyphenyl)-benzamide | white solid, 92% yield. M.p. 249.1° C. (decomposed). $^1$H NMR (DMSO-$d_6$, 300 MHz) δ 9.79 (s, 1H), 9.44 (s, 2H), 7.21 (d, 2H, J = 9.0 Hz), 6.93 (d, 4H, J = 8.7 Hz), 6.66 (d, 4H, J = 8.7 Hz), 6.58 (d, 2H, J = 9.0 Hz). MS m/z 344 (M + Na). |
| 4c<br>N,N-diphenyl-[3-(2-piperidinyl-ethoxy)]-benzamide hydrochloride | yellow solid, 57% yield. M.p. 149.5-150.0° C. $^1$H NMR (DMSO-$d_6$, 300 MHz) δ 10.76 (s, 1H), 7.33-6.92 (m, 14H), 4.32 (s, 2H), 3.42-3.40 (m, 4H), 2.94-2.92 (m, 2H), 1.78-1.67 (m, 5H), 1.38 (br, 1H). MS m/z 401 (M + H)$^+$. |
| 4d<br>N,N-diphenyl-[3-(2-piperidinyl-ethoxy)]-benzamide hydrochloride | yellow solid, 50% yield. M.p. 148.5-149.5° C. $^1$H NMR (DMSO-$d_6$, 300 MHz) δ 10.67 (s, 1H), 7.40-6.85 (m, 14H), 4.38 (s, 2H), 3.48-3.41 (m, 4H), 2.96-2.94 (m, 2H), 1.77-1.66 (m, 5H), 1.34 (br, 1H). MS m/z 401 (M + H)$^+$. |
| 3l<br>4-Hydroxy-N,N-diphenyl-phenyl-sulfonamide | white solid, 86% yield. M.p. 158.0-158.8° C. $^1$H NMR (CDCl$_3$, 300 MHz) δ 10.61 (s, 1H), 7.52-7.47 (m, 2H), 7.39-7.25 (m, 10H), 6.93-6.89 (m, 2H). MS m/z 324 (M − H)$^−$. |
| 4e<br>N-(4-Hydroxyphenyl)-N-phenyl-[4-(2-piperidin-1-ylethoxy)]-benzamide hydrochloride | yellow solid, 38% yield. M.p. 183.7-185.0° C. (decomposed). $^1$H NMR (DMSO-$d_6$, 300 MHz) δ 10.76 (s, 1H), 9.66 (s, 1H), 7.35-6.61 (m, 13H), 4.37 (m, 2H), 3.40 (m, 4H), 2.94 (m, 2H), 1.76-1.65 (m, 5H), 1.34 (m, 1H). MS m/z 417 (M + H)$^+$. |
| 4u<br>N-[4-(2-piperidin-1-ylethoxy)-phenyl]-N-phenyl-[4-(2-piperidin-1-ylethoxy)]-benzamide dihydrochloride | yellow solid, 27% yield. M.p. 210.9-212.0° C. (decomposed). $^1$H NMR (DMSO-$d_6$, 300 MHz) δ 11.07 (s, 2H), 7.35-6.84 (m, 13H), 4.38 (m, 4H), 3.40 (br, 8H), 2.95 (m, 4H), 2.05-1.65 (m, 10H), 1.34 (m, 2H). MS m/z 528 (M + H)$^+$. |
| 4b<br>N-(phenyl)-N-[4-(2-piperidin-1-ylethoxy)-phenyl]-benzamide hydrochloride | yellow solid, 89% yield. M.p. 138.3-139.5° C. $^1$H NMR (DMSO-$d_6$, 300 MHz) δ 9.52 (s, 1H), 7.42-7.39 (m, 2H), 7.33-7.16 (m, 10H), 6.89-6.91 (m, 2H), 4.17 (s, 2H), 2.76 (s, 2H), 2.51-2.49 (m, 4H), 1.61 (br, 4H), 1.43 (br, 2H). MS m/z 401 (M + H)$^+$. |
| 3m | white solid, 90% yield. M.p. 246.3-247.0° C. $^1$H NMR |

TABLE 1-continued

| Compound # and IUPAC NAME | PHYSICAL CHARACTERIZATION |
|---|---|
| 4-Hydroxy-N-(4-hydroxyphenyl)-N-(4-fluorophenyl)-benzamide | (DMSO-$d_6$, 300 MHz) δ 9.84 (s, 1H), 9.53 (s, 1H), 7.24-7.13 (m, 6H), 6.98-6.95 (m, 2H), 6.69-6.67 (m, 2H), 6.69-6.66 (m, 2H), 6.61-6.58 (m, 2H). MS m/z 324 (M + H)$^+$. |
| 4f N,N-diphenyl-bis[4-(2-piperidin-1-ylethoxy)-phenyl]-sulfonamide hydrochloride | pale-yellow solid. 79% yield. M.p. 211.6-212.5° C. $^1$H NMR (DMSO-$d_6$, 300 MHz) δ 10.78 (s, 1H), 7.65-7.17 (m, 14H), 4.52 (m, 2H), 3.36-3.47 (m, 4H), 3.00 (br, 2H), 1.67-2.50 (m, 5H), 1.38 (m, 1H). MS m/z 437 (M + H)$^+$. |
| 4g N-(4-Fluorophenyl)-N-[4-hydroxyphenyl]-[4-(2-piperidin-1-ylethoxy)]-benzamide | pale-yellow solid, 45% yield. M.p. 168.3-169.0° C. $^1$H NMR (DMSO-$d_6$, 500 MHz) δ 10.61 (s, 1H), 9.65 (s, 1H), 7.38-6.69 (m, 12H), 4.38 (m, 2H), 3.46-3.36 (m, 4H), 2.96 (m, 2H), 2.04-1.66 (m, 5H), 1.35 (br, 1H). MS m/z 435 (M + H)$^+$. |
| 4r N-(4-Fluorophenyl)-N-[4-(2-piperidin-1-ylethoxy)-phenyl]-[4-(2-piperidin-1-yl-ethoxy)]-benzamide dihydrochloride | yellow solid, 95% yield. M.p. 253.5-254.0° C. (decomposed). $^1$H NMR (DMSO-$d_6$, 300 MHz) δ 11.03 (s, 2H), 7.42-7.39 (m, 2H), 7.28-7.26 (m, 3H), 7.20-7.17 (m, 4H), 6.94-6.92 (m, 4H), 4.39 (br, 4H), 3.46-3.42 (m, 8H), 3.01-2.94 (m, 4H), 1.85-1.65 (m, 10H), 1.38-1.34 (m, 2H). MS m/z 528 (M + H)$^+$. |
| 4h N-(4-Hydroxyphenyl)-N-[4-(2-piperidin-1-ylethoxy)-phenyl]-4-fluoro-benzamide hydrochloride | yellow solid, 42% yield. M.p. 234.0-235.8° C. (decomposed). $^1$H NMR (DMSO-$d_6$, 300 MHz) δ 10.85 (s, 1H), 9.65 (s, 1H), 7.42-6.68 (m, 12H), 4.38 (m, 2H), 3.40 (m, 4H), 2.95 (m, 2H), 2.06-1.77 (m, 5H), 1.35 (m, 1H). MS m/z 435 (M + H)$^+$. |
| 4s N,N-Bis[4-(2-piperidin-1-ylethoxy)-phenyl]-4-fluoro-benzamide dihydrochloride; | yellow solid, 20% yield. M.p. 204.8-205.5° C. (decomposed). $^1$H NMR (DMSO-$d_6$, 300 MHz) δ 11.01 (s, 2H), 7.45-6.92 (m, 12H), 4.38 (m, 4H), 3.38 (m, 8H), 2.95 (m, 4H), 2.06-1.67 (m, 10H), 1.35 (m, 2H). MS m/z 546 (M + H)$^+$. |
| 3n N,N-Bis(4-hydroxyphenyl)-1-naphthylamide; (3n) | white solid, 86% yield. M.p. 215.7° C. (decomposed). $^1$H NMR (DMSO-$d_6$, 500 MHz) δ 9.54 (s, 1H), 9.35 (s, 1H), 8.11 (d, 1H, J = 9.0 Hz), 8.87 (d, 1H, J = 8.0 Hz), 7.79 (d, 1H, J = 8.5 Hz), 7.61-7.58 (m, 1H), 7.53-7.48 (m, 2H), 7.37-7.34 (m, 1H), 7.30 (s, 2H), 7.00 (s, 2H), 6.83 (s, 2H), 6.38 (s, 2H). MS m/z 356 (M + H)$^+$. |
| 4t N,N-Bis[4-(2-piperidin-1-ylethoxy)-phenyl]-benzamide dihydrochloride; (4t) | yellow solid, 28% yield. M.p. 218.6-219.5° C. (decomposed). $^1$H NMR (DMSO-$d_6$, 300 MHz) δ 11.09 (s, 2H), 7.38-6.86 (m, 12H), 4.40 (m, 4H), 3.39 (m, 8H), 2.96 (m, 4H), 2.07-1.66 (m, 10H), 1.35 (m, 2H). MS m/z 546 (M + H)$^+$. |
| 3o 4-Hydroxy-N-(1-Naphthyl)-N-(4-hydroxyphenyl)-benzamide | white solid, 84% yield. M.p. >300° C. (decomposed). $^1$H NMR (DMSO-$d_6$, 300 MHz) δ 9.84 (s, 1H), 9.47 (s, 1H), 8.07 (d, 1H, J = 7.8 Hz), 7.97 (d, 1H, J = 7.8 Hz), 7.86 (d, 1H, J = 8.1 Hz), 7.58-7.45 (m, 3H), 7.39-7.30 (m, 3H), 7.02 (d, 2H, J = 8.1 Hz), 6.66-6.56 (m, 4H). MS m/e 354 (M − H)$^−$. |
| 5a 4-Chloro-N-[4-hydroxyphenyl]-N-(4-methoxyphenyl)-benzamide | white solid. 93% yield. M.p. 237.5-238.9° C. $^1$H NMR (DMSO-$d_6$, 300 MHz) δ 9.53 (s, 1H), 7.41-7.38 (m, 2H), 7.34-7.31 (m, 2H), 7.17-7.14 (m, 2H), 7.05-7.02 (m, 2H), 6.88-6.86 (m, 2H), 6.70-6.66 (m, 2H), 3.71 (s, 3H). MS m/z 354 (M + H)$^+$. |
| 5b 4-Cyano-N-[4-hydroxyphenyl]-N-(4-methoxyphenyl)-benzamide | white solid. 71% yield. M.p. 182-182.9° C. $^1$H NMR (DMSO-$d_6$, 300 MHz) δ 9.56 (s, 1H), 7.76-7.71 (m, 2H), 7.56-7.55 (m, 2H), 7.20 (br, 2H), 7.07 (br, 2H), 6.87 (br, 2H), 6.67 (br, 2H), 3.71 (s, 3H). MS m/z 345 (M + H)$^+$. |
| 4j 4-Cyano-N-[4-(2-piperidin-1-ylethoxy)-phenyl]-N-(4-methoxyphenyl)-benzamide | colorless oil, 61% yield. M.p. C. $^1$H NMR (DMSO-$d_6$, 300 MHz) δ 7.42-7.40 (m, 2H), 7.34-7.31 (m, 2H), 7.18-7.13 (m, 4H), 6.88-6.86 (m, 4H), 4.00 (tr, 2H, J = 5.7 Hz), 3.71 (s, 3H). 2.60 (tr, 2H, J = 5.7 Hz), 2.40 (br, 4H), 1.47-1.45 (m, 4H), 1.37-1.36 (m, 2H). MS m/z 465 (M + H)$^+$. |
| 5c 3-Chloro-N-[4-hydroxyphenyl]-N-(4-methoxyphenyl)-benzamide | white solid. 74% yield. M.p. C. $^1$H NMR (DMSO-$d_6$, 300 MHz) δ 9.53 (s, 1H), 7.45-7.44 (m, 1H), 7.36-7.24 (m, 3H), 7.20-7.18 (m, 2H), 7.08-7.05 (m, 2H), 6.89 (br, 2H), 6.69 (br, 2H), 3.71 (s, 3H). MS m/z 354 (M + H)$^+$. |
| 4i 3-(2-piperidin-1-ylethoxy)-N,N-bis(4-hydroxyphenyl)-benzamide | yellow solid, 47% yield. M.p. 293.9-295.0° C. (decomposed). $^1$H NMR (DMSO-$d_6$, 300 MHz) δ 10.51 (s, 2H), 8.18-7.68 (m, 12H), 4.00 (tr, 2H, J = 5.5 Hz), 2.62 (m, 2H), 2.41 (m, 4H), 1.50-1.46 (m, 4H), 1.37-1.35 (m, 2H). MS m/e 431 (M − H)$^−$. |
| 4k 4-Chloro-N-[4-(2-piperidin-1-ylethoxy)-phenyl]-N-(4-methoxyphenyl)-benzamide | white solid, 45% yield. M.p. 285.0-287.0° C. (decomposed). $^1$H NMR (DMSO-$d_6$, 300 MHz) δ 9.55 (s, 1H), 7.40-7.39 (m, 2H), 7.34-7.32 (m, 2H), 7.20 (br, 2H), 7.02 (br, 2H), 6.95 (m, 2H), 6.68-6.67 (m, 2H), 4.28 (m, 2H), 3.34 (br, 4H), 2.99 (m, 2H), 1.72 (br, 4H), 1.46 (br, 2H). MS m/z 451 (M + H)$^+$. |
| 4l 4-Cyano-N-[4-(2-piperidin-1-ylethoxy)-phenyl]-N-(4-methoxyphenyl)-benzamide | yellow solid, 75% yield. M.p. 118.1-118.5° C. $^1$H NMR (DMSO-$d_6$, 300 MHz) δ 7.51 (br, 4H), 7.05 (br, 4H), 6.82 (br, 4H), 4.10 (m, 2H), 3.78 (s, 3H), 2.81 (m, 2H), 2.56 (m, 4H), 1.64-1.62 (m, 4H), 1.48-1.46 (m, 2H). MS m/z 456 (M + H)$^+$. |
| 4m 3-Chloro-N-[4-(2-piperidin-1-ylethoxy)-phenyl]-N-(4-methoxyphenyl)-benzamide | yellow solid, 82% yield. M.p. 114.9-115.5° C. $^1$H NMR (DMSO-$d_6$, 300 MHz) δ 7.47-7.46 (m, 1H), 7.26-7.23 (m, 2H), 7.14-7.05 (m, 5H), 6.83-6.80 (m, 4H), 4.08 (tr, 2H, J = 6.0 Hz), 3.77 (s, 3H), 2.76 (tr, 2H, J = 6.0 Hz), 2.53-2.49 (m, 4H), 1.65-1.58 (m, 4H), 1.48-1.43 (m, 2H). MS m/z 465 (M + H)$^+$. |
| 7a | yellow solid. 65% yield. M.p. 217.0-218.5° C. (decomposed). |

TABLE 1-continued

| Compound # and IUPAC NAME | PHYSICAL CHARACTERIZATION |
|---|---|
| 5-[4-methoxy-phenyl]-5H-phenanthridin-6-one | $^1$H NMR (DMSO-$d_6$, 500 MHz) δ 8.61-8.59 (m, 1H), 8.54-8.51 (m, 1H), 8.36-8.34 (m, 1H), 7.94-7.89 (m, 1H), 7.71-7.66 (m, 1H), 7.43-7.28 (m, 4H), 7.19-7.16 (m, 2H), 6.63-6.60 (m, 1H). MS m/z 302 (M + H)$^+$. |
| 3p<br>4-Cyano-N,N-Bis(4-hydroxyphenyl)-benzamide | white solid, 84% yield. M.p. 272.0-273.5° C. (decomposed). $^1$H NMR (DMSO-$d_6$, 300 MHz) δ 9.53 (s, 2H), 7.74-7.73 (m, 2H), 7.55-7.53 (m, 2H), 7.12-7.02 (m, 4H), 6.74-6.57 (m, 4H). MS m/e 329 (M − H)$^-$. |
| 7b<br>5-[4-hydroxy-phenyl]-5H-phenanthridin-6-one | yellow solid. 78% yield. M.p. 325.7-327.0° C. (decomposed). $^1$H NMR (DMSO-$d_6$, 500 MHz) δ 9.82 (s, 1H), 8.60-8.58 (m, 1H), 8.52-8.51 (m, 1H), 8.35-8.33 (m, 1H), 7.92-7.89 (m, 1H), 7.69-7.66 (m, 1H), 7.41-7.38 (m, 1H), 7.32-7.29 (m, 1H), 7.15-7.13 (m, 2H), 6.99-6.97 (m, 2H), 6.65-6.63 (m, 1H). MS m/z 310 (M + Na)$^+$. |
| 3q<br>3-Cyano-N,N-Bis(4-hydroxyphenyl)-benzamide | white solid, 84% yield. M.p. 237.5-238.0° C. $^1$H NMR (DMSO-$d_6$, 300 MHz) δ 9.53 (s, 2H), 7.81-7.80 (m, 1H), 7.75-7.74 (m, 1H), 7.73-7.72 (m, 1H), 7.69-7.68 (m, 1H), 7.67-7.7.66 (m, 1H), 7.48-7.44 (m, 1H), 7.07 (br, 4H), 6.65 (br, 4H). MS m/z 353 (M + Na)$^+$. |
| 7c<br>5-[4-(2-piperidin-1-ylethoxy)-phenyl]-5H-phenanthridin-6-one | yellow solid. 79% yield. M.p. 220.0-221.5° C. (decomposed). $^1$H NMR (DMSO-$d_6$, 300 MHz) δ 8.56-8.53 (m, 1H), 8.35-8.29 (m, 2H), 7.84-7.79 (m, 1H), 7.64-7.59 (m, 1H), 7.36-7.24 (m, 4H), 7.23-7.10 (m, 2H), 6.76-6.73 (m, 1H), 4.45 (tr, 2H, J = 5.1 Hz), 3.16 (tr, 2H, J = 5.1 Hz), 2.94 (br, 4H), 1.90-1.85 (m, 4H), 1.61-1.59 (m, 2H). MS m/z 399 (M + H)$^+$. |
| 8b<br>Cyclohexane-carboxylic acid bis(4-hydroxyphenyl)-amide; | white solid, 86% yield. M.p. 265.1-266.2° C. (decomposed). $^1$H NMR (DMSO-$d_6$, 500 MHz) δ 9.65 (s, 1H), 9.37 (s, 1H), 7.17-6.70 (m, 4H), 6.78-6.67 (m, 4H), 2.29-2.23 (m, 1H), 1.71-1.62 (m, 4H), 1.54-1.51 (m, 1H), 1.41-1.32 (m, 2H), 1.21-1.07 (m, 1H), 0.97-0.90 (m, 2H). MS m/z 334 (M + Na)$^+$. |
| 3r<br>N,N-Bis(4-hydroxyphenyl)-2-naphthylamide | white solid, 86% yield. M.p. 264.3-265.2° C. (decomposed). $^1$H NMR (DMSO-$d_6$, 500 MHz) δ 9.46 (s, 2H), 7.98 (s, 1H), 7.85-7.75 (m, 2H), 7.75-7.73 (m, 2H), 7.54-7.48 (m, 2H), 7.45-7.43 (m, 1H), 7.05 (s, 4H), 6.66 (s, 4H). MS m/z 356 (M + H)$^+$. |
| 3s<br>4-Cyano-N-[4-(2-piperidin-1-ylethoxy)-phenyl]-N-(4-hydroxyphenyl)-benzamide | white solid, 50% yield. M.p. 266.7-268.0 (decomposed). $^1$H NMR (DMSO-$d_6$, 300 MHz) δ 9.57 (s, 1H), 7.76-7.74 (m, 2H), 7.58-7.55 (m, 2H), 7.24-6.96 (m, 6H), 6.66 (s, 2H), 4.26-4.21 (m, 2H), 3.33 (br, 4H). 2.98 (br, 4H), 1.70 (br, 4H), 1.50-1.44 (m, 2H). MS m/z 442 (M + H)$^+$. |
| 3t<br>3-Chloro-N-[4-(2-piperidin-1-ylethoxy)-phenyl]-N-(4-hydroxyphenyl)-benzamide | white solid, 38% yield. M.p. 208.9-209.5° C. (decomposed). $^1$H NMR (DMSO-$d_6$, 300 MHz) δ 9.54 (s, 1H), 7.44 (s, 1H), 7.37-7.21 (m, 5H), 7.08-7.05 (m, 2H), 6.96 (s, 2H), 6.69-6.67 (s, 2H), 4.27 (s, 2H), 3.33 (br, 4H). 3.02 (br, 2H), 1.71 (br, 4H), 1.50 (br, 2H). MS m/z 451 (M + H)$^+$. |
| 10w<br>N-cyclohexyl-4-hydroxy-N-(4-hydroxyphenyl)-benzamide | white solid. 81% yield. M.p. 267.3-268.5° C. $^1$H NMR (DMSO-$d_6$, 500 MHz) δ 9.56 (s, 2H), 7.03 (d, 2H, J = 8.7 Hz), 6.83 (d, 2H, J = 8.8 Hz), 6.60 (d, 2H, J = 8.5 Hz), 6.50 (d, 2H, J = 8.3 Hz), 4.43 (m, 1H), 1.83-1.81 (m, 2H), 1.72-1.69 (m, 2H), 1.54-1.52 (m, 1H), 1.35-1.28 (m, 2H), 1.11-1.03 (m, 2H), 0.93-0.89 (m, 1H). MS m/z 312 (M + H)$^+$. |
| 10x<br>4-((4-Fluorophenyl)(4-hydroxybenzyl)-amino)phenol | yellow oil. 92% yield. $^1$H NMR (DMSO-$d_6$, 500 MHz) δ 9.29 (s, 1H), 9.24 (s, 1H), 7.09 (d, 2H, J = 8.3 Hz), 6.98 (d, 2H, J = 9.0 Hz), 6.94-6.91 (m, 2H), 6.73 (d, 2H, J = 9.0 Hz), 6.68-6.64 (m, 4H), 4.70 (s, 2H). MS m/z 308 (M − H)$^-$. |
| 10y<br>N-(4-(2-(dimethylamino)ethoxy)phenyl)-N-(4-hydroxy-phenyl)-benzamide | white solid. 57% yield. M.p. 170.0-172.0° C. $^1$H NMR (DMSO-$d_6$, 500 MHz) δ 9.50 (s, 1H), 7.37 (d, 2H, J = 8.0 Hz), 7.29-7.24 (m, 3H), 7.12 (d, 2H, J = 6.5 Hz), 7.01 (d, 2H, J = 6.5 Hz), 6.87 (s, 2H), 6.66 (s, 2H), 3.99 (s, 2H), 2.61 (t, 2H, J = 5.5 Hz), 2.21 (s, 6H). MS m/z 375 (M − H)$^-$. |
| 10z<br>3-Cyano-N-(4-hydroxyphenyl)-N-(4-(2-(piperidin-1-yl)ethoxy)phenyl)-benzamide; | pale-yellow solid. 63% yield. M.p. 160.7-162.3° C. $^1$H NMR (DMSO-$d_6$, 500 MHz) δ 9.56 (s, 1H), 7.83 (s, 1H), 7.76-7.74 (m, 1H), 7.71-7.68 (m, 1H), 7.47 (t, 1H, J = 7.5 Hz), 7.19 (br, 2H), 7.08 (br, 2H), 6.90 (br, 2H), 6.66 (br, 2H), 4.02 (br, 2H), 2.63 (br, 2H), 2.42 (br, 4H), 1.48 (br, 4H), 1.36 (br, 2H). MS m/z 442 (M + H)$^+$. |
| 11a<br>N-(4-Hydroxyphenyl)-N-(4-(2-(pyrrolidin-1-yl)ethoxy)phenyl)-benzamide | white solid. 64% yield. M.p. 163.9-165.1° C. $^1$H NMR (DMSO-$d_6$, 500 MHz) δ 9.63 (s, 1H), 7.39-7.38 (m, 1H), 7.31-7.23 (m, 3H), 7.13 (d, 2H, J = 6.0 Hz), 7.02 (d, 2H, J = 7.0 Hz), 6.88 (br, 2H), 4.03 (br, 2H), 2.82 (br, 2H), 2.56 (br, 4H), 1.69-1.68 (m, 4H). MS m/z 401 (M − H)$^-$. |
| 11b<br>N,N-Bis(4-hydroxyphenyl)-4-(trifluoromethyl)-benzamide; | white solid. 96% yield. M.p. 255.9-256.5° C. $^1$H NMR (DMSO-$d_6$, 500 MHz) δ 9.52 (s, 2H), 7.64-7.56 (m, 4H), 7.06 (br, 4H), 6.64 (br, 4H). MS m/z 374 (M + H)$^+$. |
| 11c<br>N-(4-Hydroxyphenyl)-N-(4-(2-(piperidin-1-yl)ethoxy)phenyl)-4- | white solid. 41% yield. M.p. 158.1-158.7° C. $^1$H NMR (DMSO-$d_6$, 500 MHz) δ 9.55 (s, 1H), 7.65-7.58 (m, 4H), 7.18-6.65 (m, 8H), 4.01 (br, 1H), 2.63-2.61 (m, 2H), |

TABLE 1-continued

| Compound # and IUPAC NAME | PHYSICAL CHARACTERIZATION |
|---|---|
| (trifluoromethyl)-benzamide; | 2.40-2.36 (m, 4H), 1.47 (br, 4H), 1.36 (br, 2H). MS m/z 485 (M + H)$^+$. |
| 11d<br>N,N-Bis(4-hydroxyphenyl)-4-nitro-benzamide | white solid. 92% yield. M.p. 216.0-217.0° C. (decomposed). $^1$H NMR (DMSO-d$_6$, 500 MHz) δ 9.55 (s, 2H), 8.11-8.09 (m, 2H), 7.65-7.62 (m, 2H), 7.15-7.03 (m, 4H), 6.77-6.58 (m, 4H). MS m/z 349 (M − H)$^−$. |
| 11e<br>3-Fluoro-N,N-bis(4-hydroxyphenyl)-benzamide | white solid. 87% yield. M.p. 254.1.1-254.6° C. $^1$H NMR (DMSO-d$_6$, 500 MHz) δ 9.51 (s, 2H), 7.31-7.26 (m, 1H), 7.19-7.18 (m, 2H), 7.13-7.09 (m, 1H), 7.05 (br, 4H), 6.68 (br, 4H). MS m/z 322 (M − H)$^−$. |
| 11f<br>N-(4-Hydroxyphenyl)-N-(4-(2-(piperidin-1-yl)ethoxy)phenyl)-1-naphthamide | white solid. 71% yield. M.p. 198.5-199.1° C. $^1$H NMR (DMSO-d$_6$, 500 MHz) δ 9.56 (s, 0.5H), 9.40 (s, 0.5H), 8.13-8.10 (m, 1H), 7.89-7.78 (m, 2H), 7.63-7.58 (m, 1H), 7.54-7.49 (m, 2H), 7.38-7.30 (m, 3H), 7.00 (br, 3H), 6.83 (br, 1H), 6.61 (br, 1H), 6.40 (br, 1H), 4.17-3.92 (m, 2H), 2.73-2.44 (m, 6H), 1.55-1.41 (m, 6H). MS m/z 467 (M + H)$^+$. |
| 11g<br>3-Fluoro-N-(4-hydroxyphenyl)-N-(4-(2-(piperidin-1-yl)ethoxy)phenyl)benzamide | white solid. 53% yield. M.p. 227.3-228.0° C. $^1$H NMR (DMSO-d$_6$, 500 MHz) δ 9.56 (s, 1H), 7.33-7.26 (m, 1H), 7.21-7.12 (m, 5H), 7.09-7.04 (m, 2H), 6.89 (br, 2H), 4.05 (br, 2H), 2.71 (br, 2H), 2.50 (br, 4H), 1.93 (br, 2H), 1.51-1.49 (m, 4H), 1.39-1.37 (br, 2H). MS m/z 435 (M + H)$^+$. |
| 11h<br>N-(4-Hydroxyphenyl)-4-nitro-N-(4-(2-(piperidin-1-yl)ethoxy)phenyl)benzamide | yellow solid. 49% yield. M.p. 181.7-182.3° C. $^1$H NMR (DMSO-d$_6$, 300 MHz) δ 9.55 (s, 1H), 8.07 (d, 2H, J = 8.7 Hz), 7.62 (d, 2H, J = 8.7 Hz), 7.18-6.90 (m, 4H), 6.77-6.61 (m, 4H), 4.01 (br, 2H), 2.64-2.43 (m, 6H), 1.46-1.35 (m, 6H). MS m/z 462 (M + H)$^+$. |
| 11i<br>N,N-Bis(4-hydroxyphenyl)-4-methoxy-1-naphthamide | white solid. 48% yield. M.p. 305.4° C. (decomposed). $^1$H NMR (DMSO-d$_6$, 300 MHz) δ 9.45 (s, 2H), 8.14-8.10 (m, 2H), 7.65-7.60 (m, 1H), 7.54-7.49 (m, 1H), 7.44-7.41 (m, 1H), 7.11 (br, 4H), 6.84-6.81 (m, 1H), 6.70-6.65 (m, 4H), 3.93 (s, 3H). MS m/z 386 (M + H)$^+$. |
| 11j<br>N-(4-Hydroxyphenyl)-N-(4-(2-(piperidin-1-yl)ethoxy)phenyl)-2-naphthamide | white solid. 45.0% yield. M.p. 195.8-196.3° C. $^1$H NMR (DMSO-d$_6$, 300 MHz) δ 9.49 (s, 1H), 8.01 (s, 1H), 7.87-7.84 (m, 2H), 7.77-7.74 (m, 1H), 7.56-7.43 (m, 3H), 7.19-7.16 (m, 2H), 7.08-7.06 (m, 2H), 6.88-6.85 (m, 2H), 6.67-6.65 (m, 2H), 3.99 (s, 2H), 2.61-2.57 (m, 2H), 2.39 (s, 4H), 1.46-1.45 (m, 4H), 1.37-1.35 (m, 2H). MS m/z 467 (M + H)$^+$. |
| 11k<br>2-Hydroxy-N,N,2-tris(4-hydroxyphenyl)-propanamide | white solid. 78% yield. M.p. 292.0-294.0° C. $^1$H NMR (DMSO-d$_6$, 300 MHz) δ 9.74 (s, 1H), 9.39 (s, 1H), 9.15 (s, 1H), 7.18 (d, 2H, J = 8.7 Hz), 7.09 (d, 2H, J = 8.7 Hz), 6.80 (d, 2H, J = 8.7 Hz), 6.72 (d, 2H, J = 8.7 Hz), 6.60 (d, 2H, J = 9.1 Hz), 6.53 (d, 2H, J = 9.1 Hz), 1.68 (s, 3H). MS m/z 348 (M − H$_2$O)$^+$. |
| 11w<br>N-(4-hydroxyphenyl)-4-(3-hydroxypropyl)-N-(4-methoxyphenyl)-benzamide | pale-yellow solid, M.p. 145-147° C. $^1$H NMR ((DMSO-d$_6$, 300 MHz) δ 9.50 bs, 1H), 7.28 (0 (d, J = 8.10 Hz, 2H), 7.15-7.05 (m, 4H), 6.99 (d, J = 8.62 Hz, 2H), 6.86 (d, J = 8.74 Hz, 2H), 6.66 (d, J = 8.56 Hz, 2H), 4.44 (bs, 1H), 3.71 (s, 3H), 3.35-3.33 (m, 2H), 2.57-2.49 (m, 2H), 1.69-1.60 (m, 2H). MS m/z 376.0 (M − H)$^−$. |
| 11x<br>4-fluoro-N,N-bis(4-hydroxyphenyl)-2-(trifluoromethyl)-benzamide | colorless oil. $^1$H NMR ((DMSO-d$_6$, 300 MHz) δ7.29 (d, J = 8.13 Hz, 2H), 7.13-7.09 (m, 4H), 7.00 (d, J = 8.61 Hz, 2H), 6.86 (d, J = 8.70 Hz, 2H), 6.66 (d, J = 8.49 Hz, 2H), 3.71 (s, 3H), 2.76 (t, J = 7.43 Hz, 2H), 2.51-2.45 (m, 2H). MS m/z 390.0 (M − H)$^−$. |
| 11y<br>3-fluoro-N-(4-fluorophenyl)-4-hydroxy-N-(4-hydroxyphenyl)benzamide | M.p. 110-112° C. MS m/z 364.1 (M + Na)$^+$. $^1$H NMR ((DMSO-d$_6$, 300 MHz) δ 10.14 (bs, 1H), 9.71 (bs, 1H), 7.25-7.11 (m, 5H), 7.05-6.99 (m, 3H), 6.78 (t, J = 8.61 Hz, 2H), 6.68 (d, J = 8.68 Hz, 2H). |
| 11z<br>N-(4-hydroxyphenyl)-4-methyl-N-(4-(2-(piperidin-1-yl)ethoxy)phenyl)benzamide | M.p.135-137° C. MS m/z 431.3 (M + H)$^+$. $^1$H NMR ((DMSO-d$_6$, 300 MHz) δ 9.49 (bs, 1H), 7.26 (d, J = 8.06 Hz, 2H), 7.11-6.98 (m, 6H), 6.85 (d, J = 8.72 Hz, 2H), 6.66 (d, J = 8.53 Hz, 2H), 4.00 (t, J = 5.85 Hz, 2H), 2.60 (t, J = 5.85 Hz, 2H), 2.41-2.38 (m, 4H), 1.51-1.44 (m, 4H), 1.37-1.36 (m, 2H). |
| 11aa<br>N,N-bis(4-hydroxyphenyl)-isonicotin-amide | M.p. > 240° C. MS m/z 304.9 (M − H)$^−$. $^1$H NMR ((DMSO-d$_6$, 300 MHz) δ 9.54 (bs, 2H), 8.52-8.43 (m, 2H), 7.76-7.72 (m, 1H), 7.31-7.27 (m, 1H), 7.07 (bs, 4H), 6.68 (bs, 4H). |
| 11ab<br>N-(4-hydroxyphenyl)-N-(4-(2-(piperidin-1-yl)ethoxy)phenyl-isonicotinamide | MS m/z 418.4 (M + H)$^+$. $^1$H NMR ((DMSO-d$_6$, 300 MHz) δ (s, 1H), 8.53 (d, 9.56 J = 1.65 Hz, 1H), 8.44 (dd, J = 1.61, 4.83 Hz, 1H), 7.78-7.74 (m, 1H), 7.31-7.27 (m, 1H), 6.89 (bs, 2H), 6.68 (bs, 2H), 4.02 (t, J = 7.03 Hz, 2H), 2.64 (bs, 2H), 2.43 (bs, 4H), 1.49-1.47 (m, 4H), 1.38-1.36 (m, 2H). |

Example 2

Effects of SERMs on ER-α, ER-β and AR Transactivation

Materials and Methods

Figure 6:
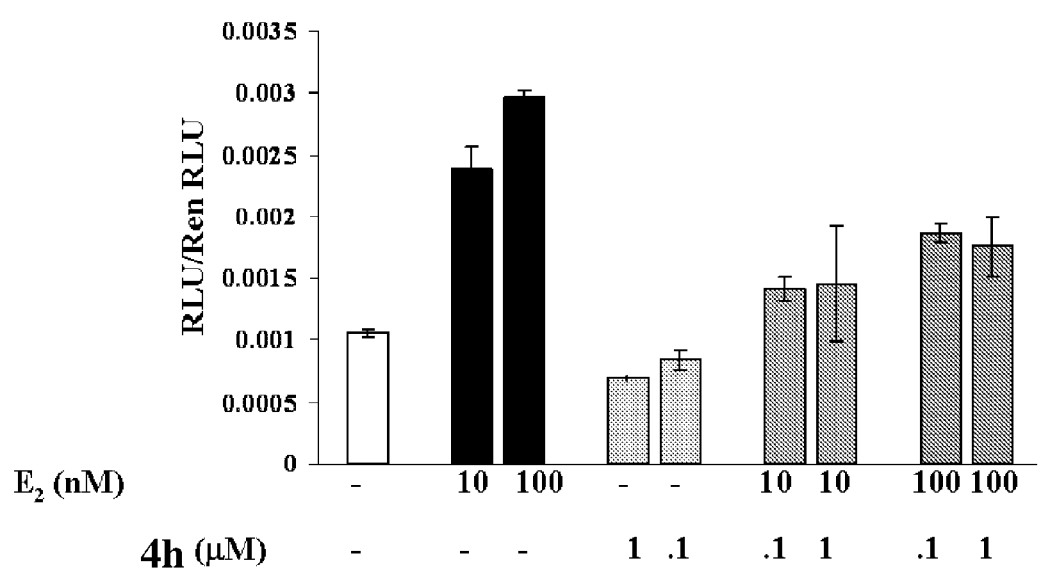
FIG. 6: Effect of the indicated compounds on ER-β transactivation. COS or 293 cells plated in DME without phenol red+10% csFBS at 90,000 cells per well of a 24 well plate were transfected with 0.25 µg ERE-LUC, 0.02 µg CMV-LUC (*Renilla*) and 50 ng of ER-β by lipofectamine. Twenty four hours after transfection, the cells were treated as indicated in the figure, harvested 48 hrs after transfection and assayed for firefly and *renilla* luciferase.

COS or 293 cells were plated in DME without phenol red+10% cs FBS at 90,000 cells per well in 24 well plates, and were transfected with 0.25 µg of the vector "ERE-LUC", where a firefly luciferase gene is driven by two estrogen responsive elements and 0.02 µg of the control CMV-LUC, *Renilla* where a luciferase gene is driven by a CMV promoter. Also 25 ng of ER-α (FIGS. 1, 5, and 9), 50 ng of ERβ (FIGS. 2, 6 and 10) or 12.5 ng of AR (FIG. 3) were introduced by lipofectamine. All the receptors were cloned from rat tissue into the PCR3.1 vector backbone. Twenty four hours post transfection, cells were treated with 4a, toremifene, 4h, estrogen, DHT, and other SERMs or combinations thereof, as indicated in figures. Cells were harvested 48 hrs after transfection, and assayed for firefly and *Renilla* luciferase activity.

Results

Treating cells with either 4a or toremifene alone had no effect on ER-α activity, under the tested conditions. However, both the compounds inhibited the estradiol ($E_2$) induced ER-α activity to basal levels, suggesting that 4a can regulate ER activity, or function as a SERM, and in this assay functions as an ER-α antagonist.

In order to determine whether the compounds can function as agonists of the ER, COS or 293 cells expressing constructs with luciferase expression under the control of an ERE were incubated with estrogen, toremifene or 4a. While estrogen addition resulted in dose-dependent luciferase expression, neither SERM alone showed any such effect. Similarly, 4h was evaluated for expression of luciferase (FIGS. 5 *a, b* and *c*).

Both 4a and 4h inhibited estrogen stimulated luciferase expression, indicating these compounds may function as SERMs in these circumstances, for example, as estrogen receptor α-antagonists. Compound 10o also inhibited estrogen stimulated luciferase expression, in 293 cells expressing ER-α similarly evaluated (FIG. 5 *d,e*).

COS or 293 cells expressing ER-β (FIGS. 2 and 6) were similarly evaluated. Under these experimental conditions, neither 4a nor 4h stimulated LUC expression, and each inhibited $E_2$-stimulated LUC expression, indicating their activity as antagonists for ER-β as well.

Figure 3:
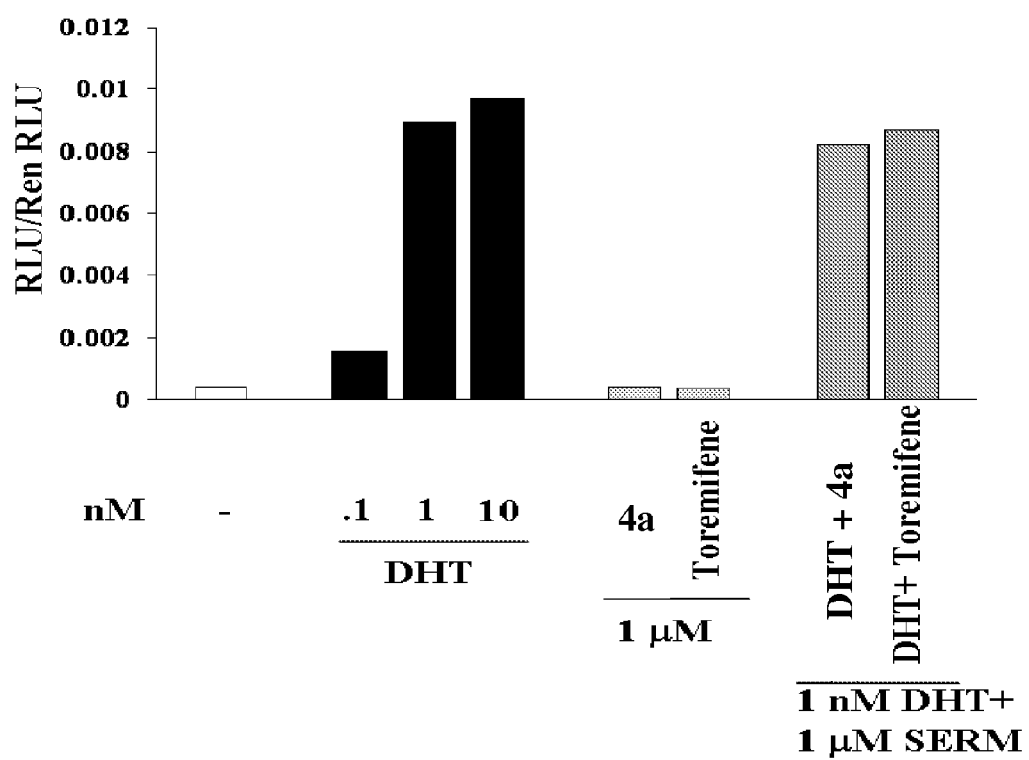
FIG. 3: Effect of the indicated compounds on AR transactivation. COS cells plated in DME without phenol red+10% csFBS at 90,000 cells per well of a 24 well plate were transfected with 0.25 µg ARE-LUC, 0.02 µg CMV-LUC (*Renilla*) and 12.5 ng of AR by lipofectamine. Twenty four hours after transfection, the cells were treated as indicated in the figure, harvested 48 hrs after transfection and were assayed for firefly and *renilla* luciferase.

Under the tested conditions, compound 4a was specific for the ER, since the compound had no effect on LUC expression in COS cells expressing an androgen receptor (AR), nor did it inhibit DHT-induced AR activation (FIG. 3).

Figure 9:
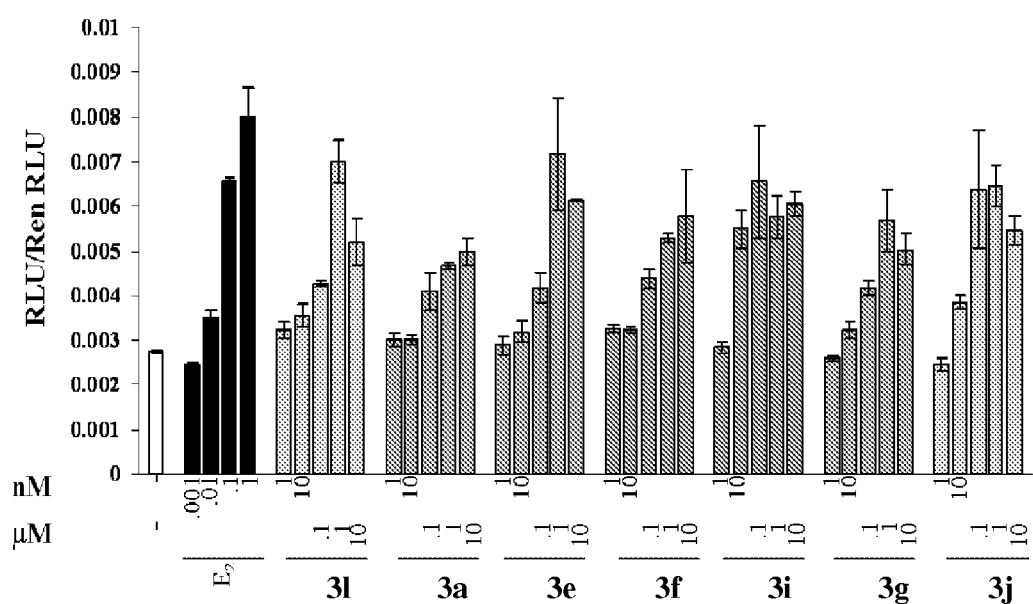
FIG. 9: Effect of the indicated compounds on ER-α transactivation. COS or 293 cells plated in DME without phenol red+10% csFBS per well of a 24 well plate were transfected with 0.25 µg ERE-LUC, 0.02 µg CMV-LUC (*Renilla*) and 25 ng of ER-α by lipofectamine. Twenty four hours after transfection, the cells were treated as indicated in the figure, harvested 48 hrs after transfection and were assayed for firefly and *renilla* luciferase.
Figure 10:
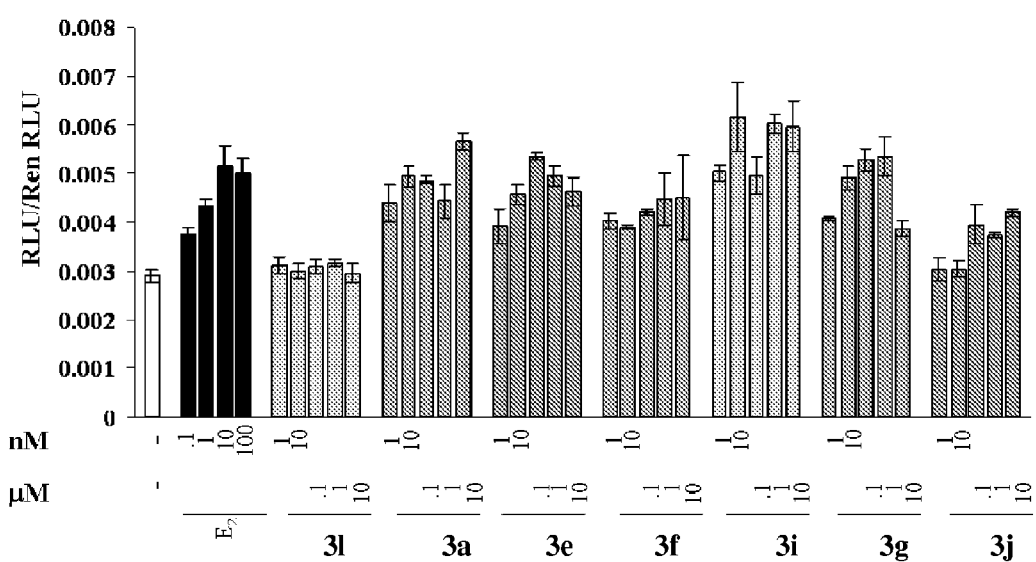
FIG. 10: Effect of the indicated compounds on ER-β transactivation. COS or 293 cells plated in DME+10% csFBS at 90,000 cells per well of a 24 well plate were transfected with 0.25 µg ERE-LUC, 0.02 µg CMV-LUC (*Renilla*) and 50 ng of ER-β by lipofectamine. Twenty four hours after transfection, the cells were treated as indicated in the figure, harvested 48 hrs after transfection and were assayed for firefly and *renilla* luciferase.

Additional SERMs were similarly tested for their ability to mediate estrogen receptor signaling in the indicated conditions (FIG. 9). Of the SERMs tested, compounds 3e and 3i were the most potent in stimulating ER-α, and compounds 3a, 3e, 3i and 3g were most potent in stimulating ER-β (FIG. 10).

Example 3

Agonist Activity of Some Embodiments of the Compounds

Materials and Methods

MCF-7 cells were plated at 500,000 cells per well of a 6 well plate. The cells were serum starved for 3 days and then were treated as above for 16 hrs. RNA was isolated and gene expression levels assessed by realtime RT-PCR, following normalization to 18S ribosomal RNA.

Results

Figure 4:
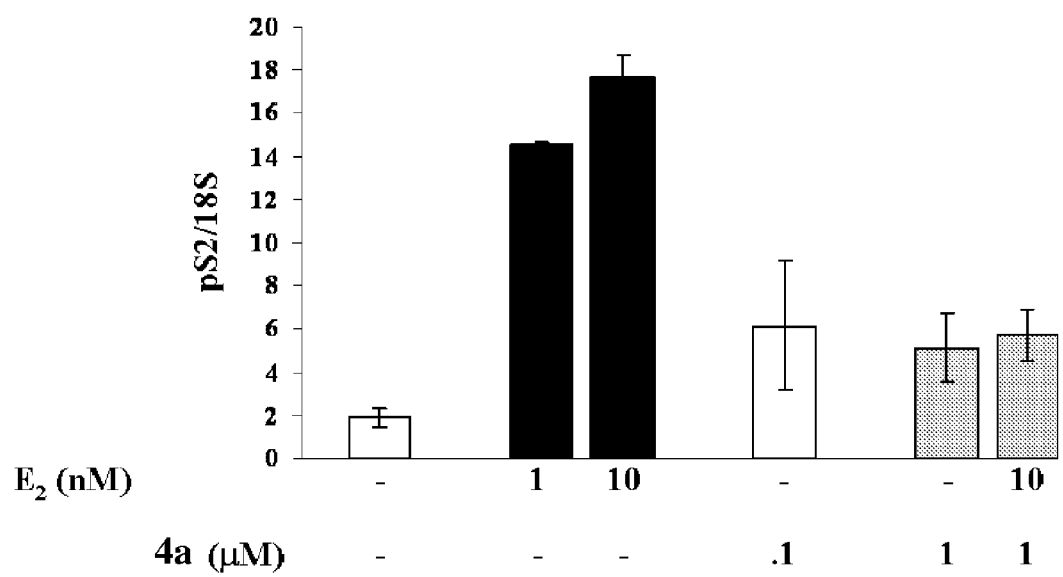
FIG. 4: Compound 4a functions as a partial agonist of ER action in MCF-7 cells. MCF-7 cells were plated at 500,000 cells per well of a 6 well plate. The cells were serum starved for 3 days and then were treated or not treated as indicated in the figure for 16 hrs. RNA was isolated and the message levels of pS2 (gene encoding the trefoil peptides) measured and normalized to 18S ribosomal RNA by realtime polymerase chain reaction (rtPCR).
Figure 5A:
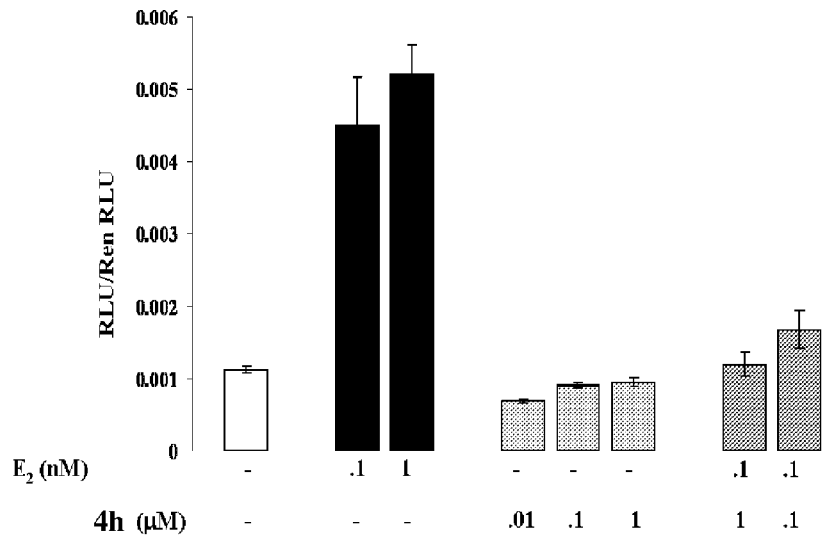
FIG. 5: Effect of the indicated compounds on ER-α transactivation. COS or 293 cells plated in DME without phenol red+10% csFBS at 90,000 cells per well of a 24 well plate were transfected with 0.25 µg ERE-LUC, 0.02 µg CMV-LUC (*Renilla*) and 5 ng of ER-α by lipofectamine. Twenty four hours after transfection, the cells were treated as indicated in the figure, harvested 48 hrs after transfection and were assayed for firefly and *renilla* luciferase.
Figure 5B:
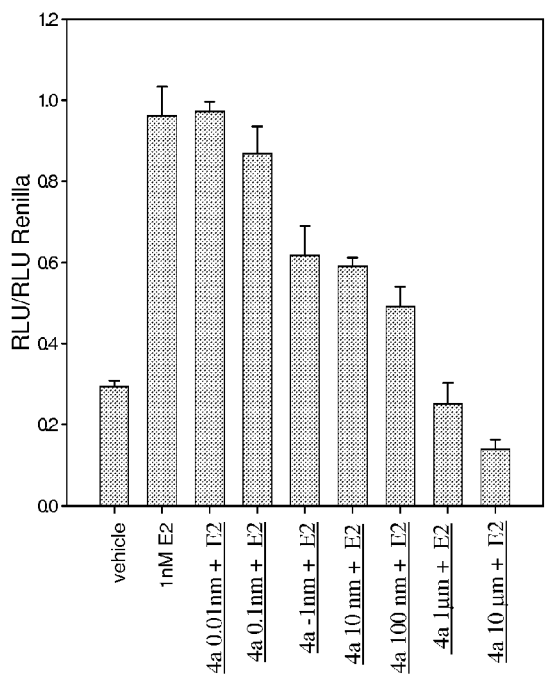
Figure 5C:
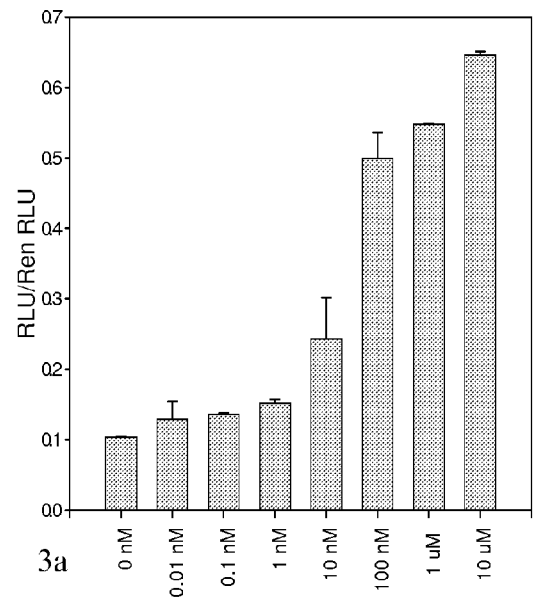
Figure 5D:
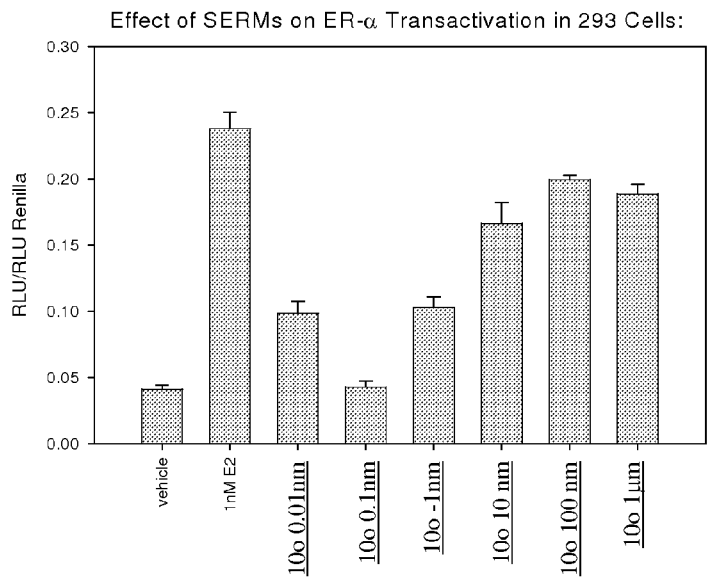
Figure 5E:
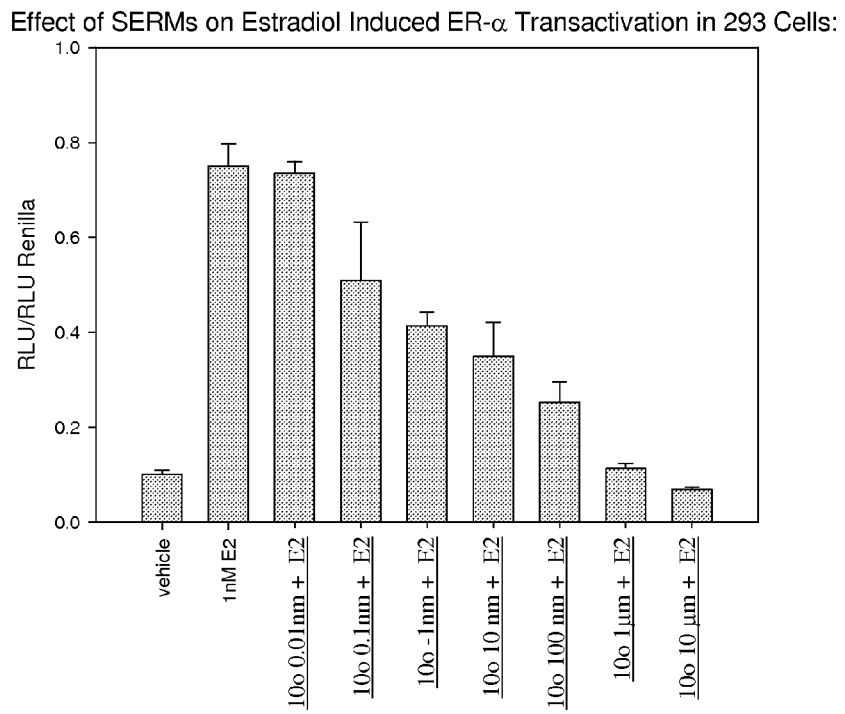
Figure 11:
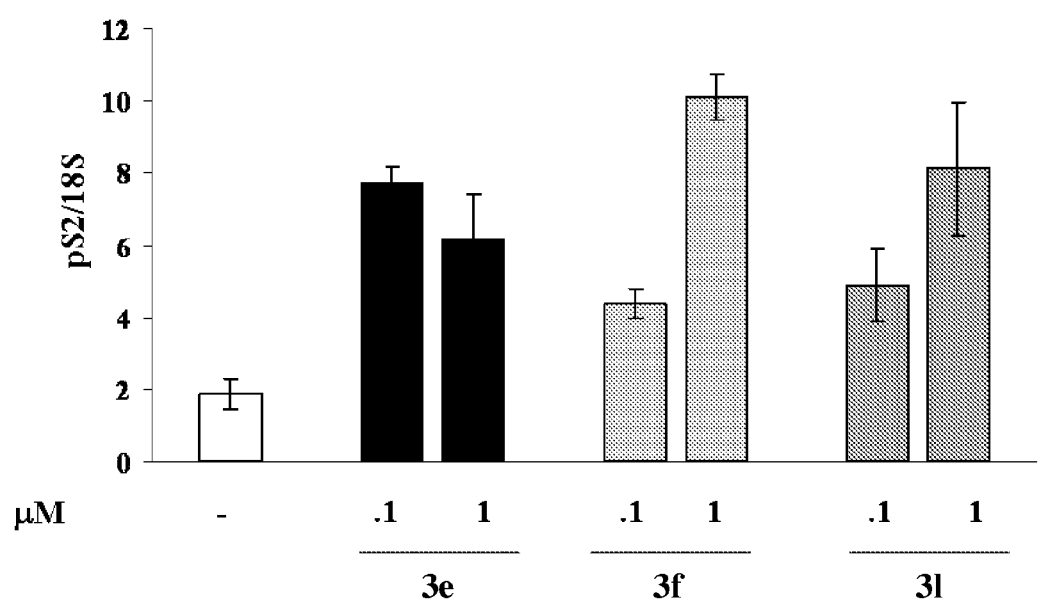
FIG. 11: Agonistic activity of the indicated compounds in MCF-7 cells. MCF-7 cells were plated at 500,000 cells per well of a 6 well plate. The cells were starved for 3 days and then were treated or not treated as indicated in the figure for 16 hrs. RNA was isolated and the message levels of pS2 gene measured and normalized to 18S ribosomal RNA by realtime rtPCR.

While estrogen increased pS2 (gene encoding the trefoil peptides) expression in MCF-7 cells under the conditions tested, 4a only minimally did so, moreover, it inhibited estrogen-induced upregulation of pS2 gene expression, indicating its role as a partial agonist or antagonist in these conditions (FIG. 4). Compounds 3e, 3f and 3l increased pS2 expression levels as well (FIG. 11).

Example 4

Effect of the Compounds on TRAP Positive Multinucleated Osteoclasts

Materials and Methods

Bone marrow cells isolated from rat femur were cultured in Alpha MEM without phenol red+10% sterile FBS without phenol red in the presence or absence of 30 ng/mL RANKL and 10 ng/ml GMCSF. The cells were treated for 12 days were stained for tartarate resistant acid phosphatase activity (TRAP) positive multinucleated osteoclasts and were counted.

Results

Figure 7:
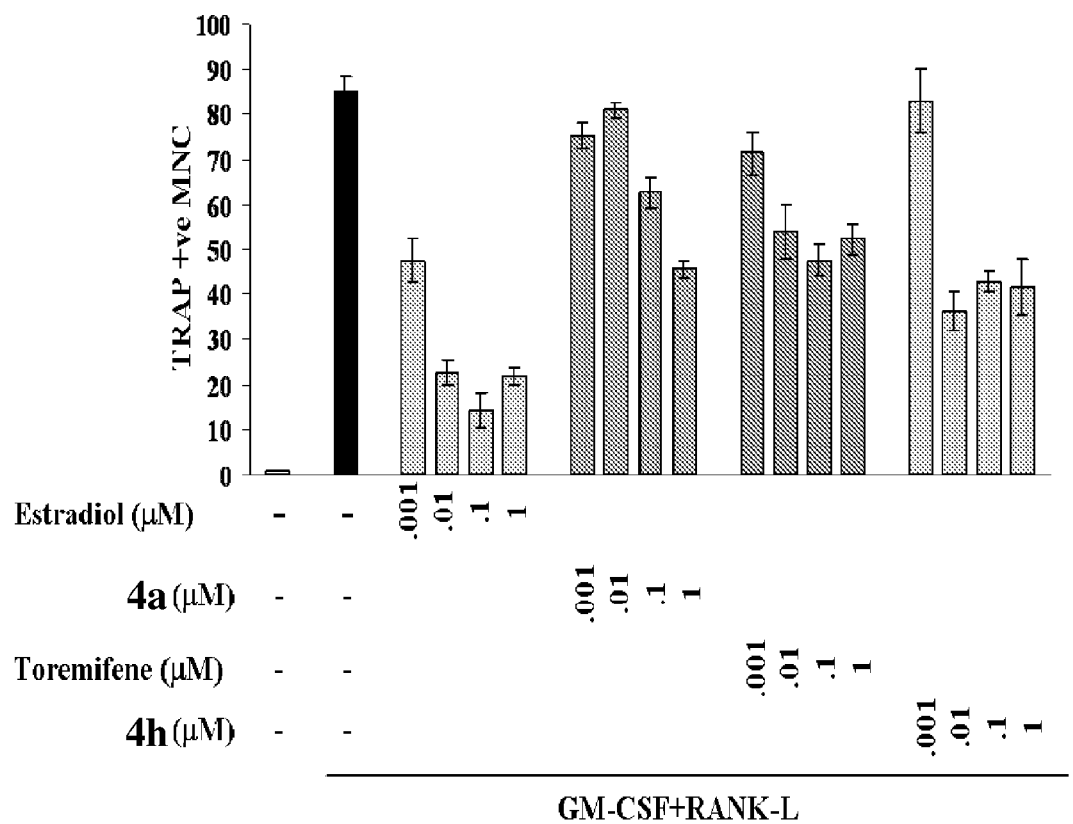
FIG. 7: Effect of the indicated compounds on TRAP positive multinucleated osteoclasts. Bone marrow cells from rat femur was cultured in Alpha MEM+10% csFBS without phenol red in the presence or absence of 30 ng/ml RANKL and 10 ng/ml GMCSF. The cells were treated for 12 days and were stained for tartarate resistant acid phosphatase activity (TRAP) and multinucleated osteoclasts were counted.

The administration of GMCSF and RANKL to pluripotent bone marrow progenitors favors their differentiation to osteoclasts. The presence of estrogen strongly suppressed osteoclast differentiation, while the administration of 4a, 4h, and toremifene under these conditions, minimally but dose-dependently suppressed the osteoclast differentiation (FIG. 7).

Figure 14:
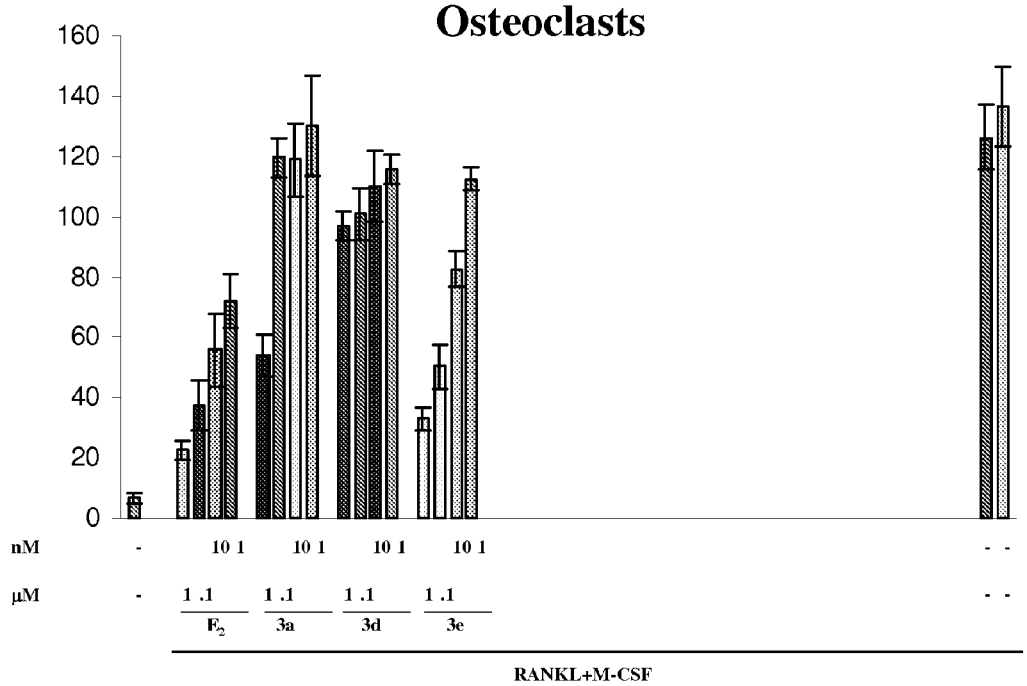
FIG. 14: Effects of the indicated compounds on TRAP positive multinucleated osteoclasts.

Compound 3e was highly suppressive of osteoclast activity and stimulated osteoblast activity, 3a suppressed osteoclasts, 3d stimulated osteoblasts and suppressed osteoclasts (FIG. 14) and 4h was highly suppressive of osteoclast activity under the tested conditions.

Example 5

The Compounds Inhibit Androgen Independent Prostate Cancer Cell Growth

Materials and Methods

The prostate cancer cell line PC-3 was plated in RPMI+ 10% csFBS at 6000 cells per well of a 96 well plate. Medium was changed to RPMI+1% csFBS without phenol red and cells were treated for 72 hrs with increasing concentrations of SERMs.

Results

Figure 8:
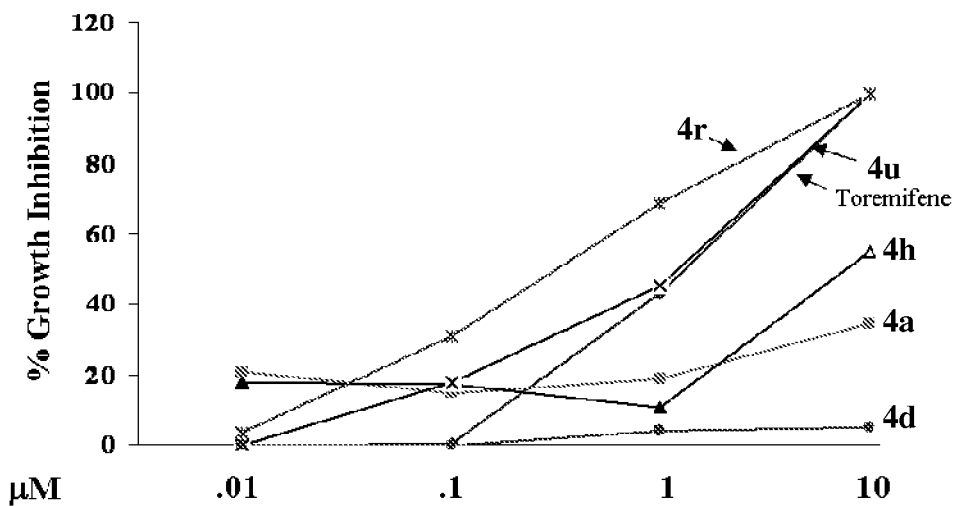
FIG. 8: Some embodiments of this invention include inhibition of androgen independent prostate cancer cell growth via the compounds of this invention. PC-3 cells were plated in RPMI+10% csFBS at 6000 cells per well of a 96 well plate. Medium was changed to RPMI+1% csFBS without phenol red and then treated for 72 hrs with increasing concentrations of SERMs.

Compounds 4r, 4u and toremifene all inhibited PC-3 cell growth by 100% at 10 µM concentrations. Compound 4h, however, under the same conditions inhibited PC-3 cell growth by 75% even at 1 µM concentration. Compound 4a partially inhibited growth by about 50% (FIG. 8). PC-3 growth inhibition was determined qualitatively, in vitro, and represented as a grading system based on the ability of the SERMs to inhibit growth. The number −4 is for compounds that induced 100% growth inhibition at 1 uM, −3 for compounds that inhibit growth by about 75-90%, −2 for about 50-70% and −1 for inhibition less than 50% growth.

Toremifene and compounds 4a, 3l, 4e, 4u, 4b, 4r and 4h each inhibited growth (data not shown). Toremifene inhibited growth to a level of −2, as did compounds 3l, and 4h. Compounds 4a, 4e and 4b showed moderate inhibition (−1); 4u and 4r demonstrated appreciably greater inhibition represented qualitatively as −3 and −4, respectively.

Example 6

In Vivo Estrogenic Activity of Some Embodiments of the Compounds

Materials and Methods

Female rats were administered increasing doses of toremifene, estrogen and the respective SERMs, and/or ICI-182,780 and uterine weights were determined Rats that were administered the vehicle alone served as controls.

Results

Figure 12:
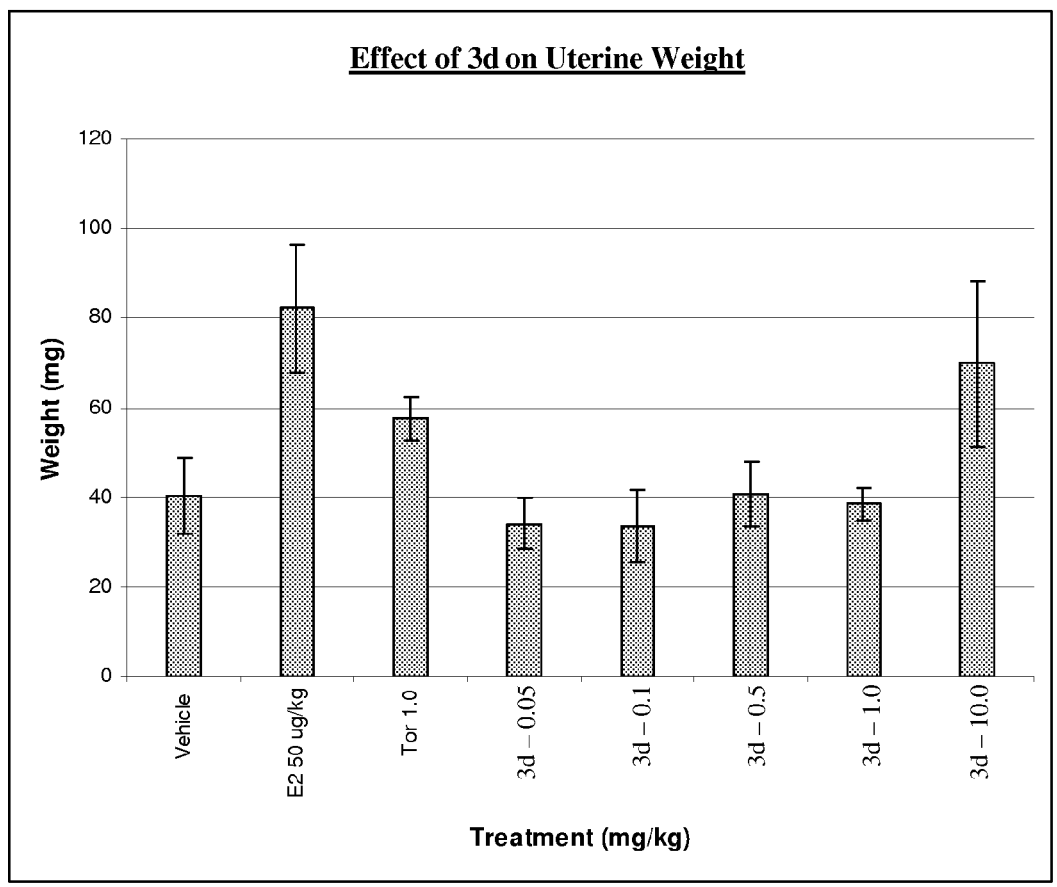
FIG. 12: Estrogenic activity of compound 3d, as compared to toremifene (Tor) and estradiol (E2), as measured by in vivo increased uterine tissue weight (mg).
Figure 13:
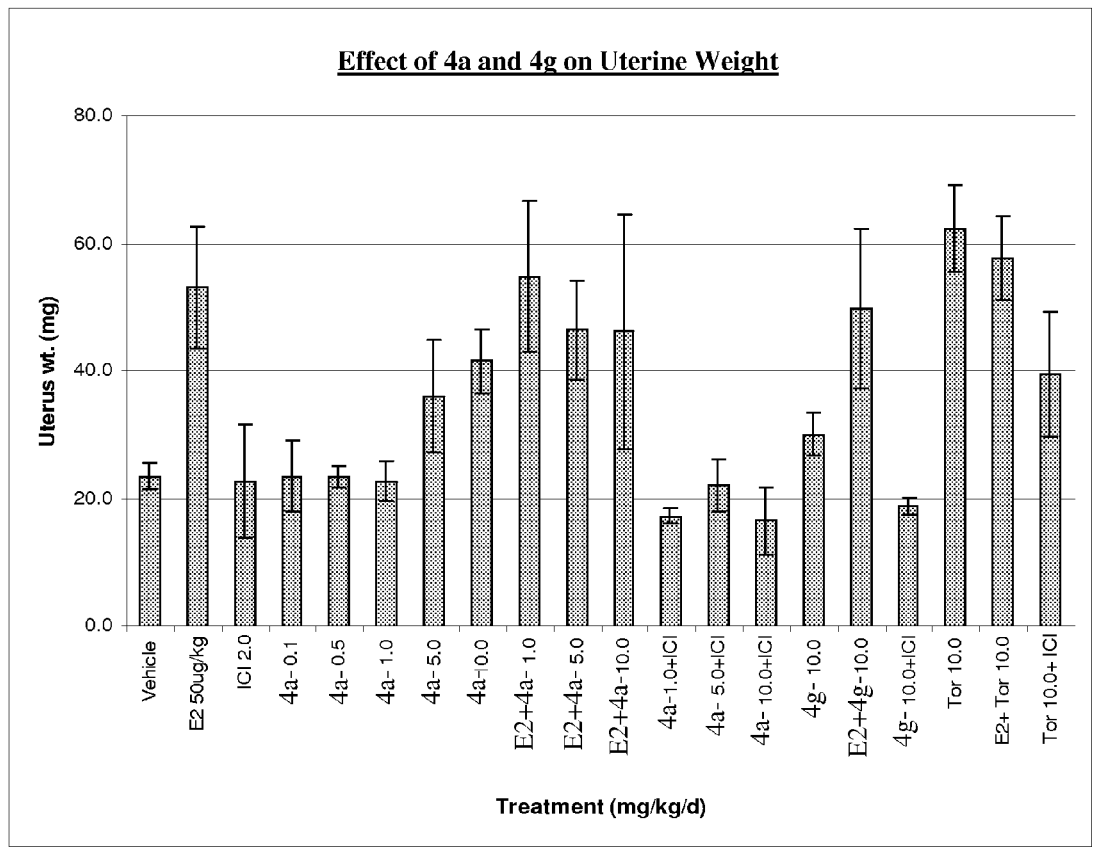
FIG. 13: Estrogenic activity of compounds 4a and 4h, as compared to toremifene (Tor) and estradiol (E2), as measured by in vivo increased uterine tissue weight (mg).

Rats given compounds 4a, 3d and 4g exhibited estrogenic activity, in terms of increased uterine weight, under the conditions tested (FIGS. 12 & 13). When 4a, 4g were coadministered with estrogen, an increase in uterine weight was observed. ICI-182,780 reversed 4a and 4g effects on uterine weight increase under these conditions.

Compounds 3e, 3l, 4h and 4e exhibited no estrogenic, or anti-estrogenic activity in uterus, and compounds 3a, 3f, 4g, and 4a exhibited estrogenic activity, in vivo (data not shown).

Example 7

Metabolic Stability of Some Embodiments of the Compounds in Human Liver Microsomes Materials and Methods Human liver microsomes were utilized as a representative system in order to assess the potential of the compounds to form pharmacologically inactive or undesired potentially toxic metabolites due to phase I metabolism.

Each substrate or reference control was dissolved at a concentration of 10 mM in DMSO, from which a 5 μM spiking solution was prepared by dilution in water. Substrates (1 μM) were incubated in the presence of human liver microsomes (Xenotech LLC, Kansas City Mo.) at 0.5 mg/mL fortified with an NADPH regenerating system at 37° C. and pH 7.4. The NADPH regenerating system consisted of glucose-6-phosphate dehydrogenase (1 units/mL) in 0.05M $K_2HPO_4$. Duplicate incubations were performed in 96-well polypropylene cluster tubes in a final volume of 250 μL per reaction. At 0, 2, 4, 6, 10, 30, and 60 minutes a stop solution (300 μL acetonitrile) was added to aliquots of the reaction mixture. Precipitated protein was removed by centrifugation (3000 rpm for 15 minutes) and the supernatants were transferred to clean 96-well plates for analysis.

LC-MS/MS Analysis:

The samples were injected onto a Phenomenex Luna hexylphenyl 50×2 mm i.d. 5 uM, column fitted with a guard column. An isocratic mobile phase consisting of 50% acetonitrile and 0.1% formic acid in water was used at a flow rate of 0.3 mL/min. The protonated molecular ion $(M+H)^+$ of the analyte was monitored by MDS/Sciex API 4000QTrap triple quadrupole mass spectrometer using electrospray positive mode ionization with a temperature of 500° C. and a spray voltage of 4000V. Total analysis time was 1.5 min per sample.

Data Evaluation:

Metabolic stability was defined as the amount of substrate metabolized by the incubation with hepatic microsomes and expressed as a percentage of the initial amount of substrate (% remaining) based on peak area. Initial substrate concentration for each analyte was 1 μM. The initial peak area of each substrate was determined at time zero and metabolic stability was assessed based on the change in analyte peak area from time 0 min to a single fixed timepoint for each sample (2-60 min, representative timepoints are shown in Table 2 below).

Results

Table 2. shows the percent of substrate remaining after designated incubation intervals (0-60 minutes)

TABLE 2

| | % Remaining | | | |
|---|---|---|---|---|
| Substrate | 0 min | 10 min | 30 min | 60 min |
| [a]Propranolol | 100 | 76 | 69 | 56 |
| [b]Verapamil | 100 | 101 | 36 | 11 |
| 3a | 100 | 140 | 118 | 103 |
| 4a | 100 | 105 | 95 | 74 |
| 3k | 100 | 119 | 120 | 94 |
| 4h | 100 | 99 | 86 | 70 |

[a]Human Liver Microsomes Slow Reference Control
[b]Human Liver Microsomes Intermediate Reference Control Four embodiments of the compounds tested showed reasonable stability in the Phase I metabolic system compared to verapamil, a known substrate for cytochrome P450-mediated inactivation in human liver microsomes (See Table 2). Compounds 3a and 3k were resistant to oxidative and reductive reactions, with 103 and 94% of the initial substrate remaining, respectively, after a 60 minute reaction time. 4a and 4h showed moderate reactivity in the assay, with 74 and 70% remaining after the incubation period. These data suggest that the piperidine ring substitution on the 4a and 4h compounds render them partially susceptible to Phase I metabolic transformation. Generally the compounds evaluated are not likely to have significant Phase I-mediated first pass hepatic extraction. As the determination of metabolic stability is but an in vitro measure to describe the rate and extent of the potential in vivo metabolic fate of the compounds, additional studies are ongoing to identify other metabolic pathways which likely contribute to the biologic inactivation of the leads, elucidate the structure of relevant metabolites, and confirm whether the in vivo pharmacokinetic profile is consistent with these preliminary in vitro data.

Example 8

General Synthesis of N,N-bis Aryl Benzamide Derivatives

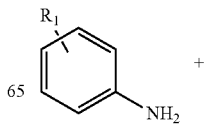

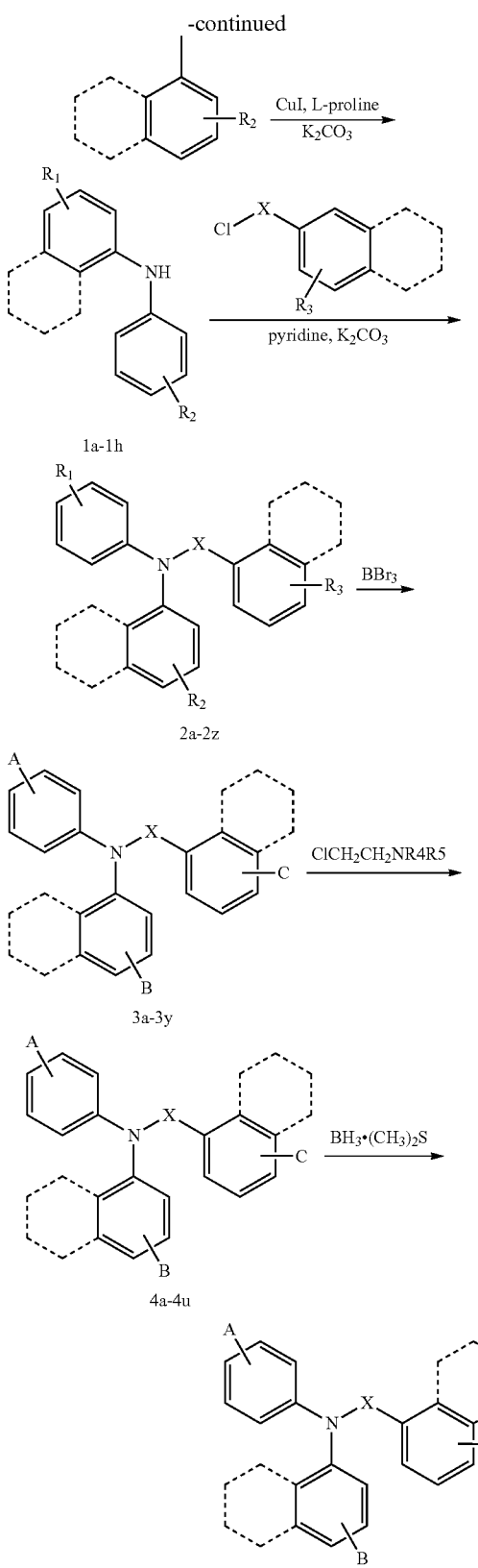

R4R5 = alkyl or together with the nitrogen atom form a heterocyclic ring
A or B or C = OCH$_2$CH$_2$NR4R5

General synthesis of diarylanilines. A mixture of arylamine (1.5 equivalent), aryl iodide (1 equivalent), K$_2$CO$_3$ (2 equivalents), CuI (0.1 equivalent) and L-proline (0.2 equivalent) were mixed together and dissolved in anhydrous DMSO at room temperature. Then, the reaction mixture was stirred and heated to 90° C. for 28 hours. The mixture was cooled to room temperature and hydrolyzed with water. EtOAc was added to partition the solution. The EtOAc layer was separated, washed with brine, dried over anhydrous MgSO$_4$. The solvent was removed under reduced pressure. The solid residue was purified by flash column chromatography (silica gel) using 5% EtOAc/hexanes as eluent to afford the corresponding diarylaniline.

Bis-(4-methoxyphenyl)amine (1a): pale-yellow solid, 73% yield. M.p. 98.6-99.0° C. $^1$H NMR (CDCl$_3$, 300 MHz) δ 6.93-6.81 (m, 8H), 5.37 (s, br, 1H), 3.78 (s, 6H). MS m/z 228.4 (M–H)$^+$.

N-(4-Methoxyphenyl)-phenylamine (1b): pale-yellow solid, 70% yield. M.p. 106.3-106.5° C. $^1$H NMR (CDCl$_3$, 300 MHz) δ 7.24-7.18 (m, 3H), 7.08-7.06 (m, 2H), 6.92-6.84 (m, 4H), 5.61 (s, br, 1H), 3.79 (s, 3H). MS m/z 200.1 (M+H)$^+$.

N-(4-Methoxyphenyl)-N-3-methoxyphenylamine (1c): pale-yellow solid, 54% yield. M.p. 69.7-70.0° C. $^1$H NMR (CDCl$_3$, 300 MHz) δ 6.93-6.81 (m, 8H), 5.37 (s, br, 1H), 3.78 (s, 6H). MS m/z 228.4 (M–H)$^+$.

N-(4-Fluorophenyl)-N4-methoxyphenylamine (1d): pale-yellow solid, 54% yield. M.p. 60.6-61.0° C. $^1$H NMR (CDCl$_3$, 300 MHz) δ 7.01-6.83 (m, 8H), 3.78 (s, 3H). MS m/z 217 (M)$^+$.

N-(4-Methoxyphenyl)-N-1-naphthylamine (1e): pale-yellow solid, 54% yield. M.p. 105.8-106.0° C. $^1$H NMR (CDCl$_3$, 500 MHz) δ 8.00 (d, 1H, J=8.0 Hz), 7.92 (d, 1H, J=8.0 Hz), 7.50-7.43 (m, 3H), 7.33-7.30 (m, 1H), 7.10 (d, 1H, J=7.5 Hz), 7.05 (d, 2H, J=8.5 Hz), 6.88 (d, 2H, J=8.5 HZ), 3.80 (s, 3H). MS m/z 249 (M)$^+$.

N-(4-Benzyloxyphenyl)-N4-methoxyphenylamine (1f): pale-yellow solid, 54% yield. M.p. 108.0-108.4° C. $^1$H NMR (CDCl$_3$, 300 MHz) δ 7.34-7.08 (m, 5H), 6.90-6.81 (s, 3H), 3.78 (s, 3H). MS m/z 306 (M+H)$^+$.

N-[4-(Benzyloxy)phenyl]biphenyl-4-amine (1g): tan solid, 40.2% yield. M.p. 136-138° C. $^1$H NMR (CDCl$_3$, 300 MHz) δ 5.04 (s, 2H, CH$_2$), 6.93-6.99 (m, 4H, ArH), 7.02-7.11 (m, 2H, ArH), 7.22-7.48 (m, 9H, ArH), 7.53-7.56 (m, 3H, ArH). MS m/z 352.2 (M+H)$^+$.

N-[4-(Benzyloxy)phenyl]biphenyl-4-amine (1h): tan solid. 40.2% yield. M.p. 136-138° C. $^1$H NMR (CDCl$_3$, 300 MHz) δ 7.56-7.53 (m, 3H, ArH), 7.48-7.22 (m, 9H, ArH), 7.11-7.02 (m, 2H, ArH), 6.99-6.93 (m, 4H, ArH), 5.04 (s, 2H, CH$_2$); MS m/z 352.2 (M+H)$^+$.

Example 9

General Synthesis of Benzamides

A mixture of arylaniline (1 equivalent), benzoyl chlorides (1.3 equivalents), and pyridine (6 equivalents) was mixed together and dissolved in anhydrous THF at room temperature. The mixture was stirred and refluxed for 24 hours. The reaction solution was cooled to room temperature, and hydrolyzed by addition of 2N HCl solution. The solution was extracted with ethyl acetate. The organic layer was washed with a saturated aqueous NaHCO$_3$ solution to remove excess acid, dried over anhydrous MgSO$_4$, filtered and concentrated under reduced pressure. The residue was purified by flash column chromatography using EtOAc/hexanes (3/7 v/v) to afford the corresponding benzamide compounds.

4-Methoxy-N,N-bis-(4-methoxyphenyl)-benzamide (2a): white solid, 98% yield. M.p. 119.5-120° C. $^1$H NMR (CDCl$_3$, 300 MHz) δ 7.42 (d, 2H, J=8.9 Hz), 7.05 (d, 4H, J=8.8 Hz), 6.81 (d, 4H, J=8.9 Hz), 6.71 (d, 2H, J=8.9 Hz), 3.77 (s, 9H). MS m/z 364 (M+H).

3-Methoxy-N,N-bis-(4-methoxyphenyl)-benzamide (2b): white solid, 99% yield. M.p. 113.5-113.6° C. $^1$H NMR (DMSO-d$_6$, 300 MHz) δ 7.17-7.14 (m, 5H), 6.97-6.95 (m, 3H), 6.87-6.84 (m, 4H). MS m/z 364 (M+H)$^+$.

4-Methoxy-N-(4-methoxyphenyl)-N-(3-methoxyphenyl)-benzamide (2c): white solid, 79% yield. M.p. 154.5-154.9° C. $^1$H NMR (CDCl$_3$, 300 MHz) δ 7.47-7.43 (m, 2H), 7.31-7.13 (m, 7H), 6.75-6.68 (m, 4H), 3.77 (s, 3H), 3.71 (s, 3H). MS m/z 356 (M+Na)$^+$.

N,N-Bis-(4-methoxyphenyl)-benzamide (2d): white solid, 98% yield. M.p. 77-77.5° C. $^1$H NMR (CDCl$_3$, 300 MHz) δ 7.46-7.42 (m, 2H), 7.29-7.17 (m, 3H), 7.09-7.06 (m, 4H), 6.81-6.78 (m, 4H), 3.76 (s, 6H). MS m/z 356 (M+Na)$^+$.

4-Methoxy-N,N-diphenyl-benzamide (2e): white solid, 99% yield. M.p. 133.5-133.9° C. $^1$H NMR (CDCl$_3$, 300 MHz) δ 7.45-7.42 (m, 2H), 7.29-7.24 (m, 4H), 7.18-7.12 (m, 6H), 6.71-6.68 (m, 2H), 3.74 (s, 3H). MS m/z 326 (M+Na)$^+$.

3-Methoxy-N,N-diphenyl-benzamide (2f): white solid, 98% yield. M.p. 122-122.2° C. $^1$H NMR (CDCl$_3$, 300 MHz) δ 7.45-7.42 (m, 2H), 7.29-7.24 (m, 4H), 7.18-7.12 (m, 6H), 6.71-6.68 (m, 2H), 3.74 (s, 3H). MS m/z 326 (M+Na)$^+$.

N,N-Diphenyl-benzamide (2g): white solid, 89% yield. M.p. 178.4-179.3° C. $^1$H NMR (CDCl$_3$, 300 MHz) δ 7.46-7.44 (m, 2H), 7.28-7.23 (m, 5H), 7.21-7.14 (m, 8H). MS m/z 296 (M+Na)$^+$.

N-(4-Methoxyphenyl)-N-phenyl-benzamide (2h): white solid, 95% yield. M.p. 153-154.2° C. $^1$H NMR (CDCl$_3$, 300 MHz) δ 7.47-7.43 (m, 2H), 7.30-7.02 (m, 8H), 6.83-6.78 (m, 2H), 3.76 (s, 3H). MS m/z 326 (M+Na)$^+$.

N-(3-Methoxyphenyl)-N-phenyl-benzamide (2i): white solid, 93% yield. M.p. 103-105.9° C. $^1$H NMR (CDCl$_3$, 300 MHz) δ 7.49-7.45 (m, 2H), 7.31-7.15 (m, 9H), 6.75-6.70 (m, 3H), 3.76 (s, 3H). MS m/z 326 (M+Na)$^+$.

4-Methoxy-N-(4-methoxyphenyl)-N-phenyl-benzamide (2j): white solid, 78% yield. $^1$H NMR (CDCl$_3$, 300 MHz) δ 7.44-7.41 (m, 2H), 7.28-7.26 (m, 2H), 7.15-7.05 (m, 5H), 6.83-6.80 (m, 2H), 6.72-6.70 (m, 2H), 3.77 (s, 6H). MS m/z 356 (M+Na)$^+$.

4-Methoxy-N-(3-methoxyphenyl)-N-phenyl-benzamide (2k): white solid, 84% yield. M.p. 119.0-119.5° C. $^1$H NMR (CDCl$_3$, 300 MHz) δ 7.47-7.43 (m, 2H), 7.31-7.13 (m, 7H), 6.75-6.68 (m, 3H), 3.77 (s, 3H), 3.71 (s, 3H). MS m/z 356 (M+Na)$^+$.

N,N-Bis(4-methoxyphenyl)-4-fluorobenzamide (2l): white solid, 98% yield. M.p. 122.2-122.4° C. $^1$H NMR (CDCl$_3$, 300 MHz) δ 7.46-7.42 (m, 2H), 7.29-7.17 (m, 3H), 7.09-7.06 (m, 4H), 6.81-6.78 (m, 4H), 3.76 (s, 6H). MS m/z 356 (M+Na)$^+$.

4-Methoxy-N,N-diphenyl-sulfonamide (2m): white solid, 89% yield. M.p. 153.0-153.5° C. $^1$H NMR (CDCl$_3$, 300 MHz) δ 7.64-7.61 (m, 2H), 7.34-7.22 (m, 10H), 6.94-6.91 (m, 2H), 3.86 (s, 3H). MS m/z 362 (M+Na)$^+$.

4-Methoxy-N-(4-methoxyphenyl)-N-(4-fluorophenyl)-benzamide (2n): white solid, 97% yield. M.p. 133.5.0-134.5° C. $^1$H NMR (CDCl$_3$, 300 MHz) δ 8.11-6.66 (m, 15H), 3.74 (s, 3H), 3.73 (s, 3H). MS m/z 384 (M+H)$^+$.

4-Methoxy-N-(4-methoxyphenyl)-N-(1-naphthyl)-benzamide (2o): white solid, 65% yield. M.p. 144.0-144.5° C. $^1$H NMR (CDCl$_3$, 300 MHz) δ 8.11-6.66 (m, 15H), 3.74 (s, 3H), 3.73 (s, 3H). MS m/z 384 (M+H)$^+$.

N-(4-Methoxyphenyl)-N-(4-benzyloxyphenyl)-1-naphthylamide (2p). white solid, 95% yield. M.p. 143.5-144.0° C. $^1$H NMR (CDCl$_3$, 300 MHz) δ 8.25-8.22 (m, 1H), 7.79-7.69 (m, 2H), 7.57-7.22 (m, 9H), 6.96-6.63 (m, 8H), 4.99 (s, 2H), 3.71 (s, 3H). MS m/z 460 (M+H)$^+$.

4-Chloro-N-(4-methoxyphenyl)-N-(4-benzyloxyphenyl)-benzamide (2q): white solid, 96% yield. M.p. 130.0-131.4° C. $^1$H NMR (DMSO-d$_6$, 300 MHz) δ. MS m/z 444 (M+H)$^+$.

4-Cyano-N-(4-methoxyphenyl)-N-(4-benzyloxyphenyl)-benzamide (2r): white solid, 85% yield. M.p. 147.6-148.0° C. $^1$H NMR (DMSO-d$_6$, 300 MHz) δ. MS m/z 435 (M+H)$^+$.

N-(4-Methoxyphenyl)-N-(4-benzyloxyphenyl)-2-naphthylamide (2s): white solid, 58% yield. M.p. 174.9-175.5° C. $^1$H NMR (CDCl$_3$, 300 MHz) δ 8.04 (s, 1H), 7.77-7.74 (m, 2H), 7.64-7.61 (m, 1H), 7.51-7.43 (m, 4H), 7.40-7.31 (m, 4H), 7.13-7.10 m, 4H), 6.88-6.78 (m, 4H), 4.99 (s, 2H), 3.74 (s, 3H). MS m/z 460 (M+H)$^+$.

4-(Benzyloxy)-N-[4-(benzyloxy)phenyl]-N-(4-methoxyphenyl)benzamide (2t): tan solid. 72.4% yield. M.p. 175-178° C. $^1$H NMR (DMSO-d$_6$, 300 MHz) δ 7.37-7.34 (m, 12H, ArH), 7.13-7.10 (m, 4H, ArH), 6.96-6.89 (m, 2H, ArH), 6.88-6.86 (m, 4H, ArH), 5.06 (s, 4H, 2×CH$_2$), 3.72 (s, 3H, OCH$_3$). MS m/z 516.3 (M+H)$^+$.

N-[4-(Benzyloxy)phenyl]-4-methoxy-N-(4-methoxyphenyl)benzamide (2u): yellow oil. 71.3% yield. $^1$H NMR (CDCl$_3$, 300 MHz) δ 7.44-7.34 (m, 7H, ArH), 7.07-7.04 (m, 4H, ArH), 6.89-6.86 (m, 2H, ArH), 6.82-6.79 (m, 2H, ArH), 6.72-6.69 (m, 2H, ArH), 5.01 (s, 2H, CH$_2$), 3.77 (s, 6H, 2 X OCH$_3$). MS m/z 462.1 (M+Na)$^+$.

N-[4-(Benzyloxy)phenyl]-N-biphenyl-4-yl-4-methoxybenzamide (2v): light-yellow foam. 78.6% yield. M.p. 70-72° C. $^1$H NMR (DMSO-d$_6$, 300 MHz) δ 7.66-7.57 (m, 4H, ArH), 7.47-7.32 (m, 10H, ArH), 7.30-7.23 (m, 2H, ArH), 7.18-7.07 (m, 2H, ArH), 7.00-6.92 (m, 2H, ArH), 6.89-6.80 (m, 2H, ArH), 5.06 (s, 2H, CH$_2$), 3.72 (s, 3H, OCH$_3$). MS m/z 508.3 (M+Na)$^+$.

4-Cyano-N-(4-methoxyphenyl)-N-phenylbenzamide (2w): pale-yellow solid. 96.3% yield. M.p. 125-128° C. $^1$H NMR (DMSO-d$_6$, 300 MHz) δ 7.77-7.74 (m, 2H, ArH), 7.61-7.58 (m, 2H, ArH), 7.34-7.21 (m, 7H, ArH), 6.88 (d, J=7.92 Hz, 2H, ArH), 3.71 (s, 3H, OCH$_3$). MS m/z 351.1 (M+Na)$^+$.

3-Methoxy-N-(4-methoxyphenyl)-N-phenylbenzamide (2x): pale-yellow oil. 98.8% yield. $^1$H NMR (CDCl$_3$, 300 MHz) δ 7.30-7.25 (m, 2H, ArH), 7.18-7.07 (m, 6H, ArH), 7.01-6.98 (m, 2H, ArH), 6.83-6.80 (m, 3H, ArH), 3.77 (s, 3H, OCH$_3$), 3.68 (s, 3H, OCH$_3$). MS m/z 356.1 (M+Na)$^+$.

4-Cyano-N-(3-methoxyphenyl)-N-phenylbenzamide (2y): brown oil. 84.8% yield. $^1$H NMR (DMSO-d$_6$, 300 MHz) δ 7.77-7.75 (m, 2H, ArH), 7.63-7.61 (m, 2H, ArH), 7.35-7.30 (m, 4H, ArH), 7.25-7.22 (m, 2H, ArH), 6.91 (s, 1H, ArH), 6.83-6.80 (m, 2H, ArH), 3.67 (s, 3H, OCH$_3$). MS m/z 351.1 (M+Na)$^+$.

4-Cyano-N,N-diphenylbenzamide (2z): tan solid. 85.2% yield. M.p. 145-147° C. $^1$H NMR (DMSO-d$_6$, 300 MHz) δ 7.76-7.74 (m, 2H, ArH), 7.61-7.59 (m, 2H, ArH), 7.34-7.22 (m, 10H, ArH). MS m/z 321.0 (M+Na)$^+$.

Example 10

General Procedure for Demethylation of Benzamide Derivatives Using BBr$_3$

A methoxybenzamide compound was dissolved in dry CH$_2$Cl$_2$. BBr$_3$ (1.0 M CH$_2$Cl$_2$ solution) was added dropwise at 0° C. The reaction solution was slowly warmed to room temperature and allowed to stir overnight at room temperature. The mixture was cooled to 0° C. in an ice bath and hydrolyzed by adding water. EtOAc was added to partition the solution. The organic layer was separated; the aqueous layer was extracted with EtOAc. The organic layer was washed with brine and dried over anhydrous MgSO$_4$. The solvent was removed under reduced pressure. The residue was purified by flash column chromatography using CH$_3$OH/CH$_2$Cl$_2$ (1/9 v/v) to afford the phenolic compounds.

The following compounds where synthesized as described herein above and characterized and summarized in Table 1: 4-Hydroxy-N,N-bis-(4-hydroxyphenyl)-benzamide (3a); 3-Hydroxy-N-bis-(4-hydroxyphenyl)-benzamide (3b); 4-Hydroxy-N-(4-hydroxyphenyl)-N-(3-hydroxyphenyl)-benzamide (3c); N,N-Bis-(4-hydroxyphenyl)-benzamide (3d); 4-Hydroxy-N,N-diphenyl-benzamide (3e); 3-Hydroxy-N,N-diphenyl-benzamide (3f); N-(4-Hydroxyphenyl)-N-phenyl-benzamide (3g); N-(3-Hydroxyphenyl)-N-phenyl-benzamide (3h); 4-Hydroxy-N-(4-hydroxyphenyl)-N-phenyl-benzamide (3i); 4-Hydroxy-N-(3-hydroxyphenyl)-N-phenyl-benzamide (3j); N,N-Bis(4-hydroxyphenyl)-4-fluorobenzamide (3k); 4-Hydroxy-N,N-diphenyl-phenylsulfonamide (3l); 4-Hydroxy-N-(4-hydroxyphenyl)-N-(4-fluorophenyl)-benzamide (3m); N,N-Bis(4-hydroxyphenyl)-1-naphthylamide (3n); 4-Hydroxy-N-(1-Naphthyl)-N-(4-hydroxyphenyl)-benzamide (3o); 4-Cyano-N,N-Bis(4-hydroxyphenyl)-benzamide (3p); 3-Cyano-N,N-Bis(4-hydroxyphenyl)-benzamide (3q); N,N-Bis(4-hydroxyphenyl)-2-naphthylamide (3r); 4-Cyano-N-[4-(2-piperidin-1-ylethoxy)-phenyl]-N-(4-hydroxyphenyl)-benzamide (3s); 3-Chloro-N-[4-(2-piperidin-1-ylethoxy)-phenyl]-N-(4-hydroxyphenyl)-benzamide (3t); N-Biphenyl-4-yl-N-(4-hydroxyphenyl)-4-methoxybenzamide (3u); N-Biphenyl-4-yl-4-hydroxy-N-(4-hydroxyphenyl)-benzamide (3v); 4-Hydroxy-N-(4-hydroxyphenyl)-N-[4-(2-piperidin-1-ylethoxy)phenyl]-benzamide (3w); 3-Hydroxy-N-(4-hydroxyphenyl)-N-phenyl-benzamide (3x); N-Biphenyl-4-yl-4-hydroxy-N-[4-(2-piperidin-1-ylethoxy)phenyl]-benzamide (3y); 4-Cyano-N-(4-hydroxyphenyl)-N-phenylbenzamide (10a); N,N-bis(4-hydroxyphenyl) biphenyl-4-carboxamide (10c), N,N-bis(4-hydroxyphenyl)-3,4-dimethylbenzamide (10d); N-(biphenyl-4-yl)-4-cyano-N-(4-hydroxyphenyl)-benzamide (10e); 3-fluoro-4-hydroxy-N-(4-hydroxyphenyl)-N-phenylbenzamide (10f); 4-hydroxy-N,N-bis(4-hydroxyphenyl)-3,5-dimethylbenzamide (10i); N,N-bis(4-hydroxyphenyl)-2,3-dimethylbenzamide (10j); 3-fluoro-4-hydroxy-N,N-bis(4-hydroxyphenyl)-benzamide (10k); N,N-bis(4-hydroxyphenyl)-4-propylbenzamide (10l); 3,4-dihydroxy-N,N-bis(4-hydroxyphenyl)-benzamide (10m); 4-hydroxy-N,N-bis(4-hydroxyphenyl)-3-methylbenzamide (10n); N,N-bis(4-hydroxyphenyl)-2,4-dimethylbenzamide (10q); N,N-bis(4-hydroxyphenyl)-4-methylbenzamide (10s); 4,4'-(2,3-dimethylbenzylazanediyl)diphenol (10t); 4-formyl-N,N-bis(4-hydroxyphenyl)-benzamide (10u); N,N-bis(4-hydroxyphenyl)-4-(trifluoromethyl)benzamide (11b); N,N-bis(4-hydroxyphenyl)-4-nitrobenzamide (11d); 3-fluoro-N,N-bis(4-hydroxyphenyl)benzamide (11e); N,N-bis(4-hydroxyphenyl)-4-methoxy-1-naphthamide (11i); 4-((hydroxyimino)methyl)-N,N-bis(4-hydroxyphenyl)benzamide (11l); N,N-bis(4-hydroxyphenyl)-4-pentylbenzamide (11p); 4-tert-butyl-N,N-bis(4-hydroxyphenyl)benzamide (11r); 3-{4-[Bis-(4-hydroxy-phenyl)-carbamoyl]-phenyl}-acrylic acid (11t); 3-{4-[Bis-(4-hydroxy-phenyl)-carbamoyl]-phenyl}-propionic acid (11u); N,N-Bis-(4-hydroxy-phenyl)-4-(3-hydroxy-propyl)-benzamide (11v); N-(4-hydroxyphenyl)-4-(3-hydroxypropyl)-N-(4-methoxyphenyl)-benzamide (11w); 4-fluoro-N,N-bis(4-hydroxyphenyl)-2-(trifluoromethyl)-benzamide (11x); 3-fluoro-N-(4-fluorophenyl)-4-hydroxy-N-(4-hydroxyphenyl) benzamide (11y); and N,N-bis(4-hydroxyphenyl)-isonicotin-amide (11aa).

General Procedures for Debenzylation of Benzyloxyphenyl-Benzamides.

Compound was dissolved in EtOH in a 250 mL hydrogenation bottle. Pd/C powder (5% mol) was added to the solution. The reaction vessel was mounted to a hydrogenation apparatus under 20 psi pressure hydrogen gas. The reaction was monitored by TLC until the disappearance of starting material. Then, the solvent was removed under reduced pressure. The residue was purified by flash column chromatography with hexanes/EtOAc=3/2 v/v to afford the desired product.

The following compounds where synthesized as described herein above and characterized and summarized in Table 1: 4-Chloro-N-[4-hydroxyphenyl]-N-(4-methoxyphenyl)-benzamide (5a); 4-Cyano-N-[4-hydroxyphenyl]-N-(4-methoxyphenyl)-benzamide (5b); 3-Chloro-N-[4-hydroxyphenyl]-N-(4-methoxyphenyl)-benzamide (5c); 4-Hydroxy-N-(4-hydroxyphenyl)-N-(4-methoxyphenyl)-benzamide (5d); N-(4-Hydroxyphenyl)-4-methoxy-N-(4-methoxyphenyl)-benzamide (5e).

Example 11

General Synthesis of O-(2-piperidin-1-ylethoxy)-Benzamides and Analogues

To a solution of hydroxyphenyl containing benzamide analogue (1 equivalent) in acetone, K$_2$CO$_3$ (3 equivalents) and N-chloroethyl-piperidine hydrochloride salt (1.2 equivalents) were added. The solution was heated to reflux for 6 hours. The solution was evaporated to dryness. The residue was hydrolyzed by adding water, and then extracted with ethyl acetate. The organic layers were separated and dried over anhydrous MgSO$_4$. The solvent was removed under reduced pressure. The residue was purified by flash chromatography with methylene chloride/methanol=9/1 v/v to give the desired compound. The hydrochloride salts were prepared by adding HCl in Et$_2$O to the methanol solution of the compounds followed by evaporation of solvents.

The following compounds where synthesized as described herein above and characterized and summarized in Table 1: N-(4-Hydroxyphenyl)-N-[4-(2-piperidin-1-ylethoxy)-phenyl]-benzamide (4a); N-(phenyl)-N-[4-(2-piperidin-1-ylethoxy)-phenyl]-benzamide (4b); N,N-diphenyl-[3-(2-piperidinylethoxy)]-benzamide hydrochloride (4c); N,N-diphenyl-[3-(2-piperidinylethoxy)]-benzamide hydrochloride (4d); N-(4-Hydroxyphenyl)-N-phenyl-[4-(2-piperidin-1-ylethoxy)]-benzamide hydrochloride (4e); N,N-diphenyl-bis[4-(2-piperidin-1-ylethoxy)-phenyl]-sulfonamide hydrochloride (4f); N-(4-Fluorophenyl)-N-[4-hydroxyphenyl]-[4-(2-piperidin-1-ylethoxy)]-benzamide (4g); N-(4-Hydroxyphenyl)-N-[4-(2-piperidin-1-ylethoxy)-phenyl]-4-fluoro-benzamide hydrochloride (4h); 3-(2-piperidin-1-ylethoxy)-N,N-bis(4-hydroxyphenyl)-benzamide (4i); 4-Cyano-N-[4-(2-piperidin-1-ylethoxy)-phenyl]-N-(4-methoxyphenyl)-benzamide (4j); 4-Chloro-N-[4-(2-piperidin-1-ylethoxy)-phenyl]-N-(4-methoxyphenyl)-benzamide (4k); 4-Cyano-N-[4-(2-piperidin-1-ylethoxy)-phenyl]-N-(4-methoxyphenyl)-benzamide (4l); 3-Chloro-N-[4-(2-piperidin-1-ylethoxy)-phenyl]-N-(4-methoxyphenyl)-benzamide (4m); 4-Methoxy-N-(4-methoxyphenyl)-N-[4-(2-piperidin- 1-ylethoxy)phenyl]-benzamide (4n); N-Biphenyl-4-yl-N-(4-hydroxyphenyl)-4-(2-piperidin-1-ylethoxy)-benzamide (4o); 4-Methoxy-N-phenyl-N-[4-(2-piperidin-1-ylethoxy)phenyl]-benzamide (4p); N-(4-Hydroxyphenyl)-N-phenyl-3-(2-piperidin-1-ylethoxy)-benzamide (4q); N-(4-hydroxyphenyl)-N-(4-(2-(piperidin-1-yl)ethoxy)phenyl)-4-propylbenzamide (10o); N-(4-hydroxyphenyl)-2,3-dimethyl-N-(4-(2-(piperidin-1-yl)ethoxy)phenyl)-benzamide (10p); N-(4-hydroxyphenyl)-N-(4-(2-(pyrrolidin-1-yl)ethoxy)phenyl)benzamide (11a); N-(4-hydroxyphenyl)-N-(4-(2-(piperidin-1-yl)ethoxy)phenyl)-4-(trifluoromethyl)benzamide (11c); N-(4-Hydroxyphenyl)-N-(4-(2-(piperidin-1-yl)ethoxy)phenyl)-1-naphthamide (11f); 3-fluoro-N-(4-hydroxyphenyl)-N-(4-(2-(piperidin-1-yl)ethoxy)phenyl)benzamide (11g); N-(4-hydroxyphenyl)-4-nitro-N-(4-(2-(piperidin-1-yl)ethoxy)phenyl)benzamide (11h); N-(4-hydroxyphenyl)-N-(4-(2-(piperidin-1-yl)ethoxy)phenyl)-2-naphthamide (11j); N-(4-hydroxyphenyl)-2,4-dimethyl-N-(4-(2-(piperidin-1-yl)ethoxy)phenyl)benzamide (11m); N-(4-hydroxyphenyl)-3,5-dimethyl-N-(4-(2-(piperidin-1-yl)ethoxy)phenyl)benzamide (11n); 4-((2,3-dimethylbenzyl)(4-(2-(piperidin-1-yl)ethoxy)phenyl)amino)phenol (11o); N-(4-hydroxyphenyl)-4-pentyl-N-(4-(2-(piperidin-1-yl)ethoxy)phenyl)benzamide (11q); 4-tert-butyl-N-(4-hydroxyphenyl)-N-(4-(2-(piperidin-1-yl)ethoxy)phenyl)benzamide (11s); N-(4-hydroxyphenyl)-4-methyl-N-(4-(2-(piperidin-1-yl)ethoxy)phenyl)benzamide (11z); and N-(4-hydroxyphenyl)-N-(4-(2-(piperidin-1-yl)ethoxy)phenyl)-isonicotinamide (11ab).

Synthesis of Two-Tailed SERMs

N-(4-Fluorophenyl)-N-[4-(2-piperidin-1-ylethoxy)-phenyl]-[4-(2-piperidin-1-yl-ethoxy)]-benzamide dihydrochloride (4r); N,N-Bis[4-(2-piperidin-1-ylethoxy)-phenyl]-4-fluoro-benzamide dihydrochloride (4s); N,N-Bis[4-(2-piperidin-1-ylethoxy)-phenyl]-benzamide dihydrochloride (4t); and N-[4-(2-piperidin-1-ylethoxy)-phenyl]-N-phenyl-[4-(2-piperidin-1-ylethoxy)]-benzamide dihydrochloride (4u).

Example 12

General Procedures for Synthesis of Cyclohexanecarboxylic Acid Bis-Arylamides

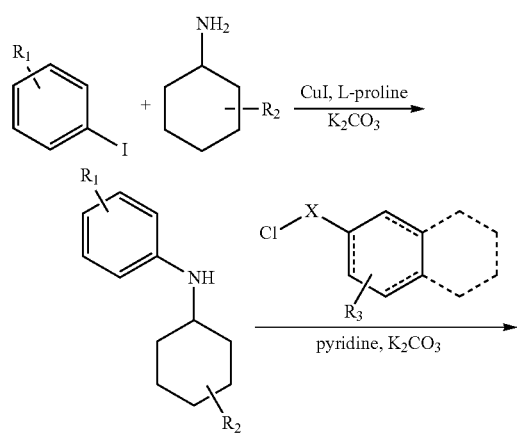

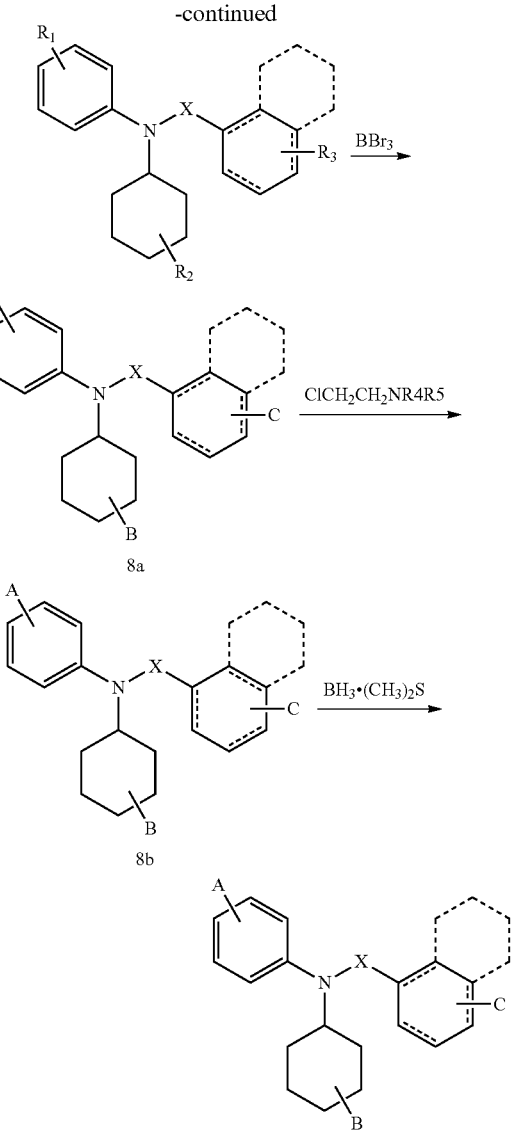

R4, R5 = alkyl or form together with the nitrogen atom a heterocyclic ring

A or B or C = OCH$_2$CH$_2$NR4R5

N-Cyclohexyl-4-methoxyphenylamine. This compound was synthesized according the literature. The NMR, MS data and melting point are consistent with those reported in literature.[ref] (D. Ma, Q. Cai, H. Zhang, Org. Lett. 2003, 5, 2453.) General Procedures for Synthesis of Cyclohexanecarboxylic Acid Bis-Aryl Amides.

Arylaniline (1 equivalent), cyclohexylcarbonyl chloride (1.3 equivalents), and pyridine (6 equivalents). The reaction mixture was stirred and heated to 90° C. for 24 hours. The reaction solution was cooled to room temperature, and hydrolyzed by addition of 2N HCl solution. The solution was extracted with ethyl acetate twice. The combined organic layers were washed with saturated aqueous NaHCO$_3$ solution to remove excess acid, dried over anhydrous MgSO$_4$, filtered and concentrated under reduced pressure. The residue was purified by flash column chromatography using EtOAc/hexanes (3/7 v/v) to afford the corresponding cyclohexylamide compound.

Cyclohexanecarboxylic acid N-(4-methoxyphenyl)-N-(4-benzyloxyphenyl)-amide (8a): white solid, 92% yield. M.p.

102.7-128.0° C. $^1$H NMR (CDCl$_3$, 300 MHz) δ 7.40-6.90 (m, 13H), 5.03 (s, 2H), 3.80 (s, 3H), 2.41-2.04 (m, 1H), 1.78-1.53 (m, 7H), 1.28-1.06 (m, 3H). MS m/z 438 (M+Na)$^+$.

General Procedure for Synthesis of Bis N-Hydroxyphenyl Cyclohexanecarboxylic Acids.

A methoxyphenylcyclohexylamide compound was dissolved in dry CH$_2$Cl$_2$. BBr$_3$ (1.0 M CH$_2$Cl$_2$ solution) was added dropwise with stirring via a syringe at 0° C. The reaction solution was slowly warmed to room temperature and allowed to stir overnight at room temperature. The mixture was cooled to 0° C. in an ice bath and hydrolyzed by adding water. EtOAc was added to partition the solution. The organic layer was separated; the aqueous layer was extracted with EtOAc twice. The organic layers were combined, washed with brine and dried over anhydrous MgSO$_4$. The solvent was removed under vacuum. The residue was purified by flash column chromatography using silica-gel with CH$_3$OH/CH$_2$Cl$_2$ (1/9 v/v) to afford the pure desired phenolic compound.

Cyclohexanecarboxylic acid bis(4-hydroxyphenyl)-amide (8b): white solid, 86% yield. M.p. 265.1-266.2° C. (decomposed). $^1$H NMR (DMSO-d$_6$, 500 MHz) δ 9.65 (s, 1H), 9.37 (s, 1H), 7.17-6.70 (m, 4H), 6.78-6.67 (m, 4H), 2.29-2.23 (m, 1H), 1.71-1.62 (m, 4H), 1.54-1.51 (m, 1H), 1.41-1.32 (m, 2H), 1.21-1.07 (m, 1H), 0.97-0.90 (m, 2H). MS m/z 334 (M+Na)$^+$.

Example 13

General Synthesis of 5-[4-methoxyphenyl]-5H-phenanthridin-6-ones

A mixture of 6-(5H)-phenathridinone (1.5 equivalent), 4-iodoanisole (1 equivalent), K$_2$CO$_3$ (2 equivalents), CuI (0.1 equivalent) and L-proline (0.2 equivalent) were mixed together and dissolved in anhydrous DMSO at room temperature. Then, the reaction mixture was stirred and heated to 150° C. for 28 hours. The mixture was cooled to room temperature and hydrolyzed with water. EtOAc was added to partition the solution. The EtOAc layer was separated, washed with brine, dried over anhydrous MgSO$_4$. The solvent was removed under reduced pressure. The residue was purified by flash column chromatography (silica gel) using EtOAc/hexanes (2/3 v/v) to afford the desired product.

5-[4-methoxyphenyl]-5H-phenanthridin-6-one (7a): yellow solid. 65% yield. M.p. 217.0-218.5° C. (decomposed). $^1$H NMR (DMSO-d$_6$, 500 MHz) δ 8.61-8.59 (m, 1H), 8.54-8.51 (m, 1H), 8.36-8.34 (m, 1H), 7.94-7.89 (m, 1H), 7.71-7.66 (m, 1H), 7.43-7.28 (m, 4H), 7.19-7.16 (m, 2H), 6.63-6.60 (m, 1H). MS m/z 302 (M+H)$^+$.

General Synthesis of 5-[4-hydroxyphenyl]-5H-phenanthridin-6-ones

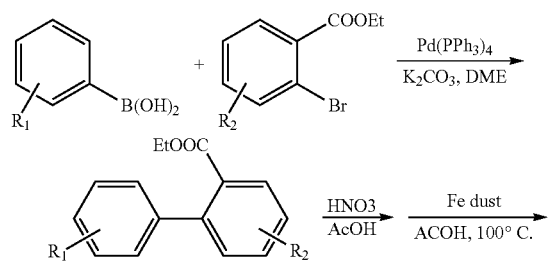

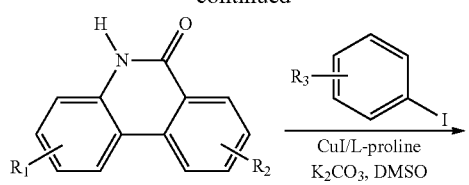

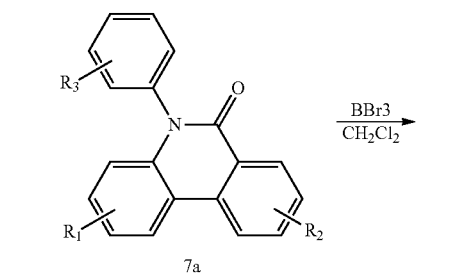

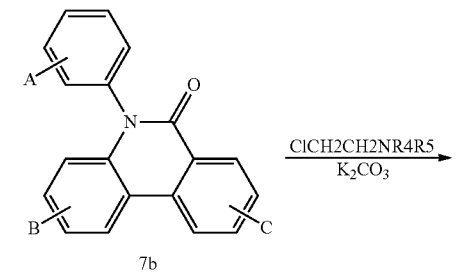

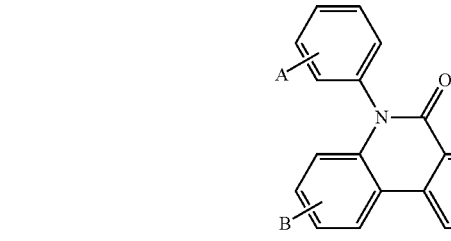

R4, R5 = alkyl or form together with the nitrogen atom a heterocyclic ring
A or B or C = OCH2CH2NR4R5

A 5-[4-methoxyphenyl]-5H-phenanthridin-6-one was dissolved in dry CH$_2$Cl$_2$. BBr$_3$ (1.0 M CH$_2$Cl$_2$ solution) was added dropwise with stirring via a syringe at 0° C. The reaction solution was slowly warmed to room temperature and allowed to stir overnight at room temperature. The mixture was cooled to 0° C. in an ice bath and hydrolyzed by adding water. EtOAc was added to partition the solution. The organic layer was separated; the aqueous layer was extracted with EtOAc twice. The organic layers were combined, washed with brine and dried over anhydrous MgSO$_4$. The solvent was removed under vacuum. The residue was purified by flash column chromatography using silica-gel with CH$_3$OH/CH$_2$Cl$_2$ (1/9 v/v) to afford the pure desired phenolic compound.

5-[4-hydroxyphenyl]-5H-phenanthridin-6-one (7b): yellow solid. 78% yield. M.p. 325.7-327.0° C. (decomposed). $^1$H NMR (DMSO-d$_6$, 500 MHz) δ 9.82 (s, 1H), 8.60-8.58 (m, 1H), 8.52-8.51 (m, 1H), 8.35-8.33 (m, 1H), 7.92-7.89 (m, 1H), 7.69-7.66 (m, 1H), 7.41-7.38 (m, 1H), 7.32-7.29 (m, 1H), 7.15-7.13 (m, 2H), 6.99-6.97 (m, 2H), 6.65-6.63 (m, 1H). MS m/z 310 (M+Na)$^+$.

General Synthesis of 5-[4-(2-piperidin-1-ylethoxy)-phenyl]-phenanthridin-6-one Derivatives To a solution of 5-[4-hydroxyphenyl]-phenanthridin-6-one (1 equivalent) in acetone, $K_2CO_3$ (3 equivalents) and N-chloroethylpiperidine hydrochloride salt (1.2 equivalents) were added. The solution was heated to reflux for 6 hours. The solution was evaporated to dryness. The residue was hydrolyzed by adding water, and then extracted with ethyl acetate. The organic layers were separated and dried over anhydrous $MgSO_4$. The solvent was removed under reduced pressure. The residue was purified by flash chromatography (silica-gel; methylene chloride/methanol=9/1 v/v) to give the desired compound. The hydrochloride salts were prepared by adding HCl in $Et_2O$ to the methanol solution of the compounds followed by evaporation of solvents.

5-[4-(2-piperidin-1-ylethoxy)-phenyl]-5H-phenanthridin-6-one (7c): yellow solid. 79% yield. M.p. 220.0-221.5° C. (decomposed). $^1H$ NMR (DMSO-$d_6$, 300 MHz) δ 8.56-8.53 (m, 1H), 8.35-8.29 (m, 2H), 7.84-7.79 (m, 1H), 7.64-7.59 (m, 1H), 7.36-7.24 (m, 4H), 7.23-7.10 (m, 2H), 6.76-6.73 (m, 1H), 4.45 (tr, 2H, J=5.1 Hz), 3.16 (tr, 2H, J=5.1 Hz), 2.94 (br, 4H), 1.90-1.85 (m, 4H), 1.61-1.59 (m, 2H). MS m/z 399 $(M+H)^+$.

Example 14

General Synthesis of 6b, 6c, 6d, 6e, 6f, and 6g

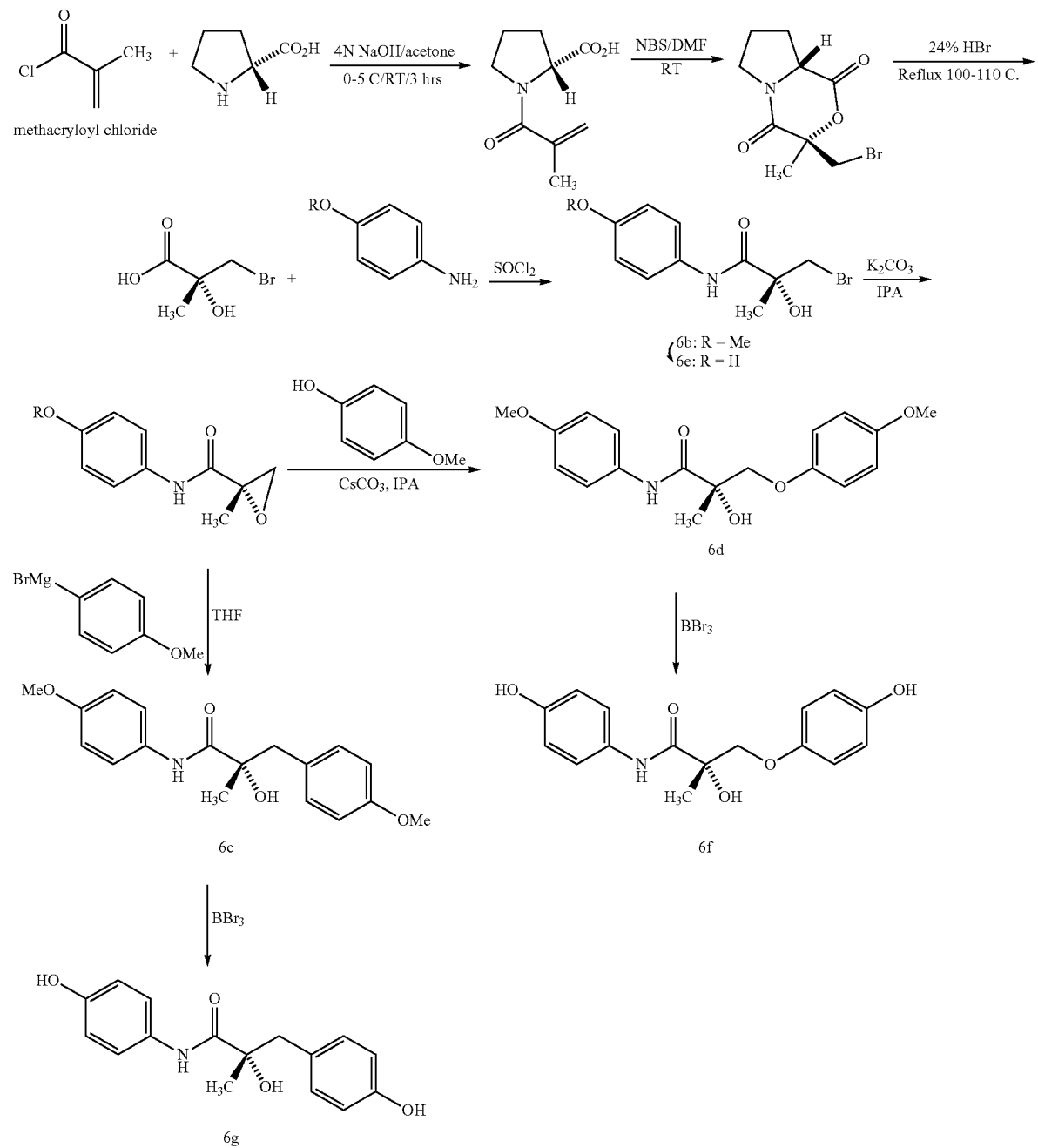

(2R)-1-Methacryloylpyrrolidin-2-carboxylic Acid. D-Proline, 14.93 g, 0.13 mol) was dissolved in 71 mL of 2 N NaOH and cooled in an ice bath; the resulting alkaline solution was diluted with acetone (71 mL). An acetone solution (71 mL) of metacryloyl chloride (13.56 g, 0.13 mol) and 2N NaOH solution (71 mL) were simultaneously added over 40 min to the aqueous solution of D-proline in an ice bath. The pH of the mixture was kept at 10-11° C. during the addition of the metacryloyl chloride. After stiffing (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite, and evaporated in vacuo to give the crude product as a colorless oil. Recrystallization of the oil from ethyl ether and hexanes afforded 16.2 (68%) of the desired compound as colorless crystals: mp 102-103° C. (lit. [214] mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[\alpha]_D^{26}$ +8.0° (c=1, MeOH); Anal. Calcd. for $C_9H_{13}NO_3$: C, 59.00; H, 7.15; N, 7.65. Found: C, 59.13; H, 7.19; N, 7.61.

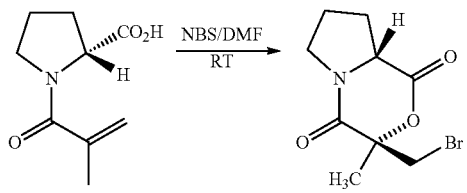

(3R,8aR)-3-Bromomethyl-3-methyl-tetrahydro-pyrrolo[2,1-c][1,4]oxazine-1,4-dione. A solution of N-bromosuccimide (NBS) (23.5 g, 0.132 mol) in 100 mL of DMF was added dropwise to a stirred solution of the (methyl-acryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 (81%) (smaller weight when dried ~34%) of the title compound as a yellow solid: mp 152-154° C. (lit. [214] mp 107-109° C. for the S-isomer); $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, $CHH_a$), 3.86 (d, J=11.4 Hz, 1H, $CHH_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[\alpha]_D^{26}$+ 124.5° (c=1.3, chloroform); Anal. Calcd. for $C_9H_{12}BrNO_3$: C, 41.24; H, 4.61; N, 5.34. Found: C, 41.46; H, 4.64; N, 5.32.

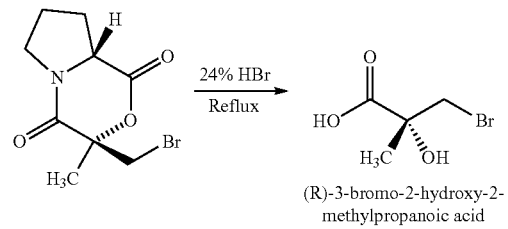

(2R)-3-Bromo-2-hydroxy-2-methylpropanoic Acid. A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated $NaHCO_3$ (100 mL×4). The aqueous solution was acidified with concentrated HCl to pH=1, which, in turn, was extracted with ethyl acetate (100 mL×4). The combined organic solution was dried over $Na_2SO_4$, filtered through Celite, and evaporated in vacuo to dryness. Recrystallization from toluene afforded 10.2 g (86%) of the desired compound as colorless crystals: mp 107-109° C. (lit. [214] mp 109-113° C. for the S-isomer); $^1$H NMR (300 MHz, DMSO-$d_6$) δ 3.63 (d, J=10.1 Hz, 1H, $CHH_a$), 3.52 (d, J=10.1 Hz, 1H, $CHH_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[\alpha]_D^{26}$ +10.5° (c=2.6, MeOH); Anal. Calcd. for $C_4H_7BrO_3$: C, 26.25; H, 3.86. Found: C, 26.28; H, 3.75.

Synthesis of (R)-3-bromo-2-hydroxy-N-(4-methoxyphenyl)-2-methylpropanamide (6b). (R)-3-Bromo-2-hydroxy-2-methylpropanic acid (8.54 g, 46.7 mmol) was placed in a 250 mL three-necked round-bottomed flask fitted with a stirring bar and an addition funnel, and dissolved in 100 mL anhydrous THF at room temperature. The solution was cooled to 0° C. Then, $SOCl_2$ (7.78 g, 65.4 mmol) was added dropwise with stiffing in 3 hours. p-Anisidine (5.00 g, 40.6 mmol) and triethylamine (6.62 g, 65.4 mmol) were added to the mixture at 0° C. The reaction mixture was stirred at room temperature overnight. The solvent was removed under reduced pressure to give a yellow residue which was dissolved in ethyl acetate and water. The organic layer was separated, washed with saturated $NaHCO_3$ solution and dried over anhydrous $MgSO_4$. The solvent was removed and residue was subjected to flash column chromatography (silica gel, EtOAc/hexanes=1/1 v/v) to give a white solid product, 8.50 g, 63.2% yield.

Synthesis of (S)-2-hydroxy-N,3-bis(4-methoxyphenyl)-2-methylpropanamide (6c). (R)-3-bromo-2-hydroxy-N-(4-methoxyphenyl)-2-methylpropanamide (6b) (5.80 g, 20.13 mmol) and $K_2CO_3$ (5.56 g, 40.26 mmol) were placed in a 500 mL round-bottomed flask fitted with a stirring bar. 150 mL of acetone was added at room temperature. The reaction solution was heated to reflux for 3 hours. The solvent was removed under reduced pressure. The residue was purified by flash column chromatography (silica gel, EtOAc/hexanes=1/1 v/v) to give a white solid product, (S)—N-(4-methoxyphenyl)-2-methyloxirane-2-carboxamide, 4.00 g, 96.0% yield.

To a 500 mL single-necked round-bottomed flask fitted with a stirring bar, rubber stopper and a nitrogen inlet was added (S)—N-(4-methoxyphenyl)-2-methyloxirane-2-carboxamide (1.00 g, 4.83 mmol) and anhydrous THF (50 mL). The solution was cooled to −78° C. in dry ice-acetone bath. 4-Methoxyphenylmagnesium bromide solution (14.50 mL of 0.5 M THF solution, 7.25 mmol) was added dropwise with stirring at −78° C. The resulted solution was stirred at −78° C.

for 30 minutes and then at room temperature for 3 hours. The reaction was quenched by adding 20 mL of saturated NH₄Cl solution at 0° C. EtOAc (3×30 mL) was added to extract the solution. The organic layers were separated, washed with brine (20 mL) and dried over anhydrous MgSO₄. The solvent was removed under reduced pressure and the residue was purified by flash column chromatography (silica gel, EtOAc/hexanes=1/1 v/v) to give a white solid product, (S)-2-hydroxy-N,3-bis(4-methoxyphenyl)-2-methylpropanamide (6c), 0.60 g, 39.5% yield.

Synthesis of (S)-2-hydroxy-3-(4-methoxyphenoxy)-N-(4-methoxyphenyl)-2-methylpropanamide (6d). (S)—N-(4-Methoxyphenyl)-2-methyloxirane-2-carboxamide (0.50 g, 2.41 mmol), 4-methylphenol (0.39 g, 3.14 mmol) and K₂CO₃ (0.67 g, 4.82 mmol) were placed in a 250 mL round-bottomed flask fitted with a stirring bar. 100 mL of isopropanol was added at room temperature. The reaction solution was heated to reflux for 3 hours. The solvent was removed under reduced pressure. The residue was purified by flash column chromatography (silica gel, EtOAc/hexanes=2/3 v/v) to give a white solid product, (S)-2-hydroxy-3-(4-methoxyphenoxy)-N-(4-methoxyphenyl)-2-methylpropanamide (6d), 0.79 g, 98.8% yield.

Synthesis of (R)-3-bromo-2-hydroxy-N-(4-hydroxyphenyl)-2-methylpropanamide (6e). (R)-3-bromo-2-hydroxy-N-(4-methoxyphenyl)-2-methylpropanamide (6b) (0.55 g, 1.91 mmol) was dissolved in 25 mL of anhydrous methylene chloride in a dry 250 mL round-bottomed flask fitted with a stirring bar, a nitrogen inlet and rubber stopper. BBr₃ solution (16.0 mL of 0.5 M CH₂Cl₂ solution, 8.0 mmol) was added dropwise with stirring at 0° C. The reaction solution was stirred at room temperature overnight. The reaction was quenched by adding 20 mL of water and extracted with EtOAc (3×30 mL). The EtOAc layers were separated and dried over anhydrous MgSO₄. The solvent was removed under reduced pressure. The residue was purified by flash column chromatography (silica gel, EtOAc/hexanes=1/1 v/v) to give a white solid product, (R)-3-bromo-2-hydroxy-N-(4-hydroxyphenyl)-2-methylpropanamide (6e), 0.51 g, 97.9% yield.

Synthesis of (S)-2-hydroxy-3-(4-hydroxyphenoxy)-N-(4-hydroxyphenyl)-2-methylpropanamide (6f). (S)-2-hydroxy-3-(4-methoxyphenoxy)-N-(4-methoxyphenyl)-2-methylpropanamide (6d) (0.20 g, 0.60 mmol) was dissolved in dry CH₂Cl₂ (30 mL). BBr₃ (4 mL of 1.0 M CH₂Cl₂ solution) was added dropwise with stirring via a syringe at room temperature. The reaction solution was allowed to stir overnight at room temperature. The mixture was cooled to 0° C. in a ice bath and hydrolyzed by adding water (25 mL). EtOAc (50 mL) was added to partition the solution. The organic layer was separated; the aqueous layer was extracted with EtOAc (2×10mL). The organic layers were combined, washed with brine and dried over anhydrous MgSO₄. The solvent was removed under vacuum. The residue was purified by flash column chromatography using silica-gel with hexanes/EtOAc (3/7 v/v) to afford a white solid product, (S)-2-hydroxy-3-(4-hydroxyphenoxy)-N-(4-hydroxyphenyl)-2-methylpropanamide (6f), 0.13 g, 67.2% yield.

Synthesis of (S)-2-hydroxy-N,3-bis(4-hydroxyphenyl)-2-methylpropanamide (6g). (S)-2-hydroxy-N,3-bis(4-methoxyphenyl)-2-methylpropanamide (6c) (0.20 g, 0.63 mmol) was dissolved in dry CH₂Cl₂ (20 mL). BBr₃ (6 mL of 1.0 M CH₂Cl₂ solution) was added dropwise with stirring via a syringe at room temperature. The reaction solution was allowed to stir overnight at room temperature. The mixture was cooled to 0° C. in a ice bath and hydrolyzed by adding water (25 mL). EtOAc (50 mL) was added to partition the solution. The organic layer was separated; the aqueous layer was extracted with EtOAc (2×10 mL). The organic layers were combined, washed with brine and dried over anhydrous MgSO₄. The solvent was removed under vacuum. The residue was purified by flash column chromatography using silica-gel with hexanes/EtOAc (3/7 v/v) to afford a white solid product, (S)-2-hydroxy-N,3-bis(4-hydroxyphenyl)-2-methylpropanamide (6g), 0.12 g, 65.6% yield.

Example 15

Synthesis of 11k

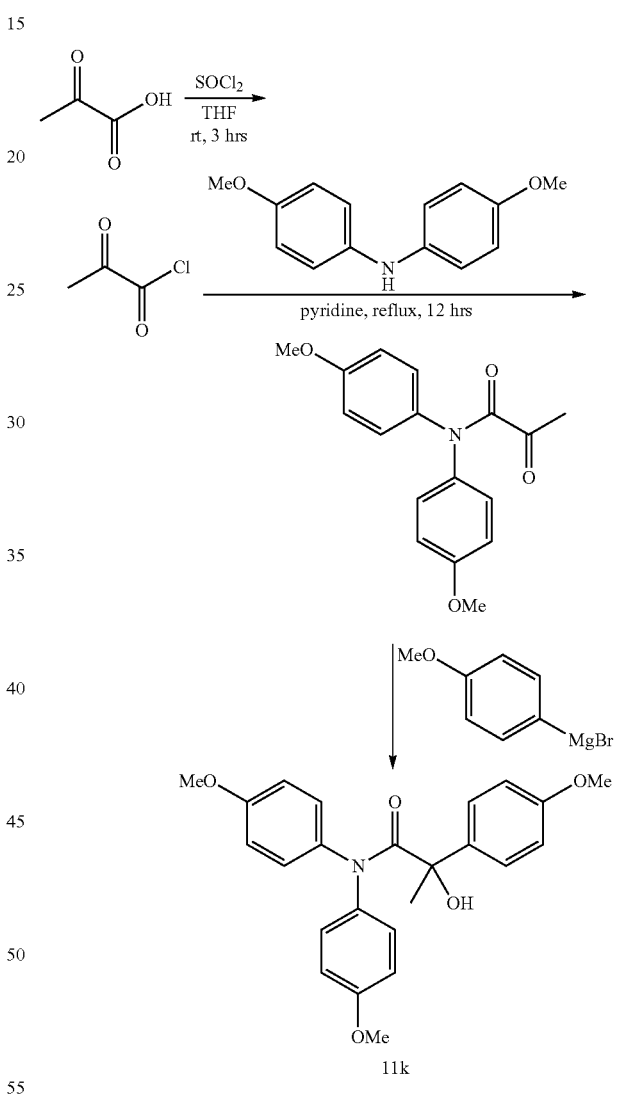

Synthesis of 2-hydroxy-N,N,2-tri(4-hydroxyphenyl)propanamide (11k). Pyruvic acid (1.00 g, 11.34 mmol) was placed in a 250 mL three-necked round-bottomed flask fitted with a stirring bar, reflux condenser and a nitrogen inlet, and dissolved in 30 mL anhydrous THF at room temperature. Then, SOCl₂ (2.03 g, 17.01 mmol) was added dropwise with stirring in 3 hours at room temperature. Bis(4-methoxyphenyl)amine (2.00 g, 8.72 mmol) was added under nitrogen protection. Pyridine (4.14 g, 52.3 mmol) were added to the mixture at 0° C. The reaction mixture was heated to reflux for 12 hours. The reaction was quenched by adding 30 mL of 2N HCl solution. The mixture was extracted with EtOAc (3×20 mL). The organic layers were separated, washed with brine (20 mL) and dried over anhydrous MgSO$_4$. The solvent was removed under reduced pressure to give a yellow residue. The solvent was removed and residue was subjected to flash column chromatography (silica gel, EtOAc/hexanes=3/7 v/v) to give a white solid product, N,N-bis(4-methoxyphenyl)-2-oxopropanamide, 2.15 g, 82.4% yield. MS: m/z 322 [M+Na]$^+$.

N,N-bis(4-methoxyphenyl)-2-oxopropanamide (0.53 g, 1.77 mmol) was placed in a 250 mL three-necked round-bottomed flask fitted with a stiffing bar, a rubber stopper and a nitrogen inlet, and dissolved in 30 mL anhydrous THF. The solution was cooled to −78° C. in dry ice-acetone bath. 4-Methoxyphenylmagnesium bromide solution (3.89 mL of 0.5 M THF solution, 7.25 mmol) was added dropwise with stiffing at −78° C. under nitrogen atmosphere. The resulted solution was stirred at −78° C. for one hour and then at room temperature for one hour. The reaction was quenched by adding 20 mL of saturated NH$_4$Cl solution. EtOAc (3×30 mL) was added to extract the solution. The organic layers were separated, washed with brine (20 mL) and dried over anhydrous MgSO$_4$. The solvent was removed under reduced pressure and the residue was purified by flash column chromatography (silica gel, EtOAc/hexanes=1/1 v/v) to give a white solid product, 2-hydroxy-N,N,2-tris(4-methoxyphenyl)propanamide, 0.61 g, 84.7% yield.

2-hydroxy-N,N,2-tris(4-methoxyphenyl)propanamide (0.60 g, 1.47 mmol) was to dissolved in 30 mL of anhydrous methylene chloride in a dry 250 mL round-bottomed flask fitted with a stiffing bar, anitrogen inlet and rubber stopper. BBr$_3$ solution (6.00 mL of 1M CH$_2$Cl$_2$ solution, 6.00 mmol) was added dropwise with stiffing at 0° C. The reaction solution was stirred at room temperature overnight. The reaction was quenched by adding 20 mL of water and extracted with EtOAc (3×30 mL). The EtOAc layers were separated and dried over anhydrous MgSO$_4$. The solvent was removed under reduced pressure. The residue was purified by flash column chromatography (silica gel, CH$_2$Cl$_2$/MeOH=9/1 v/v) to give a white solid product, 2-hydroxy-N,N,2-tri(4-hydroxyphenyl)propanamide (11k), 0.42 g, 77.8% yield.

Example 16

Toremifene Lowers Total LDL Cholesterol and Triglycerides and Raises HDL on Prostate Cancer Patients on Androgen Deprivation Therapy (ADT)

Methods:
1392 men 50 years old or more, with histologically documented prostate cancer and receiving ADT were randomized to toremifene (80 mg/day) or placebo treated groups in a human clinical trial. An interim analysis evaluated changes in circulating lipid levels from baseline to month 12 in the first 197 subjects to complete their first year to determine changes in total cholesterol, low density lipoprotein (LDL) cholesterol, high density lipoprotein (HDL) cholesterol, triglycerides and the ratio of total circulating cholesterol to HDL levels in the respective subjects.

Figure 2:
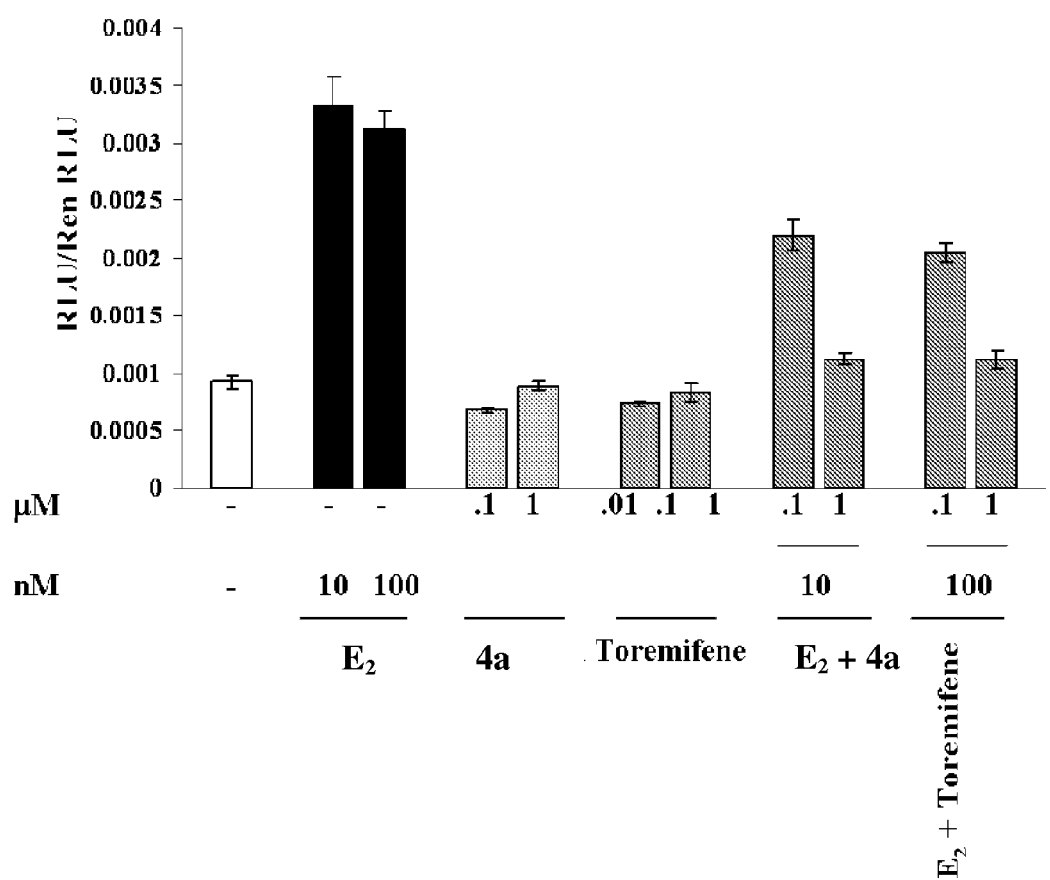
FIG. 2: Effect of the indicated compounds on ER-β transactivation. COS or 293 cells plated in DME without phenol red+10% csFBS at 90,000 cells per well of a 24 well plate were transfected with 0.25 µg ERE-LUC, 0.02 µg CMV-LUC (*Renilla*) and 50 ng of ER-β by lipofectamine. Twenty four hours after transfection, the cells were treated as indicated in the figure, harvested 48 hrs after transfection and were assayed for firefly and *renilla* luciferase.

Results:
Prostate cancer patients having undergone Androgen Deprivation Therapy (ADT) who received toremifene were compared to placebo groups. Toremifene treatment resulted in lower total circulating cholesterol (−7.1%; p=0.001), LDL (−9.0%; p=0.003), and triglyceride (−20.1%; p=0.009) levels, a reduction in the total cholesterol/HDL ratio (−11.7%; p<0.001), and higher HDL levels (+5.4%; p=0.018) (FIG. 1).

Subjects concurrently administered Statins demonstrated further reduction of total cholesterol, yet the magnitude of lipid changes elicited by toremifene treatment was greater in patients who were not concomitantly taking statins. Accordingly, patients treated with toremifene had a statistically significant improvement in all serum lipid parameters to measured.

Example 17

Exemplified SERM Compounds Lowering LDL Cholesterol Levels

Methods:
In addition to Toremifene, other SERM compounds may be similarly evaluated in clinical trial settings. The following compounds may be similarly administered as described in Example 1, and their effect in altering lipid profiles in subjects with prostate cancer, undergoing ADT may be similarly evaluated. Some of the compounds thus evaluated may comprise:
Compound (1): N,N-bis(4-hydroxyphenyl)-3,4-dimethylbenzamide;
Compound (2): N,N-bis(4-hydroxyphenyl)-4-propylbenzamide;
Compound (3): 3-fluoro-4-hydroxy-N-(4-hydroxyphenyl)-N-phenylbenzamide; Compound
(4): N,N-bis(4-hydroxyphenyl)-4-pentylbenzamide; and/or Ospemifene.

Example 18

Effects of SERMs on ER-α, ER-β and AR Transactivation
COS or 293 cells were plated in DME without phenol red+10% cs FBS at 90,000 cells per well in 24 well plates, and were transfected with 0.25 µg of the vector "ERE-LUC", where a firefly luciferase gene was driven by two estrogen responsive elements and 0.02 µg of the control CMV-LUC, Renilla where a luciferase gene was driven by a CMV promoter. Also 25 ng of ER-α, 50 ng of ER-β or 12.5 ng of AR were introduced by lipofectamine. All the receptors were cloned from rat tissue into the PCR3.1 vector backbone. Twenty four hours post transfection, cells were treated with compounds of this invention, estrogen, DHT, and other NRBAs or combinations thereof. Cells were harvested 48 hrs after transfection, and assayed for firefly and Renilla luciferase activity.

Representative examples of the NRBAs of this invention and their % estardiol activity at 100 mM

| Compound | ER-α | ER-β |
|---|---|---|
| 3a | 49.5 | 61.1 |
| 3d | 48 | 37.4 |
| 3e | 133 | 32 |
| 3l | 52.2 | 46.7 |
| 3g | 62.5 | 75.2 |
| 3j | 62 | 93.6 |
| 3i | 77.8 | 84.2 |
| 4a | 29.9 | 32.6 |
| 4d | 16.8 | 30.7 |
| 4h | 17.4 | 29.1 |
| 4u | 12.8 | 27.8 |
| 10o | 12 | 14 |
| 10d | 21.4 | 6.1 |
| 10f | 85 | 25 |
| 10l | 32 | 13 |
| 10w | 21.9 | 4.5 |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A nuclear receptor binding agent (NRBA) compound or its isomer, pharmaceutically acceptable salt, ester, or any combination thereof, represented by the structure of formula VI:

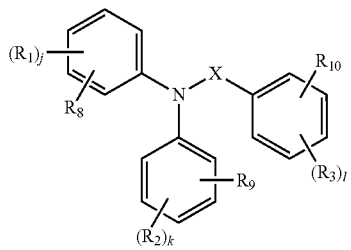

wherein
X is CO;
$R_1$ and $R_3$, are independently halogen, —CHO, —CHNOH, CH=CHCO$_2$H, hydroxyalkyl group of 1 to 7 carbon atoms, hydroxyl, alkoxy group of 1 to 7 carbon atoms, cyano, CF$_3$, NH$_2$, NHR, NHCOR, sulfonamide, SO$_2$R, aryl or protected hydroxyl;
$R_2$ is —CHO, —CHNOH, CH=CHCO$_2$H, hydroxyalkyl, hydroxyl, alkoxy, cyano, CF$_3$, NH$_2$, NHR, NHCOR, sulfonamide, SO$_2$R, aryl, or protected hydroxyl;
$R_8$, $R_9$, and $R_{10}$ are independently hydrogen, halogen, CHO, CHNOH, CH=CHCO$_2$H, hydroxyalkyl group of 1 to 7 carbon atoms, hydroxyl, alkoxy group of 1 to 7 carbon atoms, cyano, CF$_3$, NH$_2$, NHR, NHCOR, sulfonamide, SO$_2$R, aryl, or protected hydroxyl;
R is alkyl group of 1 to 7 carbon atoms, hydrogen, haloalkyl group of 1 to 7 carbon atoms, dihaloalkyl group of 1 to 7 carbon atoms, trihaloalkyl group of 1 to 7 carbon atoms, CH$_2$F, CHF$_2$, CF$_3$, CF$_2$CF$_3$, aryl, phenyl, halogen, alkenyl group of 1 to 7 carbon atoms, CN, NO$_2$, or OH; and
j, k, l are independently 1-4.

2. The nuclear receptor binding agent (NRBA) of claim 1 wherein said pharmaceutically acceptable salt is an HCl salt.

3. The nuclear receptor binding agent (NRBA) compound of claim 2 wherein said pharmaceutically acceptable salt is a chloride, phosphate, acetate, oxalate, tartrate, mandelate, citrate, sodium, potassium, ammonium, calcium, ferric hydroxides, isopropylamine, trimethylamine, 2-ethylaminoethanol, histidine, or procaine.

4. A nuclear receptor binding agent (NRBA) compound of claim 1, wherein said compound is:
4-hydroxy-N-(4-hydroxyphenyl)-N-(4-fluorophenyl)-benzamide (3m);
4-fluoro-3-hydroxy-N,N-bis(4-hydroxyphenyl)-benzamide (10g);
3-fluoro-4-hydroxy-N,N-bis(4-hydroxyphenyl)-benzamide (10k); and
4-fluoro-N,N-bis(4-hydroxyphenyl)-2-(trifluoromethyl)-benzamide (11x).

5. A pharmaceutical composition comprising the nuclear receptor binding agent (NRBA) compound of claim 1 or its pharmaceutically acceptable salt, and a suitable carrier or diluent.

6. A method of binding the nuclear receptor binding agent (NRBA) of claim 1 to an estrogen receptor or an estrogen related receptor, comprising the step of contacting an estrogen receptor with said NRBA.

7. A method of treating or reducing the severity of osteoporosis in a subject, the method comprising administering a composition comprising the nuclear receptor binding agent (NRBA) of claim 1 or its pharmaceutically acceptable salt to said subject.

8. A method of treating or reducing the risk of mortality from cardiovascular disease in a subject, the method comprising administering a composition comprising the nuclear receptor binding agent (NRBA) of claim 1 or its pharmaceutically acceptable salt to said subject.

9. A method of improving a lipid profile in a subject, the method comprising administering a pharmaceutical composition comprising the nuclear receptor binding agent (NRBA) of claim 1 or its pharmaceutically acceptable salt to said subject.

10. A method of reducing the incidence of, inhibiting, suppressing, or treating androgen-deprivation induced osteoporosis, bone fractures and/or loss of bone mineral density (BMD) in men having prostate cancer, the method comprising administering a pharmaceutical composition comprising the nuclear receptor binding agent (NRBA) of claim 1 or its pharmaceutically acceptable salt, or any combination thereof to a male subject in need, having prostate cancer.

11. A method of ameliorating symptoms and/or clinical complications associated with menopause in a female subject, the method comprising administering a pharmaceutical composition comprising the nuclear receptor binding agent (NRBA) of claim 1 or its pharmaceutically acceptable salt to a female menopausal subject.

12. A method of treating or reducing the severity of Alzheimer's disease in a subject, the method comprising administering a pharmaceutical composition comprising the nuclear receptor binding agent (NRBA) of claim 1 or its pharmaceutically acceptable salt to said subject.

13. A method of treating, suppressing, inhibiting, or reducing the incidence of hot flashes, gynecomastia, and/or hair loss in a male subject having prostate cancer, the method comprising administering a pharmaceutical composition comprising the nuclear receptor binding agent (NRBA) of claim 1 or its pharmaceutically acceptable salt to said subject.

14. A method of treating, suppressing, inhibiting or reducing the risk of developing prostate cancer in a subject, the method comprising administering a pharmaceutical composition comprising the nuclear receptor binding agent (NRBA) of claim 1 or its pharmaceutically acceptable salt, to said subject.

15. A method of treating, suppressing, inhibiting or reducing the amount of precancerous precursors of prostate adenocarcinoma lesions in a subject, the method comprising administering a pharmaceutical composition comprising the nuclear receptor binding agent (NRBA) compound of claim 1 or its pharmaceutically acceptable salt to said subject.

16. A method of claim 15, wherein said precancerous precursors of prostate adenocarcinoma is prostate intraepithelial neoplasia (PIN).

17. A method of treating, preventing, inhibiting or reducing the incidence of inflammation in a subject, comprising administering a pharmaceutical composition comprising a nuclear receptor binding agent (NRBA) of claim 1 or its pharmaceutically acceptable salt to said subject.

18. A method of treating, inhibiting or reducing the risk of breast cancer in a subject, comprising administering a pharmaceutical composition comprising a nuclear receptor binding agent (NRBA) of claim 1 or its pharmaceutically acceptable salt to said subject.

19. A method of treating, inhibiting or reducing the risk of endometrial cancer in a subject, comprising administering a pharmaceutical composition comprising a nuclear receptor binding agent (NRBA) of claim 1 or its pharmaceutically acceptable salt to said subject.

20. A method of treating, inhibiting or reducing the risk of bladder cancer in a subject, comprising administering a pharmaceutical composition comprising a nuclear receptor binding agent (NRBA) compound of claim 1 or its pharmaceutically acceptable salt to said subject.

21. A method of treating, inhibiting or reducing the risk of colon cancer in a subject, comprising administering a pharmaceutical composition comprising a nuclear receptor binding agent (NRBA) of claim 1 or its pharmaceutically acceptable salt to said subject.

22. A method of treating, inhibiting or reducing the risk of leukemia in a subject, comprising administering a pharmaceutical composition comprising a nuclear receptor binding agent (NRBA) of claim 1 or its pharmaceutically acceptable salt to said subject.

23. A method of reducing circulating lipid levels in a male subject with prostate cancer having undergone Androgen Deprivation Therapy (ADT), said method comprising administering to said subject a composition comprising a nuclear receptor binding agent (NRBA) compound of claim 1 or its pharmaceutically acceptable salt.

24. The method of claim 23, wherein said lipid levels, which are reduced comprise a triglyceride, low density lipoprotein (LDL) cholesterol, or a combination thereof.

25. The method of claim 23, wherein said method comprises increasing circulating levels of high density lipoprotein (HDL) cholesterol in said subject.

26. The method of claim 23, wherein said method further comprises reducing the ratio of total circulating cholesterol levels to high density lipoprotein (HDL) levels in said subject.

27. The method of claim 23, wherein said subject further suffers from atherosclerosis and its associated diseases, premature aging, Alzheimer's disease, stroke, toxic hepatitis, viral hepatitis, peripheral vascular insufficiency, renal disease, hyperglycemia, or any combination thereof.

28. A method of treating atherosclerosis and its associated diseases including cardiovascular disorders, cerebrovascular disorders, peripheral vascular disorders, and intestinal vascular disorders in a subject with prostate cancer having undergone Androgen Deprivation Therapy (ADT), comprising administering to said subject a composition comprising a nuclear receptor binding agent (NRBA) compound of claim 1 or its pharmaceutically acceptable salt.

29. A method of treating ischemia in a tissue of a subject with prostate cancer having undergone Androgen Deprivation Therapy (ADT), comprising administering to said subject a composition comprising a nuclear receptor binding agent (NRBA) compound of claim 1 or its pharmaceutically acceptable salt.

30. A method of treating bone loss in a subject, the method comprising administering to said subject a composition comprising a nuclear receptor binding agent (NRBA) compound of claim 1 or its pharmaceutically acceptable salt.

\* \* \* \* \*